US012703866B2

(12) United States Patent
James et al.

(10) Patent No.: US 12,703,866 B2
(45) Date of Patent: Aug. 11, 2026

(54) ENGINEERED MICROORGANISMS

(71) Applicant: Synlogic Operating Company, Inc., Cambridge, MA (US)

(72) Inventors: Michael James, Cambridge, MA (US); Aida Kalantari, Cambridge, MA (US); Tea Mirabella, Cambridge, MA (US); Lauren Renaud, Cambridge, MA (US); Lee Kristensen, Cambridge, MA (US); Vincent Isabella, Cambridge, MA (US)

(73) Assignee: Synlogic Operating Company, Inc., Winchester, MA (US)

( * ) Notice: Subject to any disclaimer, the term of this patent is extended or adjusted under 35 U.S.C. 154(b) by 604 days.

(21) Appl. No.: 18/265,002

(22) PCT Filed: Dec. 2, 2021

(86) PCT No.: PCT/US2021/061579
§ 371 (c)(1),
(2) Date: Jun. 2, 2023

(87) PCT Pub. No.: WO2022/120028
PCT Pub. Date: Jun. 9, 2022

(65) Prior Publication Data

US 2024/0110191 A1 Apr. 4, 2024

Related U.S. Application Data

(60) Provisional application No. 63/120,674, filed on Dec. 2, 2020.

(51) Int. Cl.

| | |
|---|---|
| ***C12N 15/52*** | (2006.01) |
| ***A61P 3/00*** | (2006.01) |
| ***C07K 14/245*** | (2006.01) |
| ***C12N 9/00*** | (2006.01) |
| ***C12N 9/10*** | (2006.01) |
| ***C12R 1/19*** | (2006.01) |

(52) U.S. Cl.
CPC ........... *C12N 15/52* (2013.01); *C07K 14/245* (2013.01); *C12R 2001/19* (2021.05)

(58) Field of Classification Search
None
See application file for complete search history.

(56) References Cited

FOREIGN PATENT DOCUMENTS

| | | | |
|---|---|---|---|
| WO | 2016/183531 | A1 | 11/2016 |
| WO | 2017/040719 | A1 | 3/2017 |

OTHER PUBLICATIONS

Bossuet-Grief et al., *Escherichia coli* ClbS is a colibactin resistance protein. Mol Microbiol. Mar. 2016;99(5):897-908.
Massip et al., Deciphering the interplay between the genotoxic and probiotic activities of *Escherichia coli* Nissle 1917. PLoS Pathog. Sep. 23, 2019;15(9):e1008029, 24 pages.
Olier et al., Genotoxicity of *Escherichia coli* Nissle 1917 strain cannot be dissociated from its probiotic activity. Gut Microbes. Nov.-Dec. 2012;3(6):501-9.
Pleguezuelos-Manzano et al., Mutational signature in colorectal cancer caused by genotoxic pks+ *E. coli*. Nature. Apr. 2020;580(7802):269-273.
International Search Report and Written Opinion for Application No. PCT/US2021/061579, dated Jun. 13, 2022, 17 pages.
International Preliminary Report on Patentability for Application No. PCT/US2021/061579, dated Jun. 15, 2023, 12 pages.

*Primary Examiner* — Manjunath N Rao
*Assistant Examiner* — Jae W Lee
(74) *Attorney, Agent, or Firm* — McCarter & English, LLP; Marcie B. Clarke

(57) ABSTRACT

The present invention relates to engineered microorganisms, wherein the engineered microorganisms comprise a therapeutic molecule and a modified pks island.

16 Claims, 37 Drawing Sheets

Specification includes a Sequence Listing.

Vehicle
WT EcN
ΔPks EcN
CFU/g Feces
T1
T3
T6
T24
T48
T72
Time of Collection (hours)

Vehicle
WT+ΔPks COMBO: WT selection
WT+ΔPks COMBO: ΔPks selection
CFU/g Feces
T1
T3
T6
T24
T48
T72
Time of Collection (hours)

Figure 2:
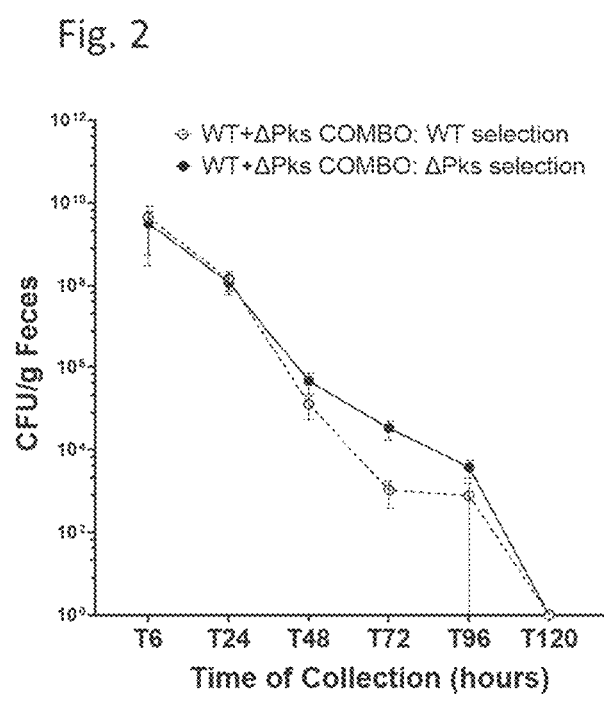

CFU/g Feces

WT+ΔPks COMBO: WT selection
WT+ΔPks COMBO: ΔPks selection

T6 T24 T48 T72 T96 T120

Time of Collection (hours)

FIG. 4

>clbQ

ATGAGTAATATCAGTTTGTATTGTTTGCCATATTCAGGTGGTTCTGCCGCCATGTATTATAAATGGCGTAGCGTGCT
GTCGGACAATATTACTTTGCGGCCTTTAGAACCTGCGGGGAGGGGAACTAGAATACGCCAGCCGCTGTGTCTTAC
GATGGTGGATGCCGTCGCTGACCTTTATCAACAATTTGTGAAACACTACACAGGTGGAGACTACGCCATTTTTGGG
CATAGTCTCGGAGGGATCATGGCCTTCGAACTGGTGCATTATATTCTCGATCATGGACATGACATGCCATGCGCGC
TGTTTTTTTCCGGCTGTCGCCCACCCGATCGGGCCTCTCATGAAGTAATACTGCATACCTTGCCCGATCAGGCGTTT
ATGGAAGAGATCGTCAAGCTGGGCGGAACTCCGGTTGATGTCTTTCGTAATAAAGAGTTAATGACAATTTTCACCC
CCATCATTAAAAACGATTATCGGCTCTATGAGCAGTATGTATTTCAGGCCAAGGCGCGCACATTAACCTGTCCGAT
CGTGCTATTTCATGGCGATGCTGACAATCTGGTAATGCAGGATGAATTACTTGCATGGGAAAAATTCACCACACGA
AAGACGCGGACTATTATATTTCCTGCTGCCGATCATTTTTTTGTCGATAAGCATTTTGAACAGGTGGTAGGTTATGT
GAACCAGACGATTGAATCACTCGAAATAGTAGGGTAG

>clbP

ATGACAATAATGGAACACGTTAGCATTAAAACATTATATCATCTCCTGTGCTGTATGCTGCTCTTTATTTCCGCTATG
TGCGCTTTGGCGCAAGAACATGAGCCTATCGGGGCGCAAGATGAGCGCCTGTCGACATTAATTCACCAACGGATG
CAGGAGGCCAAGGTCCCAGCCCTTTCCGTAAGTGTGACCATTAAGGGGGTACGTCAGCGATTTGTCTACGGTGTT
GCCGATGTGGCTAGTCAGAAAGCGAATACTCTAGACACAGTTTACGAGCTGGGATCGATGAGTAAGGCGTTTACC
GGACTTGTGGTGCAAATACTGATTCAGGAAGGCAGACTCCGGCAAGGGGATGATATCATTACCTATCTGCCGGAA
ATGCGCTTGAATTATCAGGGAAAACCTGCTTCCCTGACCGTGGCTGATTTCCTTTATCATACATCAGGATTGCCTTT
TTCAACACTGGCTCGGCTGGAAAACCCTATGCCTGGGAGCGCTGTGGCACAGCAACTGCGCAACGAGAATCTGCT
GTTTGCGCCGGGTGCGAAGTTTAGCTATGCCTCCGCCAATTATGATGTGTTGGGCGCGGTGATTGAAAATGTGAC
GGGAAAAACCTTTACAGAGGTCATTGCGGAACGACTCACGCAGCCGCTGGGCATGTCGGCGACTGTGGCAGTTA
AGGGGGATGAGATTATTGTCAACAAGGCAAGCGGCTATAAACTGGGATTCGGCAAACCCGTTCTGTTTCATGCGC
CTCTGGCCCGGAACCATGTTCCTGCCGCCTATATCCATAGCACTCTGCCTGATATGGAAATATGGATAGACGCCTG
GTTGCACAGAAAGGCTTTGCCGGCAACGCTGCGTGAGGCGATGAGTAACAGTTGGCGTGGTAATAGTGATGTTCC
GCTTGCCGCAGACAATCGTATCCTCTATGCCAGCGGTTGGTTTATCGACCAGAATCAAGGCCCTTACATCAGTCAC
GGTGGGCAGAATCCAAACTTTTCTTCTTGCATTGCGTTGCGACCGGATCAGCAGATTGGCATTGTTGCGCTGGCAA
ATATGAATTCGAATCTGATACTACAGCTTTGCGCGGATATCGATAATTATCTGCGCATTGGCAAATATGCTGACGG
CGCTGGTGATGCAATTACAGCCACCGATACCCTTTTCGTCTACCTCACGTTGTTGCTGTGTTTTTGGGGGGCGGTG
GTTGTAGTGCGCGGTGCTTTCCGTGTTTATCGCGCAACGGCGCATGGCCCTGGAAAACAGCAGAGGTTACGTTTA
CGCGTACGTGACTATATCATCGCCTTGGCGGTTCCTGGGCTCGTGGCCGCCATGCTCTATGTCGCACCGGGTATAC
TATCTCCAGGACTTGACTGGCGTTTTATCTTGGTATGGGGTCCATCGAGCGTGTTGGCGATACCGTTCGGAATTAT
CCTGTTAGCTTTCGTTCTGACATTAAATCATCAAATTAAACGAATTCTATTACACAACAAGGAGTGGGACGATGAG
TAA

>clbO

ATGGCAAAGGATGATTTTACCTGTGGCTCACTGGATATTGCCATTATTGGCATGAGCGGGCGTTTTTCCGGTGCGG
AATCGGTGCCCGAGTGGTGGGATAAGTTGCTGGCGGGTGAGGAGTTCACTCAACCGACATGCACAGAAGACGAT

FIG. 4 - Continued part 1

AATGGGAACCCTTGGATTAGGCTGCGCAATATAATCACCGCTCCCTATGACTTCGATGCTGCATTTTTCAATATTCC
GCCTGGCGAAGCCCTGTTGATGGATCCGCAACAACGAATATTTCTTGAATGCTGCTACAACGCTCTTGAGCATGCG
GGCTATATTCCCACGCAACTTAAGCGAGTCGGCGTCTATGGGGCGACCTACGCCAATAACTATTTTATCGATCGCG
TCTATCCATACCTGAAGATGAGCGGCGATCACCATTATCTTCAGGCGCAGATTGGTAACGAAAAGGATTACTTGTG
TGCTCAGGTTGCCTACAAGTTGGGGTTTACCGGACCCGCTGTGAGTGTACAGACCGCCTGTTCCAGTTCGTTGGTG
GCAGCATATTTAGCATGCGAGGGGTTATTGACTTTTCAAGCCGATGTTGCGTTGGCAGGTGGGGTCACCTTGGGT
TTTTTACAGGCGCACGGCTACAGTCCGCAAGGTGATAAGCTGGTATCGCAAGACGGACACTGCGCCCCGTTTAGC
GCTGAGGCGACCGGCACGGTATACAGCAGCGGTGCGGGAGTTGTGGTGCTAAAACGTCTTGAGGATGCACTACG
CGACCAAGACAGAGTGTATGCGGTGATTAAAGGAGGTGCGGTAAATAACGACGGCGGGCGTCGGCTGGGGTTT
GTCGCCCCCAGCGTAGAAGGACAGGTAGAAGCGATCAATACGGCGCTTGCCGCCGCAGAAGTCGTACCGACTGA
TATCGCACTGATCGAAACGCACGGTACCGGTACCCCGTTGGGTGATGAGATTGAGCTTGAAGCTCTGCACCGGGT
TTTCGCACCGGCATGTGCGCCGCACAGCATTCAATTGGGTGCGGTAAAAGCCAACTTGGGTCACCTGGGAGTCGC
TTCCGGTATCGTCAGCTTAATGAAAACCGCACTGACGCTATATACTGGTTTAGTTCCCCCGCAGATCAACCTAGTAA
ATAAACATAAAAAACTGTTGCAGCCAGCCTCGCCATTTTATCTCAGTGATGTAGTGACTTCTGTCCCACAAACGAAA
AGGATCCATGCCACCGTTAGTTCGTTTGGGCTGGGAGGGACCAATGCTCATTTGGTTCTGCAAAACTGGTGCGAG
ACGCCTGCGCAAGCGGTGCAAGAAAATGAGCGCCGCCTGTTTTTCTTCAGCGCCAAAACGCCATTAGCCCTTAGAC
AACAGTTGGATGCTCATTATCACGCTCTGGCGACCTATGCGGAAGCAGATAAAGATCGTATCGCCTATACTCTCGC
GCAACGCCGGGCACATTTCCCGTATCGCTGTGCGCTGGCGGCAGACAGTGTGGTAGCGTTGCGTGCAAGTTTGGC
GAAACTGCGGGATGCTGACATGTCTTTTACCCCTATCAATATGGAAACTACCTTGGTGTTCCTATATCCGGACCGG
GACGATAAGCTGGAGAGTGCCCTGACGCATTTGCTGGCTTGTCAACCTAACTTGCGCCAGCGGCACCAGCGCCTG
TCTCAGGATGTTGCACAAATCTGCGAACCAGCCGATTGGACGCCAGCATTGCGTCAGTTTATCCAGCAGGTGAGTC
TTAGTGAATGGCTGATCGAACAAAGTATCTCGCCTGTGCAGCACATCGGTTACCTGACGGGGGCTGCAGCAGCGC
AGTATGTTGCGCGCATCATCTCACTGGAAAACGCTGTTCAGCAGGTGATTGTGGCTGAAACGACACCGGAGCAGA
CGCTGGCCGGCAACAGTGAACTGAGCGAAATATTGGCTAATCTGGCGGTGACGGAGGGAACGCTGATGCTGGAA
ATCGGTCGCGCGGGGACGTTTTCCATATTGTATCACCAGCATGCGCAGTGGGTTGGGCAAACAGTATTTTCCCCCA
TGCTGAATACGGATACGCCTGAGGACATCCTGCCGCTGTTGGGCACTCTTTGGCAACGAGGAGTGACTATTTGTTT
ACCGGAAATGCCAGCCGTGCAGACTATAGGCTTACCCGGTTATTCGTTTGATCGCGTCCGGTATGAAATTCAGTCC
AGTGATGCGAGAGAGAACGCTATGTTACCAGTGAGTTATTTGTCGGTCAGCGACTTTGTGGAGAAAACCTGGCGT
TCATTGTTATGCATCGATCATTATGACGAACACGCGGTTATTTTCGAATACGGAGCGACCTCGATGCACGTTATCTC
TTTCGTCGACAGCTGTAACCACATTTATAAAATCGGACTGACTGCCGCCGATATTTATGCCAGACCCGCTATCCGTG
AGCACAGTGAATTTATCTCCGAATGTGTTGATGGTATTTTATGA*

>clbN

ATGATGTCGGGCAATCCGTTGTCGTGGCCACAGGAACAGTGCCACATCATTGATCAACTGTATCCTTACAGTGCCG
TAAACATCATTGGTGGTGTGGTCACCATTGAGGGAATTGTCGATCTGCCCCGACTACACGCGGCCATCCAGTCCGC
CATTCGGCAATTTGATGCGTTGCGTATGTGGTTTGTGATGGGAGAGGAGAGTGAAGTGGTCAGCCAAGTGCAGCC
TTATCACTGGCGCGATATCCGCCATTTGACTTTTTCCCCAGATTATGACAAGGAGAACCTACGCCCAGCGGCGATC
GAAACATTTGTTGATGAGTGGTTCCGGCAGCCCTTTACCCTGCTGGCGCACGATTTGTTCGAGTTTGTCACCTTTAC
GTGCGGTGAACAATACAGCGGTTATTTATTTAAAGCCCATCACGGCATTGCTGATGGTTGGTCAATGGCGTTGTTG

FIG. 4 - Continued part 2

TCAAACCATGTCAAGCGAGCATACGAACAGCAGGACGTACCAGATGATGCGTCACCAGCCTATAGCGCATTTCTG
GCGCAGCAGCAATCTTATCAGGCGTCAACGCGCTTTGCCGTTGATCGTGGCTGGTGGCGTGACTATATCGACGAA
TACCGCGACTGCTTTCCAGACAGTTCCCCCATCGTTACTACTGAGGGCATCAGTTGTTCCACTTGGCTTGAGCCAGC
CATGATTAACCGTCTCTACAGGTTGTGTAATCGTTATGGCTGTACGCTTAATACGCTGTTTATTGCACTCTTCGCTCT
CTATCGCGCCAGAGTATGGGGGGAGGAAAAAGGCGTAATAGGCGTGCCGTTAGCCAATCGGCATACTCGCGAGG
CGCGGCGTTGCTTTGGCATGTTTACTAATCAATTGCCGCTGGCCTATCGACTGGTGCGCACGGAACGATTCTGTGA
ACGGGTGGCCTTTTTCCAGCGCGAACTGAAACGCGGTTTTAAACACAGCAAATATCCCATTACCTTATTCAACCAG
GATTTGGCGGAACAGGGGGGAGGGAAGTTGCGGGCGTTCGATTATTGCGTTAATTATTATAACTTTACCTATGAA
CGCCACATTGCAGGTGCCGCGCAACGCGTGGAGAGTTACTACAGCGGCGAGCAGTCCTATAAGCTACAGATTGTT
TTGCAAACTGTTAATAATCATAAAGAAAGCCTTAGGTTGAGTCTGGAGGCGCTGCGTAGCGCTTTCACTCCGCACC
AACTGACAGCGATGAAAAATGGGCTGTTGGATTTAGTCACTGCATTGGATCGGCAACCTGACGCTCGTCTAGGCG
ATCTCGAAGTCTATCCTGCGCCGCACGTCGCATTGGCATGTGGCTCACTCAAACCCTCATTTACTTCCCGATTTGCA
GCGCAAGTTGTGGAGCATGGTGATCGCACAGCACTAATTGATAATGAACAGTCTTTGACTTATCGGCAGTTGGAT
GACGCTGTTGAGCGGGTTGCGCGTTATCTGCGCCAACAGGGGATCGGACGCGGTCAAGTGGTTGGGATTATCGCT
GAGCATAGCGCTCAAACGGTGATGGTTATTTATGGTATTTTGCGCTGCGGCGCGGCATTTCTGCCGCTAAATCCCG
CGTTGCCAACGACCCGCCTTTACGCCATGTGTCGTAAAGCGCAGGTAGCGCATATCCTTTACGATCCGGCGATGCA
TGAATTGACGCAGGCGCTGGCGTTTCCCGCGTCCAGCTTGCTCCAGGCCTTAGCCACTTCGGCGCTTGCTAGAGAA
CCTTGGCCAGCTATTGAACCGCAGGATCTGGCATATGTGCTGTTTACCTCCGGATCGACCGGCGAGCCTAAGGGC
GTGCAAGTCTCTCATGGCAATCTGGCTAACTATCTCCATTTCGCCGCCGAACGTTACTTTACAGCGCAGGACCGGG
CTGCGCTCTACTCTTCGCTGTCCTTCGATTTGACCATCACTACGCTGTTCGCCCCCTTATGTGTGGGCGCTAGCATCA
GCGTTTGTCGGCACGCCGAGAGCGAAACATTGCTGCGCATGGCCGTGGTTGATCAGCCCAACACAGTGATCAAAC
TGACGCCTGCACACCTGCGGTTGTTGTGTGCGGCTGGCATAAGCAGTGAGCAGATTCGTACCTTGGTGGTTGGCG
GGGAGGATTTCAAGCGGGATCTGGCGCGTAAGGCGGCTGCTCTCTTTCCTCAGGCCGTGATCTATAACGAATATG
GGCCGACAGAGGCCACCGTTGGTTGCATGATCTATCGCTACACCGGGCAAGAAACGCTGCCTTCATTGCCCATCG
GTATGGCGATCGACGGTTGCCAGGTAGCAATTTGCTCCCCTTGGGGCTGTCCGGTACCGGAAGGCGAAACTGGTG
AATTGGTGATTTATGGCGCGTCAGTGACGCAGGGCTATATCGATGCGCCGCAACAAACGGCCGCCGCCTACCTTA
AAGATACCAATGGGGTGATGATTGGCTATCGCAGCGGTGATATTGGCTACGCCATCGCTCCTAATACGCTGGTTTA
TCAGGGACGTAAAGACGATCAGGTCAAAATTAATGGCTATCGTATTGAGCTGTGCGAAATCGAACAAGCGTTGTT
GAGCGCACCTCAGGTAGAAAGTGCGGCGGTGGCGGTGATTGATGATGTGCAGGGGCAGCACAGCGGGTTGCTA
GCCTGCGTGACACCGTCATCTGTTGATGTAGCTACCGTAATGCAACATCTGCGTCAGCAATTACCCACCTACATGCA
ACCCAAGCAGTGCTGTGCTATCGCCCAACTGCCGCTATCGCACAATGGCAAGGTGGACGTGCGTCAGATGGTCGC
AACGGTCCGAAACACCGCGCCTGCATCGGGTAGCGAGCGGCTGGGAGATGCGGCGATAAGGCATTCAGTTCGGG
TATGTGTGGAAGGGGCGCTGGAGCAAACTGAGTTTGATGATAACGAAAATCTTTATGTCTTGGGGTTGGACTCCA
TCAAGAGTATCCAGATTGCAGCGCAGCTCAGGCACCACGGCTGGACGATGTCAGCGGTGCAGGTGATGGAGTGT
GGAACAGTGAACGCCATCTGTGAGTTTCTCGCTAGTCATACAACGGTGTCACAGCTCGCGCAGTATGCTCATAACA
CCCGTATCGATCTACCCGCATTGCGTTGGTTTACGCAGTTGGCGTTGCCAGTGCCCAATGTTTATAACCATGTCATT
GTGCTGAAAGTGTTGCCGGGCTGCCCGCTCGAGCAGTTACACAACAGGCTGCATACATTAATCCAGCAGCAGCCA
GCTTTGCACAGTGCGCTGGACGCTGAGGGGCGGTTGCTAGTATGCGACCCTAATGTGTGTTATCCCAACGAGGTG
CTCACGGAATATTCGACGGCGCAGTGGACGTTGGCAGAGGTGATCGCTCAGTGCAATAGCATGCTTGACGTGACA
AATGGTCGAGTCTTTACGGCAGCTCTGTTACACGCCCCGCAGCCTGCGTCTAGCACGCTGGTACTCTGTGCCCATC
ACTTGTGCGTCGATATGCACTCTTGGTATTTAATCCTCAGCACGCTGGACGCCGTCAGCACTGTCAATGGCACCAG
CAACAGCGGACTGCATCGCTGGAATGACTATCTGGCGAGCAAAACGGTAGATTCCGCCACACACGAAAGCTGGCG

FIG. 4 - Continued part 3

CACAGTATGTCAAACGCTACCGCTGCATTTCCCACCCGTGTCATTGCCAGATGACTCATTACCTCGTACGCGCGCTT
GGCGTGAAGACTTTCGCCATCCTTGCGTCAGGAGGTTGTTTGAATCCAGTGGTAATACCGCGTACAGCGCCGAAA
CCTATGTGCTAACGGCATTGGCGCTGGTGCTGCGTTACTACAGCGAAGAGCCTTGGTGTCGCATCGAGATGGAAG
GCATGGGACGCGGCTGCTGGCCCGATGAGCCTGACGTTGCGGATACGGTCGGGTGGTTTACTCTATTTTATCCTTG
GGCGATCCCTCTGCATGGCGATATGGCGACACTGTTATCTGCGATCGCTTCCGATTTGGCAAAACGCACGCATGGT
GGGGGAGATTACGGTCTGCTGCAAATGCGGCATGCACCGGAAGACTCTCTTGCGCAAGGGATCCGAATGAATTAC
ATCGGTGTGCAGGCGCAACCTTCACTCCGCTATTTTCATATTGATCACTTTAATAGTGATATCTATACCGCGCCTGA
AAACGCGCTCGGCTGCGTGCTGGAGTTTAATATTGCGCGCTCGGCAGCTGATGGTCTCTCCTTCCACTGCCGTTTC
GATCCCACGCGCATTGCGCTGAATGATGTGCAACTCCTGCTGGCGCGCTACAAGAACAGCCTCACTGATCTGGATG
CCTGGCTGTGCCAACACAGCGCCACGCTGACGGGCGCGCCGACTTTGTGGACACTATAA*

>clbM

ATGACGGTGAATAAGCTTGAGCCAGACAACGGCACGCCGAACGATGAGCTGTTCACGGTGGCGGGTATGTTTGA
CGGCTCGCTGTATAAATTACTCCTGCGCATGGCGTTGCCGATGTTTGTCGGTATGTTAACGCAGGTGACCTATGCC
ATCGCCGATATTTTTTGGCTGAGCCACATTGATGTCACCAACAGCGGCATCATTGCCGGTGTGGGGCTGGTTTTCC
CCGTTGGAATGGGGTTATTTGCCATCGCCAACGGCATTCAAATCGGTATGGGATCTTTGCTGTCCCGCGCCATCGG
CATGCAGCGGTTGGATCGTGCACAGCGGATTTTGTCGGTCGGTATCATCATCGCGCTATTCTTTGCGATCGTGATC
ACCGTACTTGGCTATGTTTATGCCCAGCCGCTATTGCGCTCACTGGGGGCCACGAAGAGCATCATCGGCTACGCAA
CGGAGTTCTATTATTATTCGCTGCTGACCGTGTTCAGCATCATGTTGATTGGCGTCATGATGGGGCTGTTTCAAGG
CGCGGGTAAGATCATGGTCATCATGAAGGCCTCATTGTTGGGGGCGTTGGTAAATATTATGCTCGATCCAATCATG
ATCTTTGTATTCGATTTTGGTGTGAAAGGGGTGGCATTGGCGTCGTTTCTGGCGCAACTGAGTATGGTCGCCTATT
TCATCTACACATTGATGGGATTACATATCGGGTTGAGTATACGCATCGCGTTACGCCCATTCTCCTGGAAAATCTAC
CGAGAGTTTCTCTCCGTCGGCATGGCGCAGATGCTGATGCAACTGATCATTGCGGTCGGCATAGTGATTTATAATT
TTTTTATCGTCAGGCTGGACGTAAACGCGATGGCAGCGTTTACGCTCACTGGTCGCATCGACTATTTCATCATCACG
CCGATGCTGGCTATCGCGACCGCGTTGCTGACTGTGGTGGGGCAAAACTGGGGACACGGAAATGTCACCCGCAC
GCTGAATGCCTATTGGGCCGCCGTCGCGCTGGCCTTCTCTATTGTGCTGGTGTTAGCCGTTATGCATATTGTACTGG
CACCCTGGATGTATCCCCTGTTTACTCGTGTTGTTGCCGTGAGTGACTATGCGGTACTGCAAACCCGTATCATGGCA
CTGGCACTACCCTTTGTCGCTATCAGCCTGTTAGCAAGTGAATATTATCAGGCCATTGGTAAGCCTTGGTATTCGGT
GTTGTTGACGCTGATGCGTCACGTGTTTATATCTGTCCCTGTCGTATACCTGCTGGCGATTGTGTTAGAGATGCGTA
TTACCGGCGTCTATTTTGGGGCGATGAGCGGCACTTTTGTGGCTGCGTTGTTGGCGTGGCGTCTGCTGCGTCTTTC
ACCTCGTCTGCTGCGATGGAATCAGGAGGCGGTGCGCTCCCAACACTTGGATATGGAGGTGGCACCATGA*

>clbL

ATGAGTGAGCAGAGCTATCGTAGCGCAGGGACACTGTTGGCACAGTTGGCGTCCGGAGAAACCACCTCAGTGGC
GTTGGTGAATCACTATTTTTCACGTATGGCGCAGTTTAACAAGCCGTTGAATGCGGTGGTGCAGCAGCACTATGCG
TTGGCGTTGGAGGCCGCCGCGCGCGCCGATCGTGAGCGACTGGAGGGGCGCGCAAGGGGCGTGTTGCACGGAT
TACCTTGTACTGTTAAGGAGTCGTTTGACGTGCAAGGGTGGTTAACCACGTCCGGTGCCCATTATCTGAAAGATAA
CCGGGCGACGCAGGATGCTCCTTCCATCGCACGCTTACGCGCTGCCGGGGCGATCCTGATGGGAAAAACCAATGT
GCCGATGATGACTGCCGATTGGCAAACCTATAACGATCTGTATGGCACCACCCATAACCTGTGGGATAGGCAACG

FIG. 4 - Continued part 4

TTCACCCGGCGGATCGTCCGGAGGAGCGGCGGTGGCGGTGGCGGCGGATTTCACCCCCGTGGAATTTGGCAGCG
ATTTGTTTGGCTCACTGCGCATTCCCGCACACTACACAGGTGTCTATGCCCATCGTTGTAGCTTGGGGTTGATGTCG
GTCAGAGGACATGTGCCCGGTGGTGGTCCGCAAGCGACTGATGAGCCGGATCTCTCGACGGCGGGCCCCATGGC
GCGCAGCGCGGCGGATCTGCGTCTGATGATGCGCGCATTGAGCACATTCTGGGTGGAACCGCCGCGTATTCCCGA
TTTTAGCCGTTATCAGGCCAAAGCAAACTACCGCGTGTGCACGTGGTTTAGTGCGCCCCACCATGAGATAGATCAA
CAGATCGCACAGCGTTTTCAATCGTTTATCGACAAGTTACGCGCACAGCCTGGCGTGGAGGTTGATGATGCTATGC
CCGCCGATATCGATCCCGACGCACTGTTTGATATAGCAGTCAAACTCAGTGGTCGGCTGGTAAGTACGGCGCTCAA
TGGACGCCAGCGTCTTACAGCCGGGCTGGCTGCGCTGGGCTTCAGGCTTGTGGGCAAGCTGGCGGATGTGCCTG
AGGGGATAACGAGCTATTACCAGGGCATGCTGAAAGACAGTGGCGAACAGCGGAATACAGACAAACTCCGCCAC
GAATACAGCCGGGTGATAGAAACCCTTTTCGCGCGTTATGACGTGTTGTTGACACCTGTCAGCCCGGTGCTGGCGT
TTGCGCACATGCAGCAGCCGGTGCGTAAGCGCAAGCTTATCGTCAATGGCGAACCGCAAGATTACAACGAACATT
TGTTCTGGAACATGTTAGCAACGGTTTTTGGTTTGCCTGCCACCGTTTACCCATTGGCGAAAACGATGGATGAGCT
TCCGTGCGGCATACAGATCATTTCCGGGCATTTTCACGATGATGTGACGATTAACTTTGCTGAGTTCTGCGAAAGC
ATCAGTGGCGGATTCACGGTACCGGAAGGGTACTAG*

>clbK

ATGACTTACAGTGAAAGCGATATTGCCATTGTTGGCATGAACTGCCGGTACCCCGGCGTGCACAGCGTTGCGGCA
TTCGAAACGGTGCTTCGCACCGGATGCAACATTTTGGACCCCAAAGTGACCCCGAGCAACGGCCACAATCACATTA
CGCTGAACAACGTCTATGAGCACATGGCGGAGTTCGATGCCAACTTTTTTGGCTACAGCCGTGCAGAAGCAGAAA
TCATGGATCCACAGCAGCGCGTATTTCTGACCTGTGCTTGGGAGATGTTTGAACAAAGCGGTTACAACCCGAAGC
AGCACGATGCGCGCGTCGGCCTATATGCGGGCGTGAGTACCAGCTTCTATTTGCTTACTCACCTGATGAACAACCC
AGACAAGCTTGCACAACTCGGTGGTCTCCAAATCATGGTCGGCAATGACAAAGATCATTTGACGTCCCAACTGGCT
TACCGCCTGAATATTACCGGCCCTTGCGTGACGGTTCAGGCCAGTTGTGCCACCTCGCTGGTGGCAGTGCATCTGG
CCTGCGAAGGGCTGCTGAGCGGTCAGTGCGATATGGCGCTAGCGGGTGGCGTCACGTTTCGCATGGAGGAGCAG
CGCAGCTATGAATCGCACGGTGATGGGCTGCAAGCAGAGGATGGCCTGATTCATACTTTTGATGCGCAGGCGAGC
GGTACGGTCTACAGCAGTGGTTTGGGCATGGTGCTGCTCAAACGGGCTACAGACGCGCAGGTGCAAGGGGATAA
CATCCTTGCCGTCATCAAGGGAAGCGCCATCAACAATGATGGCGGTGCGCGCAGTGGTTATACCGTGCCGGGTGT
TGATGGTCAGGAAGCTGTGATGATTGAGGCGCATAGCTTGGCGGAGGTGACGCCGCAGCAAATTCAGTATCTAG
AACTGCATGGCAGCGGCACGCCGTTGGGTGACGCTATCGAATTCGCGGCCATCAAACGTGTGTTTGGGACGCCAG
CGCCGAATGCGACACCGTGGCGTCTGGGGGCTGTGAAACCTAACGTGGGTCACGTAGAAATGGCATCTGGCATC
ACCAGTCTCATAAAAACGGTGCTGAGTCTTACTAACCGGGTGTTTTACCCTACGCTGAATTTTCAACGGGCTAATCC
GCAACTGGGGTTGGAGGACAGCCCGTTTGAAGTGGTGTCCCGTTTAACGCCTTGGCCGGAGGGCACCACGCCAC
GCACCGCTGGTGTGAGTGCGTTCGGATTGGGCGGCACCAACGCACATCTGGTGGTACAAGCGCCGTTATCGACGC
CGCAGGCGAGGGCGCAGCAGATGGGGCCTTGTGTCGTTGTACTCTCGGCAAAAAACCACAATGCCCTGGAACAG
ATGCAAAACGCCCTGCTGGCGAAACTGGCCGCACATCCAGAGATACGCTTACAGGACGTGGCTTACACCCTGCGT
CACGGGCGTTTCTCCGCCCCGGTACGTAAGTGTGTCATCGCAGAGAATTGCACCCAGCTAGCCCGACAACTCCGCG
ACGCACCGATGGTGGAGGCAACCACGGGTTGCACGATCTACTGGAGATTGGGGCACCGTTTCGTTGTTGCACTCG
AGACGCTTAGTGACTGGCTGGCGTGCTCTGAGGTGTTGTCACAGGCGGTGGGACAACTGCTCGAGCATTTTCCGC
TCGAACCAGCCTGTCTGCAAGATCTCTCCCCTGCGCAACGGACGTTTATCAGCCAGTATGCGCTGATCGCGTTGAT
TGACGAACGGGAAACGTTGAATGTGGTGCTATGCGGCGACGGTGATGGTGGCTATGCTGCCGCCGTACTACGAG
GAGACTGCACACTAGAGCAAGCATGGCACAGGTTGAATGCGGGCCAACCGTTTGATGATGTGCCGACGAATCCCC

FIG. 4 - Continued part 5

TCTTGCAGCCCGATGTCTGCTCTTTGATGCTGGACGACGCGGCGAGTGATGCCAATCGCACCGCGCTAGAGGCGT
TAGGGCAGTTATGGTTGGCTGGCGTCAGCCTAGATTGGCGCTGGGTGGATGCGGCGGAGCGTATGTTGGGCAGT
CAACGCATCGCCCTGCCGGGGACCGTTTTTACACCGCAGCGCTATTGGGTCGAGGCCGTACGGCCTGCCACGTTCT
CCCACGAATCGTCGAATAATCTCTTATCCCGCGCAACAAAATCCGATATTATTGCAGTGGTGACGGAGATATGGGA
ACGCACGCTTGGTGTCAGCATTGATGATCACCACGCCAGCTTCTTCGAACTGGGTGGGCATTCGCTGTTAGCGTCA
ACCATTTTATATGATATTCAGCAACGTTACGGCATCACCTGTACGCTAAGCGCATTCTTTGCCGATCCCACCATCGA
GGGATTAAGTTGCTATCTGCTCGAACAAGGCGGCAGTGAGACAGCGGTTTCAGCATTGCCTGATACGGTCTTTGC
CCCTGACCAGCAGCACCTACCTTTTCCGCTGACTGACGTGCAACAGGCCTATTGGGTTGGGCGGCGAAAATCCTTG
GGATTGGGCAATATTTCCACCCATATCTATGTGGAATATGAACTACAGGGGCTAGATGAAACAGCGTTCAACCGC
GCGCTCAATGCGGTGATTGCGCGGCACAGCATGTTGCGTGCAATTGTCAACGATGACGGTATGCAGCAGATATTG
CCAAACGTGCCGGAATACCACGTTGCCTTCTATACCACCCAGTGCGAGGATGCGTTTCAACAGCGTTGCCGTGAGC
TGCGTGACACCCTCTCACATCAGATGATTGATTGTAGTCGCTGGCCTCTGTTTCAGATGGAGGTCGTGGTTGATCC
GCAGCAAAAAGCCCGGCTACATGTATCTATCGACCTGCTGATAGCCGATGCATGGAGTCTGGAGTTGTTCATTCGG
GAACTAGCTTATCACTACCGCCATCCGCAGGCGGCATTGCCTACATTGACGTACAGTTTCCGCGACTATGTGCTGA
CCTTAAAATCCTACGAGAAAACGCCGCAGTTTGAACGGGCACGTGACTACTGGCGCGCCCGCATCGAAACTCTGC
CGCCGGGGCCACGATTGCCGCTGCGTACCGACCCCACGAAGCTGGAAAACCCCACATTCGTGCGCCGTAGCTATT
GTCTATCTCGTGCTATCTGGCAGCGCTTGAAAACGCAGGCGGGTCAGATGAGTATCACGCCTACTACACTGCTGCT
CACGGGGTTTGCTCAGGTGTTGGCGCGCTTTAGTTCCTCGCCGCACTTTAGCCTTAACCTGACGCTGTTTAATCGTC
TGCCGTTGCACGCAGATATCAATCACTTAATTGGCGATTTTACTGCACTGACGTTGCTGGAGATTGATATGTCGCA
GGGAGAAACCTTGCAGGCGCGGGCAAACGTGATCCACTCTCAACTGTGGCGCGATTTGGATAACCGCTTGTTTGG
CGGTATCCAGGTCTCTCGACTGCTGGTACAAACTCACCGCGATCCGGCGAAATCGGTGATTCCTATCGTGTTCACC
AGCTTGCTCAATCAATATGAGGCGAGCTGGGAAACGGATGATACGCTGTTCAACCAACCGCAGGATGATCTGTAC
AGTATTTCACAGACACCGCAGGTGTGGCTCGATCATCAGGTAATGGAGCGTAACGGGGAATTGCACTTTAATTGG
GACGTGGTGGAACAATTGTTTGAACCGGCGCTAATGGATCAGATGTTCCAGTGTTATTGCCAACTCCTGCACGCCC
TAGCCCAGCGACCACAGCTCTGGCATGAGACTCAAGATGTGCTGGCGCTGCCCACCGTTAGTGCACCGGTCACGC
AGGCTCCTGCACCTACGGCCTTGTTGCACCATGGGTTACTGCGTCAGGCAGCACTGACGCCACAGGAAACTGCGC
TGATCAGTCCTATCCGTGAATTGACCTATCGCCAACTGTCGACGGCGGCGGATCATGTGGCCCGCGCCCTGTTAGC
GCTGGGCGTGCAGCATGGCGACCGCGTGGCGGTGGTGATGGAAAAAGGCTGGCAGCAGATTGCCGCCGTACAC
GGCATTTTACGACTGGGTGCGGTCTATCTGCCAGTGGATCCGGTGCTACCGCCACAGCGTCGCCAGCTTTTGCTGA
CGGTGGGCGAGGTGCGGGTACAAGTAACGCAGCCGGGTCTCACGCAATTGGAGCCGTCGCTGCCCGTGCTGATC
ATCGACGACGGAATGCTGGACACGCCTGCTGCGCCGTTGCCTGAAGTGGCTGGGGATGTCACGGATCTGGCCTAT
ATCATTTTCACTTCCGGCTCCACCGGTACCCCGAAAGGAGTGATGATCGACCACCGTGCGGCCATGAACACACTGG
AAGACATCAACGAACGCTTTGGCCTCAATGCGCAGGATAGGGTGTTCGGGCTGTCATCATTGAGCTTTGACCTGTC
GGTTTACGATGCCTTTGCGCCTTTTATGGTGGGTGCAGCGCTGGTACTGCCGGAAGCAGGACGGGAAAAAGATCC
GCGTCATTGGCAGACAGTTATGGCACACGGTCATGTAAGCGTCTGGAATGCAGTGCCCGCACTGATGCAGATGCT
GTGCGAATACCACAGCGGCGATCGGATGAGTTATCCGACGTTGCGTCTGGCACTGTTGAGCGGCGACTGGATCCC
GCTAACGTTACCGGAGCAGATGCGCGAGCGGCTCAATGAAACGATGGACATCATCAGTCTGGGTGGAGCGACCG
AGTGCGCCATCTGGTCGGTCTACTACCCGATAGGTGAGGTGGAATCGACGTGGACCAGTATTCCCTACGGTCGGG
GCCTGCGCAACCAGCCAGTATACGTGCTAAATGCGCAACTGGAGGAATGTCCGGTCGGGGTGGAAGGAGAGATT
TGCATTGGCGGGATGGGGCTGGCACAAGGCTACCTGAACGACGCAGAGAAAACGGCGGCGAGCTTTGTCTGGCG
CGAAGCGAGTGGTGAGCGAATTTACCGCACTGGGGATCGCGGGCGCTACTTTGCTGACGGGCAAGTCGCCTTTTT
GGGGCGCAACGATACCCAAGTGAAGGTGAATGGTTACCGTATCGAACTGGGGGAAATCGAGCGCTGCATTGCGC

FIG. 4 - Continued part 6

GACATCCCGATGTGGAGCAGTCAGTGGTGGTGGCAGTGGGTAATTCTCAACATCGTCGGCTGGTCGCTTTTGCCA
AACTGCACGATCGCCACCAGGCGCAGGCATTGCAAGCTAAGGAAGCGGAGGCGGCGGCACTGGCGCAGGGTATT
ATTGTGAATCCGGCACAGCGTCTAGCGTTCAAACTCAAGGAGCCACATATTCGCGCGCTGGATGGTCTGGGCATT
GCACTGACGGCACCGGCGGATAGCACACGTTACATCAAACGCCGCAGCTATCGTCATTTCAGCGCGCAAAAAACC
ACGCTGGCACAGTTGGGGCAATTGCTGTCGGGCTTGGGGCAGATGCGTCTACCCGGTCTACCTTTTGCCAAGTAT
GCCTATGCGTCCGCCGGGGGGCTATACCCGGTGCAAACCTACGTGTACCTGCATCCAGACAAGATCGAAGAGGGA
GTATCCGGTATTTACTACTTCGACCCGCGACAGAGCTGTCTTATGCCGGTAGCACCAGAAGTCGAGCTGAACAGTG
GTTTTCATGCCGGACCTAATCAGTCTATTGCCGATCGGGCGGCATTCACGCTGTTTATGGTGGCTGATATGGCGGT
GATCTCGCCATTCTATGGGCAAGAGGCAGCTTGGCACTTCTCGGTGATGGAAGCAGGTACTCTCTGCCATTTACTG
GAAGAAGATGCGCCGCGCTACGGATTGGGGCTGTGCCAACTTGGGATGGCAGACTTTTCCGCTGTGGCATCGCAT
TTTCAATTGTCGCCACATCATCGCTATGTCCATTGCACCGTGGGGGGCGCGATAGGGCAAGAGGCGGCAAGTGCT
GCAGCATTGCTGCGCGATTTCTCCACCTATGAGAAACCGAAGGAAACCGCTGCGCCGCTGGACATGCAGAGCTAC
AAAGATGCCATGCTGCGCGGCCTGCGTCAGCAACTGCCTGACTATATGGTGCCGAGTGATCTGATGTTAGCGACC
GATTTTCCGTTAACCGCTAACGGCAAGCTAGATCGGCAAAAATTACAGCTGCAGGGCGAACAAATTGCCCACCAG
CGTGACGGCGTGGGTCCAATCCAGGTGGACAGTGCGTTACAACAGCGGCTGGTGGCGCTCTGGCAGGAGGTACT
CGGCGTGAGCCACGTGTCGGCCGAAGACGATTTCTTCTCGCTGGGGGGCAGTTCTATAGAATTGGTGCGTATTCA
GCAGGCACTTGAGGCGATTATCGGGCAGGAGATTCCCATTGTCGATCTGTTCCGTCTGCCAACCATCGCGGATGTG
GCGCGTTACCTTGATGAGCAACTGCACAATCTACCCGCCGCCCACGATATCGTATTAGCGCAGGCTGAGGTTTCGC
AGGTCAGCGCTGCGCGCGAGAATCTGGCGTTGCGGCGTAAACGTGCCCAACAGGGAGAAAAGGGCGATGAGTG
A*

>clbJ

ATGACGATACATCATGCCGCATTGGCGCGAATGTTACCGGCGGAAAAAAAGGAAAAGCTATTACGACAGTTGGCG
CAATCAGGCGTGTCGCCCAGCCGCATTCCCATCATCAAAGCGGATCCGGCGCAGGCAATCCCGCTGTCGTTTAATC
AGGAGCGGTTGTGGTTTTTGCAAAAATACGACAGTACCGCCACTAACTACAACCTTTATGTGGTGTATCGTTTGCA
TGGCGTGGTGGATATGCCGATGCTCACGGAGGCATTGCGCCATGTGCAAGCACGCCACGCCATCTTGCGTACCCG
TATCATAGTACGTAACGATCGGCCTTGCCAGGTGATAGATGATGCGTCTTCGTTAGTTCTCGATACGGTCACGCTG
GCAGCGCAGGCCCCAACTTCAGCGCTAGATGCGGTAATTCAGCAGGTGATAAACACCCGGTTCGATCTGGCACGC
GGTCCTCTGTGGGGGGTAACTCAGATTATTCAACCCGATCAAGGTTGTCATTTGGTGTTTTGCGCGCACCATATCAT
CATCGACGGTATCTCGTTACGGCTATTGTTCGATGAGTTACAGCAGCAGTATGCTCGATTGCATGCTGGTAATGAA
ACGTCGCTGCCTCCGCCGCCGCTGCAATATGCCGATTATGCCTTCTGGCAGCGCGAATGGTTCCAGGATACCTTGC
TGGCGAACGAACTTGCCTACTGGCGTGCGCGTTTGCAAGACGCGCCTCTGCTGTCGACATTTCCATCGCTGCACCC
GCGCCCGGCACAACCCTCTACACATGGTTCCCGGTTCAGCATCACCCTGGATGAAACATTAAGCCTCGCGTTGAAA
CACGTAGCCCGCACGCAGGAAACAACGCCGTTCGTGCTGATGCTGACTGCCTTCCAACTGGTGCTGATGCGTTACG
CTCAGCAACAGCGATTGGTGATAGGCATGCCAGTATCGGGGCGCATTCGCCCGGAATTGCAGAGTAGCATTGGTT
ATTATGCCAGCACTGCGGTTATCTACACCGATTTTAATGGGGTTGAGGTAGGGCGCGAGGCGCTCCAGCGTGTGA
AGGCCAGCGTGAAAGAGACGCAGGGGCGCCAGCAACTGCCGTTTGAAAACTTGGTGAATATGCTGGATCTCCCTC
GCAGCCTTTCCCATTCACCGTTGTTCCAGATCCTCTATATCTACCATAACCACGTGACCCCACGCGCTTTTACCTTGG
CTGGTGCGTATTGGGAGCAGGTGACGTATCACAATCAGACCGTCAAATACGACATGACAGTCGAGGTGTTCCAAA
ACGACGCCACGTTCGACGTCTCCTTTGAGTACGATTTGGGGTTATACGATGCTGATGTGGTGAAGCAGATTGCCGA
GGCGCTGCGTCAGCACTGCTTATCGTTGACATCATCACTGGAGACCCCGATAGGGGCGATCCCTCTGCATGCACCG

FIG. 4 - Continued part 7

GAGACCGCAACGCCGCGGCGTGATCCGCTCAACGCCACTAACGTCCCGTGGCTCGGGCCGCAGGATGTGCTGCGT
ATCATTGAACAGCGCTGTGTGCAGCACCCAAAGCAACTGGCAATACAGCAGCATGACGGCACACTGACCTACGCT
GAGCTCTGGGCGCGTGTGCAGTTCATCGCGATGCGTTTTCGAGCGCATGGCATACAACCGGGCGATCGTATTGGC
GTGCTGTTGCCACGTCACAGGGATGTGATTGCAACCATGTTGGCGACGTGGTTTGTGGGGGCGTGCTACGTGCCG
TTCGATATTCATCAGCCTGCCGCGCGTTTGCAACGCCTTATGCAACGCGCGCGTTTGGTCTGTCTGGTGGTCCGTCA
GCCGGGAGAGTGGGGTGAAATTGTACAACTGTCGTTGCCGGAATTGATGCAGGACATGTCGAATGCGATCCGGT
ATTCTACACCTTGCGCGCTGTTGCCGGATATGCAGGCCTACCTGTTGTTTACCTCCGGCAGTACCGGTGAACCTAAA
GGCGTGTGCGTTGTTCACCGCGGGTTGCTGAACTTGTTGTTGGATATGCAGCGTACCTTTGCGGTTGGCTCGCAAG
ACCGGCTGCTCTCGGTGACGACGCCAACATTTGATATCTCATTCTTGGAGTATCTGTTGCCGCTGATCTCCGGTGCG
AGTCTCTATCTGACAGAGGCGGAACGCGCCGCAGACAGCTTCCGTATGATTCCGCTGATTGCCGACTATCGACCAA
CGCTGATGCAGGCGACGCCCTCGTTCTGGCACGGGCTGTTGATGGCGGGTTGGCGTGGCGACCCGGAACTATGT
GTGCTGGCAGGCGGTGAAGCGCTGCCAACGAAAGTGGCGGAAGAACTGTTGCGCTGTTGTGGTTCATTGTGGAA
CCTCTACGGTCCCACCGAAACAACCATTTGGTCGCTGAAATCGCAGATAACCCAAGCGGAAAACATCACCCTCGGC
GCTCCCATTGCCAATACCCGTATATACATTCTGGACAATGAGGGCCATCCAGTGCCGCAAGGCGTTGACGGCGAG
CTTTACATCGCCGGGGATGGTGTGGCGCAAGGGTATGATGGGCAGCCTGAGTTGAACGCACAGTTCTTCTTGTCA
GAACCAGGGGTCCCCGGTGGCAGGATGTTCCGCACTGGCGATCTGGTCAGGAGTGATGCGCAGGGGCAGTTGTT
TTTTGTTGGGCGCAAAGATAGCCAGATCAAACTGCGCGGTTATCGTATTGAGTTAGGCGAAATTGAACGGACGTT
GGCACGGCATCCGCATGTGGACGCCGCGGTGGTGGCCTGTATTGAAAGAGCACCGTTACACAAAGCACTGGCAG
CATTCATCATCACCAGTGAGCCTCCCTCGCTATTCGAGCAACTGAAAAACGAGCTTCGGCAGCAACTGCCAGACTA
TATGGTGCCAACGCTGTGGCAGAGGGTGGCCGACTTCCCGAACACTGACAACGGTAAAATCGATCGTAAGCGGTT
AGCGGAAAATTTCGTTGCCGATAGCTCCCTTGTGTCGCCGCAGACGCAAGCGCTGAGCGACACGGAACAGATGTT
GCTGGCGCTGTGGATGCGCTATTTGCCGATAAAAAACGTCGATCCTGAGTGCGATTTCTTTCGCTTGGGGGGACAT
TCGCTGTTGGCGGTAACGTTGGTAGCAGAGATCAACCGCACTTTTCACTGCGCCTTGACCCTGAAGGACATTTTCC
ACTACTCCACACTACGGGCACTGAGTGCGCGTATTGCACAGCAATCTATCACGGACGCTGCCGCGTCTCAGGATGA
CTGGGTGATAGTGCACGACCCTGAGCATCGTCATCAACCGTTCCCATTGACGGATGTTCAGCGCGCCTACTGGCTT
GGACGACAGACGGGTGCTACCTCGATCGCGACCCACATCTACCATGAATTTGACGTAGAACACTTTAATGTTACGC
GTTTTACCCATGCGGTGAATGCGCTGATCGCTCGCCATGAAATGCTACGTGCGCGGGTACTCCCCGACGGTACTCA
GCAGATTCTGGCGCAAGTGCCGGCGTATCAGTTAGAGCAGCGCGATCTGAGTGCTTTGTCCCCTAACGCACGAAA
CGATGCCTTGATGGCGATCCGCGATCGGCTGTCGCATCATGTGCATCCCGCAGATCGTTGGCCGCTGTTTGATTTC
AGTTATTCGGCTTGCACGGCGCAACATGGCCGCTTGCATTTCAGTCTCGATCTGCTGATTGCCGATGCTCTGAGTAT
GCGCACGCTACAGCAGGAGTTGATGATGCTGTACCGTGAGCCCCATGTGTCACTGCCGTTGCTACCGTTCTCTTTTC
GTGACTACGTGCAGGCGCTGTTGGTAGAGCAGGCGAGTGAAGCCTATGCACGCGATCAGGCCTATTGGCAACGG
GCGCTGCCGCAGCTGTATGGCCCACCAACGCTGCCCGTACAGGGCGATTTGGCGCAACTGTCTGCGATCAGGTTC
GTACGTCGCCGTCATCGGCTGTCAGCCCACAACTGGGGAGTGCTGAGCGCGCTGGCCCAACGCACACGTATCACC
AAGACGGCATTGTTGTTGACAGTCTTTAGCCAAGTGCTGGCACGTTGGAGCCTTAGCCCGACGTTTACGCTCAATC
TGACGTTGTTCAACCGCCCGCAGGGTTACCCCAACGCAGAGGCAGTTATTGGTGATTTTACCGCTGTCAGCTTGCT
GAATGTTTGTTACGACAGCCAGCACTCTTATGCCCACAACGCTCAGCGTATTCAGGTGCAACTGTGGGAAGATCTC
GAACATCGTCGTTTCAGTGGGATCCGCGCCAGCGAGGCGCTGATCCATAGCGGTCGTTTCCATGCGCCGATGCCG
GTGGTATTCACTAGTATGTTGGATATCGACGGGGAGACGACTGCGCAAGACCCTCGGGACACAACCCGTTTTACT
CTGTGTCCGGACGCCAATATTACCCAAACACCGCAGGTGTGGCTCGATCACCAGGTGATCGAGTTGGCTGGGGAG
TTGCATTTCAACTGGGACGCGGTCGAGCAACTGTTTGATACCACGCTGCTGGATCAGATGTTTGGTGCTTATTGTC
ATGCGCTGCAGGCGCTGGTTGCCATGCCGCAAAGTTGGTGGGGGGTAAATAGTTCTCTGGCGCTGCCCACCGTTA

FIG. 4 - Continued part 8

GTGCACCGGTCACGCAGGCTCCTGCACCTACGGCCTTGTTGCACCATGGATTACTGCGTCAGGCAGCACTGACGCC
ACAGGAAACTGCGCTGATCAGTCCTATCCGTGAATTGACCTATCGCCAACTGTCGACGGCGGCGGATCATGTGGC
CCGCGCCCTGTTAGCGCTGGGCGTGCAGCATGGCGACCGCGTGGCGGTGGTGATGGAAAAAGGCTGGCAGCAG
ATTGCCGCCGTACACGGCATTTTACGACTGGGTGCGGTCTATCTGCCAGTGGATCCGGTGCTACCGCCACAGCGTC
GCCAGCTTTTGCTGACGGTGGGCGAGGTGCGGGTACAAGTAACGCAGCCGGGTCTCACGCAATTGGAGCCGTCG
CTGCCCGTGCTGATCATCGACGACGGAATGCTGGACACGCCTGCTGCGCCGTTGCCTGAAGTGGCTGGGGATGTC
ACGGATCTGGCCTATATCATTTTCACTTCCGGCTCCACCGGTACCCCGAAAGGAGTGATGATCGACCACCGTGCGG
CCATGAACACGCTGGAAGACATCAACGAACGCTTTGGCCTCAATGCGCAGGATAGGGTGTTCGGGCTGTCATCAT
TGAGCTTTGACCTGTCGGTTTACGATGCCTTTGCGCCTTTTATGGTGGGTGCAGCGCTGGTACTGCCGGAAGCAGG
ACGGGAAAAAGATCCGCGTCATTGGCAGACAGTTATGGCACACGGTCATGTAAGCGTCTGGAATGCAGTGCCCGC
ACTGATGCAGATGCTGTGCGAATACCACAGCGGCGATCGGATGAGTTATCCGACGTTGCGTCTGGCACTGTTGAG
CGGCGACTGGATCCCGCTAACGTTACCGGAGCAGATGCGCGAGCGGCTCAATGAAACGATGGACATCATCAGTCT
GGGTGGAGCGACCGAGTGCGCCATCTGGTCGGTCTACTACCCGATAGGTGAGGTGGAATCGACGTGGACCAGTA
TTCCCTACGGTCGGGGCCTGCGCAACCAGCCAGTATACGTGCTAAATGCGCAACTGGAGGAATGTCCGGTCGGGG
TGGAAGGAGAGATTTGCATTGGCGGGATGGGGCTGGCACAAGGCTACCTGAACGACGCAGAGAAAACGGCGGC
GAGCTTTGTCTGGCGCGAAGCGAGTGGTGAGCGAATTTACCGCACTGGGGATCGCGGGCGCTACTTTGCTGACG
GGCAAGTCGCCTTTTTGGGGCGCAACGATACCCAAGTGAAGGTGAATGGTTACCGTATCGAACTGGGGGAAGTC
AAAAGCCACCTTGAACAGCTCGACAGCGTAGGGAGTGCCGCCGTGGTGTGCCACCAGGGACAGCTGTATGCCTTT
ATCACTGCCGCAGAAAACCTGCATCCTGACGATACTGACGCCCTGTTAGCGCGTGTTCGTGCTCAGTTAGCCGTGC
AGTTGCCGTATTACCTGCTGCCCCAACATTTCTTTCTTCTCAAGGTGCTGCCGATGACAGGCAACGGCAAAATTGAT
CAGGCGGCAATGGTTCAAGAGGTTATCCAACGTATGTCGCAATCTACATCACAGAAGTCGAGGGCCCTCGCGCAC
GCCTCGCCCTATGAACAGCAGGTGGCCGCTCTCTGGTGCGAGGTACTACAACGAGAACAGATCGGACTGAATGAC
AACTTTTTTGAAGCGGGGGGCGGCTCAATCCAGATCGTGCTGTTGCATCGCCGTATTGAGGAGATTTTTAAGGTTA
CGGTACCTATTGCTGAGCTATTTCGCTTAACCACCGTGAAAAGAATTGCCGGTTATTTGCAGGCTATGCAGGACAA
TGCACGGGCGGTGAATCAAACACAGCAGCGTGATGCTTCCCGATCCCGCGCCCAGCAACGACTTGTACGTCGTCA
CCAGCGTCAGCGTTAA*

>clbI

ATGGCAGAGAATGATTTTGGTATAGCTATCATTGGGATGGCGGGGCGTTTCCCTCAAGCCGATACGGTACAGGCG
TTTTGGGAAAATCTTCTGGCAAGCCGAGAGTGCATTTCCTTTTACAGCGATGAGGAACTGCTGGCGATGGGAATC
AGTCCTGAATTTGTTCAGCACCCAGATTACGTCAAGGCCAAAGGGGAGGTAGCTGACATCGATAAATTTGATGCT
GCTTTCTTCGGTATCGCACCCCGAGAGGCGGAGCTGATGGATCCTCAGCACCGTGTCCTGTTGGAAACCGCGTGG
GCAGCCTTCGAAGATGCGGGCTATGTGGCTGCCGATTATCCGGGGGATGTGGGTATTTTTGCTGGCAAAAGCATG
GATTCCTATTTGATGCTGAACTTGATGCCGCACTTTAAACGCGTTTTCTCTTCTGGCAGTTTGCAGGCGGCCATTGG
TAACGACAAAGACAGTATCACTACTACCATCGCCTATCACCTCAACCTGCGCGGCCCGGCGATCACGGTGCAGACT
TCCTCATCGACATCCTTGGTGGCGGTGTGCGTGGCATGCCAAAGTCTGTTGACTTGGCAGTGTGACATGGCGATTG
CTGGCGGAGTAACGCTGGGGCCACCAGCAAAAACCGGCTACTTGTCGCAGGAAGGTGGGATCACCGCCGCCGAT
GGCCACTGTCGGGCGTTTTCCGATAACAGCAGCGGATTTGTGCCCGGCACCGGCGCGGGGCTGGTGGTGTTAAA
GCGTGTTGATGAAGCGCTGCGTGATGGCGATAACATCTATGCGGTCATCAAAGGATTTGCCGTCAACAACGACGG
TTCGGAGAAGATCAGTTATACCGCGCCGAGCGTGGATGCCCAAGCGCGCGCCATTGCTCAGGCACAGCGGTTGGC
AGGTTTGACACCGCAGGATATCACTTATGTGGAAGCCCACGGTACCGGTACGCGTTTGGGCGATCCGGTTGAGTT

FIG. 4 - Continued part 9

TTCTGCGCTAAGCCAAGCCTTTGCGGGCGCGTCACAAAAGCAGTACTGTGCGCTGGGGTCGGTAAAAACCAATAT
CGGCCATTTGGATACGGCAGCGGGCGTCGCAGGGTTGATAAAAACCGCGCTGGCAGTGCAGCAGGGAATAATTC
CCGCAACATTGCACTTTGAACGGCCCAATGCACAGATCGATCTGACCAATAGTCCGTTTTACATCAACACTACCTGT
CAACCGTGGCAACCGGAAAGCGGCATCCGTCGCGCGGGCGTCACCTCGCTTGGCATGGGCGGCACCAATGCCCAT
GTTGTGCTGGAACAAGCGCCAGCCGTTGACTTGCAAGCGCGAGCGCCTGTACCTGCCTACAGTATTTTGCCGTTTT
CTGCCAAGACCGACAGTGCCTTATCCTCGGGGCTGGCGCGTTTTGCCGATTTTCTGCAACATGAATCGCTGCCGGA
TAGGCGGGATCTGGCGTGGACACTCTCACAGGGACGTAAAGCCTTCGCACATCGCGCCGCGCTCGTAACCAGAGA
TCTACATGCTGCCGGGACGCTGTTGCAGCAGGCCGCGACAGCGCCGTTTGCTCGTGGTGTAGCGCAGACACAGCT
CGGGCTGGGGCTGTTGTTTTCCGGGCAGGGTAGCCAATATCAGCGCATGGGCCATCAGCTCTATCAGGTTTGGCC
GGCCTACGCCGATGCCTTCGACCGTTGCGCGACGTTACTCGAGCGTGAATACCAACTGGATATCCGCCATGAGTTG
TTCAGAGCAGAAGTCTCGTTAGCCCAAGGCGAACGCCTTGCGCAAACCTGCCTCACACAACCGCTGCTGTTCAGCG
TCGAGTATGCCTTAGCCCAATTGTGGCTCAGTTGGGGAATCACGCCAACGGTAATGATTGGTCATTCGCTGGGCG
AATGGGTGGCAGCGACGTTGGCAGGCGTGTTCTCTTTAGAGGATGCGTTGCGCTTGGTGGCGCGTCGAGCAGAG
CTGATGCATCAGGCACCAAGCGGTGCCATGTTGATGGTGGCGCTGCCCGAAGCACAGATTCGCGCACTGATTACC
GCCCCGCTGGCGATTGCCGCTGTTAACGCCCCTGACTATTCGGTTATCGCCGGGCCTACGTCGGAGATCCTCGCCG
TCAGCCAGCGTCTGACGGAGCAGAACATCATCAACAAACGATTGCATACCTCTCATGCCTTCCACTCTAGCATGAT
GCAAGATGCGGCGCAGGCGCTACGTCAGGCATTTGAGAATGTACGACTGAACCCGCCGACGCTCACCATCATCTC
TACCGTAACCGGCGCGCACGTCAGTGCCGACACTCTCACCACACCGGACTACTGGATTGAACAGATGCTGATGCCT
GTGCAGTTCTCCGCTGCACTGCAAGAGGCGCAAGCTACATTTGATGTCGATTTTCTGGAAATCGGGCCAGGTGCCA
CCCTGACCCAGCTGACCAACGGTCATGCATTAGGTGATCGTCTCGCGTTCAGCTCGCTGCCAGCAGGTGCCCGCAG
CAGCGATGAGCACAAACATATCTTAGATACCGTGGCAGCGCTTTGGGTGCGAGGGCATAACATCGATTTGTCTGC
GTTTGCAGGTGAGCAACCGCGCCGTGTCTCTCTACCGACCTACGCCTTTGACAAAATCCGTTACTGGGTCGACAGT
CCAGAAGAACAGAGGAGCGCCGTAACGCCGGTGGCGGACGCGGGAAGTGTCATCCCTAGCGAACCGTCGGTGC
GCCGTCAGCCGCGTCCGGCGTTTTCGGTGCCTTACGCGGCTCCAGAGAGCAAAACGCAGCGCGGCTTAGTGGCGA
TTTGTGAAGCATTGCTGGGAATTGACGGCTTGGGCATTGACGACAACTTCTTCGAAGCTGGCGGACATTCATTGAT
GCTGGGCATGTTGCTGGCGCAGGTACAGGAACGGTTCGCCGTCACTCTTTCCTTTTTCGACGTGATGGAGGATGCC
AGCGTGCGCGCGTTAGCGCAGTTGGTCGAGCAGGAGCAGCAGGATGATGGAGGGTCCGCACTTGCCGTGCTAGT
TAACGACATGATTAATGAGTGA*

>clbH

ATGGAACAGCAAGGGATTATGAGACAGTTGCCTACCGACGACCAAACGATAGTCGACTATTTGTATCGTATCGCC
GGAGAATATGGGGAAAAAGCCGCTGTATTGATGGGGGACGCGGCGCTGAGCTATCACGATCTTAATGCACGCTC
TAACCAACTGGCGCATTATCTGCGTGGGCTGGGGATCGGCGAGGATCGTGTGGTAGCTATCCGCCTGCCGCGCGG
CATGGCAATGCTGATTGCCATTTTCGCTATTGTAAAAGCTGGTGGTGCCTATTTACCGCTGGCGTACAATGCACCG
CGCAGCCGCATTGAAAATATACTGAGCAACAGCGGCGCTGTTTGTCTGATCGGTACTGACGATGGTGATCGCTGG
CCGATTCCTCGCGTCGAAATCGACAGCGCGGCGGTCAGTGCCATGCCAACGACGGATCTGCGTTACCGACCACAT
GCGCGGCAACTGGCGTATATTATTTACACCTCCGGTTCCACCGGTGTCCCTAAAGGGGTGGCGACGGAACATGCA
GCGCTGCTAAACCGAATTGTCTGGATGCAGAACGCTTATCCTATCAGTTCTCAGGACGTGCTGTTTCAGAAGACGG
TGTACACCTTTGACGTCTCTGTCTGGGAGATGTTCTGGTGGGCGATGTACGGCGCATCTGTAGTGCTGTTACCGTC
CGGACTGGAGAGCGATCCGCGAACCTTGGCTCGACTGATTCAGCGTCACCGCGTGTCGGTTGTGCACTTTGTCCCT
TCGATGCTGAACCTGTTTGTCGAGTATCTGGAGATGAAACAGGATCCTCGTTTGACCGCCTCATTGCGATTAGTGT

FIG. 4 - Continued part 10

TTTCCAGCGGTGAGAAACTCACGGTCCACAGTGTGGCTCGCTTTTATCAATCGGTGGCGCAGGGTGATCTTATAAA
TCTCTATGGCCCGACCGAAGCAGCAATCGATGTCAGTCATCACCGCTGCCTGCGCGGGTACGACTACGACGATATC
CCTATCGGTCAAGCGATTGACGGTTGCCGACTCTATGTGCTGGATGACCATGGTAATCCGGTAGCAGACGGCGAA
GAGGGCGAACTGTATCTCGCTGGTATCGGGCTGGCACGTGGCTATCTCAACAACGTGGCGTTAACTGATCGCTGT
TTTACTATACATCCAACTTTGCGCCATTTAGGGAAACCGGAGCGGCTGTATAAAACTGGAGATCTGGTGTGGCGCG
ACGGGGAAAGCCAACAAATTCATTACATTGGCCGTAATGATTTTCAGATTAAAATTAGAGGGTTGCGCGTTGAATT
GGGAGAAATCGAAGCCCATGCGATGCGTTTCCCGGGGGTACAGCAGGCAGTCGTGGTGGCGGATCAGGATGATC
CCGACAATCAGTTGATTTACGCTTTTGTCGTCAGTAGCGTGCCGCTCAATTTGGCGGCCTTAATGGACGCACTGTCC
AAAAACTTGCCTGCCTACATGCTGCCGAACCGTTTGTTGGCAATGTCAGAGTTACCACTCTCCGACAATGGCAAGT
GCTGTCGTAAAACGTTGCTCGACTTGGCGCGGGCGTACTCAGCCAGTCGCGTCGATTTACGTGAAACTCCCGCCGT
GCGCTACCTACCGTTGTCATCGGCTCAATCGTCGATGTGGTTTATGCAACAATTGGCGCCGCATACTGCACTATACA
ATAACCCCACCGCCTTGCTGCTTGAAGGAGAACTGGATCGCACGCGGATGGACGGCGCGATTCGTCAATTGATGA
GTCGGCATACTCTGTTACGTGCTATGGCGGAAACCCACAATGGACAACCAGTATTGGCGGTGCCTCAGTGCGTATC
GTCGCAGGCGTTGCTGACCATAGTGCCACTCCCCTCGGTGAGTGATGATAACGCGCTACAGGCGATGATCAACCA
GCGTGCGGCACACCCCATGCCCTTAACGTCAGGCACACCGCTGTGCCGGTTTGAACTGTTGACGCTCGATGACGAT
CGTAGCGTATTGTTGATTCATCTGCACCACATCATCAGTGATGGCTGGTCGAAAGGCGTTTTGTTACGCGAATTGC
AGGCCGCATATAACGGTGAATCGCTGACGCCAGAACCGTTGTTGGAGTATGCCGACTACATGGAGTACCAAGAAG
AGTGGCGTCAGAGTGACGCCTATCAGGACGCGATGCGTTACTGGCAAAATACCCTGGCGGGGACGTTGCCGATTC
TTGATATCCCCACCGATCAACCGCGTCAGAAGGTGGCACGTTACCAAGGCGCGTTTGTTGCCTTCGCATTGTCTGC
CAACACATGCGAGCGAGTGTTGGCGGCGGCGCGTGCGCAGCGCGTGTCGTTGTATAACTATCTGCTGACCGCCTT
CGTCCTCCTGCTGCATCGTAATGCGCGTCAACAGGAATACATCGTCGGTATGCCGATTGCTGCGCGGCTGACGAAA
GAACAGGAGCATATGATCGCGCCGCTGGTCAACGTACTACCGCTGCGCTTACCTCTTGACGAAGCGGCATCGTTTT
CCGAGTTAGTACAGACGATCAGAGGTATTCTGTTTGCCGCTTTCAGGCACCAGCGTCTCGAATTTACCGACATAGT
GCGCGCAGTGAATGTGGATCGCAGCGCCGGACATTTCCCAATATATCAGTGCATGTTCCAACTCGACAATATGCCT
CTGGCGAGCCCGACACTAAACGGTGTCAACGTTACACCATTATTGTTGGATACCAGTGCATCTCAGGTGGATATTT
CGCTAAGTATGCAGCATATCGATGGGCGCATCACCGGCACTTTCGAATACGACGCTGGGTTATACAGTGCGGATC
GTATTCAGCACCTGGTGGCGCAGTGGAGAGAACTGCTAGATGAGGCCAGCAGCCAACCCACGCAGTTAGTCCGC
GATTTGATTCGTTTCACCCCTCGAGAGCACGCTTGGCTGGCGCGGCACAACGCCACTGAAGTTGCTCTGCCGCCCG
TAGATAACCTGCTGGCGCTAGTGTTACCGCACTGCCAGCAGCGCCCTACACAGGTGGCTTTGCGCCACGCTGACG
ACGCCATGACCTATGGCGAATTGCAACAGGCCACGATGCAGATGTGTACTTGGCTGCGTGCGCAAGGCGTAAAAC
GCGGAGAATCTGTCGCACTGCAACTGCCTTTTTGTTTCGAATTGATTATCGCACAATTGGCGATCCTCTCTTTGGGG
GCGAGCTATGTGCCGCTGGATGGTAACGCGCCAGCGGCCCGCAATGCCCTGATCTTGGCGCAGGCAACGCCGTGC
ATGCTGCTGGTGGCGCAACCGCTGGAATCCCCTCATGGGCTGACGATACCTTGGGTGCTAGTGCCTGACTGGCGT
AGCCTGCTGACAGAAATACCGAACCTGCCAGTTAGTGTTGCGCCAGATGCTTTAGATTGCGATGCGGTGGTGATCT
TTACCTCCGGTACTACCGGGCAGCCCAAAGGCGTCCGACTCAGCCAACGTAATCTGGTCAACTTAACCGCATCCTT
TATATCCAGCTATCAAGTGACGCATCAGGATGTTTTGCTACCCATTACCTCAGTCGCGTCTGCTAGCTTTGTCGGGG
AGGTACTGCCGCTGCTCGCCGCTGGCGGTACCTTAGTATTGGCGCAAAAAGCGCAGAGTTTGGATAGTGATGCGC
TCATTGCGCTGCTGGCATCTCAGCGGGTGACTATCCTGAGCACCACCCCATCGCTTTCTGCCAGCCTCTCTGTGCTG
GCTCAGTCGATGGGATCGCTGCGCTTGTTTCTGTGCGGTGGTGAAGCGTTAGAGTATGAGCAGATAGCGCCGCTT
CTGCCGCACATGGCAGTGGTTAACGGTTATGGCCTGACCGAAAGCGGTATCTGCTCGACCTACTTTCCTGTCGCAA
AGCGTAGGGAGCAAGAAACGGGAGCATTGCCCATTGGCCGCCCGATTCAGAACACCCAAGCTTATGTGGTGGAT
GCATATAATCGTTTGGTACCGCCAGGTGCCTGTGGAGAACTCTGTTTCTCTGGTCTGGGCATTTCGCCCGGCTACCT

FIG. 4 - Continued part 11

TGATGCACGACAGGATCCCGAGCGCTTTGTCGAGTTGCCGGAATACCCTGGCGTTCGGGTGCTGAAAACTGGCGA
TCGTGCTCGTTGGGCAACCGACGGGATGTTGTTCTATCTCGGCAGACAAGATCGCCAAGTGCAGATCCGTGGATA
CCGAGTTGAACTGGGCGACATCGAAAGCCTACTGAAACAGCATCCGGATATTGCTGATGCGTGGGTCGATGTGCG
ACGCAATGCGGCGGCAACGCCGCTACTAGTGGCCTTCTATTGCAGCGTCAACGGCGTTGCGCTGGATGCTCAGCA
ATTGCGCGTATGGCTCAGCCTGCGGCTTCCGTTGCATATGCTGCCGTTGCTCTACGTGCCGCTGAGCGCCATGCCG
CTAGGTGTAAACGGCAAAATCGATCCCCAGTGCCTGCCGCTGGTCGATCTGCGGCAGTTGGAAGGGCCGGGCGA
GTATGTCCCTCCGGCAACCGAACTGGAACAGCGTCTGGCGGAGATCTGGCAGCAGTTGCTTGGCCTGGAGCGTGT
CGGCACCACCACAAATTTCTTCGATCTCGGTGGACACTCACTTCTGCTAGTACAGATGCAGCAATACATCGGGCAG
CAGTGCGGTCAGCACGTGGCGTTGGTTGACCTGCTGCGCTTCACTACCATCAAACGCTTGGCGGAATTTCTGCTGG
CCCCGGACGCAGCGCAAGGGACCACAGGAGATCAGACACAACTGCGTGCGGCGAAGCAGCGTTTGGCCTTTGGT
CACACGCGCTGGGCAGCCACAACCGACAGTCATCACTGA*

>clbG

ATGACGAAGGATGTCGCACTGATGTTCCCTGGCTCCGGTTCGCAATATGTAGGCATGGCACGGTGGCTGTATGAG
CGTTATCCGCAGGTGCGTACTCTGTTTGATGAAGCTAGCCAGATCACGGAACGGGACATGGCAGCGCTGTGCCTG
TCGGGTACTTTGGTACAACTTGCTGAGCCGACGGCAATGGCGCTGGCTATCTATACCACCAGCGTGGCCCACTTTG
TCGCGTGGCAGCAGTTTTTGGCGCAAACCGGTGTCCATGTCAACCTACGTTATATGTTGGGTCATAGTTTGGGCGA
ATATGCTGCGCTGACCTGTAGTGGTGCGCTGAGCTTTTCCCAAGCACTGGCGCTGGTGGCGATGCGTAGCCGTTTA
GCCAGTGAGATCGCCCGCGAAATGGACGCGAGTACCACTATCATCAAGCAAGGGAATCAGGCACTGGTGGCAGC
GGCGTGCGAGGTGGCGGAGCGTGAAACCCGACAGCAGGTCGGTATTGCCTGCTTCAATTCGCCGCAACAGTTTAT
GTTATCCGGACAAAACTCGGCCATTATCGCCGCCGAGCAATACCTGCTGGATCATGATCGCCAAGTCGAAGTAGT
GCCGCTGATTGGTGGTGTTCCTTACCACAGCCCACTATTGAAACCTTGCGGACAGCAATTGCGCAAGGCGCTGGAT
CGCTGCGAATGGCGACGTCCGTGCTGCCCAGTGATCTCCAATGTCAACGCTCAACCCTATCCCGATACGGTCACGC
CAGTCCAGTGGCTAGAACAACAGCTCTCTCAGCCAGTGCAGTGGCAGCGCTCTCTCACCTACCTGACAGGACACTT
GTCACCGATCGCGATAGAGATCGGTCCGCAAAGTGTGCTGAAAAACCTGCTGCTGGAGAATCGCTATCCAGCACC
AGTTTACGCATTTGACAATCGTCATGATCGTGCGCAACTAGCATTGGTGCTGGGGGATAACATGGCGGTGAAGAC
CGATCCGGAAGCCGTGCGCCGCCAACGCATCACGCTGCTCACTAACGCCCTGACAGCCACACGCCATCACCGCGCC
GCCGATGTGGCTGCCAGTGCGCAATTGAAAGAATTGCTCAGTCGTTTTTTTGAGCGCATCCAGCAGATTGAGCAGC
GCGGCACATCCAGCGAAGAGGACATTGCTTTTTTGCATGAGCTTCTTGAACAGGGATTTCAACTCAAAGGCAGTA
GTCAGGCAGAAATCGACGCCTGCCACGCGCGGTTGGCTTCCGACAACGGCGGACAGGCGTAA*

>clbF

ATGTGCACTGAAAATTATGAGCTGGCTCAGCAAGAGGCAGTCCTGTTTGCCAAACAACATCTCGCCCTGGCTGCAC
AGAATATTGAACGTCAGCAGTTTATTGTGCCAGACATTATTTCTTGCGTGGCGCAGGCCGGGTACTTAGGTGCGTC
AATCCCCCAAAAATATGGCGGACGAGGTTACGATTCTTATCAACTGTGCGCTTTGCATGAAGTGATGGCTGGGGTT
CACGGTTCGTTAGAAAATCTCATAACAGTGACTGGCATGGTCAGCACGCTGCTGCAACGCGTGGGCAGCGCAGCG
CAAAAAGCCCATTATTTGCCAAAGCTGGCAACGGGGGAATTGATCGGCGCGATTGCCCTCACAGAGCCGAATATC
GGCAGTGACTTAGTGAACGTGGAAACAGAATTACAGCAGGATGGCGACGGTTGGCGGCTGAACGGAAAAAGA
AATGGATCACGCTAGGGCAGATTGCTGATTTTTTTATTGTTTTAATCCACTGTGGTAATCAATTAGCGACAGTGCTT

FIG. 4 - Continued part 12

ATCGATCGCAATACCGACGGCTTTACTATCACTCCACTCAACGACATGTTGGGGTTACGCGGCAATATGTTGGCAG
AGCTGCATTTTAATGACTGCCGCCTGAAGGAGGATGCATTGCTCGGTCCGCTCACCCCTGGGGTACCGCTGGCGG
TGAATTTTGCGCTCAATGAAGGGCGGTTCACCACCGCTTGTGGCAGCCTAGGATTATGTCGGGCCGCTGTGGATG
TGGCAGCGCGCTACATCCGCCAGCGTAAACAGTTCAAGCGGCGGTTATTTTCTCATGGCATTGTTCAGCACTTGTTT
GCCACAATGCTGACCCAAACGCGCAGTGCGCAACTAATGTGCTTCAGCGCGGCGGAATACCGCGAAACGCTGCAC
CCGGCCATGATAAACCAAATCCTGATGGCGAAGTATGTCGCTTCCAAAGCTGCGGTGGACGTGGCCGGGAAGGC
GGTGCAACTGCTCGGTGCGAATGGTTGCCATGCCGATTATGCCGTCGAACGTTACTACCGCGACGCCAAAATCAT
GGAAATCATCGAAGGGACATCGCAAATTCATGAAATCCAAATTGCGATGAATTACATGATGGGGAGTGAAGCATG
A*

>clbE

ATGAAAAAGCAAGATATGAAAGCCGCCATTCGGGAATTTCTTTCACGCTCATTACGTGGGCATACGTTGAACGATG
ATGACGATATTTTTTCTCTCGGGCTTGTCCATTCGTTATTTACTGTGCAAATCATACTGTTTATAGAAAAAAATTTTC
AGGTTGAGCTGGAAGTGAGTGAGTTGAAAACAGAACAGATTGCTACCGTCAATAAAATAGTGGAGCTCATTCAGC
GACAAACAGGCCTGGAGTAA*

>clbD

ATGATGAACGTGGCGGTAATAGGTGCAGGAGTAATGGGAACTGGCGTCGCTCATAACATGGCGCAATACGGCAT
ATCAACTAACGTTGTGGATATTTCTCAATCTCAGTTGGATAAATGCCGACAGATGATCGAAGCGAACTTACGCTTA
TATAATTTTCACCCGCAGCATAAAAAAAAGACGCATAGCACAGCGGAGATAATGGAAAATATCCGTTTCACAACTG
AGTTGGACGACATTGTAGAATGTGATTTGGTGATTGAGAATATTACTGAGGATATAGAGAAAAAAAATGCACTAT
ACACACGGATGAATACGATCTGCGGCGCGTCGACAGTGTTTGGTGTTAATACGTCCGCCATATCTATCACTGCGTT
GTCAAAATTAATGCGACATCCGGAGAATGTAGTCGGCGTCCATTTTATGAACCCGGTACCGCTGATGCACACCGTC
GAATTAATCCGTGGTGTACATACTGCAGAGCGTACACTGAACATATTTCACCACTTATTTGCTCAGTTGAATAAAAC
CGGCATCGTGGTCAATGATTCTCCGGGCTTTGTCACTAATCGTGCCATGATGATTTTTGTTAACGAAGCCATATTTA
TGGTGCAGGAGCAGATCGCCCGTGCTGAGGATATCGATACGTTGTTTAAAACCTGCTTCGGGCACAAGATGGGGC
CACTACAAACTGCCGATTTGATTGGCTTGGATACGATTTTGCAATCGTTGCAGGTGCTATATGAAAGTTTTAATGAT
GATAAGTATCGCCCCAGCTTTTTATTAAAGAAAATGGTCGATGCAGGGTATTTGGGCGTGAAATCAGGGCAGGGG
TTTTATCGCTATCAACAGACGTACGCCGAGCAGTGA*

>clbC

ATGGAATACGCAAGCGAAATGAACGGCATGGAAATCGCCATTATTGGTATGGCGGTCCGTTTCCCGCAGTCCCGG
ACGTTACACGAATTCTGGCATAACATCGTTCAGGGTAAAGAGTGCGTCACCTTCTTTAGCGAGGAGGAGTTGCTG
GCCGAAGGCGTCGAACAGAGTACTCTGGACAACCCGGCCTATGTACGGGCCAAGCCCTATATCGAGGGCATATGC
GACTTTGATGCTGCATTTTTCGGTTACAGTCACAAAGAGGCGCAGACTCTGGATCCGAAATCCCGCGTATTACATG
AAGTTGCCTACCATGCGCTGGAAGATGCAGGCTATGCCCAACGTACCAGCGATCTGATCACCGGGGTATTCGTGG
GGGCGTCAGAAGATGTGGATTGGCTACGGCGTTCGCTGTCACAGATTGGCGGCGATGCGCTGAATCGTTTTGAGT

FIG. 4 - Continued part 13

CTGGCATCTATGGTCATAAGGATCTGCTCGCACATCTCATTGCCTACAGTCTCAATCTCAACGGTCCGGTGTATAGT
CTCTACACCAGTTGTTCGACTTCTCTGAGTGCAACGCATATCGCTTGCCGCAGCTTGTTGTTTGGCGAATGTGATCT
GGCGTTGGCGGGTGGAATTACTATCGATTTACCGCAGAAGTCAGGCTACTTCTGTCAACAGGGCATGATCCACTCC
ACCGATGGCCACTGCCGTCCTTTTGACAGTCAGGCTTCTGGCACCCTGTTTGGCGATGGCGCGGGTGTGGTTGTGC
TTCGGCGTTTGGAAGATGCTCTGGCAGCGGGCGATCGCATCTATGCGGTGATCCGGGGTAGCGCGGTCAACAATG
ACGGTAAACAAAAAATCGGTTTTGTCGCGCCTGGTCATGAGGGACAGAAGGCGGTCATTTGTGCGGCCTGTCATC
TGGCAGAAGTAAGCCCAGAAAGCATCGGCTACGTTGAAACCCACGGTACCGGCACCCGTATTGGCGATCCTATCG
AGTTCGCTGCGTTGACGGAGGCGTTCGATACTTCACACCGCCAATACTGTGCACTAGGGGCTGTAAAGGCGAATA
TTGGCCACACCCACGCGGCGGCGGGCGTGGCTGGGTTAATCAAGACGGCGCTGGTACTTCATCACCGGACCATTC
CGCCGCTCGCCAACTATCAAATGCCTAACTCGAAGCTGGATCTGGCGCATTCACCGTTTTATATCCCGATACAGCCG
CAGGAGTGGCCCGCATCGCGGATGCCGCCCCGCGCTGGCGTCAGTTCTTTTGGCATTGGCGGTACTAATGTGCAT
ATGATTTTGGAAGGGCTGAATCCTGCGGTGCGCGATGACCATGACCAAGTGCGAGCACCGGTGTTTATCCCTCTCT
CCGCGCCGTCTTTCGAGCAGTTGGATGAGCTGACGCAACAGCTTACCCCGTTGCTGGCTACCCTTGATGCGTCAAC
GCTAGCCTACACACAACAAGTGGCGCGCCCCGTGTTTGATTGCCGCCGAGTGATACAAGTGGAAAACGATGGTAC
GCAAGCGATGCTGGCATCGCTGGATAACCTAATGCCCGACGCTCCTTGGGGCCTACACTGTCCAGATCTACGTACT
ACGAACGATTGTACTTACGCACAGTGGCTGGCGCATTCGGCACATTATCAACGCGAAGCGACTGCTCTGACGGCA
TTACTCGACGGCATGAATATTCCACCCGCTTATTGCCACGCTGAAACGTGGGCGGCACAAGCGAACAGCAGCCTG
CTAATCAGAGGCTGCCAGACTATCGCCGCGCTAAAAACCTGGATGAACCTGCTACCGACATTAACACTGCTGTCGG
GTGCTGGAACAGGCCTTTTGCCTGCCGCTGCAGCCAGTGGCATGATTGCGACGCAAGACGTGTTGCATTTGCTGT
GGGAAATGGAGCAAAAGGCGCTTCATCTCTGGCTTCCTGAGCGCCATGAACCTATCCCCGGCTACGTGCTGGCTT
GGCAAGGAAATCCCATCACCGATGCACAGCGTAACGACAGAGGGTTTTGGAGTGAAGCGCTGTTGGCAGATACC
CGAGAACTGGGGGAGGGCGTTCACAGTATCAACTGGGTTAGGCTGCCGCCGGAAATAAGAGAAGACGTTGATGT
ATTGCGCTACGTGGCGCAACTGTGGTGTGCAGGTATCAATGTGGATTGGGCCGTGTGGTACGGCACTCCGCTGCC
GCAACGCGGGAGCGCATCAGCATATCCCTTCGCACACAACCACTACCCATTGCCTGGACGGGTAATGGGTAGTGT
GGAGACCCAACCCGAAGCAGGACCCGAAACGCACCACCCTTATCAGGCACGTCCCGTGTTAAGCGTACCTTTCGTA
GCCGCACACTCGCGGGGTATGCAGTATATCACAGGTCTGATGGAACTGTTGCTGGAAATATCGCCGGTCGGGGTG
GACGACGACTTTTTTGAATTAGGCGGGCATTCGCTGCTGGTGACGCAATTGACCTCCCGTTTAGAACGCGATTTCA
ACGTACATATCGATCTTTTGACCCTGATGGAAAACCCCAATCCGCGCAATATCTACGCGCATATCGCGGCGCAACT
GGGGGGCGAAGACAACCTCGAAATAGCCTGTCAGTAA*

>clbB

ATGGATAATACCTCTGGAGATTTTCCATGTAATAAGATGGACACGCGTAAGCAGTTACCGCTAACACCAAGTCAAC
AGGGGTTTTTATTCCATTCCTTAAAGGATAAGAAAAGGAGTAACTACCATGAGCATTTTACATGCATTTTTTCTCAG
CATGTAGATAGCGCCCACTTCAAGTGGGCGCTGGAAACGTTATTTCGAAAGCATGAGTGTTTTCGCACTGATTATA
ACTGGGAGATTGATGAGCGCCCTTGTCAGGTGGTGAAGACCGATGTGTTGCCGGATATATATGTGTTAGACTGTG
AGCAAGAGGAAATACGTTTTCTACTAGCTAATGATGACATTATCATTCCTGTCCCGCAGGATGACGGTATTGATGC
TATAATTCCTCAACTGCTACAGGCTGATTTAAAATACCCATTTTCCTTGAAAACGATCCCAGTCCGGGCCTACCTTAT
TCAGTCAACGAAAGAAAGTGCTTTTATACTATCATACCATCATATTGTGATGGATGGCTGGAGCTTATCCCTTTTCA
TTAAACAGTTGCTCCAACTCTATGGAGCGGCTGTGGTCAGTGGTGTGAGGGATGATAGCGCCATTATCCCCTCATC
TCTGAAACCCCTTGTAGACACACTGTCGGCCCGACGTCACACCTTTCAGCACGACTATTGGGCTGCATATCTTCGG
GAGGGAACACCAACTTGTATCGTGCCGCTGTCACAATATCACACAGATACTGAAGCCGAGAACAATTCTTACGTTA

FIG. 4 - Continued part 14

ATCAAACAAATCATGTGGAGATCAATTTGTCTCCGGATGTGTGTCAGAAAATACAGACGCTATGCAGCGATTATCG
TATCACCCCCGCAGTAATCTTCTATGTGGCCTGGGGCATCCTGCTACAACGTTGGTGCTATGCTGACGATGTGTTAT
TCGGCGCGACAATATCAGGGCGAAATATACCAATTGATGGTATAGAAGAAACACTAGGGCTATTTATTAACACGTT
GCCGCTGCGTCTGCGTGATGATGGGGCGACACTGTTGCAACACTTACAACGTATGCACCAAACACTAATAGCTCAC
TACAGCAATGAACATGATGCCTTAGCCAGCATACAACGGTTGGTACATAAAGAAGGTCATGCTGGGGATCTTTTTA
ATACCTTAGTGGTGTTGGAGAATTATCCCGTTGATATGACATTATTGTCATGCGCGTCGCCCGTGGCAATTCGCCAT
CTCAGTGTACATGAACAAACGCACTATCCGCTGACCTTGACCATCACTCAACAGAAGGGATTCCGTTTCAGTATTG
CATATGCCCTTAACTACCTGACCAACAACATGGCGCAAGCGTTGCTGATGCACCTGAGTTATCTGCTTGAACAACT
GGTGGACAATCCGCAGCGCCCCATTGCTGCGTTGGTAAACTTGTCCCCATGCCAGCAGGCGCAGGTACTTCAACCC
TATCTGGAACGCATGGCATGCCGGGATTGGGATAGTCAATCCAACGTCATCGAACAATTTCATCAAGTTGCTGCGA
CTTCGCCAGCACAGGTCGCAGTGGTTGATGAATTGTGCGCGTTGACCTATTCGGAGTTGGCAGCACAAGCTGAGC
AGCTCGCGGCTTATTTGGTACAGCAGGGTGTTATGGTTGGCGATACTGTAGGCATAATTAGCGAACGCCGGGTAA
ACACCGTGGTTGCCATCATCGCCATCATGTTGATCGGGGCTGCTTATGTGCCCATCAGCCCCGACTACCCAGTGGG
TAGGATGCAGGAAATTATTGATGACAGCGGCTTGGCGCTGTTGCTGGTACATGGCAAACCGCTAGATGCATTAAA
CGTTGCGCAGAGTGACCTCTGTGCATTTCCCGTCGCGCCCTCGGTGGTATTTCCGGTTATCACACCAGATTCTCGCG
CTTATGTGATTTATTCATCGGGGTCGACGGGTAAGCCAAAAGGTATCGCGGTGGCGCACCGCGGTTTATTGCGCCT
GATACAAGGCGACAGCCCGCTGAAGGTGGAGAGCGGTGAGACAACGCTGCTGACCTGCCCATTTGAGTTTGATG
TTTCGGTGTTTGAGATGTGGTCTACCTTGCTCAACCACGGCAAACTAGTATTACTCAGCAAACAGGCATTACTTGAT
ATCAATCACATTCGCCGCACGATCGCTGATGAACAGGTGGCGCGCGCCTGGTTTACCTCATCCTTGTTTAACTCCTA
TGTGGCAGAAGGTGCCGATTTCTTCGGTATGTTACAACACATTACGGTGGGCGGCGAAGCAGTATCTGCGTGGCA
TGTCAACGACGTGATGCAAAAATACCCGCATCTGGTGGTGACAAACGGTTATGGGCCGACGGAAAACACTATTTT
TACCACCGCATATCGTTTCAACGGGTTGCAACCCGCCCGAGTCCCGATAGGATACGCGGTACCGGGCACCTCGCTC
TACATTACCGATCTCCATGGGCATTTGTTGCCTATCGGTGCCACCGGTGAACTAGTGGCGGGTGGAGTGGGGGTC
GCCATCGGCTATCAGAACAACCCGGCGCTAAGTGCGACGGTTTTTGTCCCTGATCCTTTTATTCCCGGCGGTATGAT
GTACAAAACTGGCGATTATGCCCGGTTGCTGGATGATGGCTGTGTTGACTGTTTTGGGCGTAAAGACGGTCAAAT
TAAGATCAATGGACAACGAATTGAAACCGGAGAGATCGAGCAGCGCCTGCTGGAGTGCTCCGGCATTATCGAGG
CGGTAGTGGTTCCTTACCGCGTACGTGAAACGCTGCATATTGCGGCAGTGGTCTGCGTCAATGATAGCTATGATGA
GGTGGAAGTTCGAGGGCAATTGGCTGACAGATTGCCGCCATTCGCTATTCCGGAATCCTTGGTGGTGGTGACGGA
GATTGCAAAAAGCCATAGTGGCAAGGCCGACTTGGCGCAGTTGCGGTATCTCCTGCCCGCAACTCAGTGCAACGC
CGTGTCCACCACGATATCAGAGGTGCATAGTGACATGGAACATGCGCTGCATGCTATCTGGCAACGCGTACTTGAT
AGACAAGACATTGATAGCAATGCCTCCTTTTTCGCCCTCGGTGGCACCTCATTGGATACCATCAGGGTTAAAGGGG
ATATTAAGCGGCAACTTGGCTTGGAGATTGATATTACCGATCTCTTTAAGTACCCAACGCTCACGGCGTTAGCACA
TTTTCTCGATACTGCCGTATCGCCGGAGGATGCAATTCCAACGCGTGCTGTTGTCTACAGCGACATGCCGGTGGCG
ATTGTCGGTATGGCGGGACGTTTCCCCGGTGCGGCGAATATTGCAGCGTTGTGGACGCTGGTTGTAGGAGGGGA
ATCGGGATTAACACTGTTCAGTGATGAAGAGTTGCGCGCGCATGGTGTGACACCTGACACGCTTAAACAAGCGAA
TTATATAAAAACCAAAGGGATTGTTGATGATCACGAATGGTTTGATGCGGATTTCTTTGGTTATACTCCCAACGAG
GCGGAATGTATGGATCCGCAAATTCGCTTATTGCATCAGTGCTGCTGGCAAACTCTGGAACACGCTGGGTGCGAT
CCTGCCACCTTTACTGGTGCGATTGGCATTTATGCCGGACTGCTGACATCCCCCCACTGGCTTAATGCGGTAATGCA
AGACACTACCGACTCTACCGCCCTGTACAAGGCCAGTATCCTGAATATCCATTCCGTCACAGCATTGATTGCCCATG
CGCTTAACCTCACCGGCCCTGCCGTGACGCTTGACACCGCCTGCTCCACTTCGGCAGTGGCTATCCACCAGGCCTG
CATCGCACTACGTAACCGGGATTGCGATGCGGCATTGGCGGGCGGCGTTTCTATCGAGATGCCTGCGTACCGGGG
CTATGAATATCATGAAGGCATGATCAATGCGCGAGATGGTGTCTGTCGTCCTTTCGATAGCCAAGCCTCTGGCACA

FIG. 4 - Continued part 15

GTCACCGGTGATGGCTTAGGAATGCTGCTGCTAAAACGTCTGGACGACGCGCTGGCGGATCGGGACTGCATCTAT
GGTGTGATCAAAGGTTCGGCGGTCAATAATGATGGCAATAACAAAATCGGCTATACCGCGCCGAGTGTGATCGG
GCAATCAACGGTAATCCGCACCAGTTTGCGCCGTGCCGGTTTTGATAGCGACAGTATCGGATTGGTGGAAGCGCA
CGGCACCGGTACGGTGCTGGGTGATCCTATTGAGTTACGTGCGCTTAATGAGGTGTTTGGCCCAACACCTGTTCCG
TTTTGTGTGGTTTCAGCGCTGAAAAGTAATATTGGCCACCTCAACTCCGCTGCGGGAGTGGCGGGCGTCATCAAAA
CAACGCTCGCCCTGCATCATCAAGTGTTGCCACCAACAGCGCACTTTCGCCAACTCAATCCTGCTATAGATCTATCG
CGTTCTGCATTGTACGTTAACCAGCAAGTCCAACCGTGGCCGTCGACGCGTCCTCGTCGTGCACTGGTGAGCTCCT
TCGGCATCGGCGGCACCAATGCCAGCATCGCACTAGAAGCACATCAACATGAGGACGACCCTTCAGCGACGGGG
GTACGCGACAGCTATCTGTTGTTGTTCTCCGCTAAAACACCCGCTGCGTTAGAGTTGCGCGTGGCCTCCACACTGG
AATATGTCAAGCATGGAGTAGGGGTGCGCCTGCCGGATGTGGCTTATACATTGCAAACTGGACGCACAGCCTTTG
ACCATCGGCGGGCTTATTTGGTGAGTCGTGGGTCGAAAATCGATCTCTCCTGTGCCACGATATTGCAAGCGGAAAT
CTTCAATGGTCAGCGCACGACAGCGGAGATCTGCTTCATGTTTCCTGGTCAAGGTAGCCAATATCACGGCATGGCC
AGCGCGCTCTATGCTCATCAACCCATGTTTCGCCAGCACATGGATCGCTGCTTTGCTGCATTCCAACGCTATTCGAC
GGTCGATCTCAAGGCGTTGTTGTTTGACGATGAGGATACGCGGGATATTGATCAAACGCAGTTCACACAACCGGC
GTTGTTCTGTGTCGAATACAGCCTAGCGCGCACCTTGATTGATCTGGGGATTACGCCGGACAGTATGATCGGGCAC
AGTCTGGGCGAGTATGTTGCGGCCTGTATTGCTGGCGTATTTACTCTTGAGGATGCGCTGCACGTCATTGAGGCGC
GCGGACGTTTGATGCAGTCCATGCGTCCCGGTAGCATGATGGCGGTCTACCTTAGTCGCGAACAGTTGACCCCAT
GGCTAGCTGCAGAACGGGGTATTGAACTGGCAGCTAATAATAGCGCGCATTTTTGCGTAGTCGCGGGCGAGCAG
GCGGCCATTTCCCGTTTGAGCACACGCTTAGTCGAGGGCGGGATACAGCACAGGCGCCTGAAAACCTCTCACGCA
TTCCACTCGGCCATGATGACGCCGATGCTGCACGATTTTGCACAGTTGCTGGGGCAAATCCCGATGCACGCGCCGC
ACAAGCGCTTTATATCTAATGTAAGCGGTACATGGATTACTGAGGAGCAAGCTACCTCGCCGGATTACTGGGTGC
AGCAAGTGCGCAACGCGGTGCTGTTTAGCGAAGGTGCGGCGCAACTGTTGGTACAACCCACGCTGTTTATCGAAT
GTGGGCCGGGTAATACGCTCTCTACCTTTATTCAAGGACATAACCAATACAGCGATCAGCCGACCCTGTTGACGCT
ACGCAAAGCCAACGCGGCGATCGATGATGAGCACATGTTGCATCGTACGCTGGCGGCGCTGTGGGTCAGGGGGG
AGAATATTGATTGGAGACGCTTTAACCAGACGGCACTCGGCAAGCACATTCCATTGCCGGATTACCCCTTCGAACA
GACTTATTACTATCGCTATGGTGCTGCACTTTCCGGTTATCGCCAGTATCCAAATCCTCTGCGCCGTCCGCAAGATG
AGTGGCTCCAGCGTGTGCTGTGGCGGATGCACGACACATCCTTGCGGGAGGCGTTCTATGCGCCGGGCGAATTGA
TCATCATTATTAGTGCTGACGGCGACAAGTTACAGCAGACGCTGATGAGTAGTGGTGTCGACAGCATCACAATGC
CGCTGCCGATATCGTCAGAGGACGACGTGTGGGATAATGACCGTATTCTGACGCATTTCCACGACATCTGCGCACT
TTTAGCACACAAAACCTACCGACAGTTACATTGCTTGTATGCTCCCGGTGCGGAGGCAGGATCATCGTTGACACAG
TCGCTCTCGGGACTTTATCGTGTTGCTCGCTGGTGTATGCACAGCACCACGCCGCTGGCGTCCTTAACAGTATTGAC
CCATGGTGCGTTTCGCGTACAGGAAGAGGATAATCCCGAACCGACGCTGGCAGCGTTGTCGGGCGCAGTAAACG
TGTTTGCCCAAGAGCTGCACCCGACCGAAGTACGATTGATCGATATCGATGCGCAGAGCAGTGATGAGAATCTGA
ACTTGCTAACCCAGCGTCTGGCCCCGAAACAAGAAACGGTAATGGCGCTCAGGCAGGGGATGCTTTACCTGCGAC
GCTTTATCCCGACACGGCTGTTGGCGCACTTACCCCCTCAAACAGGGTGTATACCGGGCAACGTACTGTGGATTAT
CGGCGGTGAAAAGGGGATTGGCCGCATGATCGGCGAAGCGCTTGCTCAGCGTGAGGGAGTCCGTGTGGTACTGA
GCAGCCGCACAGGTTATCACCATGAAGCGGTGCAGCAGGACGCATTAGACGTTATCCACTGCGACGTGACGCAG
GCGGAGGCGGTTAGAGCTTGTCTGGCAACTCTGCTCGAACGCTATGGACGGTTGGATGGCGTGATTTTTGCTGCC
GACGCTACCACCACATTGACACTGCATCAATTGAGCGAATCTGCGCTACGCGACACGCTAACGGTGAAAGAACGG
GGTACTGCTAATGTGCTGCATGCGTTAGCGCAACGGAATCTGCTGGATGAGCGTCTGCTACTGCTGTTCTGTAACT
CGTTGGCTGCCGTGAATGCGGAGATTGGCCAGACAGGCTATGCTACCGCCAGCGCCTATTTGGATGCACTGGCAC
AGCAACTGCGTACCCGCTACAAGGTGAATGCGCTCAGTATCGGGTTGGATGCATTGCGTGAGCAGGGCATGTTGT

FIG. 4 - Continued part 16

TGGATGCTATAAACGGCAGTGAATACGATGTCTTGCGTGGACTGCGCCCATTGATGACGGGAACGTTGCTACAGG
CTTATAAACAACAAGGGGCTGACACCAGCTACTACGCGCGATTATCCCCCGAGTCCGATTGGCTGCTGGATGAGC
ACCGGATATCCGGTATCGCCACGCTGCCGGGAACCGGCTATCTGGCGCTGGCGTATGAAGCTCTGCGCCATTACTT
TGTGCAAGACCAAATCTGCATTGATGAATTGGTCTTTTTGGCACCGTTGACTGTGATGGACAACTGCAGTGTTGAC
GTTTTTGTTGACATTTCACCTAACGGGCAAGGAGTTAGTGTCGAGGTGAAATCAATGACGGAGCGCTTTAGTGGC
ACGTTAACAACCCATGCCAGAGGCAGGGCGACGCGTCTGATGGTAGACGATAATGTTGTGTGCGATCTCACGGG
GCTGATGCGCGAGATGCACACTATCACTCCTCCAACAAAGGAATTATCGAGCACGCACTTCCACTATGGGCCGCGC
TGGCACAGCGTACAACAACTGTATGGCAATACCGCCCAGACTCAGGTTTTCGCAACGCTGGCCCTGCCCACCGTTG
CCGCTAATGATACGATCGCACTGCACCCTGCGCTGTTGGACATCGCCAGCAGTGTTGTCGAACAACTGCCTGGTTT
TCATACTGATTCGGTACCTTTCCTTTATCAGGATTTACGCCTGTACCGCCCGTTGCCGAACACCTTACATGTGGCGCT
GACTGTCAATCGGCACGATGAGGAGGGTGACAGCTACGCTTTCACGCTCTACGACATGGCAGGCGAGATGGTTGC
CCGCTGTGCGGCAATGGTGAAGCGCAAGGTACAGCTCCACATACAAGATGTCGATGACGACACGCGACTGCGCG
TGCCCAGTGCCGATAACTACCAACTGCGGCTGGCCGCTGAGGGGGAGGGGGCAGGAAAGCTAGCGTTGTGCCCT
ACGCCGCGCTTAGCGCTGGGGGATTCACAAGTAGAGATTGAGGTACTGGCCACCGGACTGAACTTTAAGGATGTG
CTGTTCACCACGGGATTGCTCCGGCAGCAGCCGGGTGAGGCTCCGCTGCAATTGGGACTGGAGTGCGCCGGACG
CATTACTCGCGTGGGTAAAAATGTCACTGAATTTGCCCCGGGAGAGGATGTTATGGCGGTGCTAAACGGTGGTTT
TGTCCAGTACGCACGGGTAGAAAGCGATTGCGTAGTGAGAAAACCAGCCCATTGTCGCATCGAACAGGCGGCTG
CGCTGCCTATCGCATACCTCACCGCCTATTACGCACTGGTGGTGCGCGCTAATTTGCAACCCGGAGAACGAGTATT
GATCCACAGTGCGGCGGGGGGCGTTGGCTTGGCTGCGCTACATATTGCCAAACGCTGCGGAGCACAGATTTTCGC
CACAGCAGGTAGCGAGCAGAAACGCGATTACTTGCTTTCGCTAGGCGTACATGCCGTAGCTGATTCACACGACGA
ACAGTTCGCTGCCACTCTGCTGACCGCATCGGACGGACAGGGGATGGATGTGATCCTTAACTCCCTCACAGGCCGT
CTGCTTGACGCTAGCCTCGCGCTGCTGGCACCGCTGGGCCGTTTTCTTGAGCTGGGCAGCAAGGACATTGTGGAA
GACAAAGCGCTACCGATGCGTTTCTTCGCCCAAGGCGGCACCTTTATTCCGATTAATTTTCACGCGGCGCATGGTG
CGTTTAGTCGCTACCTGCAACAGATTGTCGCTTGGATAGATGATAACACGCTACCGCTCCTTCCATGCAAATCCGTA
CCATTGCCCGAGGTTGCACGCGCCTTCGCCACCCTGACCACGCCGCAGCATATTGGCAAGGTGGTGGTAACGCAT
CGCACTGCGGCAGGCATGGACCGGCTGAACGCCATGATAGCAGAAAGGCGCCTCGGCGGCTATGCGCTCAGCAT
GAGCAATGCCGAGGTGATGCGCCAATTGTGGCCGATACTGAACACTCGCAGTCCGTGGGCGCAACTGCTGCTCTC
ACCTCGGGCGATCGATAGATTAGCGCGGGGCAACCGGGTGGATCGCGGTGTACCGTCTGCCGCTAACGATACGA
TTACTCAGCAGACAGTGAAAAAGCGGCCCCGTCCGGAAATTGGCGTGCCTTACAGCCCCGCGACACGTGAAGTGG
AACGCGTGCTCTGCCAAATCCTGGAAGAGTATCTGGGTCTGGATAGAGTAGGCATTGACGACAACTATGCCGAAT
TAGGGGCAACCTCACTCGATATGGTGCAACTGAGTGGGCAAATGGCGCGTCACTATCCGCAAGTGAGCGTGGTGT
CGCTGTACAACCACGCCACCGTGCGCCAGCTGGCGACGTTTTGCCAGCCCCCGGAGGGCGAGTCAAATGCGCCAT
CACCACAGCCTGCAGTACAGACGAATACGCGCGCGAATCAGATAGCAAAACGTGCTTTGCAAATTGCGAAAAATA
CTGCGCGCAGTCACACGTCTTTGCATTAA*

>clbR

ATGGATAAGTTCAAAGAAAAAAACCCGTTATCTCTGCGTGAAAGACAAGTATTGCGCATGCTGGCACAAGGTGAT
GAGTACTCTCAAATATCACATAATCTTAACATATCAATAAACACAGTAAAGTTTCATGTGAAAAACATCAAACATAA
AATACAAGCTCGGAATACGAATCACGCTATACACATTGCTAACAGGAATGAGATTATCTAA*

FIG. 4 - Continued part 17

>clbA

ATGAGGATTGATATATTAATTGGACATACTAGTTTTTTTCATCAAACCAGTAGAGATAACTTCCTTCACTATCTCAAT
GAGGAAGAAATAAAACGCTATGATCAGTTTCATTTTGTGAGTGATAAAGAACTCTATATTTTAAGCCGTATCCTGC
TCAAAACAGCACTAAAAAGATATCAACCTGATGTCTCATTACAATCATGGCAATTTAGTACGTGCAAATATGGCAA
ACCATTTATAGTTTTTCCTCAGTTGGCAAAAAAGATTTTTTTTAACCTTTCCCATACTATAGATACAGTAGCCGTTGC
TATTAGTTCTCACTGCGAGCTTGGTGTCGATATTGAACAAATAAGAGATTTAGACAACTCTTATCTGAATATCAGTC
AGCATTTTTTTACTCCACAGGAAGCTACTAACATAGTTTCACTTCCTCGTTATGAAGGTCAATTACTTTTTTGGAAAA
TGTGGACGCTCAAAGAAGCTTACATCAAATATCGAGGTAAAGGCCTATCTTTAGGACTGGATTGTATTGAATTTCA
TTTAACAAATAAAAAACTAACTTCAAAATATAGAGGTTCACCTGTTTATTTCTCTCAATGGAAAATATGTAACTCATT
TCTCGCATTAGCCTCTCCACTCATCACCCCTAAAATAACTATTGAGCTATTTCCTATGCAGTCCCAACTTTATCACCA
CGACTATCAGCTAATTCATTCGTCAAATGGGCAGAATTGA*

>clbS

ATGGCTGTTCCATCATCAAAAGAAGAGTTAATTAAAGCTATTAATAGTAATTTTTCTTTATTAAATAAGAAGCTAGA
ATCTATTACGCCCCAACTCGCCTTTGAACCTCTATTGGAAGGGCACGCGAAGGGGACTACGATTAGCGTAGCGAAT
CTGGTTTCCTATCTGATTGGCTGGGGAGAGCTGGTGTTACACTGGCATGACCAAGAGGCAAAAGGAAAAACTATT
ATTTTTCCTGAGGAAGGATTTAAATGGAATGAATTGGGGCGTTTAGCACAGAAATTCTACCGTGACTATGAGGATA
TTACAGAGTACGAAGTTTTATTGGCACGGTTAAAGGAAAATAAGCAGCAACTCGTGGCTTTGATTGAACGATTCA
GTAACGACGAGCTTTACGGTAAACCTTGGTATAATAAATGGACCCGAGGTCGTATGATTCAATTTAATACCGCCTC
GCCTTATAAAAATGCTTCGGGGAGGTTAAATAAACTGCAGAAATGTCTTGCAGAATAG

FIG. 5

>clbQ

MSNISLYCLPYSGGSAAMYYKWRSVLSDNITLRPLEPAGRGTRIRQPLCLTMVDAVADLYQQFVKHYTGGDYAIFGHSL
GGIMAFELVHYILDHGHDMPCALFFSGCRPPDRASHEVILHTLPDQAFMEEIVKLGGTPVDVFRNKELMTIFTPIIKNDY
RLYEQYVFQAKARTLTCPIVLFHGDADNLVMQDELLAWEKFTTRKTRTIIFPAADHFFVDKHFEQVVGYVNQTIESLEIV
G*

>clbP

MTIMEHVSIKTLYHLLCCMLLFISAMCALAQEHEPIGAQDERLSTLIHQRMQEAKVPALSVSVTIKGVRQRFVYGVADV
ASQKANTLDTVYELGSMSKAFTGLVVQILIQEGRLRQGDDIITYLPEMRLNYQGKPASLTVADFLYHTSGLPFSTLARLEN
PMPGSAVAQQLRNENLLFAPGAKFSYASANYDVLGAVIENVTGKTFTEVIAERLTQPLGMSATVAVKGDEIIVNKASGY
KLGFGKPVLFHAPLARNHVPAAYIHSTLPDMEIWIDAWLHRKALPATLREAMSNSWRGNSDVPLAADNRILYASGWFI
DQNQGPYISHGGQNPNFSSCIALRPDQQIGIVALANMNSNLILQLCADIDNYLRIGKYADGAGDAITATDTLFVYLTLLL
CFWGAVVVVRGAFRVYRATAHGPGKQQRLRLRVRDYIIALAVPGLVAAMLYVAPGILSPGLDWRFILVWGPSSVLAIPF
GIILLAFVLTLNHQIKRILLHNKEWDDE*

>clbO

MAKDDFTCGSLDIAIIGMSGRFSGAESVPEWWDKLLAGEEFTQPTCTEDDNGNPWIRLRNIITAPYDFDAAFFNIPPGE
ALLMDPQQRIFLECCYNALEHAGYIPTQLKRVGVYGATYANNYFIDRVYPYLKMSGDHHYLQAQIGNEKDYLCAQVAY
KLGFTGPAVSVQTACSSSLVAAYLACEGLLTFQADVALAGGVTLGFLQAHGYSPQGDKLVSQDGHCAPFSAEATGTVYS
SGAGVVVLKRLEDALRDQDRVYAVIKGGAVNNDGGRRLGFVAPSVEGQVEAINTALAAAEVVPTDIALIETHGTGTPLG
DEIELEALHRVFAPACAPHSIQLGAVKANLGHLGVASGIVSLMKTALTLYTGLVPPQINLVNKHKKLLQPASPFYLSDVVT
SVPQTKRIHATVSSFGLGGTNAHLVLQNWCETPAQAVQENERRLFFFSAKTPLALRQQLDAHYHALATYAEADKDRIAY
TLAQRRAHFPYRCALAADSVVALRASLAKLRDADMSFTPINMETTLVFLYPDRDDKLESALTHLLACQPNLRQRHQRLS
QDVAQICEPADWTPALRQFIQQVSLSEWLIEQSISPVQHIGYLTGAAAAQYVARIISLENAVQQVIVAETTPEQTLAGNS
ELSEILANLAVTEGTLMLEIGRAGTFSILYHQHAQWVGQTVFSPMLNTDTPEDILPLLGTLWQRGVTICLPEMPAVQTIG
LPGYSFDRVRYEIQSSDARENAMLPVSYLSVSDFVEKTWRSLLCIDHYDEHAVIFEYGATSMHVISFVDSCNHIYKIGLTA
ADIYARPAIREHSEFISECVDGIL*

>clbN

MMSGNPLSWPQEQCHIIDQLYPYSAVNIIGGVVTIEGIVDLPRLHAAIQSAIRQFDALRMWFVMGEESEVVSQVQPYH
WRDIRHLTFSPDYDKENLRPAAIETFVDEWFRQPFTLLAHDLFEFVTFTCGEQYSGYLFKAHHGIADGWSMALLSNHVK
RAYEQQDVPDDASPAYSAFLAQQQSYQASTRFAVDRGWWRDYIDEYRDCFPDSSPIVTTEGISCSTWLEPAMINRLYR
LCNRYGCTLNTLFIALFALYRARVWGEEKGVIGVPLANRHTREARRCFGMFTNQLPLAYRLVRTERFCERVAFFQRELKR
GFKHSKYPITLFNQDLAEQGGGKLRAFDYCVNYYNFTYERHIAGAAQRVESYYSGEQSYKLQIVLQTVNNHKESLRLSLE
ALRSAFTPHQLTAMKNGLLDLVTALDRQPDARLGDLEVYPAPHVALACGSLKPSFTSRFAAQVVEHGDRTALIDNEQSL
TYRQLDDAVERVARYLRQQGIGRGQVVGIIAEHSAQTVMVIYGILRCGAAFLPLNPALPTTRLYAMCRKAQVAHILYDP

FIG. 5 - Continued part 1

AMHELTQALAFPASSLLQALATSALAREPWPAIEPQDLAYVLFTSGSTGEPKGVQVSHGNLANYLHFAAERYFTAQDRA
ALYSSLSFDLTITTLFAPLCVGASISVCRHAESETLLRMAVVDQPNTVIKLTPAHLRLLCAAGISSEQIRTLVVGGEDFKRDL
ARKAAALFPQAVIYNEYGPTEATVGCMIYRYTGQETLPSLPIGMAIDGCQVAICSPWGCPVPEGETGELVIYGASVTQG
YIDAPQQTAAAYLKDTNGVMIGYRSGDIGYAIAPNTLVYQGRKDDQVKINGYRIELCEIEQALLSAPQVESAAVAVIDDV
QGQHSGLLACVTPSSVDVATVMQHLRQQLPTYMQPKQCCAIAQLPLSHNGKVDVRQMVATVRNTAPASGSERLGD
AAIRHSVRVCVEGALEQTEFDDNENLYVLGLDSIKSIQIAAQLRHHGWTMSAVQVMECGTVNAICEFLASHTTVSQLA
QYAHNTRIDLPALRWFTQLALPVPNVYNHVIVLKVLPGCPLEQLHNRLHTLIQQQPALHSALDAEGRLLVCDPNVCYPN
EVLTEYSTAQWTLAEVIAQCNSMLDVTNGRVFTAALLHAPQPASSTLVLCAHHLCVDMHSWYLILSTLDAVSTVNGTS
NSGLHRWNDYLASKTVDSATHESWRTVCQTLPLHFPPVSLPDDSLPRTRAWREDFRHPCVRRLFESSGNTAYSAETYV
LTALALVLRYYSEEPWCRIEMEGMGRGCWPDEPDVADTVGWFTLFYPWAIPLHGDMATLLSAIASDLAKRTHGGGDY
GLLQMRHAPEDSLAQGIRMNYIGVQAQPSLRYFHIDHFNSDIYTAPENALGCVLEFNIARSAADGLSFHCRFDPTRIALN
DVQLLLARYKNSLTDLDAWLCQHSATLTGAPTLWTL*

>clbM

MTVNKLEPDNGTPNDELFTVAGMFDGSLYKLLLRMALPMFVGMLTQVTYAIADIFWLSHIDVTNSGIIAGVGLVFPVG
MGLFAIANGIQIGMGSLLSRAIGMQRLDRAQRILSVGIIIALFFAIVITVLGYVYAQPLLRSLGATKSIIGYATEFYYYSLLTVF
SIMLIGVMMGLFQGAGKIMVIMKASLLGALVNIMLDPIMIFVFDFGVKGVALASFLAQLSMVAYFIYTLMGLHIGLSIRI
ALRPFSWKIYREFLSVGMAQMLMQLIIAVGIVIYNFFIVRLDVNAMAAFTLTGRIDYFIITPMLAIATALLTVVGQNWGH
GNVTRTLNAYWAAVALAFSIVLVLAVMHIVLAPWMYPLFTRVVAVSDYAVLQTRIMALALPFVAISLLASEYYQAIGKP
WYSVLLTLMRHVFISVPVVYLLAIVLEMRITGVYFGAMSGTFVAALLAWRLLRLSPRLLRWNQEAVRSQHLDMEVAP*

>clbL

MSEQSYRSAGTLLAQLASGETTSVALVNHYFSRMAQFNKPLNAVVQQHYALALEAAARADRERLEGRARGVLHGLPC
TVKESFDVQGWLTTSGAHYLKDNRATQDAPSIARLRAAGAILMGKTNVPMMTADWQTYNDLYGTTHNLWDRQRSP
GGSSGGAAVAVAADFTPVEFGSDLFGSLRIPAHYTGVYAHRCSLGLMSVRGHVPGGGPQATDEPDLSTAGPMARSAA
DLRLMMRALSTFWVEPPRIPDFSRYQAKANYRVCTWFSAPHHEIDQQIAQRFQSFIDKLRAQPGVEVDDAMPADIDP
DALFDIAVKLSGRLVSTALNGRQRLTAGLAALGFRLVGKLADVPEGITSYYQGMLKDSGEQRNTDKLRHEYSRVIETLFA
RYDVLLTPVSPVLAFAHMQQPVRKRKLIVNGEPQDYNEHLFWNMLATVFGLPATVYPLAKTMDELPCGIQIISGHFHD
DVTINFAEFCESISGGFTVPEGY*

>clbK

MTYSESDIAIVGMNCRYPGVHSVAAFETVLRTGCNILDPKVTPSNGHNHITLNNVYEHMAEFDANFFGYSRAEAEIMD
PQQRVFLTCAWEMFEQSGYNPKQHDARVGLYAGVSTSFYLLTHLMNNPDKLAQLGGLQIMVGNDKDHLTSQLAYRL
NITGPCVTVQASCATSLVAVHLACEGLLSGQCDMALAGGVTFRMEEQRSYESHGDGLQAEDGLIHTFDAQASGTVYSS
GLGMVLLKRATDAQVQGDNILAVIKGSAINNDGGARSGYTVPGVDGQEAVMIEAHSLAEVTPQQIQYLELHGSGTPL
GDAIEFAAIKRVFGTPAPNATPWRLGAVKPNVGHVEMASGITSLIKTVLSLTNRVFYPTLNFQRANPQLGLEDSPFEVVS
RLTPWPEGTTPRTAGVSAFGLGGTNAHLVVQAPLSTPQARAQQMGPCVVVLSAKNHNALEQMQNALLAKLAAHPEI

FIG. 5 - Continued part 2

RLQDVAYTLRHGRFSAPVRKCVIAENCTQLARQLRDAPMVEATTGCTIYWRLGHRFVVALETLSDWLACSEVLSQAVG
QLLEHFPLEPACLQDLSPAQRTFISQYALIALIDERETLNVVLCGDGDGGYAAAVLRGDCTLEQAWHRLNAGQPFDDVP
TNPLLQPDVCSLMLDDAASDANRTALEALGQLWLAGVSLDWRWVDAAERMLGSQRIALPGTVFTPQRYWVEAVRP
ATFSHESSNNLLSRATKSDIIAVVTEIWERTLGVSIDDHHASFFELGGHSLLASTILYDIQQRYGITCTLSAFFADPTIEGLSC
YLLEQGGSETAVSALPDTVFAPDQQHLPFPLTDVQQAYWVGRRKSLGLGNISTHIYVEYELQGLDETAFNRALNAVIAR
HSMLRAIVNDDGMQQILPNVPEYHVAFYTTQCEDAFQQRCRELRDTLSHQMIDCSRWPLFQMEVVVDPQQKARLH
VSIDLLIADAWSLELFIRELAYHYRHPQAALPTLTYSFRDYVLTLKSYEKTPQFERARDYWRARIETLPPGPRLPLRTDPTKL
ENPTFVRRSYCLSRAIWQRLKTQAGQMSITPTTLLLTGFAQVLARFSSSPHFSLNLTLFNRLPLHADINHLIGDFTALTLLEI
DMSQGETLQARANVIHSQLWRDLDNRLFGGIQVSRLLVQTHRDPAKSVIPIVFTSLLNQYEASWETDDTLFNQPQDDL
YSISQTPQVWLDHQVMERNGELHFNWDVVEQLFEPALMDQMFQCYCQLLHALAQRPQLWHETQDVLALPTVSAPV
TQAPAPTALLHHGLLRQAALTPQETALISPIRELTYRQLSTAADHVARALLALGVQHGDRVAVVMEKGWQQIAAVHGI
LRLGAVYLPVDPVLPPQRRQLLLTVGEVRVQVTQPGLTQLEPSLPVLIIDDGMLDTPAAPLPEVAGDVTDLAYIIFTSGST
GTPKGVMIDHRAAMNTLEDINERFGLNAQDRVFGLSSLSFDLSVYDAFAPFMVGAALVLPEAGREKDPRHWQTVMA
HGHVSVWNAVPALMQMLCEYHSGDRMSYPTLRLALLSGDWIPLTLPEQMRERLNETMDIISLGGATECAIWSVYYPI
GEVESTWTSIPYGRGLRNQPVYVLNAQLEECPVGVEGEICIGGMGLAQGYLNDAEKTAASFVWREASGERIYRTGDRG
RYFADGQVAFLGRNDTQVKVNGYRIELGEIERCIARHPDVEQSVVVAVGNSQHRRLVAFAKLHDRHQAQALQAKEAE
AAALAQGIIVNPAQRLAFKLKEPHIRALDGLGIALTAPADSTRYIKRRSYRHFSAQKTTLAQLGQLLSGLGQMRLPGLPFA
KYAYASAGGLYPVQTYVYLHPDKIEEGVSGIYYFDPRQSCLMPVAPEVELNSGFHAGPNQSIADRAAFTLFMVADMAVI
SPFYGQEAAWHFSVMEAGTLCHLLEEDAPRYGLGLCQLGMADFSAVASHFQLSPHHRYVHCTVGGAIGQEAASAAAL
LRDFSTYEKPKETAAPLDMQSYKDAMLRGLRQQLPDYMVPSDLMLATDFPLTANGKLDRQKLQLQGEQIAHQRDGV
GPIQVDSALQQRLVALWQEVLGVSHVSAEDDFFSLGGSSIELVRIQQALEAIIGQEIPIVDLFRLPTIADVARYLDEQLHNL
PAAHDIVLAQAEVSQVSAARENLALRRKRAQQGEKGDE*

>clbJ

MTIHHAALARMLPAEKKEKLLRQLAQSGVSPSRIPIIKADPAQAIPLSFNQERLWFLQKYDSTATNYNLYVVYRLHGVVD
MPMLTEALRHVQARHAILRTRIIVRNDRPCQVIDDASSLVLDTVTLAAQAPTSALDAVIQQVINTRFDLARGPLWGVTQ
IIQPDQGCHLVFCAHHIIIDGISLRLLFDELQQQYARLHAGNETSLPPPPLQYADYAFWQREWFQDTLLANELAYWRAR
LQDAPLLSTFPSLHPRPAQPSTHGSRFSITLDETLSLALKHVARTQETTPFVLMLTAFQLVLMRYAQQQRLVIGMPVSGR
IRPELQSSIGYYASTAVIYTDFNGVEVGREALQRVKASVKETQGRQQLPFENLVNMLDLPRSLSHSPLFQILYIYHNHVTP
RAFTLAGAYWEQVTYHNQTVKYDMTVEVFQNDATFDVSFEYDLGLYDADVVKQIAEALRQHCLSLTSSLETPIGAIPLH
APETATPRRDPLNATNVPWLGPQDVLRIIEQRCVQHPKQLAIQQHDGTLTYAELWARVQFIAMRFRAHGIQPGDRIG
VLLPRHRDVIATMLATWFVGACYVPFDIHQPAARLQRLMQRARLVCLVVRQPGEWGEIVQLSLPELMQDMSNAIRYS
TPCALLPDMQAYLLFTSGSTGEPKGVCVVHRGLLNLLLDMQRTFAVGSQDRLLSVTTPTFDISFLEYLLPLISGASLYLTEA
ERAADSFRMIPLIADYRPTLMQATPSFWHGLLMAGWRGDPELCVLAGGEALPTKVAEELLRCCGSLWNLYGPTETTIW
SLKSQITQAENITLGAPIANTRIYILDNEGHPVPQGVDGELYIAGDGVAQGYDGQPELNAQFFLSEPGVPGGRMFRTGD
LVRSDAQGQLFFVGRKDSQIKLRGYRIELGEIERTLARHPHVDAAVVACIERAPLHKALAAFIITSEPPSLFEQLKNELRQQ
LPDYMVPTLWQRVADFPNTDNGKIDRKRLAENFVADSSLVSPQTQALSDTEQMLLALWMRYLPIKNVDPECDFFRLG
GHSLLAVTLVAEINRTFHCALTLKDIFHYSTLRALSARIAQQSITDAAASQDDWVIVHDPEHRHQPFPLTDVQRAYWLG
RQTGATSIATHIYHEFDVEHFNVTRFTHAVNALIARHEMLRARVLPDGTQQILAQVPAYQLEQRDLSALSPNARNDAL
MAIRDRLSHHVHPADRWPLFDFSYSACTAQHGRLHFSLDLLIADALSMRTLQQELMMLYREPHVSLPLLPFSFRDYVQ
ALLVEQASEAYARDQAYWQRALPQLYGPPTLPVQGDLAQLSAIRFVRRRHRLSAHNWGVLSALAQRTRITKTALLLTVF

FIG. 5 - Continued part 3

SQVLARWSLSPTFTLNLTLFNRPQGYPNAEAVIGDFTAVSLLNVCYDSQHSYAHNAQRIQVQLWEDLEHRRFSGIRASE
ALIHSGRFHAPMPVVFTSMLDIDGETTAQDPRDTTRFTLCPDANITQTPQVWLDHQVIELAGELHFNWDAVEQLFDTT
LLDQMFGAYCHALQALVAMPQSWWGVNSSLALPTVSAPVTQAPAPTALLHHGLLRQAALTPQETALISPIRELTYRQL
STAADHVARALLALGVQHGDRVAVVMEKGWQQIAAVHGILRLGAVYLPVDPVLPPQRRQLLLTVGEVRVQVTQPGLT
QLEPSLPVLIIDDGMLDTPAAPLPEVAGDVTDLAYIIFTSGSTGTPKGVMIDHRAAMNTLEDINERFGLNAQDRVFGLSS
LSFDLSVYDAFAPFMVGAALVLPEAGREKDPRHWQTVMAHGHVSVWNAVPALMQMLCEYHSGDRMSYPTLRLALL
SGDWIPLTLPEQMRERLNETMDIISLGGATECAIWSVYYPIGEVESTWTSIPYGRGLRNQPVYVLNAQLEECPVGVEGEI
CIGGMGLAQGYLNDAEKTAASFVWREASGERIYRTGDRGRYFADGQVAFLGRNDTQVKVNGYRIELGEVKSHLEQLD
SVGSAAVVCHQGQLYAFITAAENLHPDDTDALLARVRAQLAVQLPYYLLPQHFFLLKVLPMTGNGKIDQAAMVQEVIQ
RMSQSTSQKSRALAHASPYEQQVAALWCEVLQREQIGLNDNFFEAGGGSIQIVLLHRRIEEIFKVTVPIAELFRLTTVKRI
AGYLQAMQDNARAVNQTQQRDASRSRAQQRLVRRHQRQR*

>clbI

MAENDFGIAIIGMAGRFPQADTVQAFWENLLASRECISFYSDEELLAMGISPEFVQHPDYVKAKGEVADIDKFDAAFFG
IAPREAELMDPQHRVLLETAWAAFEDAGYVAADYPGDVGIFAGKSMDSYLMLNLMPHFKRVFSSGSLQAAIGNDKDS
ITTTIAYHLNLRGPAITVQTSSSTSLVAVCVACQSLLTWQCDMAIAGGVTLGPPAKTGYLSQEGGITAADGHCRAFSDNS
SGFVPGTGAGLVVLKRVDEALRDGDNIYAVIKGFAVNNDGSEKISYTAPSVDAQARAIAQAQRLAGLTPQDITYVEAHG
TGTRLGDPVEFSALSQAFAGASQKQYCALGSVKTNIGHLDTAAGVAGLIKTALAVQQGIIPATLHFERPNAQIDLTNSPF
YINTTCQPWQPESGIRRAGVTSLGMGGTNAHVVLEQAPAVDLQARAPVPAYSILPFSAKTDSALSSGLARFADFLQHES
LPDRRDLAWTLSQGRKAFAHRAALVTRDLHAAGTLLQQAATAPFARGVAQTQLGLGLLFSGQGSQYQRMGHQLYQV
WPAYADAFDRCATLLEREYQLDIRHELFRAEVSLAQGERLAQTCLTQPLLFSVEYALAQLWLSWGITPTVMIGHSLGEW
VAATLAGVFSLEDALRLVARRAELMHQAPSGAMLMVALPEAQIRALITAPLAIAAVNAPDYSVIAGPTSEILAVSQRLTE
QNIINKRLHTSHAFHSSMMQDAAQALRQAFENVRLNPPTLTIISTVTGAHVSADTLTTPDYWIEQMLMPVQFSAALQE
AQATFDVDFLEIGPGATLTQLTNGHALGDRLAFSSLPAGARSSDEHKHILDTVAALWVRGHNIDLSAFAGEQPRRVSLP
TYAFDKIRYWVDSPEEQRSAVTPVADAGSVIPSEPSVRRQPRPAFSVPYAAPESKTQRGLVAICEALLGIDGLGIDDNFFE
AGGHSLMLGMLLAQVQERFAVTLSFFDVMEDASVRALAQLVEQEQQDDGGSALAVLVNDMINE*

>clbH

MEQQGIMRQLPTDDQTIVDYLYRIAGEYGEKAAVLMGDAALSYHDLNARSNQLAHYLRGLGIGEDRVVAIRLPRGMA
MLIAIFAIVKAGGAYLPLAYNAPRSRIENILSNSGAVCLIGTDDGDRWPIPRVEIDSAAVSAMPTTDLRYRPHARQLAYIIY
TSGSTGVPKGVATEHAALLNRIVWMQNAYPISSQDVLFQKTVYTFDVSVWEMFWWAMYGASVVLLPSGLESDPRTL
ARLIQRHRVSVVHFVPSMLNLFVEYLEMKQDPRLTASLRLVFSSGEKLTVHSVARFYQSVAQGDLINLYGPTEAAIDVSH
HRCLRGYDYDDIPIGQAIDGCRLYVLDDHGNPVADGEEGELYLAGIGLARGYLNNVALTDRCFTIHPTLRHLGKPERLYK
TGDLVWRDGESQQIHYIGRNDFQIKIRGLRVELGEIEAHAMRFPGVQQAVVVADQDDPDNQLIYAFVVSSVPLNLAAL
MDALSKNLPAYMLPNRLLAMSELPLSDNGKCCRKTLLDLARAYSASRVDLRETPAVRYLPLSSAQSSMWFMQQLAPHT
ALYNNPTALLLEGELDRTRMDGAIRQLMSRHTLLRAMAETHNGQPVLAVPQCVSSQALLTIVPLPSVSDDNALQAMIN
QRAAHPMPLTSGTPLCRFELLTLDDDRSVLLIHLHHIISDGWSKGVLLRELQAAYNGESLTPEPLLEYADYMEYQEEWRQ
SDAYQDAMRYWQNTLAGTLPILDIPTDQPRQKVARYQGAFVAFALSANTCERVLAAARAQRVSLYNYLLTAFVLLLHR
NARQQEYIVGMPIAARLTKEQEHMIAPLVNVLPLRLPLDEAASFSELVQTIRGILFAAFRHQRLEFTDIVRAVNVDRSAG

FIG. 5 - Continued part 4

HFPIYQCMFQLDNMPLASPTLNGVNVTPLLLDTSASQVDISLSMQHIDGRITGTFEYDAGLYSADRIQHLVAQWRELLD
EASSQPTQLVRDLIRFTPREHAWLARHNATEVALPPVDNLLALVLPHCQQRPTQVALRHADDAMTYGELQQATMQM
CTWLRAQGVKRGESVALQLPFCFELIIAQLAILSLGASYVPLDGNAPAARNALILAQATPCMLLVAQPLESPHGLTIPWV
LVPDWRSLLTEIPNLPVSVAPDALDCDAVVIFTSGTTGQPKGVRLSQRNLVNLTASFISSYQVTHQDVLLPITSVASASFV
GEVLPLLAAGGTLVLAQKAQSLDSDALIALLASQRVTILSTTPSLSASLSVLAQSMGSLRLFLCGGEALEYEQIAPLLPHMA
VVNGYGLTESGICSTYFPVAKRREQETGALPIGRPIQNTQAYVVDAYNRLVPPGACGELCFSGLGISPGYLDARQDPERF
VELPEYPGVRVLKTGDRARWATDGMLFYLGRQDRQVQIRGYRVELGDIESLLKQHPDIADAWVDVRRNAAATPLLVA
FYCSVNGVALDAQQLRVWLSLRLPLHMLPLLYVPLSAMPLGVNGKIDPQCLPLVDLRQLEGPGEYVPPATELEQRLAEI
WQQLLGLERVGTTTNFFDLGGHSLLLVQMQQYIGQQCGQHVALVDLLRFTTIKRLAEFLLAPDAAQGTTGDQTQLRA
AKQRLAFGHTRWAATTDSHH*

>clbG

MTKDVALMFPGSGSQYVGMARWLYERYPQVRTLFDEASQITERDMAALCLSGTLVQLAEPTAMALAIYTTSVAHFVA
WQQFLAQTGVHVNLRYMLGHSLGEYAALTCSGALSFSQALALVAMRSRLASEIAREMDASTTIIKQGNQALVAAACEV
AERETRQQVGIACFNSPQQFMLSGQNSAIIAAEQYLLDHDRQVEVVPLIGGVPYHSPLLKPCGQQLRKALDRCEWRRP
CCPVISNVNAQPYPDTVTPVQWLEQQLSQPVQWQRSLTYLTGHLSPIAIEIGPQSVLKNLLLENRYPAPVYAFDNRHDR
AQLALVLGDNMAVKTDPEAVRRQRITLLTNALTATRHHRAADVAASAQLKELLSRFFERIQQIEQRGTSSEEDIAFLHELL
EQGFQLKGSSQAEIDACHARLASDNGGQA*

>clbF

MCTENYELAQQEAVLFAKQHLALAAQNIERQQFIVPDIISCVAQAGYLGASIPQKYGGRGYDSYQLCALHEVMAGVHG
SLENLITVTGMVSTLLQRVGSAAQKAHYLPKLATGELIGAIALTEPNIGSDLVNVETELQQDGDGWRLNGKKKWITLGQI
ADFFIVLIHCGNQLATVLIDRNTDGFTITPLNDMLGLRGNMLAELHFNDCRLKEDALLGPLTPGVPLAVNFALNEGRFTT
ACGSLGLCRAAVDVAARYIRQRKQFKRRLFSHGIVQHLFATMLTQTRSAQLMCFSAAEYRETLHPAMINQILMAKYVA
SKAAVDVAGKAVQLLGANGCHADYAVERYYRDAKIMEIIEGTSQIHEIQIAMNYMMGSEA*

>clbE

MKKQDMKAAIREFLSRSLRGHTLNDDDDIFSLGLVHSLFTVQIILFIEKNFQVELEVSELKTEQIATVNKIVELIQRQTGLE*

>clbD

MMNVAVIGAGVMGTGVAHNMAQYGISTNVVDISQSQLDKCRQMIEANLRLYNFHPQHKKKTHSTAEIMENIRFTTE
LDDIVECDLVIENITEDIEKKNALYTRMNTICGASTVFGVNTSAISITALSKLMRHPENVVGVHFMNPVPLMHTVELIRGV
HTAERTLNIFHHLFAQLNKTGIVVNDSPGFVTNRAMMIFVNEAIFMVQEQIARAEDIDTLFKTCFGHKMGPLQTADLIG
LDTILQSLQVLYESFNDDKYRPSFLLKKMVDAGYLGVKSGQGFYRYQQTYAEQ*

FIG. 5 - Continued part 5

>clbC

MEYASEMNGMEIAIIGMAVRFPQSRTLHEFWHNIVQGKECVTFFSEEELLAEGVEQSTLDNPAYVRAKPYIEGICDFDA
AFFGYSHKEAQTLDPKSRVLHEVAYHALEDAGYAQRTSDLITGVFVGASEDVDWLRRSLSQIGGDALNRFESGIYGHKD
LLAHLIAYSLNLNGPVYSLYTSCSTSLSATHIACRSLLFGECDLALAGGITIDLPQKSGYFCQQGMIHSTDGHCRPFDSQAS
GTLFGDGAGVVVLRRLEDALAAGDRIYAVIRGSAVNNDGKQKIGFVAPGHEGQKAVICAACHLAEVSPESIGYVETHGT
GTRIGDPIEFAALTEAFDTSHRQYCALGAVKANIGHTHAAAGVAGLIKTALVLHHRTIPPLANYQMPNSKLDLAHSPFYIP
IQPQEWPASRMPPRAGVSSFGIGGTNVHMILEGLNPAVRDDHDQVRAPVFIPLSAPSFEQLDELTQQLTPLLATLDAST
LAYTQQVARPVFDCRRVIQVENDGTQAMLASLDNLMPDAPWGLHCPDLRTTNDCTYAQWLAHSAHYQREATALTA
LLDGMNIPPAYCHAETWAAQANSSLLIRGCQTIAALKTWMNLLPTLTLLSGAGTGLLPAAAASGMIATQDVLHLLWE
MEQKALHLWLPERHEPIPGYVLAWQGNPITDAQRNDRGFWSEALLADTRELGEGVHSINWVRLPPEIREDVDVLRYV
AQLWCAGINVDWAVWYGTPLPQRGSASAYPFAHNHYPLPGRVMGSVETQPEAGPETHHPYQARPVLSVPFVAAHS
RGMQYITGLMELLLEISPVGVDDDFFELGGHSLLVTQLTSRLERDFNVHIDLLTLMENPNPRNIYAHIAAQLGGEDNLEI
ACQ*

>clbB

MDNTSGDFPCNKMDTRKQLPLTPSQQGFLFHSLKDKKRSNYHEHFTCIFSQHVDSAHFKWALETLFRKHECFRTDYN
WEIDERPCQVVKTDVLPDIYVLDCEQEEIRFLLANDDIIIPVPQDDGIDAIIPQLLQADLKYPFSLKTIPVRAYLIQSTKESAFI
LSYHHIVMDGWSLSLFIKQLLQLYGAAVVSGVRDDSAIIPSSLKPLVDTLSARRHTFQHDYWAAYLREGTPTCIVPLSQYH
TDTEAENNSYVNQTNHVEINLSPDVCQKIQTLCSDYRITPAVIFYVAWGILLQRWCYADDVLFGATISGRNIPIDGIEETL
GLFINTLPLRLRDDGATLLQHLQRMHQTLIAHYSNEHDALASIQRLVHKEGHAGDLFNTLVVLENYPVDMTLLSCASPV
AIRHLSVHEQTHYPLTLTITQQKGFRFSIAYALNYLTNNMAQALLMHLSYLLEQLVDNPQRPIAALVNLSPCQQAQVLQ
PYLERMACRDWDSQSNVIEQFHQVAATSPAQVAVVDELCALTYSELAAQAEQLAAYLVQQGVMVGDTVGIISERRVN
TVVAIIAIMLIGAAYVPISPDYPVGRMQEIIDDSGLALLLVHGKPLDALNVAQSDLCAFPVAPSVVFPVITPDSRAYVIYSS
GSTGKPKGIAVAHRGLLRLIQGDSPLKVESGETTLLTCPFEFDVSVFEMWSTLLNHGKLVLLSKQALLDINHIRRTIADEQ
VARAWFTSSLFNSYVAEGADFFGMLQHITVGGEAVSAWHVNDVMQKYPHLVVTNGYGPTENTIFTTAYRFNGLQPA
RVPIGYAVPGTSLYITDLHGHLLPIGATGELVAGGVGVAIGYQNNPALSATVFVPDPFIPGGMMYKTGDYARLLDDGCV
DCFGRKDGQIKINGQRIETGEIEQRLLECSGIIEAVVVPYRVRETLHIAAVVCVNDSYDEVEVRGQLADRLPPFAIPESLVV
VTEIAKSHSGKADLAQLRYLLPATQCNAVSTTISEVHSDMEHALHAIWQRVLDRQDIDSNASFFALGGTSLDTIRVKGDI
KRQLGLEIDITDLFKYPTLTALAHFLDTAVSPEDAIPTRAVVYSDMPVAIVGMAGRFPGAANIAALWTLVVGGESGLTLF
SDEELRAHGVTPDTLKQANYIKTKGIVDDHEWFDADFFGYTPNEAECMDPQIRLLHQCCWQTLEHAGCDPATFTGAI
GIYAGLLTSPHWLNAVMQDTTDSTALYKASILNIHSVTALIAHALNLTGPAVTLDTACSTSAVAIHQACIALRNRDCDAA
LAGGVSIEMPAYRGYEYHEGMINARDGVCRPFDSQASGTVTGDGLGMLLLKRLDDALADRDCIYGVIKGSAVNNDGN
NKIGYTAPSVIGQSTVIRTSLRRAGFDSDSIGLVEAHGTGTVLGDPIELRALNEVFGPTPVPFCVVSALKSNIGHLNSAAGV
AGVIKTTLALHHQVLPPTAHFRQLNPAIDLSRSALYVNQQVQPWPSTRPRRALVSSFGIGGTNASIALEAHQHEDDPSA
TGVRDSYLLLFSAKTPAALELRVASTLEYVKHGVGVRLPDVAYTLQTGRTAFDHRRAYLVSRGSKIDLSCATILQAEIFNG
QRTTAEICFMFPGQGSQYHGMASALYAHQPMFRQHMDRCFAAFQRYSTVDLKALLFDDEDTRDIDQTQFTQPALFC
VEYSLARTLIDLGITPDSMIGHSLGEYVAACIAGVFTLEDALHVIEARGRLMQSMRPGSMMAVYLSREQLTPWLAAERG
IELAANNSAHFCVVAGEQAAISRLSTRLVEGGIQHRRLKTSHAFHSAMMTPMLHDFAQLLGQIPMHAPHKRFISNVSG
TWITEEQATSPDYWVQQVRNAVLFSEGAAQLLVQPTLFIECGPGNTLSTFIQGHNQYSDQPTLLTLRKANAAIDDEHM
LHRTLAALWVRGENIDWRRFNQTALGKHIPLPDYPFEQTYYYRYGAALSGYRQYPNPLRRPQDEWLQRVLWRMHDT

FIG. 5 - Continued part 6

SLREAFYAPGELIIIISADGDKLQQTLMSSGVDSITMPLPISSEDDVWDNDRILTHFHDICALLAHKTYRQLHCLYAPGAEA
GSSLTQSLSGLYRVARWCMHSTTPLASLTVLTHGAFRVQEEDNPEPTLAALSGAVNVFAQELHPTEVRLIDIDAQSSDE
NLNLLTQRLAPKQETVMALRQGMLYLRRFIPTRLLAHLPPQTGCIPGNVLWIIGGEKGIGRMIGEALAQREGVRVVLSS
RTGYHHEAVQQDALDVIHCDVTQAEAVRACLATLLERYGRLDGVIFAADATTTLTLHQLSESALRDTLTVKERGTANVL
HALAQRNLLDERLLLLFCNSLAAVNAEIGQTGYATASAYLDALAQQLRTRYKVNALSIGLDALREQGMLLDAINGSEYDV
LRGLRPLMTGTLLQAYKQQGADTSYYARLSPESDWLLDEHRISGIATLPGTGYLALAYEALRHYFVQDQICIDELVFLAPL
TVMDNCSVDVFVDISPNGQGVSVEVKSMTERFSGTLTTHARGRATRLMVDDNVVCDLTGLMREMHTITPPTKELSST
HFHYGPRWHSVQQLYGNTAQTQVFATLALPTVAANDTIALHPALLDIASSVVEQLPGFHTDSVPFLYQDLRLYRPLPNT
LHVALTVNRHDEEGDSYAFTLYDMAGEMVARCAAMVKRKVQLHIQDVDDDTRLRVPSADNYQLRLAAEGEGAGKLA
LCPTPRLALGDSQVEIEVLATGLNFKDVLFTTGLLRQQPGEAPLQLGLECAGRITRVGKNVTEFAPGEDVMAVLNGGFV
QYARVESDCVVRKPAHCRIEQAAALPIAYLTAYYALVVRANLQPGERVLIHSAAGGVGLAALHIAKRCGAQIFATAGSEQ
KRDYLLSLGVHAVADSHDEQFAATLLTASDGQGMDVILNSLTGRLLDASLALLAPLGRFLELGSKDIVEDKALPMRFFAQ
GGTFIPINFHAAHGAFSRYLQQIVAWIDDNTLPLLPCKSVPLPEVARAFATLTTPQHIGKVVVTHRTAAGMDRLNAMIA
ERRLGGYALSMSNAEVMRQLWPILNTRSPWAQLLLSPRAIDRLARGNRVDRGVPSAANDTITQQTVKKRPRPEIGVPY
SPATREVERVLCQILEEYLGLDRVGIDDNYAELGATSLDMVQLSGQMARHYPQVSVVSLYNHATVRQLATFCQPPEGE
SNAPSPQPAVQTNTRANQIAKRALQIAKNTARSHTSLH*

>clbR

MDKFKEKNPLSLRERQVLRMLAQGDEYSQISHNLNISINTVKFHVKNIKHKIQARNTNHAIHIANRNEII*

>clbA

MRIDILIGHTSFFHQTSRDNFLHYLNEEEIKRYDQFHFVSDKELYILSRILLKTALKRYQPDVSLQSWQFSTCKYGKPFIVFP
QLAKKIFFNLSHTIDTVAVAISSHCELGVDIEQIRDLDNSYLNISQHFFTPQEATNIVSLPRYEGQLLFWKMWTLKEAYIKY
RGKGLSLGLDCIEFHLTNKKLTSKYRGSPVYFSQWKICNSFLALASPLITPKITIELFPMQSQLYHHDYQLIHSSNGQN*

>clbS

MAVPSSKEELIKAINSNFSLLNKKLESITPQLAFEPLLEGHAKGTTISVANLVSYLIGWGELVLHWHDQEAKGKTIIFPEEG
FKWNELGRLAQKFYRDYEDITEYEVLLARLKENKQQLVALIERFSNDELYGKPWYNKWTRGRMIQFNTASPYKNASGRL
NKLQKCLAE*

FIG. 9A
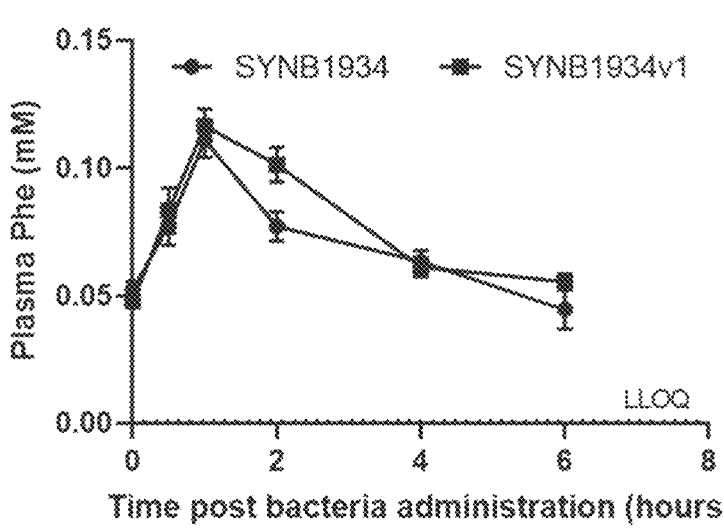
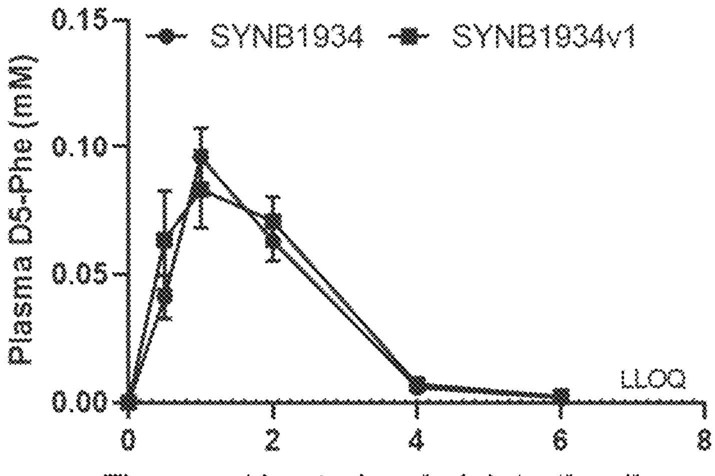

FIG. 9B
Plasma TCA
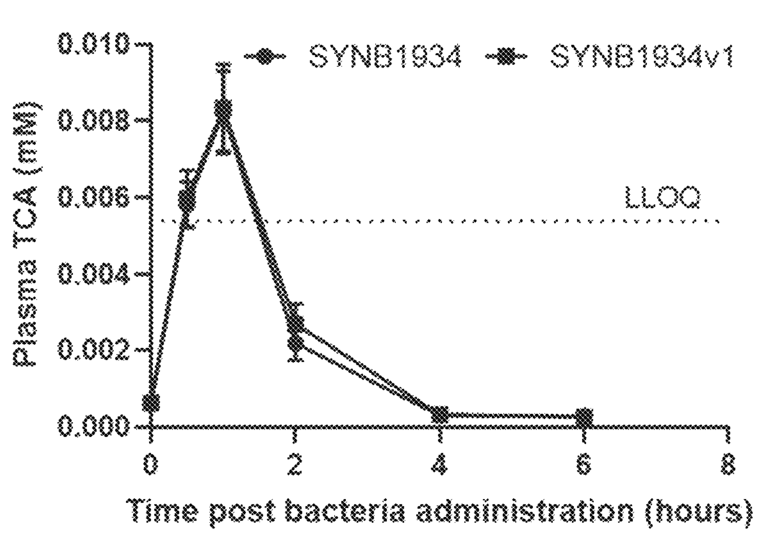
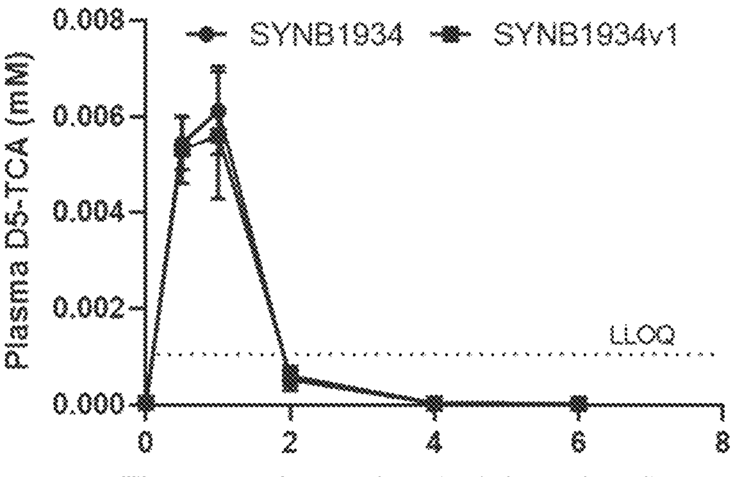

FIG. 9C
Urine HA
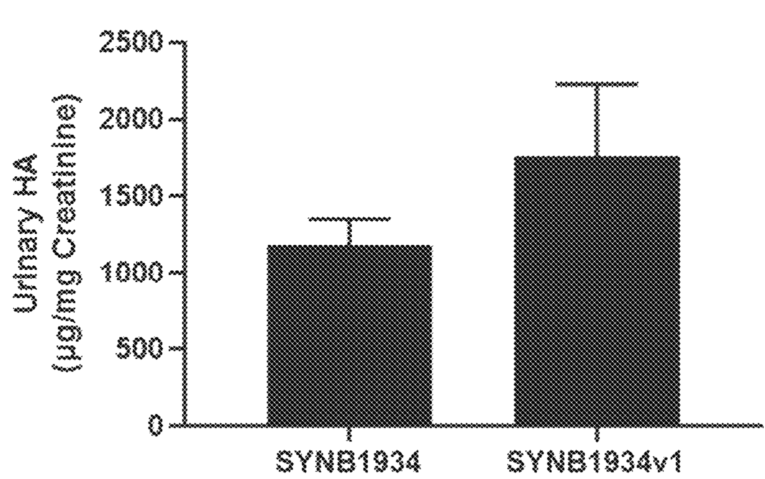
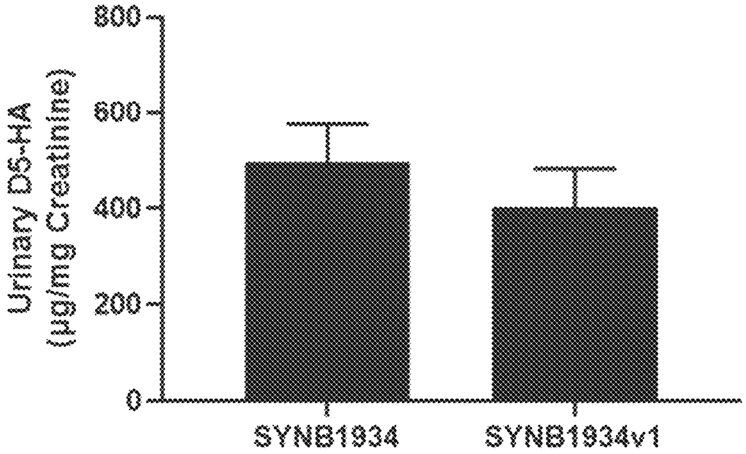

ENGINEERED MICROORGANISMS

RELATED APPLICATIONS

This application is a 35 U.S.C. § 371 national stage filing of International Application No. PCT/US2021/061579, filed on Dec. 2, 2021, which in turn claims the benefit of U.S. Provisional Application No. 63/120,674, filed on Dec. 2, 2020. The entire contents of each of the foregoing applications are expressly incorporated herein by reference.

SEQUENCE LISTING

The instant application contains a Sequence Listing which has been submitted electronically in .txt format and is hereby incorporated by reference in its entirety. Said .txt copy, created on Mar. 27, 2023, is named SL.txt and is 339,211 bytes in size.

BACKGROUND

Cyclomodulins are microorganismal toxins that are capable of interfering with the eukaryotic cell cycle. Fais 2018. Colibactin is a cyclomodulin that is synthetized by enzymes encoded by the pks genomic island. Id. The pks genomic island is "highly conserved" in Enterobacteriaceae. Id. In *Escherichia coli*, a 54-kilobase pks genomic island contains 19 genes, clbA to clbS, and encodes various enzymes that have been described as an "assembly line responsible for colibactin synthesis." Id. The pks genomic island assembly line for colibactin synthesis includes three polyketide synthases (ClbC, ClbI, ClbO), three non-ribosomal peptide synthases (ClbH, ClbJ, ClbN), two hybrid non-ribosomal peptide/polyketide synthases (ClbB, ClbK), and nine accessory, tailoring, and editing proteins. The polyketide synthases, non-ribosomal peptide synthases, and hybrid enzymes "are usually organized in mega-complexes as an assembly line, in which the synthesized compound is transferred from one enzymatic module to the following one." Id. Colibactin undergoes a prodrug activation mechanism that incorporates an N-terminal structural motif, which is removed during the final stage of biosynthesis.

The pks genomic island is found in various microorganisms such as members of the Enterobacteriaceae family, e.g., *Escherichia, Klebsiella, Enterobacter*, and *Citrobacter*. Id. Microorganisms such as *Escherichia coli* containing the pks genomic island have been identified in the gut microbiota as commensal bacteria as well as in disease states. Id. Colibactin-producing microorganisms such as *Escherichia coli* have been reported as overrepresented in colorectal cancer. Id. Colibactin-producing microorganisms are capable of inducing chromosomal instability, cell cycle arrest, DNA damage, epithelial cell senescence, and/or immune cell apoptosis. Id. However, colibactin-producing microorganisms have also been reported to exhibit anti-inflammatory, antibiotic, and analgesic effects. Id. In some models, a functional pks genomic island is important for probiotic microorganisms such as *Escherichia coli* Nissle (a strain characterized by its harmlessness and GRAS (generally recognized as safe) status) to exert anti-inflammatory effects. Id., Schultz 2008, Reister 2014. In colibactin-producing microorganisms, the production of colibactin may help promote bacterial growth and maintenance.

Microorganisms, including engineered microorganisms, may have therapeutic uses. As early as in 1917, for example, *Escherichia coli* Nissle was packaged into medicinal capsules, called Mutaflor, for treating gut conditions. Ukena 2007. These microorganisms may be impacted by the "pleiotropic effects" of colibactin, which include potentially beneficial and potentially deleterious effects. Rais 2018. Thus, there is a significant unmet need for effective microorganisms, including engineered microorganisms, in which potentially deleterious effect(s) of colibactin are reduced while potentially beneficial effect(s) of the microorganism are maintained.

SUMMARY

The disclosure provides an engineered microorganism, e.g., an engineered bacterium, comprising a modified pks island, and compositions and formulations thereof. In some embodiments, the disclosure provides methods for treating a subject suffering from a disease or disorder by administering an engineered microorganism, e.g., an engineered bacterium, comprising a modified pks island, and compositions and formulations thereof. In some embodiments, the engineered microorganism, e.g., an engineered bacterium, comprising a modified pks island further comprises gene(s) for producing a therapeutic molecule. In some embodiments, the therapeutic molecule is capable of reducing one or more deleterious molecules in the subject, e.g., deleterious phenylalanine, deleterious ammonia, deleterious oxalate, deleterious methionine or deleterious leucine. In some embodiments, the engineered microorganism, e.g., an engineered bacterium, comprising a modified pks island further comprises gene(s) for producing a phenylalanine metabolizing enzyme (PME); or comprises gene(s) for producing an oxalate catabolismenzyme; or comprises gene(s) encoding a modified arginine biosynthesis pathway, e.g., deleted arginine repressor, modified arginine repressor binding sites, and/or arginine feedback resistant N-acetylglutamate synthase mutation; or comprises gene(s) for producing an anti-cancer molecule, e.g., a deadenylate cyclase gene or an enzyme capable of producing a stimulator of interferon gene agonist; or comprises an oxalate metabolic enzyme, e.g., acetyl-CoA:oxalate CoA transferase. In some embodiments, the microorganism comprising a modified pks island is capable of reducing hyperphenylalaninemia in a subject and/or treating a disease or disorder associated with hyperphenylalaninemia, e.g., phenylketonuria (PKU); or is capable of reducing oxalate in a subject and/or treating a disease or disorder associated with hyperoxaluria (HOX); or is capable of reducing excess ammonia in a subject and/or treating a disease or disorder associated with hyperammonemia, e.g., a urea cycle disorder (UCD); or is capable of producing an anti-cancer molecule, e.g., a deadenylate cyclase or an enzyme capable of producing a stimulator of interferon gene (STING) agonist, and/or treating cancer.

In some embodiments, the engineered microorganism, e.g., an engineered bacterium, comprising a modified pks island further comprises gene(s) for producing a phenylalanine metabolizing enzyme (PME); or comprises gene(s) for producing a methionine catabolism enzyme, e.g., methionine gamma lyase (MGL) or methionine decarboxylase (MDC); or comprises gene(s) for producing an oxalate metabolic enzyme, e.g., scaaE3, frc, and oxdC; or comprises gene(s) for producing a uric acid catabolismenzyme; or comprises gene(s) for producing a leucine catabolismenzyme, e.g., a decarboxylase enzyme; or comprises gene(s) for producing enzymes for the production of lactate. In some embodiments, the microorganism comprising a modified pks island is capable of reducing the levels of methionine in a subject and or is capable of treating diseases associated with amino acid metabolism, such as homocystinaria, cancer, and metabolic syndromes/diseases; or is capable of reducing the levels of uric acid in a subject and/or is capable of treating diseases associated with uric acid, such as hyperuricemia or gout; or is capable of reducing the levels of leucine in a subject and/or is capable of treating a metabolic disorder associated with the abnormal catabolism of branched chain amino acids in subjects, such as isovaleric acidemia, propionic acidemia, methylmalonic acidemia, maple syrup urine disease (MSUD), and diabetes ketoacidosis and other disorders; or is capable of elevating levels in a subject and/or is capable of treating diseases associated with inflammation in the gut, including but not limited to ulcerative colitis and Crohn's disease.

In some embodiments, the engineered microorganism, e.g., an engineered bacterium, comprising a modified pks island further comprises gene(s) for producing a methionine catabolismenzyme, e.g., methionine gamma lyase (MGL) or methionine decarboxylase (MDC), and a gene for producing a methionine transporter, e.g., metP. In some embodiments, the engineered microorganism, e.g., an engineered bacterium, comprising a modified pks island further comprises gene(s) for producing an oxalate metabolic enzyme, e.g., scaaE3, fre, and oxdC, and a gene for producing an oxalate transporter, e.g., oxIT.

In some embodiments, the engineered microorganism, e.g., an engineered bacterium, comprising the modified pks island produces less colibactin as compared a control microorganism comprising the native or unmodified pks island. In some embodiments, the engineered microorganism, e.g., an engineered bacterium, is less genotoxic compared a control microorganism comprising the native or unmodified pks island. Methods of detecting colibactin precursor(s) and metabolite(s) are also provided herein. In some embodiments, a measurement of a colibactin precursor or metabolite provides a proxy for colibactin levels. In some embodiments, the method detects N-myristoyl-D-asparagine.

In some embodiments, the engineered microorganism, e.g., an engineered bacterium, comprises a modification, e.g., a partial or full deletion, in one or more of the clb genes in the pks island, e.g., as compared to the microorganism's native clb gene(s). In some embodiments, the engineered microorganism, e.g., an engineered bacterium, comprises a modification, e.g., a partial or full deletion, in one or more of clbA, clbB, clbC, clbD, clbE, clbF, clbG, clbH, clbI, clbJ, clbK, clbL, clbM, clbN, clbO, clbP, clbQ, clbR, and clbS or operably linked promoter(s) thereof, e.g., as compared to the microorganism's native clb gene(s) and operably linked promoter(s). In some embodiments, the engineered microorganism, e.g., an engineered bacterium, comprises a modification, e.g., a partial or full deletion, in one or more of clbA, clbB, clbC, clbD, clbE, clbF, clbG, clbH, clbI, clbJ, clbK, clbL, clbM, clbN, clbO, clbP, clbQ, and clbR, or operably linked promoter(s) thereof, e.g., as compared to the microorganism's native clb gene(s) and operably linked promoter(s). In some embodiments, the engineered microorganism, e.g., an engineered bacterium, comprises a modification, e.g., a partial or full deletion, in each of clbA, clbB, clbC, clbD, clbE, clbF, clbG, clbH, clbI, clbJ, clbK, clbL, clbM, clbN, clbO, clbP, clbQ, and clbR, or operably linked promoter(s) thereof, e.g., as compared to the microorganism's native clb gene(s) and operably linked promoter(s). In some embodiments, the engineered microorganism, e.g., an engineered bacterium, comprises a partial deletion of each of clbA, clbB, clbC, clbD, clbE, clbF, clbG, clbH, clbI, clbJ, clbK, clbL, clbM, clbN, clbO, clbP, clbQ, and clbR, and operably linked promoter(s) thereof, and produces less colibactin as compared to a microorganism comprising the native clb gene(s) and operably linked promoters(s). In some embodiments, the engineered microorganism, e.g., genetically engineered bacterium, comprises a full deletion of each of clbA, clbB, clbC, clbD, clbE, clbF, clbG, clbH, clbI, clbJ, clbK, clbL, clbM, clbN, clbO, clbP, clbQ, and clbR, and operably linked promoter(s) thereof, and produces less colibactin as compared a microorganism comprising the native clb gene(s) and operably linked promoters(s). In some embodiments, the microorganism retains the native or unmodified clbS gene, optionally with a partial or full deletion of the operably linked promoter.

In another aspect, the present disclosure provides a pharmaceutical composition comprising the engineered microorganism as provided herein.

In another aspect, the present disclosure provides a method of reducing a deleterious molecule comprising administering the pharmaceutical composition as provided herein to a subject in need thereof.

In another aspect, the present disclosure provides a method of reducing a deleterious molecule comprising administering the pharmaceutical composition as provided herein to a subject in need thereof.

In another aspect, the present disclosure provides a method of reducing oxalate comprising administering the pharmaceutical composition as provided herein to a subject in need thereof, wherein the therapeutic molecule is a oxalate metabolic enzyme.

In another aspect, the present disclosure provides a method of treating HOX comprising administering the pharmaceutical composition as provided herein to a subject in need thereof, wherein the therapeutic molecule is a oxalate metabolic enzyme.

In another aspect, the present disclosure provides a method of reducing phenylalanine comprising administering the pharmaceutical composition as provided herein to a subject in need thereof, wherein the therapeutic molecule is a phenylalanine metabolizing enzyme.

In another aspect, the present disclosure provides a method of treating hyperphenylalaninemia comprising administering the pharmaceutical composition as provided herein to a subject in need thereof, wherein the therapeutic molecule is a phenylalanine metabolizing enzyme.

In another aspect, the present disclosure provides a method of treating PKU comprising administering the pharmaceutical composition as provided herein to a subject in need thereof, wherein the therapeutic molecule is a phenylalanine metabolizing enzyme.

In another aspect, the present disclosure provides a method of reducing methionine levels comprising administering the pharmaceutical composition as provided herein to a subject in need thereof, wherein the therapeutic molecule is a methionine metabolizing enzyme.

In another aspect, the present disclosure provides a method of treating homocysteinuria comprising administering the pharmaceutical composition as provided herein to a subject in need thereof, wherein the therapeutic molecule is a methionine metabolizing enzyme.

In another aspect, the present disclosure provides a method of assessing pks island activity comprising detecting N-myristoyl-D-asparagine using LC-MS/MS.

BRIEF DESCRIPTION OF THE DRAWINGS

FIG. 2 shows an exemplary pharmacokinetic profile of the Δpks strain (deleted clbA-clbR gene and promoter sequences, intact clbS gene sequence with the operably linked promoter deleted) in Non-Human Primate.

FIG. 3A depicts an intact pks island.

FIG. 4 shows exemplary clb nucleotide sequences of the pks island. In one embodiment, an engineered bacterium contains deletions in all of these clb sequences except for the clbS sequence. clbQ (SEQ ID NO: 133); clbP (SEQ ID NO: 134); clbO (SEQ ID NO: 135); clbN (SEQ ID NO: 136); clbM (SEQ ID NO: 137); clbL (SEQ ID NO: 138); clbK (SEQ ID NO: 139); clbJ (SEQ ID NO: 140); clbI (SEQ ID NO: 141); clbH (SEQ ID NO: 142); clbG (SEQ ID NO: 143); clbF (SEQ ID NO: 144); clbE (SEQ ID NO: 145); clbD (SEQ ID NO: 146); clbC (SEQ ID NO: 147); clbB (SEQ ID NO: 148); clbR (SEQ ID NO: 149); clbA (SEQ ID NO: 150); and clbB (SEQ ID NO: 151).

FIG. 5 shows exemplary clb amino acid sequences of the pks island. In one embodiment, an engineered bacterium contains deletions in all of these clb sequences except for the clbS sequence. clbQ (SEQ ID NO: 152); clbP (SEQ ID NO: 153); clbO (SEQ ID NO: 154); clbN (SEQ ID NO: 155); clbM (SEQ ID NO: 156); clbL (SEQ ID NO: 157); clbK (SEQ ID NO: 158); clbJ (SEQ ID NO: 159); clbI (SEQ ID NO: 160); clbH (SEQ ID NO: 161); clbG (SEQ ID NO: 162); clbF (SEQ ID NO: 163); clbE (SEQ ID NO: 164); clbD (SEQ ID NO: 165); clbC (SEQ ID NO: 166); clbB (SEQ ID NO: 167); clbR (SEQ ID NO: 168); clbA (SEQ ID NO: 169); and clbB (SEQ ID NO: 170).

FIGS. 9A-C depicts graphs showing a time course of plasma levels of phenylalanine (Phe) (9A) and trancinnamic acid (TCA) (9B), and urinary hippurate (HA) at 6 hours post dose (9C) in NHPs upon administration of SYNB1934 and a SYNB 1934 derivative strain having Δpks (SYNB1934v1, also referred to herein as SYN8256).

DETAILED DESCRIPTION

Figures 1A, 1B:
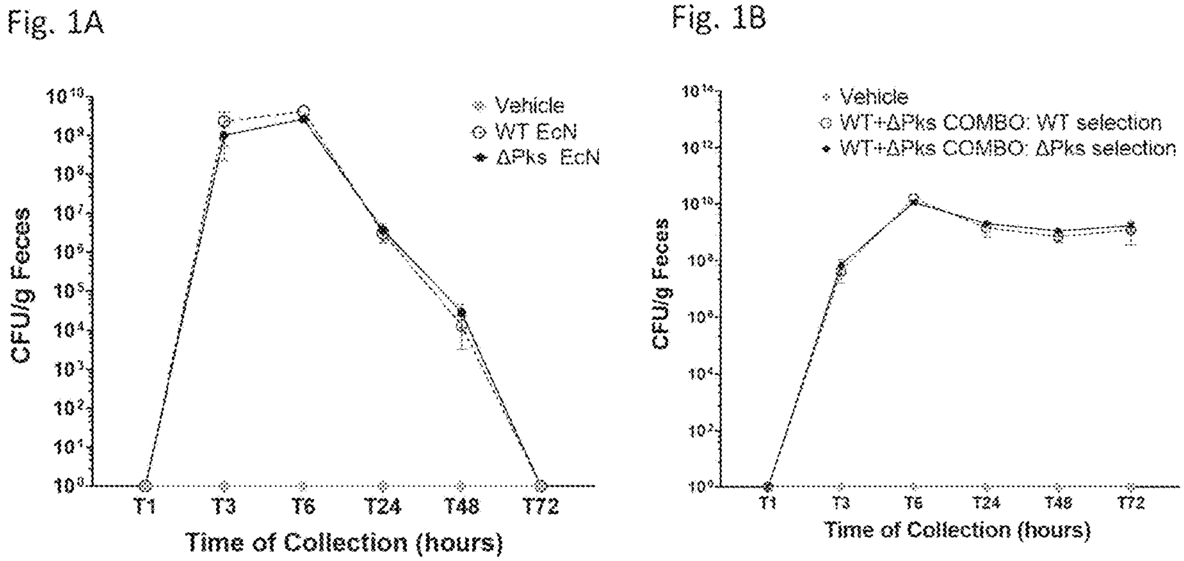
FIG. 1A and FIG. 1B show an exemplary pharmacokinetic profile of a Δpks strain in mouse. The Δpks *E. coli* Nissle (EcN) strain contains deletions in the clb sequences of the clbA-clbR genes and operably linked promoters, with the clbS gene sequence unmodified (intact) but its operably linked promoter deleted.

The present disclosure relates to, inter alia, engineered microorganisms, e.g., engineered bacteria, comprising a modified pks island as compared to a suitable control, e.g., the native pks island in an unmodified bacterium of the same strain and/or subtype, and optionally one or more gene(s) for producing a desired therapeutic molecule, and compositions, formulations, and methods of use thereof.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, "pks genomic island" and "pks island" are used to refer to a genomic region in a microorganism, e.g., bacterium, that comprises sequences encoding proteins capable of synthesizing colibactin. The pks island contains clb sequences, e.g., clb genes and associated regulatory elements, e.g., operably linked promoters. In *Escherichia coli*, the 54-kilobase pks genomic island contains 19 genes, clbA to clbS, and encodes three polyketide synthases (ClbC, ClbI, ClbO), three non-ribosomal peptide synthases (ClbH, ClbJ, ClbN), two hybrid non-ribosomal peptide/polyketide synthases (ClbB, ClbK), and nine accessory, tailoring, and editing proteins. Exemplary proteins encoded by an exemplary pks island is shown in Table 1. See Fais 2018, the contents of which are hereby incorporated by reference. In some embodiments, the pks island refers to a 54-kb genomic region comprising the following genes and operably linked promoters: clbA, clbB, clbC, clbD, clbE, clbF, clbG, clbH, clbI, clbJ, clbK, clbL, clbM, clbN, clbO, clbP, clbQ, clbR, or clbS. The pks island is found in various microorganisms such as members of the Enterobacteriaceae family, e.g., *Escherichia, Klebsiella, Enterobacter*, and *Citrobacter*. Id. The pks island is "highly conserved" in Enterobacteriaceae. Id.

Exemplary clb nucleotide sequences are provided in FIG. 4. Exemplary clb amino acid sequences are provided in FIG. 5.

TABLE 1

| Protein | Description |
|---|---|
| ClbA | Accessory protein: phosphopantetheinyl transferase<br>Activates other enzymes (favors placement of cofactor) |
| ClbR | Putative regulatory protein |
| ClbB | Synthesis enzyme: hybrid NRPS-PKS |
| ClbC | Synthesis enzyme: PKS |
| ClbD | Synthesis enzyme: hydroxyl acyl coA dehydrogenase |
| ClbE | Synthesis protein: acyl carrier protein |
| ClbF | Synthesis enzyme: αβ dehydrogenase |
| ClbG | Synthesis enzyme: acyl transferase |
| ClbH | Synthesis enzyme: NRPS |
| ClbI | Synthesis enzyme: PKS |
| ClbI | Synthesis enzyme: PKS |
| ClbJ | Synthesis enzyme: NRPS |
| ClbK | Synthesis enzyme: hybrid PKS-NRPS |
| ClbL | Synthesis enzyme: amidase |
| ClbM | Accessory protein: MATE transporter<br>Transports precolibactin across the cytoplasmic membrane |
| ClbN | Synthesis enzyme: NRPS |
| ClbO | Synthesis enzyme: PKS |
| ClbP | Accessory protein: fmtA peptidase<br>Transports precolibactin from the cytoplasm to the periplasm and clives precolibactin into genotoxic colibactin |

TABLE 1-continued

| Protein | Description |
|---|---|
| ClbQ | Synthesis enzyme: thioesterase |
| ClbS | Accessory protein<br>Inactivates colibactin in order to protect bacterial cell |

Colibactin is a cyclomodulin, which is a microorganismal toxin capable of interfering with the eukaryotic cell cycle. Fais 2018. Colibactin-producing microorganisms such as *Escherichia coli* have been identified in the gut microbiota as commensal bacteria as well as in disease states, e.g., colorectal cancer. Id. Colibactin-producing microorganisms are capable of inducing chromosomal instability, cell cycle arrest, DNA damage, epithelial cell senescence, and/or immune cell apoptosis. Id. However, colibactin-producing microorganisms are also capable of exhibiting anti-inflammatory, antibiotic, and analgesic effects. Id.

As used herein, a modified pks island refers to a change, e.g., in the clb sequence of a clb gene and/or regulatory element, that differs from the pks island of a suitable control, e.g., the native pks island in an unmodified bacterium of the same strain and/or subtype. For example, an engineered bacterium comprises a synthetic clbS gene or a synthetic clbS promoter in the pks island and differs from the corresponding clbS gene or promoter sequence in the pks island of a suitable control, e.g., the native pks island in an unmodified bacterium of the same strain and/or subtype.

As used herein, a partial or full deletion in the pks island refers to clb sequence, e.g., a gene and/or regulatory element, that is removed at least in part as compared to the corresponding clb sequence in the pks island of a suitable control, e.g., the native pks island in an unmodified bacterium of the same strain and/or subtype. A partial or full deletion in the pks island may be referred to as a "knockout" or "delta" (Δ) pks island. The clb sequence, e.g., clb gene and/or regulatory element, in the native pks island may be deleted by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, the clb sequence, e.g., clb gene and/or regulatory element, in the native pks island may be 100% deleted. For example, an engineered bacterium comprises a 100% deletion of the clbA gene in the pks island as compared to the clbA gene sequence in the pks island of a suitable control, e.g., the native pks island in an unmodified bacterium of the same strain and/or subtype. Or, for example, an engineered bacterium comprises a 50% deletion of the clbA promoter in the pks island as compared to the clbA promoter sequence in the pks island of a suitable control, e.g., the native pks island in an unmodified bacterium of the same strain and/or subtype.

As used herein, the term "N-myristoyl-D-asparagine" refers to a small molecule that is produced by the pks island during colibactin synthesis. In some embodiments, ClbN uses asparagine to generate N-myristoyl-D-asparagine, which is accepted by ClbB. In some embodiments, (s) and metabolite(s) are also provided herein. In some embodiments, activity of the pks island and/or levels of colibactin may be assessed by measuring levels of N-myristoyl-D-asparagine.

As used herein, a "therapeutic" molecule, e.g., protein, refers to a molecule that is capable of producing a therapeutic effect in a subject. For example, a therapeutic molecule such as IL-10 may be capable of reducing inflammation in a subject. In some embodiments, the therapeutic molecule is capable of reducing one or more deleterious molecules in the subject, e.g., a phenylalanine-metabolizing enzyme is capable of metabolizing excess and/or deleterious phenylalanine in a subject with PKU. In some embodiments, the therapeutic molecule is capable of reducing one or more deleterious molecules in the subject, e.g., a oxalate metabolizing enzyme is capable of catabolizing excess and/or deleterious oxalate in a subject with HOX. In some embodiments, the deleterious molecule is methionine, and the therapeutic molecule is a methionine catabolismenzyme capable of catabolizing excess and/or deleterious methionine, e.g., in a subject with homocystinuria. In some embodiments, the deleterious molecule is uric acid, and the therapeutic molecule is a uric acid degrading enzyme capable of degrading excess and/or deleterious uric acid, e.g., in a subject with as hyperuricemia or gout. In some embodiments, the deleterious molecule is leucine, and the therapeutic molecule is a leucine metabolic enzyme, e.g., leucine decarboxylase enzyme, capable of catabolizing excess and/or deleterious leucine, e.g., in a subject with isovaleric acidemia, propionic acidemia, methylmalonic acidemia, maple syrup urine disease (MSUD), and diabetes ketoacidosis and other amino acid metabolism disorders. In some embodiments, the therapeutic molecule is capable of elevating levels of a beneficial metabolite in a subject. In one embodiment, the therapeutic molecule is an enzyme for the production of lactate, e.g., for the treatment of inflammatory disorders. In some embodiments, the engineered microorganism, e.g., engineered bacterium, disclosed herein expresses one or more therapeutic molecule(s). In some embodiments, the engineered microorganisms disclosed herein, e.g., genetically engineered bacteria, express one or more therapeutic molecule(s) prior to administration to a subject. In some embodiments, the engineered microorganisms disclosed herein, e.g., genetically engineered bacteria, express one or more therapeutic molecule(s) after administration to a subject, e.g., the gene(s) for producing the therapeutic molecule are induced after administration to the subject.

As used herein, "activity" refers to a desired parameter, e.g., output of a molecule, of a cell or composition, e.g., a bacterium or a bacterial composition. In some embodiments, "therapeutic activity" refers to the production of a desired therapeutic molecule from the cell, e.g., as measured in vitro or in vivo in a cellular model, animal model, or human patient. In some embodiments, activity refers to the amount or function of a desired therapeutic molecule from the cell. In some embodiments, activity refers to the rate at which one or more desired therapeutic molecules is produced. In some embodiments, activity refers to the rate at which one or more deleterious compounds, e.g. a deleterious compound outside of the cell, is metabolized or reduced, e.g., as measured by levels of the deleterious compound or an intermediate.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

Phenylalanine metabolizing enzyme" or "PME" are used to refer to an enzyme which is able to degrade phenylalanine. Any phenylalanine metabolizing enzyme known in the art may be encoded by the engineered microorganisms, genetically engineered bacteria. PMEs include, but are not limited to, phenylalanine hydroxylase (PAH), phenylalanine ammonia lyase (PAL), aminotransferase, L-amino acid deaminase (LAAD), and phenylalanine dehydrogenases, glutamic-oxaloacetic transaminase 1 (GOT1), glutamic-oxaloacetic transaminase 2 (GOT2), dopa carboxylase (DDC) or tyrosine transaminase (TAT).

Phenylalanine hydroxylase ("PAH") converts phenylalanine into tyrosine. PAH utilizes a co-factor known as tetrahydrobiopterin ($BH_4$) to convert phenylalanine into tyrosine.

Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, PAL is encoded by a PAL gene derived from *Anabaena variabilis* and referred to as "PALI" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., Rhodosporidium toruloides (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99 (20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability. In some embodiments, the engineered microorganism, e.g., engineered bacterium, comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the engineered microorganism, e.g., engineered bacterium, is localized to the plasma membrane, facing into the periplasmic space and with the catalytic activity occurring in the periplasmic space.

As used herein, "GOT1," "GOT2," and "TAT" convert phenylalanine into phenylpyruvate.

As used herein, "DDC" converts phenylalanine into phenylethylamine.

As used herein, the term "transporter" is meant to refer to a mechanism, e.g., protein or proteins, for importing a molecule, e.g., amino acid, toxin, metabolite, substrate, etc. into the microorganism from the extracellular milieu. For example, a phenylalanine transporter such as PheP imports phenylalanine into the microorganism.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the engineered microorganism, e.g., engineered bacterium, comprise more than one type of phenylalanine transporter, selected from pheP, aroP, and the LIV-I/LS system.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the engineered microorganism, e.g., engineered bacterium, encoding a PME.

PMEs and phenylalanine transporters, as well as the nucleotide and amino acid sequences of representative examples of such enzymes and transporters, as well as exemplary promoters, are provided in WO2016183531A1 and WO2017087580A1, the contents of which are hereby incorporated by reference in their entirety. Any suitable enzymes and/or phenylalanine transporters may be used in the engineered microorganism, e.g., engineered bacterium, of the disclosure. In one embodiment, expression of one or more PME(s), e.g., PAL and/or LAAD, and/or Phe transporter(s), e.g., PheP, and/or transcriptional regulator(s), e.g., FNRS24Y, is driven by one or more thermoregulated promoter(s).

"Hyperammonemia." "hyperammonemic." or "excess ammonia" is used to refer to increased concentrations of ammonia in the body. Hyperammonemia is caused by decreased detoxification and/or increased production of ammonia. Decreased detoxification may result from urea cycle disorders (UCDs), such as argininosuccinic aciduria, arginase deficiency, carbamoylphosphate synthetase deficiency, citrullinemia, N-acetylglutamate synthetase deficiency, and ornithine transcarbamylase deficiency; or from bypass of the liver, e.g., open ductus hepaticus; and/or deficiencies in glutamine synthetase. See, e.g., Hoffman et al., 2013; Haberle et al., 2013. Increased production of ammonia may result from infections, drugs, neurogenic bladder, and intestinal bacterial overgrowth. See, e.g., Häberle et al., 2013. Increased production of ammonia may also be associated with a tumor microenvironment. See, e.g., Spinelli et al., 2017. Other disorders and conditions associated with hyperammonemia include, but are not limited to, liver disorders such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders: valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; and chemotherapy. See, e.g., Hoffman et al., 2013; Haberle et al., 2013; Pham et al., 2013; Lazier et al., 2014. In healthy subjects, plasma ammonia concentrations are typically less than about 50 μmol/L. See, e.g., Leonard, 2006. In some embodiments, a diagnostic signal of hyperammonemia is a plasma ammonia concentration of at least about 50 μmol/L, at least about 80 μmol/L, at least about 150 μmol/L, at least about 180 μmol/L, or at least about 200 μmol/L. See, e.g., Leonard, 2006; Hoffman et al., 2013; Haberle et al., 2013. Methods of modifying arginine biosynthesis, e.g., in engineered microorganisms, e.g., engineered bacteria, to reduce hyperammonemia, e.g., by deleting the arginine repressor, modifying the arginine repressor binding sites, and/or using arginine feedback resistant N-acetylglutamate synthase, are known in the art. See, e.g., WO2016200614, the contents of which are hereby incorporated by reference.

An "anti-cancer molecule" refers to one or more therapeutic substances or drugs of interest to be produced by an engineered microorganism, e.g., engineered bacterium, which are capable of reducing and/or inhibiting cell growth or replication. In some embodiments, the anti-cancer molecule is a therapeutic molecule that is useful for modulating or treating a cancer. In some embodiments, the anti-cancer molecule is a therapeutic molecule encoded by a gene. In alternate embodiments, the anti-cancer molecule is a therapeutic molecule produced by a biochemical or biosynthetic pathway, wherein the biosynthetic or biochemical pathway may optionally be endogenous to the microorganism. In some embodiments, the genetically engineered microorganism is capable of producing two or more anti-cancer molecules. Non-limiting examples of anti-cancer molecules include immune checkpoint inhibitors (e.g., CTLA-4 antibodies, PD-1 antibodies, PDL-1 antibodies), cytotoxic agents (e.g., Cly A, FASL, TRAIL, TNF-alpha), immunostimulatory cytokines and co-stimulatory molecules (e.g., OX40, CD28, ICOS, CCL21, IL-2, IL-18, IL-15, IL-12, IFN-gamma, IL-21, TNFs, GM-CSF), antigens and antibodies (e.g., tumor antigens, neoantigens, CtxB-PSA fusion protein, CPV-OmpA fusion protein, NY-ESO-1 tumor antigen, RAFI, antibodies against immune suppressor molecules, anti-VEGF, Anti-CXR4/CXCL12, anti-GLP1, anti-GLP2, anti-galectin1, anti-galectin3, anti-Tie2, anti-CD47, antibodies against immune checkpoints, antibodies against immunosuppressive cytokines and chemokines), DNA transfer vectors (e.g., endostatin, thrombospondin-1, TRAIL, SMAC, Stat3, Bcl2, FLT3L, GM-CSF, IL-12, AFP, VEGFR2), and enzymes (e.g., *E. coli* CD, HSV-TK). In some embodiments, the anti-cancer molecule includes nucleic acid molecules that mediate RNA interference, microRNA response or inhibition, TLR response, antisense gene regulation, target protein binding (aptamer or decoy oligos), gene editing, such as CRISPR interference. In some embodiments, bacteria or virus can be used as vectors to transfer DNA into mammalian cells, e.g., by bactofection. See, e.g., Bernardes et al., 2013. Engineered microorganisms, e.g., engineered bacteria, that are capable of producing an anti-cancer molecule, e.g., a deadenylate cyclase gene (e.g., dacA from *Listeria monocytogenes*) or an enzyme capable of producing a stimulator of interferon gene (STING) agonist, are known in the art. See, e.g., WO2018129404, the contents of which are hereby incorporated by reference.

The term "oxalate" as used herein, refers to the dianion of the formula $C_2O_4^{2-}$. Oxalate is the conjugate base of oxalic acid. The term "oxalic acid," as used herein, refers to a dicarboxylic acid with the chemical formula $H_2C_2O_4$.

In one embodiment, a "disorder in which oxalate is detrimental" is a disease or disorder involving the abnormal, e.g., increased, levels of oxalate and/or oxalic acid or molecules directly upstream, such as glyoxylate. In one embodiment, the disorder in which oxalate is detrimental is a disorder or disease in which hyperoxaluria is observed in the subject. In one embodiment the disorder in which oxalate is detrimental refers to any condition(s), disorder(s), disease(s), predisposition(s), and/or genetic mutations(s) that result in daily urinary oxalate excretion over 40 mg per 24 hours. In one embodiment the disorder in which oxalate is detrimental is a disorder or disease selected from the group consisting of: PHI, PHII, PHII, secondary hyperoxaluria, enteric hyperoxaluria, syndrome of bacterial overgrowth, Crohn's disease, inflammatory bowel disease, hyperoxaluria following renal transplantation, hyperoxaluria after a jejunoileal bypass for obesity, hyperoxaluria after gastric ulcer surgery, chronic mesenteric ischemia, gastric bypass, cystic fibrosis, short bowel syndrome, biliary/pancreatic diseases (e.g., chronic pancreatitis).

As used herein, the term "oxalate catabolismenzyme" or "oxalate metabolic enzyme" refers to any enzyme that is capable of metabolizing oxalate or capable of reducing accumulated oxalate or that can lessen, ameliorate, or prevent one or more diseases, or disease symptoms in which oxalate is detrimental. Examples of oxalate enzymes include, but are not limited to, formyl-CoA:oxalate CoA-transferase (also called formyl-CoA transferase), e.g., Frc from *O. formigenes*, oxalyl-CoA synthetase (also called oxalate-CoA ligase), e.g., *Saccharomyces cerevisiae* acyl-activating enzyme 3 (ScAAE3) from *Saccharomyces cerevisiae*, Oxalyl-CoA Decarboxylase, e.g., Oxc from *O. formigenes* (also referred to herein is oxdC or oxalate decarboxylase), acetyl-CoA:oxalate CoA-transferase (ACOCT), e.g., YfdE from *E. coli* and any other enzymes that catabolizes oxalate, oxalyl-CoA or any other metabolite thereof. Catabolism enzymes also include alanine glyoxalate aminotransferase (AGT, encoded by the AGXT gene, e.g. the human form), glyoxylate/hydroxypyruvate reductase (GRHPR; an enzyme having glyoxylate reductase (GR), hydroxypyruvate reductase (HPR), and D-glycerate dehydrogenase (DGDH) activities, e.g., the human form), and 4-hydroxy 2-oxoglutarate aldolase (encoded by the HOGA1 gene, e.g. in humans, and which breaks down 4-hydroxy 2-oxoglutarate into pyruvate and glyoxalate). Functional deficiencies in these proteins result in the accumulation of oxalate or its corresponding α-keto acid in cells and tissues. Oxalate metabolic enzymes of the present disclosure include both wild-type or modified oxalate metabolic enzymes and can be produced using recombinant and synthetic methods or purified from nature sources. Oxalate metabolic enzymes include full-length polypeptides and functional fragments thereof, as well as homologs and variants thereof. oxalate metabolic enzymes include polypeptides that have been modified from the wild-type sequence, including, for example, polypeptides having one or more amino acid deletions, insertions, and/or substitutions and may include, for example, fusion polypeptides and polypeptides having additional sequence, e.g., regulatory peptide sequence, linker peptide sequence, and other peptide sequence.

As used herein, the term "catabolism" refers to the cellular uptake of oxalate, and/or degradation of oxalate into its corresponding oxalyl CoA, and/or the degradation of oxalyl CoA formate and carbon dioxide. In one embodiment, the cellular uptake of oxalate occurs in the kidney. In one embodiment, the cellular uptake occurs in the liver. In one embodiment, the cellular uptake of oxalate occurs in the intestinal tract. In one embodiment, the cellular uptake of oxalate occurs in the stomach. In one embodiment, the cellular uptake is mediated by a SLC26 transporting protein (see Robijn et al. (2011). In one embodiment, the cellular uptake is mediated by the transport protein SLC26A1. In one embodiment, the cellular uptake is mediated by the transport protein SLC26A6. In one embodiment, the cellular uptake of oxalate is mediated by a paracellular transport system. In one embodiment, the cellular uptake of oxalate is mediated by a transcellular transport system.

As used herein, the term "methionine catabolismenzyme" refers to an enzyme involved in the catabolism of methionine. Specifically, when a methionine catabolismenzyme is expressed in a recombinant bacterial cell, the bacterial cell hydrolyzes more methionine into 3-methylthiopropylamine when the catabolismenzyme is expressed than unmodified bacteria of the same bacterial subtype under the same conditions. In some embodiments, methionine transporters may also be expressed or modified in the recombinant bacteria to enhance methionine import into the cell in order to increase the catabolism of methionine by the methionine catabolismenzyme. In other embodiments, methionine exporters may be knocked-out in the recombinant bacteria to decrease export of methionine and/or increase cytoplasmic concentration of methionine. In some embodiment the genetically engineered bacterial cell comprises a gene sequence encoding a methionine decarboxylase (MDC) gene sequence. In some embodiments, the bacterial cell comprises genetic modification that reduces export of methionine from the bacterial cell, e.g., a knockout of an endogenous methionine efflux pump, such as yjeH. In some embodiments, the bacterial cell further comprises a methionine importer, such as metNIQ. Non-limiting examples of such recombinant or genetically engineered bacteria are disclosed in International Patent Application PCT/US2021/017775, filed on Feb. 12, 2021, and International Patent Application PCT/US2016/032565, filed on May 13, 2016, the contents of each of which is herein incorporated by reference its entirety.

the contents of which is herein incorporated by reference its entirety.

As used herein, the term "uric acid degrading enzyme" or "uric acid degradation enzyme" refers to an enzyme capable of processing, breakdown, and/or degradation of uric acid. In one embodiment, a uric acid degradation enzyme refers to the processing, breakdown, and/or degradation of uric acid into, for example, hydroxyisourate and/or allantoin. In other embodiments, a "uric acid degrading enzyme" or "uric acid degradation enzyme" may refer to an enzyme which works upstream to degrade a precursor of uric acid, thereby decreasing downstream levels of uric acid. For example, in one embodiment, a uric acid degradation enzyme degrades guanosine. In another embodiment, a uric acid degradation enzyme degrades adenosine. Non-limiting examples of such recombinant or genetically engineered bacteria are disclosed in International Patent Application PCT/US2021/019625, filed on Feb. 25, 2021, the contents of which is herein incorporated by reference its entirety.

As used herein, the term "leucine catabolismenzyme" or "leucine catabolismenzyme" or "catabolismenzyme" or "leucine metabolic enzyme" refers to any enzyme that is capable of metabolizing leucine, and/or capable of reducing accumulated leucine, and/or that can lessen, ameliorate, or prevent one or more diseases associated with leucine catabolism or disease symptoms. Examples of leucine catabolism enzymes include, but are not limited to, leucine decarboxylase (LCD). In one embodiment, the LDC enzyme is E.C. 4.1.1.14. Non-limiting examples of such recombinant or genetically engineered bacteria are disclosed in International Patent Application PCT/US2021/022676, filed on Mar. 17, 2021, the contents of which is herein incorporated by reference its entirety.

"Operably linked" refers a nucleic acid sequence, e.g., a gene encoding a therapeutic molecule, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive. A "constitutive promoter" refers to a promoter that allows for continual transcription of the coding sequence or gene under its control.

An "inducible promoter" refers to a regulatory region that is operably linked to one or more genes, wherein expression of the gene(s) is increased in the presence of an inducer of said regulatory region.

In some embodiments, the engineered microorganism, e.g., engineered bacterium, comprise one or more gene(s) whose expression is controlled by a temperature sensitive mechanism. Thermoregulators are advantageous because of strong transcriptional control without the use of external chemicals or specialized media (see, e.g., Nemani et al., Magnetic nanoparticle hyperthermia induced cytosine deaminase expression in microencapsulated *E. coli* for enzyme-prodrug therapy: J Biotechnol. 2015 Jun. 10; 203: 32-40, and references therein). Thermoregulated protein expression using the mutant cI857 repressor and the pL and/or pR phage λ promoters may be used to engineer recombinant bacterial strains. The gene of interest is cloned downstream of the λ promoters and can be efficiently regulated by the mutant thermolabile cI857 repressor of bacteriophage λ. At temperatures below 37° C., cI857 binds to the oL or oR regions of the pR promoter and blocks transcription by RNA polymerase. At higher temperatures, the functional cI857 dimer is destabilized, binding to the oL or oR DNA sequences is abrogated, and mRNA transcription is initiated.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., WO2017087580; Castiglione et al., 2009; Eiglmeier et al., 1989; Galimand et al., 1991; Hasegawa et al., 1998; Hoeren et al., 1993; Salmon et al., 2003). In some embodiments, the FNR-responsive promoter is PfnrS derived from the *E. coli* Nissle fumarate and nitrate reductase gene S (fnrS) that is known to be highly expressed under conditions of low or no environmental oxygen (Durand and Storz, 2010; Boysen et al, 2010).

As used herein, a "non-native" nucleic acid sequence refers to a nucleic acid sequence not normally present in a bacterium, e.g., an extra copy of an endogenous sequence, or a heterologous sequence such as a sequence from a different species, strain, or sub-strain of bacteria, or a sequence that is modified and/or mutated as compared to the unmodified sequence from bacteria of the same subtype. In some embodiments, the non-native nucleic acid sequence is a synthetic, non-naturally occurring sequence. See, e.g., Purcell et al., 2013, Towards a whole-cell modeling approach for synthetic biology. The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. In some embodiments, the engineered microorganism, e.g., engineered bacterium, are engineered to comprise multiple copies of the same regulatory region, promoter, gene, and/or gene cassette in order to enhance copy number or to comprise multiple different components of a gene cassette performing multiple different functions. In some embodiments, the engineered microorganism, e.g., engineered bacterium, of the invention comprise a gene encoding a phenylalanine-metabolizing enzyme that is operably linked to a inducible promoter that is not associated with said gene in nature, e.g., an FNR promoter operably linked to a gene encoding PAL or a ParaBAD promoter operably linked to LAAD.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines. In some embodiments, the engineered microorganism, e.g., engineered bacterium, are active (e.g., express one or more heterologous genes) in the gut. In some embodiments, the engineered microorganism, e.g., engineered bacterium, are active (e.g., express one or more heterologous genes) in the large intestine. In some embodiments, the engineered microorganism, e.g., engineered bacterium, are active (e.g., express one or more heterologous genes) in the small intestine. In some embodiments, the engineered microorganism, e.g., engineered bacterium, are active in the small intestine and in the large intestine.

As used herein, the term "gene" or "gene sequence" is meant to refer to a genetic sequence, e.g., a nucleic acid sequence. The gene, gene sequence or genetic sequence is meant to include a complete gene sequence or a partial gene sequence. The gene, gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

An "engineered" or "genetically engineered" microorganism refers to a microorganism, e.g., bacterium, that has been genetically modified from its native state. Thus, an "engineered" or "genetically engineered" bacterium refers to a bacterium that has been genetically modified from its native state, e.g., to perform a specific function, e.g., to metabolize a metabolite, e.g. phenylalanine, oxalate, methionine or leucine. In certain embodiments, the engineered microorganism, e.g., bacterium, is modified to express one or more molecules, e.g., therapeutic molecules, e.g., therapeutic proteins that have a therapeutic activity or serve a therapeutic purpose. The engineered microorganism, e.g., bacterium, may additionally have the ability to stop growing or to destroy itself once the protein(s) of interest have been expressed.

"Non-pathogenic" refers to microorganisms, for example bacteria, that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, Bifidobacteria, *Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, a "heterologous" gene or "heterologous sequence" refers to a nucleotide sequence that is not normally found in a given cell in nature. As used herein, a heterologous sequence encompasses a nucleic acid sequence that is exogenously introduced into a given cell and can be a native sequence (naturally found or expressed in the cell) or non-native sequence (not naturally found or expressed in the cell) and can be a natural or wild-type sequence or a variant, non-natural, or synthetic sequence. "Heterologous gene" includes a native gene, or fragment thereof, that has been introduced into the host cell in a form that is different from the corresponding native gene. For example, a heterologous gene may include a native coding sequence that is a portion of a chimeric gene to include non-native regulatory regions that is reintroduced into the host cell. A heterologous gene may also include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature. As used herein, the term "endogenous gene" refers to a native gene in its natural location in the genome of an organism. As used herein, the term "transgene" refers to a gene that has been introduced into the host organism, e.g., host bacterial cell, genome.

As used herein, the terms "treat" and "modulate" and their cognates refer to an amelioration of a disease, disorder, and/or condition, or at least one discernible symptom thereof. In another embodiment, "treat" and "modulate" refer to an amelioration of at least one measurable physical parameter, not necessarily discernible by the patient. In another embodiment, "treat" and "modulate" refer to inhibiting the progression of a disease, disorder, and/or condition, either physically (e.g., stabilization of a discernible symptom), physiologically (e.g., stabilization of a physical parameter), or both. In another embodiment, "treat" and "modulate" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. For example, primary hyperphenylalaninemia, e.g., PKU, is caused by inborn genetic mutations for which there are no known cures, and hyperphenylalaninemia can also be secondary to other conditions, e.g., liver diseases. Treatment may encompass reducing or eliminating one or more disease features, e.g., excess phenylalanine in primary hyperphenylalaninemia, and does not necessarily encompass the elimination of the underlying disease.

As used herein a "pharmaceutical composition" refers to a preparation of engineered microorganisms, e.g., engineered bacteria, of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperphenylalaninemia. A therapeutically effective amount may, for example, be sufficient to treat, prevent, reduce the severity, delay the onset, and/or reduce the risk of occurrence of one or more symptoms of a disease or condition associated with excess phenylalanine levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides." "tripeptides, "oligopeptides," "protein," "amino acid chain," or any other term used to refer to a chain or chains of two or more amino acids, are included within the definition of "polypeptide." and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the engineered microorganisms, e.g., genetically engineered bacteria or virus, of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure.

Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

The term "about", when used before a list, modifies each member of the list. The term "about" or "approximately" means an acceptable error for a particular value as determined by one of ordinary skill in the art, which depends in part on how the value is measured or determined.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

References cited herein are incorporated by reference in their entireties.

Engineered Microorganism Comprising Modified PKS Island

In some embodiments, the disclosure provides an engineered microorganism, e.g., engineered bacterium, comprising a modified pks island, and compositions and formulations thereof. In some embodiments, the disclosure provides an engineered microorganism, e.g., engineered bacterium, comprising a modified pks island and further comprising one or more gene(s) or gene cassettes(s) encoding a therapeutic molecule, and compositions and formulations thereof.

In some embodiments, the engineered microorganism, e.g., engineered bacterium, comprises a modified pks island. In some embodiments, the engineered microorganism, e.g., engineered bacterium, comprises a modified clb sequence selected from one or more of the clbA, clbB, clbC, clbD, clbE, clbF, clbG, clbH, clbI, clbJ, clbK, clbL, clbM, clbN, clbO, clbP, clbQ, clbR, and clbS gene sequences and/or operably linked promoter sequences, as compared to a suitable control, e.g., the native pks island in an unmodified bacterium of the same strain and/or subtype. In some embodiments, the modified clb sequence is an insertion, a substitution, and/or a deletion as compared to the control.

In some embodiments, the engineered microorganism, e.g., engineered bacterium, comprises a modification in one or more of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the engineered microorganism, e.g., engineered bacterium, comprises a modification in one or more of the promoter sequences operably linked to the clbA, clbB, clbC, clbD, clbE, clbF, clbG, clbH, clbI, clbJ, clbK, clbL, clbM, clbN, clbO, clbP, clbQ, and clbR genes as compared to the suitable control.

In some embodiments, the engineered microorganism, e.g., engineered bacterium, comprises a modification in each of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the engineered microorganism, e.g., engineered bacterium, comprises a modification in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises a modification in one or more of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the engineered microorganism, e.g., engineered bacterium, comprises a modification in one or more of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises a modification in each of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the engineered microorganism, e.g., engineered bacterium, comprises a modification in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises an unmodified clbS gene sequence, a modification in each of the clbA, clbB, clbC, clbD, clbE, clbF, clbG, clbH, clbI, clbJ, clbK, clbL, clbM, clbN, clbO, clbP, clbQ, and clbR gene sequences, and a modification in the clbS promoter sequence, as compared to the suitable control.

In some embodiments, the engineered microorganism, e.g., engineered bacterium, comprises a full or partial deletion in the pks island, e.g., a full or deletion in a clb sequence, e.g., a clb gene or promoter sequence. In some embodiments, the engineered microorganism, e.g., engineered bacterium, comprises a full or partial deletion in a clb sequence selected from one or more of the clbA, clbB, clbC, clbD, clbE, clbF, clbG, clbH, clbI, clbJ, clbK, clbL, clbM, clbN, clbO, clbP, clbQ, clbR, and clbS gene sequences and/or operably linked promoter sequences, as compared to a suitable control, e.g., the native pks island in an unmodified bacterium of the same strain and/or subtype. In some embodiments, the clb sequence, e.g., clb gene or promoter sequence, may be deleted by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared to the control, e.g., the corresponding clb sequence in the native pks island in an unmodified bacterium of the same strain and/or subtype. In some embodiments, the clb sequence, e.g., clb gene or promoter sequence, may be 100% deleted as compared to the control, e.g., the corresponding clb sequence in the native pks island in an unmodified bacterium of the same strain and/or subtype In some embodiments, the engineered microorganism, e.g., engineered bacterium, comprises a partial or full deletion in one or more of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the engineered microorganism, e.g., engineered bacterium, comprises a partial or full deletion in one or more of the promoter sequences operably linked to the clbA, clbB, clbC, clbD, clbE, clbF, clbG, clbH, clbI, clbJ, clbK, clbL, clbM, clbN, clbO, clbP, clbQ, and clbR genes as compared to the suitable control.

In some embodiments, the engineered microorganism, e.g., engineered bacterium, comprises a partial or full deletion in each of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the engineered microorganism, e.g., engineered bacterium, comprises a partial or full deletion in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises a partial or full deletion in one or more of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the engineered microorganism, e.g., engineered bacterium, comprises a partial or full deletion in one or more of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises a partial or full deletion in each of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the engineered microorganism, e.g., engineered bacterium, comprises a partial or full deletion in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the engineered microorganism, e.g., engineered bacterium, comprises an unmodified clbS gene sequence, a partial or full deletion in each of the clbA, clbB, clbC, clbD, clbE, clbF, clbG, clbH, clbI, clbJ, clbK, clbL, clbM, clbN, clbO, clbP, clbQ, and clbR gene sequences, and a partial or full deletion in the clbS promoter sequence, as compared to the suitable control In some embodiments, the engineered microorganism, e.g., engineered bacterium comprising the modified pks island, expresses less colibactin compared to a suitable control, e.g., the native pks island in an unmodified bacterium of the same strain and/or subtype of the comprising the native pks island. In some embodiments, the engineered microorganism, e.g., engineered bacterium comprising the modified pks island, expresses less colibactin compared to control. In some embodiments, the engineered microorganism, e.g., engineered bacterium comprising the modified pks island, expresses less N-myristoyl-D-asparagine compared to control. In some embodiments, the engineered microorganism, e.g., engineered bacterium comprising the modified pks island, exhibits decreased accessory protein activity as compared to control. In some embodiments, the engineered microorganism, e.g., engineered bacterium comprising the modified pks island, exhibits decreased phosphopantetheinyl transferase activity as compared to control. In some embodiments, the engineered microorganism, e.g., engineered bacterium comprising the modified pks island, exhibits decreased polyketide synthase activity as compared to control. In some embodiments, the engineered microorganism, e.g., engineered bacterium comprising the modified pks island, exhibits decreased non-ribosomal peptide synthase activity as compared to control. In some embodiments, the engineered microorganism, e.g., engineered bacterium comprising the modified pks island, exhibits decreased activity of hybrid non-ribosomal peptide/polyketide synthase as compared to control. In some embodiments, the engineered microorganism, e.g., engineered bacterium comprising the modified pks island, exhibits decreased hydroxyl acyl coA dehydrogenase activity as compared to control. In some embodiments, the engineered microorganism, e.g., engineered bacterium comprising the modified pks island, exhibits decreased acyl carrier protein activity as compared to control. In some embodiments, the engineered microorganism, e.g., engineered bacterium comprising the modified pks island, exhibits decreased αβ dehydrogenase activity as compared to control. In some embodiments, the engineered microorganism, e.g., engineered bacterium comprising the modified pks island, exhibits decreased acyl transferase activity as compared to control. In some embodiments, the engineered microorganism, e.g., engineered bacterium comprising the modified pks island, exhibits decreased amidase activity as compared to control. In some embodiments, the engineered microorganism, e.g., engineered bacterium comprising the modified pks island, exhibits decreased MATE transporter activity as compared to control. In some embodiments, the engineered microorganism, e.g., engineered bacterium comprising the modified pks island, exhibits decreased fmtA peptidase activity as compared to control. In some embodiments, the engineered microorganism, e.g., engineered bacterium comprising the modified pks island, exhibits decreased thioesterase activity as compared to control. In some embodiments, the engineered microorganism, e.g., engineered bacterium comprising the modified pks island, exhibits decreased precolibactin transport across the cytoplasmic membrane as compared to control. In some embodiments, the engineered microorganism, e.g., engineered bacterium comprising the modified pks island, exhibits decreased precolibactin transport across the periplasm as compared to control. In some embodiments, the engineered microorganism, e.g., engineered bacterium comprising the modified pks island, exhibits decreased precolibactin cleavage into colibactin as compared to control.

In some embodiments, the engineered microorganism, e.g., engineered bacterium comprising the modified pks island, exhibits a similar growth rate as compared to a corresponding control comprising an unmodified pks island, e.g., in a growth and competition assay. In some embodiments, the engineered microorganism, e.g., engineered bacterium comprising the modified pks island, exhibits a similar viability as compared to a corresponding control comprising an unmodified pks island, e.g., after competitive growth. In some embodiments, the engineered microorganism, e.g., engineered bacterium comprising the modified pks island, exhibits similar ability to express therapeutic molecule as compared to a corresponding control comprising an unmodified pks island. In some embodiments, there is minimal fitness cost to an engineered bacterium comprising the modified pks island as compared to a corresponding control comprising an unmodified pks island.

In some embodiments, the engineered microorganism, e.g., engineered bacterium, further comprise one or more gene(s) for producing a desired therapeutic molecule. Engineered microorganisms, e.g., engineered bacteria, comprising one or more gene(s) for producing a desired therapeutic molecule that may further comprise a modified pks island are described in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety.

In some embodiments, the one or more gene(s) is operably linked to an inducible promoter. In some embodiments, the therapeutic molecule is capable of producing a therapeutic effect in a subject. For example, a therapeutic molecule such as IL-10 may be capable of reducing inflammation in a subject. In some embodiments, the therapeutic molecule is an anti-cancer molecule. In some embodiments, the therapeutic molecule is an enzyme capable of producing a STING agonist. In some embodiments, the therapeutic molecule is a deadenylate cyclase, e.g., dacA. In some embodiments, the therapeutic molecule is capable of reducing one or more deleterious molecules in the subject, e.g., a phenylalanine-metabolizing enzyme is capable of metabolizing excess and deleterious phenylalanine in a subject with PKU or an oxalate metabolic enzyme is capable of catabolizing excess and deleterious oxalate in a subject with HOX. In some embodiments, the engineered microorganism, e.g., engineered bacterium, comprise gene(s) encoding a modified arginine biosynthesis pathway (e.g., deleted arginine repressor, modified arginine repressor binding sites, and/or arginine feedback resistant N-acetylglutamate synthase mutation) and is capable of reducing deleterious ammonia, e.g., in a subject with UCD or in a subject with cancer. In some embodiments, the therapeutic molecule works in conjunction with another molecule to produce a therapeutic effect, e.g., a phenylalanine transporter works in conjunction with a phenylalanine-metabolizing enzyme to reduce deleterious phenylalanine in a subject with PKU. In some embodiments, the engineered microorganism, e.g., engineered bacterium, disclosed herein expresses one or more therapeutic molecule(s). In some embodiments, the engineered microorganism, e.g., engineered bacterium, disclosed herein expresses one or more therapeutic molecule(s) prior to administration to a subject. In some embodiments, the engineered microorganism, e.g., engineered bacterium, disclosed herein expresses one or more therapeutic molecule(s) after administration to a subject, e.g., the gene(s) for producing the therapeutic molecule are induced after administration to the subject.

In some embodiments, the engineered microorganism, e.g., engineered bacterium, comprises a modified pks island as described herein and one or more gene(s) and/or gene cassette(s) encoding a therapeutic molecule. In some embodiments, the engineered microorganism, e.g., engineered bacterium, comprises a modified pks island as described herein and one or more gene(s) and/or gene cassette(s) encoding at least one phenylalanine metabolizing enzyme. In some embodiments, the engineered microorganism, e.g., engineered bacterium, comprises a modified pks island as described herein and one or more gene(s) and/or gene cassette(s) encoding at least one oxalate metabolic enzyme.

In some embodiments, the engineered microorganism, e.g., engineered bacterium, comprises a modified pks island and a gene encoding PAH. In some embodiments, the engineered microorganism, e.g., engineered bacterium, comprise a gene encoding PAH, wherein the PAH gene is operably linked to an inducible promoter. In some embodiments, the microorganisms, e.g., bacteria, comprise a non-native PAH gene. In some embodiments, the microorganisms, e.g., bacteria, comprise additional copies of a native PAH gene. In some embodiments, the promoter is not associated with the PAH gene in nature. In some embodiments, the promoter is any one or more of the promoters disclosed herein. In some embodiments, the engineered microorganism, e.g., engineered bacterium that express PAH, convert phenylalanine into tyrosine.

In some embodiments, the engineered microorganism, e.g., engineered bacterium, comprises a modified pks island and a gene encoding PAL. In some embodiments, the engineered microorganism, e.g., engineered bacterium, comprise a gene encoding PAL, wherein the PAL gene is operably linked to an inducible promoter. In some embodiments, the microorganisms, e.g., bacteria, comprise a non-native PAL gene. In some embodiments, the microorganisms, e.g., bacteria, comprise additional copies of a native PAL gene. In some embodiments, the promoter is not associated with the PAL gene in nature. In some embodiments, the promoter is any one or more of the promoters disclosed herein. In some embodiments, the engineered microorganism, e.g., engineered bacterium that express PAL, convert phenylalanine into trans-cinnamate and ammonia.

In some embodiments, the engineered microorganism, e.g., engineered bacterium, comprises a modified pks island and a gene encoding LAAD. In some embodiments, the LAAD gene is operably linked to an inducible promoter. In some embodiments, the microorganisms, e.g., bacteria, comprise a non-native LAAD gene. In some embodiments, the microorganisms, e.g., bacteria, comprise additional copies of a native LAAD gene. In some embodiments, the promoter is not associated with the LAAD gene in nature. In some embodiments, the engineered microorganism, e.g., engineered bacterium that express LAAD, convert phenylalanine into phenylpyruvic acid.

In some embodiments, the engineered microorganism, e.g., engineered bacterium, comprise a modified pks island and a gene encoding a phenylalanine transporter, e.g., PheP. In some embodiments, the PheP gene is operably linked to an inducible promoter. In some embodiments, the engineered microorganism, e.g., engineered bacterium, comprise a gene encoding a non-native phenylalanine transporter gene, e.g., additional copies of a native phenylalanine transporter. In some embodiments, the microorganisms, e.g., bacteria, comprise additional copies of a native PheP gene. In some embodiments, the promoter is not associated with the PheP gene in nature. In some embodiments, the engineered microorganism, e.g., engineered bacterium that express PheP, transport phenylalanine into the bacterial cell.

In some embodiments, a single promoter controls expression of the one or more gene(s) encoding the PME and the phenylalanine transporter. In some embodiments, separate copies of the same promoter controls expression of the expression of the PME and the phenylalanine transporter. In some embodiments, different promoters control expression of the PME and the phenylalanine transporter. In some embodiments, the promoter that controls expression of PME is different from the promoter(s) that controls expression of the phenylalanine transporter. In some embodiments, the promoter(s) operably linked to the gene(s) encoding the PME and the gene(s) encoding the phenylalanine transporter are induced by exogenous environmental conditions found in a mammalian gut. In some embodiments, the promoter(s) operably linked to the gene(s) encoding the PME and the gene(s) encoding the phenylalanine transporter are induced under low-oxygen or anaerobic conditions, e.g., an FNR-responsive promoter, an ANR-responsive promoter, and a DNR-responsive promoter. In some embodiments, the promoter(s) operably linked to the gene(s) encoding the PME and the gene(s) encoding the phenylalanine transporter is a thermoregulated promoter. In some embodiments, the promoter(s) operably linked to the gene(s) encoding the PME and the gene(s) encoding the phenylalanine transporter are induced by arabinose, IPTG, tetracycline, or rhamnose. In some embodiments, the gene(s) encoding the PME, e.g., PAL and/or LAAD, is operably linked to a promoter selected from a promoter that is induced under low-oxygen or anaerobic conditions, a thermoregulated promoter, and a promoter that is induced by arabinose, IPTG, tetracycline, or rhamnose. In some embodiments, the thermoregulated promoter is capable of being induced at a temperature between 37° C. and 42° C. In some embodiments, the thermoregulated promoter is a lambda CI inducible promoter. In some embodiments, the genetically engineered bacteria further comprise one or more gene(s) encoding a temperature sensitive CI repressor mutant, which, in some embodiments, is CI857.

In some embodiments, the engineered microorganism, e.g., engineered bacterium, comprise a modified pks island and a gene encoding GOT1. In some embodiments, the engineered microorganism, e.g., engineered bacterium, comprise a gene encoding GOT1, wherein the GOT1 gene is operably linked to an inducible promoter. In some embodiments, the microorganisms, e.g., bacteria, comprise a non-native GOT1 gene. In some embodiments, the microorganisms, e.g., bacteria, comprise additional copies of a native GOT1 gene. In some embodiments, the promoter is not associated with the GOT1 gene in nature. In some embodiments, the promoter is any one or more of the promoters disclosed herein. In some embodiments, the engineered microorganism, e.g., engineered bacterium that express GOT1, convert phenylalanine into phenylpyruvate.

In some embodiments, the engineered microorganism, e.g., engineered bacterium, comprise a modified pks island and a gene encoding GOT2. In some embodiments, the engineered microorganism, e.g., engineered bacterium, comprise a gene encoding GOT2, wherein the GOT2 gene is operably linked to an inducible promoter. In some embodiments, the microorganisms, e.g., bacteria, comprise a non-native GOT2 gene. In some embodiments, the microorganisms, e.g., bacteria, comprise additional copies of a native GOT2 gene. In some embodiments, the promoter is not associated with the GOT2 gene in nature. In some embodiments, the promoter is any one or more of the promoters disclosed herein. In some embodiments, the engineered microorganism, e.g., engineered bacterium that express GOT2, convert phenylalanine into phenylpyruvate.

In some embodiments, the engineered microorganism, e.g., engineered bacterium, comprise a modified pks island and a gene encoding TAT. In some embodiments, the engineered microorganism, e.g., engineered bacterium, comprise a gene encoding TAT, wherein the TAT gene is operably linked to an inducible promoter. In some embodiments, the microorganisms, e.g., bacteria, comprise a non-native TAT gene. In some embodiments, the microorganisms, e.g., bacteria, comprise additional copies of a native TAT gene. In some embodiments, the promoter is not associated with the TAT gene in nature. In some embodiments, the promoter is any one or more of the promoters disclosed herein. In some embodiments, the engineered microorganism, e.g., engineered bacterium that express TAT, convert phenylalanine into phenylpyruvate.

In some embodiments, the engineered microorganism, e.g., engineered bacterium, comprise a modified pks island and a gene encoding DDC. In some embodiments, the engineered microorganism, e.g., engineered bacterium, comprise a gene encoding DDC, wherein the DDC gene is operably linked to an inducible promoter. In some embodiments, the microorganisms, e.g., bacteria, comprise a non-native DDC gene. In some embodiments, the microorganisms, e.g., bacteria, comprise additional copies of a native DDC gene. In some embodiments, the promoter is not associated with the DDC gene in nature. In some embodiments, the promoter is any one or more of the promoters disclosed herein. In some embodiments, the engineered microorganism, e.g., engineered bacterium that express DDC, convert phenylalanine into phenylethylamine.

In some embodiments, the engineered microorganism, e.g., engineered bacterium, comprises a modified pks island and one or more gene(s) and/or gene cassette(s) encoding at least one oxalate catabolismenzyme. In some embodiments, the engineered bacteria comprise one or more gene(s) and/or gene cassette(s) encoding at least one oxalate catabolismenzyme and are capable of converting oxalate into oxalyl-CoA. In some embodiments, the engineered bacteria comprise one or more gene(s) and/or gene cassette(s) encoding at least one oxalate catabolismenzyme and are capable of converting oxalyl-CoA into formate and carbon dioxide. In some embodiments, the engineered bacteria comprise one or more gene(s) and/or gene cassette(s) encoding at least one oxalate catabolismenzyme and are capable of converting oxalate into oxalyl-CoA, and oxalyl-CoA into formate and carbon dioxide. In some embodiments, the engineered bacteria of the disclosure comprise one or more gene(s) and or gene cassette encoding one or more oxalate catabolismenzyme(s) which convert oxalate and formyl CoA into oxalyl-CoA and formate. In some embodiments, the engineered bacteria of the disclosure comprise one or more gene(s) and/or gene cassette(s) encoding one or more oxalate catabolismenzyme(s) which convert oxalate and acetyl-coA into oxalyl-CoA and acetate. In some embodiments, the engineered bacteria of the disclosure comprise one or more gene(s) and/or gene cassette(s) encoding one or more oxalate catabolismenzyme(s) which convert oxalate and CoA into oxalyl-CoA (e.g., by converting one ATP to AMP plus diphosphate). In some embodiments, the engineered bacteria of the disclosure comprise one or more gene(s) and/or gene cassette(s) encoding one or more oxalate catabolismenzyme(s) which convert oxalyl-CoA to carbon dioxide and formyl-CoA. In some embodiments, the engineered bacteria produce formate as a result of oxalate catabolismin some embodiments, the engineered bacteria produce formate and carbon dioxide as a result of oxalate catabolismin some embodiments, the engineered bacteria produce acetate as a result of oxalate catabolismin some embodiments, the engineered bacteria produce acetate and carbon dioxide as a result of oxalate catabolismin some embodiments, the engineered bacteria produce formate, acetate, and carbon dioxide as a result of oxalate catabolism.

In some embodiments, the engineered bacteria comprise a modified pks island, as disclosed herein, and one or more gene(s) and/or gene cassette(s) encoding at least one oxalate catabolismenzyme and are capable of converting oxalate into oxalyl-CoA. In some embodiments, the engineered bacteria comprise a modified pks island, as disclosed herein, and one or more gene(s) and/or gene cassette(s) encoding at least one oxalate catabolismenzyme and are capable of converting oxalyl-CoA into formate and carbon dioxide. In some embodiments, the engineered bacteria comprise a modified pks island, as disclosed herein, and one or more gene(s) and/or gene cassette(s) encoding at least one oxalate catabolismenzyme and are capable of converting oxalate into oxalyl-CoA, and oxalyl-CoA into formate and carbon dioxide. In some embodiments, the engineered bacteria comprise a modified pks island, as disclosed herein, and one or more gene(s) and/or gene cassette(s) encoding at least one oxalate catabolism enzyme(s) which convert oxalate and formyl CoA into oxalyl-CoA and formate In some embodiments, the engineered bacteria comprise a modified pks island, as disclosed herein, and one or more gene(s) and/or gene cassette(s) encoding at least one oxalate catabolismenzyme(s) which convert oxalate and acetyl-coA into oxalyl-CoA and acetate. In some embodiments, the engineered bacteria comprise a modified pks island, as disclosed herein, and one or more gene(s) and/or gene cassette(s) encoding at least one oxalate catabolismenzyme(s) which convert oxalate and CoA into oxalyl-CoA (e.g., by converting one ATP to AMP plus diphosphate). In some embodiments, the engineered bacteria comprise a modified pks island, as disclosed herein, and one or more gene(s) and/or gene cassette(s) encoding at least one oxalate catabolismenzyme(s) which convert oxalyl-CoA to carbon dioxide and formyl-CoA. In some embodiments, the engineered bacteria, comprising a modified pks island as disclosed herein, produce formate as a result of oxalate catabolismin some embodiments, the engineered bacteria, comprising a modified pks island as disclosed herein, produce formate and carbon dioxide as a result of oxalate catabolismin some embodiments, the engineered bacteria, comprising a modified pks island as disclosed herein, produce acetate as a result of oxalate catabolismin some embodiments, the engineered bacteria, comprising a modified pks island as disclosed herein, produce acetate and carbon dioxide as a result of oxalate catabolismin some embodiments, the engineered bacteria, comprising a modified pks island as disclosed herein, produce formate, acetate, and carbon dioxide as a result of oxalate catabolism.

In some embodiments, the one or more oxalate catabolismenzyme(s) increases the rate of oxalate and/or oxalyl-CoA catabolismin the cell. In some embodiments, the one or more oxalate catabolismenzyme(s) decreases the level of oxalate in the cell. In some embodiments, the one or more oxalate catabolismenzyme(s) decreases the level of oxalyl-CoA in the cell. In some embodiments, the one or more oxalate catabolismenzyme(s) decreases the level of oxalic acid in the cell.

In some embodiments, the one or more oxalate catabolismenzyme(s) increases the rate of oxalate and/or oxalyl-CoA catabolismin the cell. In some embodiments, the one or more oxalate catabolismenzyme(s) decreases the level of oxalate in the cell. In some embodiments, the one or more oxalate catabolismenzyme(s) decreases the level of oxalyl-CoA in the cell. In some embodiments, the one or more oxalate catabolismenzyme(s) decreases the level of oxalic acid in the cell.

In some embodiments, the one or more oxalate catabolismenzyme(s) increases the level of oxalyl-CoA in the cell as compared to the level of its corresponding oxalate in the cell. In some embodiments, the one or more oxalate catabolismenzyme(s) increases the level of formate and carbon dioxide in the cell as compared to the level of its corresponding oxalyl-CoA in the cell. In some embodiments, the one or more oxalate catabolismenzyme(s) decreases the level of the oxalate and/or oxalyl CoA as compared to the level of oxalate in the cell.

Enzymes involved in the catabolism of oxalate may be expressed or modified in the bacteria of the invention in order to enhance catabolism of oxalate. Specifically, when at least one oxalate catabolismenzyme is expressed in the engineered bacterial cells of the invention, the engineered bacterial cells convert more oxalate into oxalyl-CoA, or convert more oxalyl-CoA into formate and carbon dioxide when the catabolismenzyme is expressed than unmodified bacteria of the same bacterial subtype under the same conditions. Thus, the genetically engineered bacteria comprising a heterologous gene encoding an oxalate catabolismenzyme can catabolize oxalate and/or oxalyl-CoA to treat disorders in which oxalate is detrimental, such as PHI, PHII, PHIII, and secondary hyperoxaluria, enteric hyperoxaluria, and idiopathic hyperoxaluria.

In one embodiment, the bacterial cell of the invention comprises at least one heterologous gene encoding at least one oxalate catabolismenzyme. In one embodiment, the bacterial cell of the invention comprises at least one heterologous gene encoding an importer of oxalate and at least one heterologous gene encoding at least one oxalate catabolismenzyme. In one embodiment, the bacterial cell of the invention comprises at least one heterologous gene encoding an exporter of formate and at least one heterologous gene encoding at least one oxalate catabolismenzyme. In one embodiment, the bacterial cell of the invention comprises at least one heterologous gene encoding an oxalate: formate antiporter and at least one heterologous gene encoding at least one oxalate catabolismenzyme.

Oxalate catabolism enzymes are known in the art. In some embodiments, AN oxalate catabolismenzyme is encoded by at least one gene encoding at least one oxalate catabolism enzyme derived from a bacterial species. In some embodiments, an oxalate catabolismenzyme is encoded by a gene encoding an oxalate catabolismenzyme derived from a non-bacterial species. In some embodiments, an oxalate catabolismenzyme is encoded by a gene derived from a eukaryotic species, e.g., a yeast species or a plant species. In one embodiment, an oxalate catabolismenzyme is encoded by a gene derived from a human. In one embodiment, the gene sequence(s) encoding the one or more oxalate catabolismenzyme(s) is derived from an organism of the genus or species that includes, but is not limited to, *Bifidobacterium, Bordetella, Bradyrhizobium, Burkholderia, Clostridium, Enterococcus, Escherichia, Eubacterium, Lactobacillus, Magnetospirillium, Mycobacterium, Neurospora, Oxalobacter*, e.g., *Oxalobacter formigenes, Ralstonia, Rhodopseudomonas, Shigella, Thermoplasma*, and *Thauera*, e.g., *Bifidobacterium animalis, Bifidobacterium bifidum, Bifidobacterium infantis, Bifidobacterium lactis, Bifidobacterium longum, Bordatella bronchiseptica, Bordatella parapertussis, Burkholderia fungorum, Burkholderia xenovorans, Bradyrhizobium japonicum, Clostridium acetobutylicum, Clostridium difficile, Clostridium scindens, Clostridium sporogenes, Clostridium tentani, Enterococcus faecalis, Escherichia coli, Eubacterium lentum, Lactobacillus acidophilus, Lactobacillus bulgaricus, Lactobacillus casei, Lactobacillus gasseri, Lactobacillus plantarum, Lactobacillus rhamnosus, Lactococcus lactis, Magnetospirillium magentotaticum, Mycobacterium avium, Mycobacterium intracellulare, Mycobacterium kansasii, Mycobacterium leprae, Mycobacterium smegmatis, Mycobacterium tuberculosis, Mycobacterium ulcerans, Neurospora crassa, Oxalobacter formigenes, Providencia rettgeri, Eubacterium lentum, Ralstonia eutropha, Ralstonia metallidurans, Rhodopseudomonas palustris, Shigella flexneri, Thermoplasma volcanium*, and *Thauera aromatica*.

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.). In one embodiment, the gene or protein is at least 90%, 91%, 92%, 93%, 94$, 95%, 96%, 97%, 98%, 99% or 100% identical to a gene or protein disclosed herein.

In some embodiments, the gene encoding an oxalate catabolismenzyme is mutagenized; mutants exhibiting increased activity are selected; and the mutagenized gene encoding the oxalate catabolismenzyme is isolated and inserted into the bacterial cell. In one embodiment, spontaneous mutants that arise that allow bacteria to grow on oxalate as the sole carbon source can be screened for and selected. The gene comprising the modifications described herein may be present on a plasmid or chromosome. Non-limiting examples of oxalate catabolism enzymes of the disclosure are listed in Table 2.

TABLE 2

Oxalate Catabolism Enzyme Polynucleotide Sequences

| Description | Sequence | SEQ ID NO |
|---|---|---|
| frc (formyl-CoA transferase from *O. formigenes* | ATGACTAAACCATTAGATGGAATTAATGTGCTTG ACTTTACCCACGTCCAGGCAGGTCCTGCCTGTAC ACAGATGATGGGTTTCTTGGGCGCAAACGTCATC AAGATTGAAAGACGTGGTTCCGGAGATATGACTC GTGGATGGCTGCAGGACAAACCAAATGTTGATTC CCTGTATTTCACGATGTTCAACTGTAACAAACGTT CGATTGAACTGGACATGAAAACCCCGGAAGGCA AAGAGCTTCTGGAACAGATGATCAAGAAAGCCG ACGTCATGGTCGAAAACTTCGGACCAGGCGCACT GGACCGTATGGGCTTTACTTGGGAATACATTCAG GAACTGAATCCACGCGTCATTCTGGCTTCCGTTA AAGGCTATGCAGAAGGCCACGCCAACGAACACC TGAAAGTTTATGAAAACGTTGCACAGTGTTCCGG CGGTGCTGCAGCTACCACCGGTTTCTGGGATGGT CCTCCAACCGTTTCCGGCGCTGCTCTGGGTGACTC | SEQ ID NO: 1 |

TABLE 2-continued

| Oxalate Catabolism Enzyme Polynucleotide Sequences | | |
|---|---|---|
| Description | Sequence | SEQ ID NO |
| | CAACTCCGGTATGCACCTGATGATCGGTATTCTG<br>GCCGCTCTGGAAATGCGTCACAAAACCGGCCGTG<br>GTCAGAAAGTTGCCGTCGCTATGCAGGACGCTGT<br>TCTGAATCTGGTTCGTATCAAACTGCGTGACCAG<br>CAACGTCTGGAAAGAACCGGCATTCTGGCTGAAT<br>ACCCACAGGCTCAGCCTAACTTTGCCTTCGACAG<br>AGACGGTAACCCACTGTCCTTCGACAACATCACT<br>TCCGTTCCACGTGGTGGTAACGCAGGTGGCGGCG<br>GCCAGCCAGGCTGGATGCTGAAATGTAAAGGTTG<br>GGAAACCGATGCGGACTCCTACGTTTACTTCACC<br>ATCGCTGCAAACATGTGGCCACAGATCTGCGACA<br>TGATCGACAAGCCAGAATGGAAAGACGACCCAG<br>CCTACAACACATTCGAAGGTCGTGTTGACAAGCT<br>GATGGACATCTTCTCCTTCATCGAAACCAAGTTC<br>GCTGACAAGGACAAATTCGAAGTTACCGAATGGG<br>CTGCCCAGTACGGCATTCCTTGCGGTCCGGTCAT<br>GTCCATGAAAGAACTGGCTCACGATCCTTCCCTG<br>CAGAAAGTTGGTACCGTCGTTGAAGTIGTCGACG<br>AAATTCGTGGTAACCACCTGACCGTTGGCGCACC<br>GTTCAAATTCTCCGGATTCCAGCCGGAAATTACC<br>CGTGCTCCGCTGTTGGGCGAACATACCGACGAAG<br>TTCTGAAAGAACTGGGTCTTGACGATGCCAAGAT<br>CAAGGAACTGCATGCAAAACAGGTAGTTTGA | |
| oxc (oxalylCoA decarboxylase from *O. formigenes*) also referred to as oxdc (oxalate decarboxylase) | ATGAGTAACGACGACAATGTAGAGTTGACTGATG<br>GCTTTCATGTTTTGATCGATGCCCTGAAAATGAAT<br>GACATCGATACCATGTATGGTGTTGTCGGCATTC<br>CTATCACGAACCTGGCTCGTATGTGGCAAGATGA<br>CGGTCAGCGTTTTTACAGCTTCCGTCACGAACAA<br>CACGCAGGTTATGCAGCTTCTATCGCCGGTTACA<br>TCGAAGGAAAACCTGGCGTTTGCTTGACCGTTTC<br>CGCCCCTGGCTTCCTGAACGGCGTGACTTCCCTG<br>GCTCATGCAACCACCAACTGCTTCCCAATGATCC<br>TGTTGAGCGGTTCCAGTGAACGTGAAATCGTCGA<br>TTTGCAACAGGGCGATTACGAAGAAATGGATCAG<br>ATGAATGTTGCACGTCCACACTGCAAAGCTTCTTT<br>CCGTATCAACAGCATCAAAGACATTCCAATCGGT<br>ATCGCTCGTGCAGTTCGCACCGCTGTATCCGGAC<br>GTCCAGGTGGTGTTTACGTTGACTTGCCAGCAAA<br>ACTGTTCGGTCAGACCATTTCTGTAGAAGAAGCT<br>AACAAACTGCTCTTCAAACCAATCGATCCAGCTC<br>CGGCACAGATTCCTGCTGAAGACGCTATCGCTCG<br>CGCTGCTGACCTGATCAAGAACGCCAAACGTCCA<br>GTTATCATGCTGGGTAAAGGCGCTGCATACGCAC<br>AATGCGACGACGAAATCCGCGCACTGGTTGAAGA<br>AACCGGCATCCCATTCCTGCCAATGGGTATGGCT<br>AAAGGCCTGCTGCCTGACAACCATCCACAATCCG<br>CTGCTGCAACCCGTGCTTTCGCACTGGCACAGTG<br>TGACGTTTGCGTACTGATCGGCGCTCGTCTGAACT<br>GGCTGATGCAGCACGGTAAAGGCAAAACCTGGG<br>GCGACGAACTGAAGAAATACGTTCAGATCGACAT<br>CCAGGCTAACGAAATGGACAGCAACCAGCCTATC<br>GCTGCACCAGTTGTTGGTGACATCAAGTCCGCCG<br>TTTCCCTGCTCCGCAAAGCACTGAAAGGCGCTCC<br>AAAAGCTGACGCTGAATGGACCGGCGCTCTGAAA<br>GCCAAAGTTGACGGCAACAAAGCCAAACTGGCT<br>GGCAAGATGACTGCCGAAACCCCATCCGGAATGA<br>TGAACTACTCCAATTCCCTGGGCGTTGTTCGTGAC<br>TTCATGCTGGCAAATCCGGATATTTCCCTGGTTAA<br>CGAAGGCGCTAATGCACTCGACAACACTCGTATG<br>ATTGTTGACATGCTGAAACCACGCAAACGTCTTG<br>ACTCCGGTACCTGGGGTGTTATGGGTATTGGTAT<br>GGGCTACTGCGTTGCTGCAGCTGCTGTTACCGGC<br>AAACCGGTTATCGCTGTTGAAGGCGATAGCGCAT<br>TCGGTTTCTCCGGTATGGAACTGGAAACCATCTG<br>CCGTTACAACCTGCCAGTTACCGTTATCATCATGA<br>ACAATGGTGGTATCTATAAAGGTAACGAAGCAGA<br>TCCACAACCAGGCGTTATCTCCTGTACCCGTCTGA<br>CCCGTGGTCGTTACGACATGATGATGGAAGCATT<br>TGGCGGTAAAGGTTATGTTGCCAATACTCCAGCA<br>GAACTGAAAGCTGCTCTGGAAGAAGCTGTTGCTT<br>CCGGCAAACCATGCCTGATCAACGCGATGATCGA<br>TCCAGACGCTGGTGTCGAATCTGGCCGTATCAAG<br>AGCCTGAACGTTGTAAGTAAAGTTGGCAAGAAAT<br>AA | SEQ ID NO: 2 |

TABLE 2-continued

| Oxalate Catabolism Enzyme Polynucleotide Sequences | | |
|---|---|---|
| Description | Sequence | SEQ ID NO |
| ScAAE3 (oxalate-CoA ligase from *S. cerevisiae*) | ATGACCAGTGCAGCTACGGTGACCGCGAGCTTTA<br>ATGACACTTTTTCTGTGAGCGATAATGTCGCGGT<br>AATCGTACCGGAAACCGATACGCAGGTCACCTAC<br>CGTGATCTTTCCCACATGGTAGGACACTTTCAAA<br>CAATGTTCACGAACCCGAATAGTCCTCTGTACGG<br>GGCGGTCTTTCGTCAAGACACGGTAGCGATTAGC<br>ATGCGTAACGGCCTTGAATTTATTGTGGCTTTCCT<br>TGGAGCCACGATGGATGCGAAAATTGGTGCGCCA<br>CTGAATCCCAATTATAAAGAGAAGGAGTTTAATT<br>TTTACCTGAATGACTTAAAGTCCAAAGCCATCTG<br>CGTGCCGAAAGGCACCACCAAACTGCAAAGTTCA<br>GAAATTCTTAAGAGTGCGTCCACGTTCGGGTGCT<br>TTATTGTGGAACTGGCGTTTGACGCCACCCGTTTT<br>CGTGTTGAATATGACATTTACTCCCCGGAGGACA<br>ATTATAAACGTGTGATCTACCGCAGCCTTAACAA<br>TGCTAAGTTTGTCAACACAAACCCTGTCAAGTTC<br>CCGGGTTTCGCCCGCAGCTCGGATGTTGCACTTAT<br>TTTGCATACCTCAGGCACCACTAGTACCCCAAAG<br>ACCGTACCCCTCTTGCATCTGAATATTGTCCGTTC<br>AACCCTGAATATCGCCAACACTTACAAACTTACC<br>CCGCTGGATCGCTCCTATGTTGTAATGCCGCTGTT<br>TCATGTACATGGATTAATCGGCGTCTTACTGAGT<br>ACGTTCCGCACCCAGGGCAGTGTAGTCGTCCCGG<br>ACGGCTTTCATCCGAAGCTCTTCTGGGATCAGTTT<br>GTTAAATATAACTGCAATTGGTTTAGTTGCGTCCC<br>AACGATCTCTATGATTATGTTGAATATGCCCAAA<br>CCGAATCCGTTTCCGCACATTCGCTTTATCCGCTC<br>ATGTAGCAGCGCGCTGGCGCCAGCAACGTTTCAC<br>AAGCTGGAAAAAGAATTTAATGCCCCAGTTCTGG<br>AAGCGTACGCGATGACAGAAGCATCTCATCAGAT<br>GACCAGTAACAATCTGCCTCCCGGTAAACGTAAA<br>CCGGGGACCGTGGGCCAACCTCAAGGTGTAACCG<br>TAGTAATCCTGGATGACAACGATAACGTTCTGCC<br>GCCCGGCAAAGTTGGCGAGGTGTCGATCCGTGGG<br>GAGAACGTCACCCTGGGCTACGCTAATAACCCGA<br>AAGCTAACAAAGAAAACTTCACTAAACGTGAAA<br>ACTATTTCCGTACCGGGGATCAGGGCTACTTCGA<br>CCCGGAGGGCTTTCTCGTGCTGACCGGCCGCATT<br>AAAGAATTGATCAATCGCGGTGGTGAAAAAATTA<br>GTCCTATTGAACTGGACGGAATCATGCTCTCGCA<br>TCCTAAAATCGACGAGGCGGTGGCGTTCGGCGTT<br>CCAGATGATATGTATGGCCAAGTCGTTCAGGCGG<br>CAATCGTGTTGAAAAAGGGGGAAAAGATGACCT<br>ATGAAGAATTAGTGAATTTCCTGAAAAAGCATTT<br>AGCAAGCTTTAAAATCCCAACCAAAGTCTACTTT<br>GTGGATAAGCTGCCTAAAACGGCCACCGGGAAG<br>ATTCAACGTCGCGTAATCGCCGAAACCTTCGCGA<br>AATCTAGTCGCAACAAAAGCAAACTTtaa | SEQ ID NO: 3 |
| yfdE (Acetyl-CoA:oxalate CoA-transferase from *E coli*) | atgACAAATAATGAAAGCAAAGGGCCGTTTGAAGGS<br>CTTATTAGTTATCGATATGACACATGTCCTTAATG<br>GACCTTTCGGAACTCAACTTCTTTGTAATATGGGC<br>GCAAGGGTAATTAAAGTTGAGCCGCCGGGTCATG<br>GTGATGATACCCGCACATTTGGTCCCTATGTGGA<br>TGGACAGTCACTCTATTACAGTTTTATTAATCATG<br>GCAAAGAGAGTGTGGTTCTTGATTTAAAGAATGA<br>TCACGATAAAAGTATATTTATAAATATGCTCAAA<br>CAAGCTGATGTATTAGCTGAGAATTTTCGCCCAG<br>GTACAATGGAAAAACTGGGGTTTTCATGGGAAAC<br>GCTTCAAGAAATCAACCCGCGCCTCATATATGCT<br>TCATCGTCAGGTTTCGGACATACCGGTCCGCTAA<br>AAGATGCTCCTGCCTACGATACCATCATTCAGGC<br>AATGAGCGGGATAATGATGGAAACAGGATATCCT<br>GATGCTCCGCCAGTGCGCGTTGGTACATCTCTTGC<br>GGATCTATGCGGCGGTGTCTATTTATTCAGCGGA<br>ATAGTGAGTGCACTTTATGGCCGCGAAAAGAGCC<br>AGAGAGGGGCGCATGTCGATATAGCGATGTTTGA<br>TGCCACGCTGAGTTTTCTGGAGCATGGTCTGATG<br>GCATATATCGCAACTGGGAAGTCACCACAACGTC<br>TGGGAAATCGCCATCCCTACATGGCACCTTTTGA<br>TGTTTTCAATACTCAGGATAAGCCGATTACGATTT<br>GTTGTGGTAATGACAAGCTTTTTTCTGCGTTATGC<br>CAGGCACTGGAGCTTACGGAACTGGTTAATGATC<br>CCCGATTTAGCAGCAATATTTTACGCGTACAAAA<br>CCAGGCTATTCTTAAACAATATATTGAGCGGACG<br>TTAAAAACGCAGGCAGCTGAAGTTTGGTTAGCCA<br>GAATACATGAAGTTGGTGTACCCGTCGCGCCGTT | SEQ ID NO: 4 |

TABLE 2-continued

| Oxalate Catabolism Enzyme Polynucleotide Sequences | | |
|---|---|---|
| Description | Sequence | SEQ ID NO |
| | ATTAAGTGTGGCTGAGGCCATTAAATTGCCACAA ACTCAGGCGAGAAATATGTTGATTGAAGCCGGGG GAATAATGATGCCGGGTAATCCGATAAAAATCAG CGGCTGCGCGGACCCGCATGTTATGCCGGGAGCG GCAACGCTCGACCAGCATGGGGAACAAATTCGCC AGGAGTTCTCATCAtaa | |

In one embodiment, the gene sequence(s) encoding the one or more oxalate catabolism enzyme(s) comprises a formyl-CoA:oxalate CoA-transferase sequence. In one embodiment, the formyl-CoA:oxalate CoA-transferase is frc, e.g., from *O. formigenes*. Accordingly, in one embodiment, the frc gene has at least about 80% identity with the entire sequence of SEQ ID NO: 1. Accordingly, in one embodiment, the frc gene has at least about 90% identity with the entire sequence of SEQ ID NO: 1. Accordingly, in one embodiment, the frc gene has at least about 95% identity with the entire sequence of SEQ ID NO: 1. Accordingly, in one embodiment, the frc gene has at least about 85%, 86%, 87%, 88%, 89%, 90%, 91%, 92%, 93%, 94%, 95%, 96%, 97%, 98%, or 99% identity with the entire sequence of SEQ ID NO: 1. In another embodiment, the frc gene comprises the sequence of SEQ ID NO: 1. In yet another embodiment the frc gene consists of the sequence of SEQ ID NO:1.

In one embodiment, the gene sequence(s) encoding the one or more oxalate catabolism enzyme(s) comprises a oxalyl-CoA decarboxylase sequence. In one embodiment, the oxalyl-CoA decarboxylase is oxc, e.g., from *O. formigenes*. Accordingly, in one embodiment, the oxc gene has at least about 80% identity with the entire sequence of SEQ ID NO: 2. Accordingly, in one embodiment, the oxc gene has at least about 90% identity with the entire sequence of SEQ ID NO: 2. Accordingly, in one embodiment, the oxc gene has at least about 95% identity with the entire sequence of SEQ ID NO: 2. Accordingly, in one embodiment, the oxc gene has at least about 85%, 86%, 87%, 88%, 89%, 90%, 91%, 92%, 93%, 94%, 95%, 96%, 97%, 98%, or 99% identity with the entire sequence of SEQ ID NO: 2. In another embodiment, the oxc gene comprises the sequence of SEQ ID NO: 2. In yet another embodiment the oxc gene consists of the sequence of SEQ ID NO: 2. In another embodiment, the oxc gene consists of the sequence of SEQ ID NO: 2.

In one embodiment, the at least one gene encoding the at least one oxalate catabolism enzyme comprises an oxalate-CoA ligase sequence. In one embodiment, the oxalate-CoA ligase is ScAAE3 from *S. cerevisiae*. Accordingly, in one embodiment, the ScAAE3 gene has at least about 80% identity with the entire sequence of SEQ ID NO: 3. Accordingly, in one embodiment, the ScAAE3 gene has at least about 90% identity with the entire sequence of SEQ ID NO: 3. Accordingly, in one embodiment, the ScAAE3 gene has at least about 95% identity with the entire sequence of SEQ ID NO: 3. Accordingly, in one embodiment, the ScAAE3 gene has at least about 85%, 86%, 87%, 88%, 89%, 90%, 91%, 92%, 93%, 94%, 95%, 96%, 97%, 98%, or 99% identity with the entire sequence of SEQ ID NO: 3. In another embodiment, the ScAAE3 gene comprises the sequence of SEQ ID NO: 3. In yet another embodiment the ScAAE3 gene consists of the sequence of SEQ ID NO: 3.

In one embodiment, the at least one gene encoding the at least one oxalate catabolism enzyme comprises an acetyl-CoA:oxalate CoA-transferase sequence. In one embodiment, the acetyl-CoA:oxalate CoA-transferase is YfdE from *E. coli* from *S. cerevisiae*. Accordingly, in one embodiment, the YfdE gene has at least about 80% identity with the entire sequence of SEQ ID NO: 4. Accordingly, in one embodiment, the YfdE gene has at least about 90% identity with the entire sequence of SEQ ID NO: 4. Accordingly, in one embodiment, the YfdE gene has at least about 95% identity with the entire sequence of SEQ ID NO: 4. Accordingly, in one embodiment, the YfdE gene has at least about 85%, 86%, 87%, 88%, 89%, 90%, 91%, 92%, 93%, 94%, 95%, 96%, 97%, 98%, or 99% identity with the entire sequence of SEQ ID NO: 4. In another embodiment, the YfdE gene comprises the sequence of SEQ ID NO: 4. In yet another embodiment the YfdE gene consists of the sequence of SEQ ID NO: 4.

TABLE 3

| Polypeptide Sequences of Oxalate Catabolism Enzymes | | |
|---|---|---|
| Description | Sequence | SEQ ID NO |
| Frc (Formyl-CoA transferase from *O. formigenes*) | MTKPLDGINVLDFTHVQAGPACTQMMGFLGANVIKIERR GSGDMTRGWLQDKPNVDSLYFTMFNCNKRSIELDMKTPE GKELLEQMIKKADVMVENFGPGALDRMGFTWEYIQELNP RVILASVKGYAEGHANEHLKVYENVAQCSGGAAATTGF WDGPPTVSGAALGDSNSGMHLMIGILAALEMRHKTGRGQ KVAVAMQDAVLNLVRIKLRDQQRLERTGILAEYPQAQPN FAFDRDGNPLSFDNITSVPRGGNAGGGGQPGWMLKCKG WETDADSYVYFTIAANMWPQICDMIDKPEWKDDPAYNTF EGRVDKLMDIFSFIETKFADKDKFEVTEWAAQYGIPCGPV MSMKELAHDPSLQKVGTVVEVVDEIRGNHLTVGAPFKFS GFQPEITRAPLLGEHTDEVLKELGLDDAKIKELHAKQVV* | SEQ ID NO: 5 |
| Oxc (oxalylCoA decarboxylase from *O. formigenes*) | MSNDDNVELTDGFHVLIDALKMNDIDTMYGVVGIPITNL ARMWQDDGQRFYSFRHEQHAGYAASIAGYIEGKPGVCLT VSAPGFLNGVTSLAHATTNCFPMILLSGSSEREIVDLQQGD YEEMDQMNVARPHCKASFRINSIKDIPIGIARAVRTAVSGR | SEQ ID NO: 6 |

TABLE 3-continued

Polypeptide Sequences of Oxalate Catabolism Enzymes

| Description | Sequence | SEQ ID NO |
|---|---|---|
| | PGGVYVDLPAKLFGQTISVEEANKLLFKPIDPAPAQIPAED<br>AIARAADLIKNAKRPVIMLGKGAAYAQCDDEIRALVEETG<br>IPFLPMGMAKGLLPDNHPQSAAATRAFALAQCDVCVLIG<br>ARLNWLMQHGKGKTWGDELKKYVQIDIQANEMDSNQPI<br>AAPVVGDIKSAVSLLRKALKGAPKADAEWTGALKAKVD<br>GNKAKLAGKMTAETPSGMMNYSNSLGVVRDFMLANPDI<br>SLVNEGANALDNTRMIVDMLKPRKRLDSGTWGVMGIGM<br>GYCVAAAAVTGKPVIAVEGDSAFGFSGMELETICRYNLPV<br>TVIIMNNGGIYKGNEADPQPGVISCTRLTRGRYDMMMEA<br>FGGKGYVANTPAELKAALEEAVASGKPCLINAMIDPDAG<br>VESGRIKSLNVVSKVGKK* | |
| ScAAE3<br>(Oxalate-CoA<br>ligase from<br>*S. cerevisiae*) | MTSAATVTASFNDTFSVSDNVAVIVPETDTQVTYRDLSH<br>MVGHFQTMFTNPNSPLYGAVFRQDTVAISMRNGLEFIVAF<br>LGATMDAKIGAPLNPNYKEKEFNFYLNDLKSKAICVPKGTT<br>KLQSSEILKSASTFGCFIVELAFDATRFRVEYDIYSPEDNY<br>KRVIYRSLNNAKFVNTNPVKFPGFARSSDVALILHTSGTTS<br>TPKTVPLLHLNIVRSTLNIANTYKLTPLDRSYVVMPLFHVH<br>GLIGVLLSTFRTQGSVVVPDGFHPKLFWDQFVKYNCNWF<br>SCVPTISMIMLNMPKPNPFPHIRFIRSCSSALAPATFHKLE<br>KEFNAPVLEAYAMTEASHQMTSNNLPPGKRKPGTVGQPQG<br>VTVVILDDNDNVLPPGKVGEVSIRGENVTLGYANNPKAN<br>KENFTKRENYFRTGDQGYFDPEGFLVLTGRIKELINRGGE<br>KISPIELDGIMLSHPKIDEAVAFGVPDDMYGQVVQAAIVL<br>KKGEKMTYEELVNFLKKHLASFKIPTKVYFVDKLPKTAT<br>GKIQRRVIAETFAKSSRNKSKL* | SEQ ID NO: 7 |
| yfdE (Acetyl-<br>CoA:oxalate<br>CoA-transferase<br>from *E. coli*) | MTNNESKGPFEGLLVIDMTHVLNGPFGTQLLCNMGARVI<br>KVEPPGHGDDTRTFGPYVDGQSLYYSFINHGKESVVLDLK<br>NDHDKSIFINMLKQADVLAENFRPGTMEKLGFSWETLQEI<br>NPRLIYASSSGFGHTGPLKDAPAYDTIIQAMSGIMMETGYP<br>DAPPVRVGTSLADLCGGVYLFSGIVSALYGREKSQRGAH<br>VDIAMFDATLSFLEHGLMAYIATGKSPQRLGNRHPYMAPF<br>DVFNTQDKPITICCGNDKLFSALCQALELTELVNDPRFSSN<br>ILRVQNQAILKQYIERTLKTQAAEVWLARIHEVGVPVAPL<br>LSVAEAIKLPQTQARNMLIEAGGIMMPGNPIKISGCADPHV<br>MPGAATLDQHGEQIRQEFSS* | SEQ ID NO: 8 |
| yfdW (formyl<br>CoA transferase<br>from *E. coli*) | SYYHHHHHHLESTSLYKKAGLMSTPLQGIKVLDFTGVQS<br>GPSCTQMLAWFGADVIKIERPGVGDVTRHQLRDIPDIDAL<br>YFTMLNSNKRSIELNTKTAEGKEVMEKLIREADILVENFHP<br>GAIDHMGFTWEHIQEINPRLIFGSIKGFDECSPYVNVKAYE<br>NVAQAAGGAASTTGFWDGPPLVSAAALGDSNTGMHLLIG<br>LLAALLHREKTGRGQRVTMSMQDAVLNLCRVKLRDQQR<br>LDKLGYLEEYPQYPNGTFGDAVPRGGNAGGGGQPGWILK<br>CKGWETDPNAYIYFTIQEQNWENTCKAIGKPEWITDPAYS<br>TAHARQPHIFDIFAEIEKYTVTIDKHEAVAYLTQFDIPCAP<br>VLSMKEISLDPSLRQSGSVVEVEQPLRGKYLTVGCPMKFSA<br>FTPDIKAAPLLGEHTAAVLQELGYSDDEIAAMKQNHAI | SEQ ID NO: 9 |
| yfdU (oxalyl-<br>CoA<br>decarboxylase<br>*E. coli*) | MSDQLQMTDGMHIIVEALKQNNIDTIYGVVGIPVTDMAR<br>HAQAEGIRYIGFRHEQSAGYAAAASGFLTQKPGICLTVSA<br>PGFLNGLTALANATVNGFPMIMISGSSDRAIVDLQQGDYE<br>ELDQMNAAKPYAKAAFRVNQPQDLGIALARAIRVSVSGR<br>PGGVYLDLPANVLAATMEKDEALTTIVKVENPSPALLPCP<br>KSVTSAISLLAKAERPLIILGKGAAYSQADEQLREFIESAQ<br>IPFLPMSMAKGILEDTHPLSAAAARSFALANADVVMLVGA<br>RLNWLLAHGKKGWAADTQFIQLDIEPQEIDSNRPIAVPVV<br>GDIASSMQGMLAELKQNTFTTPLVWRDILNIHKQQNAQK<br>MHEKLSTDTQPLNYFNALSAVRDVLRENQDIYLVNEGAN<br>TLDNARNIIDMYKPRRRLDCGTWGVMGIGMGYAIGASVT<br>SGSPVVAIEGDSAFGFSGMEIETICRYNLPVTIVIFNNGG<br>IYRGDGVDLSGAGAPSPTDLLHHARYDKLMDAFRGVGYNV<br>TTTDELRHALTTGIQSRKPTIINVVIDPAAGTESGHITKL<br>NPKQVAGN | SEQ ID NO:<br>10 |

In one embodiment, one or more polypeptide(s) encoded by the oxalate catabolism cassette(s) and expressed by the genetically engineered bacteria comprises a formyl-CoA transferase, e.g. frc from *O. formigenes*. In one embodiment the polypeptide(s) have at least about 80% identity with SEQ ID NO: 5. In another embodiment, one or more polypeptide(s) encoded by the oxalate catabolism gene(s) or gene cassette(s) and expressed by the genetically engineered bacteria have at least about 85% identity with SEQ ID NO: 5. In one embodiment, one or more polypeptide(s) encoded by the oxalate catabolism gene(s) or gene cassette(s) and expressed by the genetically engineered bacteria have at least about 90% identity with SEQ ID NO: 5. In one embodiment, one or more polypeptide(s) encoded by the oxalate catabolism gene(s) or gene cassette(s) and expressed by the genetically engineered bacteria have at least about 95% identity with SEQ ID NO: 5. In another embodiment, one or more polypeptide(s) encoded by the oxalate catabolism gene(s) or gene cassette(s) and expressed by the genetically engineered bacteria have at least about 96%, 97%, 98%, or 99% identity with SEQ ID NO: 5. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 5. In another embodiment, one or more polypeptide(s) encoded by the oxalate catabolism gene(s) or gene cassette(s) and expressed by the genetically engineered bacteria comprise the sequence of SEQ ID NO: 5. In yet another embodiment one or more polypeptide(s) encoded by the oxalate catabolism gene(s) or gene cassette(s) and expressed by the genetically engineered bacteria consist of the sequence of SEQ ID NO: 5.

In one embodiment, one or more polypeptide(s) encoded by the oxalate catabolism cassette(s) and expressed by the engineered bacteria comprises a oxalyl-CoA decarboxylase, e.g. oxc from *O. formigenes*. In one embodiment the polypeptide(s) have at least about 80% identity with SEQ ID NO: 6. In another embodiment, one or more polypeptide(s) encoded by the oxalate catabolism gene(s) or gene cassette (s and expressed by the engineered bacteria have at least about 85% identity with SEQ ID NO: 6. In one embodiment, one or more polypeptide(s) encoded by the oxalate catabolism gene(s) or gene cassette(s) and expressed by the engineered bacteria have at least about 90% identity with SEQ ID NO: 6. In one embodiment, one or more polypeptide(s) encoded by the oxalate catabolism gene(s) or gene cassette(s) and expressed by the engineered bacteria have at least about 95% identity with SEQ ID NO: 6. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 6. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 6. In another embodiment, one or more polypeptide(s) encoded by the oxalate catabolism gene(s) or gene cassette(s) and expressed by the engineered bacteria comprise the sequence of SEQ ID NO: 6. In yet another embodiment one or more polypeptide(s) encoded by the oxalate catabolism gene(s) or gene cassette(s) and expressed by the genetically engineered bacteria consist of the sequence of SEQ ID NO: 6.

In one embodiment, one or more polypeptide(s) encoded by the oxalate catabolism gene(s) or gene cassette(s) and expressed by the engineered bacteria comprises an oxalate-CoA ligase, e.g. ScAAE3 from *S cerevisiae*. In one embodiment the polypeptide(s) have at least about 80% identity with SEQ ID NO: 7. In another embodiment, one or more polypeptide(s) encoded by the oxalate catabolism gene(s) or gene cassette (s and expressed by the engineered bacteria have at least about 85% identity with SEQ ID NO: 7. In one embodiment, one or more polypeptide(s) encoded by the oxalate catabolism gene(s) or gene cassette(s) and expressed by the engineered bacteria have at least about 90% identity with SEQ ID NO: 7. In one embodiment, one or more polypeptide(s) encoded by the oxalate catabolism gene(s) or gene cassette(s) and expressed by the engineered bacteria have at least about 95% identity with SEQ ID NO: 7. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 7. Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 7. In another embodiment, one or more polypeptide(s) encoded by the oxalate catabolism gene(s) or gene cassette(s) and expressed by the engineered bacteria comprise the sequence of SEQ ID NO: 7. In yet another embodiment one or more polypeptide(s) encoded by the oxalate catabolism cassette(s) and expressed by the genetically engineered bacteria consist of the sequence of SEQ ID NO: 7.

In one embodiment, one or more polypeptide(s) encoded by the oxalate catabolism cassette(s) and expressed by the engineered bacteria comprises an Acetyl-CoA:oxalate CoA-transferase from, e.g. YfdE from *E. coli*. In one embodiment the polypeptide(s) have at least about 80% identity with SEQ ID NO: 8. In another embodiment, one or more polypeptide(s) encoded by the oxalate catabolism gene(s) or gene cassette (s and expressed by the engineered bacteria have at least about 85% identity with SEQ ID NO: 8. In one embodiment, one or more polypeptide(s) encoded by the oxalate catabolism gene(s) or gene cassette(s) and expressed by the engineered bacteria have at least about 90% identity with SEQ ID NO: 8. In one embodiment, one or more polypeptide(s) encoded by the oxalate catabolism gene(s) or gene cassette(s) and expressed by the engineered bacteria have at least about 95% identity with SEQ ID NO: 8. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 8. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 8. In another embodiment, one or more polypeptide(s) encoded by the oxalate catabolism gene(s) or gene cassette(s) and expressed by the engineered bacteria comprise the sequence of SEQ ID NO: 8. In yet another embodiment one or more polypeptide(s) encoded by the oxalate catabolism gene(s) or gene cassette(s) and expressed by the engineered bacteria consist of the sequence of with SEQ ID NO: 8.

In one embodiment, one or more polypeptide(s) encoded by the oxalate catabolism gene(s) or gene cassette(s) and expressed by the genetically engineered bacteria comprises a formyl CoA transferase, e.g., yfdW from *E. coli*. In one embodiment the polypeptide(s) have at least about 80% identity with SEQ ID NO: 9. In another embodiment, one or more polypeptide(s) encoded by the oxalate catabolism gene(s) or gene cassette (s and expressed by the engineered bacteria have at least about 85% identity with SEQ ID NO: 9. In one embodiment, one or more polypeptide(s) encoded by the oxalate catabolism gene(s) or gene cassette(s) and expressed by the engineered bacteria have at least about 90% identity with SEQ ID NO: 9. In one embodiment, one or more polypeptide(s) encoded by the oxalate catabolism gene(s) or gene cassette(s) and expressed by the engineered bacteria have at least about 95% identity with SEQ ID NO: 9. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 9. Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 919%, 92%, 93%, 94%, 95%, 96%, 97%, 98%, or 99% identity with SEQ ID NO: 9. In another embodiment, one or more polypeptide(s) encoded by the oxalate catabolism gene(s) or gene cassette(s) and expressed by the engineered comprise the sequence of SEQ ID NO: 9. In yet another embodiment one or more polypeptide(s) encoded by the oxalate catabolism gene(s) or gene cassette(s) and expressed by the engineered bacteria consist of the sequence of SEQ ID NO: 9.

In one embodiment, one or more polypeptide(s) encoded by the oxalate catabolism gene(s) or gene cassette(s) and expressed by the engineered bacteria comprises a oxalyl-CoA decarboxylase, e.g., yfdU from *E. coli*. In one embodiment the polypeptide(s) have at least about 80% identity with SEQ ID NO: 10. In another embodiment, one or more polypeptide(s) encoded by the oxalate catabolism gene(s) or gene cassette (s and expressed by the engineered bacteria have at least about 85% identity with SEQ ID NO: 10. In one embodiment, one or more polypeptide(s) encoded by the oxalate catabolism gene(s) or gene cassette(s) and expressed by the engineered bacteria have at least about 90% identity with SEQ ID NO: 10. In one embodiment, one or more polypeptide(s) encoded by the oxalate catabolism gene(s) or gene cassette(s) and expressed by the engineered bacteria have at least about 95% identity with SEQ ID NO: 10. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 10. Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 10. In another embodiment, one or more polypeptide(s) encoded by the oxalate catabolism gene(s) or gene cassette(s) and expressed by the engineered bacteria comprise the sequence of SEQ ID NO: 10. In yet another embodiment one or more polypeptide(s) encoded by the oxalate catabolism gene(s) or gene cassette(s) and expressed by the engineered bacteria consist of the sequence of SEQ ID NO: 10.

In some embodiments, the engineered microorganisms, e.g., genetically engineered bacteria, comprising a modified pks island are non-pathogenic bacteria. In some embodiments, the engineered microorganisms, e.g., genetically engineered bacteria, are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacteroides, Bifidobacterium, Clostridium, Escherichia, Lactobacillus*, and *Lactococcus*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added).

Unmodified *E. coli* Nissle or genetically engineered bacteria may be destroyed, e.g., by defense factors in the gut or blood serum (Sonnenborn et al., 2009) or by activation of a kill switch, several hours or days after administration. Thus, the composition may require continued administration. In some embodiments, the residence time is calculated for a human subject.

In some embodiments, the therapeutic molecule, e.g., PAL, may be expressed on a low-copy plasmid, a high-copy plasmid, or on the chromosome, e.g., at one or more of the following insertion sites in *E. coli* Nissle: malE/K, insB/I, araC/BAD, lacZ, agal/rsmI, thyA, and malP/T. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the therapeutic molecule, e.g., PAL, is integrated into the bacterial chromosome at one or more integration sites in the engineered microorganisms, e.g., genetically engineered bacteria. In some embodiments, the engineered microorganisms, e.g., genetically engineered bacteria, comprise one or more gene(s) encoding a phenylalanine metabolizing enzyme (PME); one or more gene(s) for producing an anti-cancer molecule, e.g., a deadenylate cyclase gene (e.g., dacA) or an enzyme capable of producing a STING agonist; and one or more gene(s) encoding a modified arginine biosynthesis pathway, e.g., deleted arginine repressor, modified arginine repressor binding sites, and/or arginine feedback resistant N-acetylglutamate synthase mutation, for producing arginine. In some embodiments, the engineered microorganisms, e.g., genetically engineered bacteria, comprise a gene encoding PME, wherein the PME gene is operably linked to an inducible promoter. In some embodiments, the microorganisms, e.g., bacteria, comprise a non-native PME gene. In some embodiments, the microorganisms, e.g., bacteria, comprise additional copies of a native PME gene. In some embodiments, the promoter is not associated with the PME gene in nature.

In some embodiments, the engineered microorganisms, e.g., genetically engineered bacteria, are auxotrophs for one or more essential genes. For example, a mutation of, modification of, or excision of an essential gene may result in the engineered microorganisms, e.g., genetically engineered bacteria, becoming an auxotroph. An auxotrophic modification is intended to cause bacteria to die in the absence of an exogenously added nutrient essential for survival or growth because they lack the gene(s) necessary to produce that essential nutrient. In some embodiments, any of the engineered microorganisms, e.g., genetically engineered bacteria, described herein also comprise a deletion or mutation in a gene required for cell survival and/or growth.

Exemplary auxotrophs are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety. In one embodiment, the essential gene is a DNA synthesis gene, for example, thyA. Thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the microorganism, e.g., bacterial cell, is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the microorganism, e.g., bacterial cell, is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

In another embodiment, the engineered microorganisms, e.g., genetically engineered bacteria, are auxotrophs in a cell wall synthesis gene, for example, dapA. Diaminopimelic acid (DAP) is an amino acid synthetized within the lysine biosynthetic pathway and is required for bacterial cell wall growth (Meadow et al., 1959; Clarkson et al., 1971). In some embodiments, any of the engineered microorganisms, e.g., genetically engineered bacteria, described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the microorganism, e.g., bacterial cell, does not survive in the absence of the auxotrophic gene product (e.g., outside of the gut).

In some embodiments, the engineered microorganism, e.g., genetically engineered bacterium, comprises a gene encoding phenylalanine ammonia lyase (PAL), e.g., a gene encoding PAL from *Photorhabdus luminescens*, e.g., stlA. Williams et al., 2005. In some embodiments, the PAL gene, e.g., stlA gene, is operably linked to an inducible promoter. In some embodiments, the PAL gene, e.g., stlA gene, is operably linked to a promoter that is inducible under low oxygen conditions, e.g., PfnrS promoter. In some embodiments, the PAL gene, e.g., stlA gene, is operably linked to a promoter that is inducible by isopropyl β-d-1-thiogalactopyranoside (IPTG), e.g., Ptac promoter. In some embodiments, the engineered microorganism, e.g., genetically engineered bacterium, comprises a gene encoding a phenylalanine transporter, e.g., a gene encoding a phenylalanine transporter from *Escherichia coli*, e.g., pheP. In some embodiments, the phenylalanine transporter gene, e.g., pheP gene, is operably linked to an inducible promoter. In some embodiments, the phenylalanine transporter gene, e.g., pheP gene, is operably linked to a promoter that is inducible under low oxygen conditions, e.g., PfnrS promoter. In some embodiments, the engineered microorganism, e.g., genetically engineered bacterium, comprises a gene encoding L-amino acid deaminase (LAAD), e.g., pma. In some embodiments, the LAAD gene is operably linked to an inducible promoter. In some embodiments, the LAAD gene is operably linked to a promoter that is inducible by arabinose, e.g., PBAD promoter. In some embodiments, the engineered microorganism, e.g., genetically engineered bacterium, comprises multiple copies of the genes encoding PAL, phenylalanine transporter, and/or LAAD. In some embodiments, the genes encoding PAL, phenylalanine transporter, and/or LAAD are chromosomally integrated.

In some embodiments, the genetically engineered bacterium is SYNB1618 and comprises three copies of stlA, each operably linked to a PfnrS promoter; two copies of stlA, each operably linked to a Ptac promoter; two copies of pheP, each operably linked to a PfnrS promoter; and one copy of pma operably linked to a PBAD promoter. See, e.g., Isabella et al., Development of a synthetic live bacterial therapeutic for the human metabolic disease phenylketonuria, Nature Biotechnology (2018), which is incorporated by reference in its entirety herein.

In some embodiments, the engineered microorganism, e.g., genetically engineered bacterium, comprises a PAL gene that encodes a polypeptide having modifications S92G, H133M, I167K, L432I, and V470A as compared to wild-type *Photorhabdus luminescens* PAL, e.g., mPAL1. See, e.g., PCT/US2021/023003, which is incorporated by reference in its entirety herein.

```
mPAL1:
MKAKDVQPTIIINKNGLISLEDIYDIAIKQKKVEISTEITELLTHGREKL
EEKLNSGEVIYGINTGFGGNANLVVPFEKIAEHQQNLLTFLGAGTGDYMS
KPCIKASQFTMLLSVCKGWSATRPIVAQAIVDMINHDIVPLVPRYGSVGA
SGDLIPLSYIARALCGKGKVYYMGAEIDAAEAIKRAGLTPLSLKAKEGLA
LINGTRVMSGISAITVIKLEKLFKASISAIALAVEALLASHEHYDARIQQ
VKNHPGQNAVASALRNLLAGSTQVNLLSGVKEQANKACRHQEITQLNDTL
QEVYSIRCAPQVLGIVPESLATARKILEREVISANDNPLIDPENGDVLHG
GNFMGQYVARTMDALKLDIALIANHLHAIVALMMDNRFSRGLPNSLSPTP
GMYQGFKGVQLSQTALVAAIRHDCAASGIHTIATEQYNQDIVSLGLHAAQ
DVLEMEQKLRNIVSMTILVACQAIHLRGNISEIAPETAKFYHAVREISSP
LITDRALDEDIIRIADAIINDQLPLPEIMLEE
```

In some embodiments, the mPAL1 gene is operably linked to an inducible promoter. In some embodiments, the mPAL1 gene is operably linked to a promoter that is inducible by isopropyl β-d-1-thiogalactopyranoside (IPTG), e.g., Ptac promoter. In some embodiments, the engineered microorganism, e.g., genetically engineered bacterium, comprises a gene encoding a phenylalanine transporter, e.g., a gene encoding a phenylalanine transporter from *Escherichia coli*, e.g., pheP. In some embodiments, the phenylalanine transporter gene, e.g., pheP gene, is operably linked to an inducible promoter. In some embodiments, the phenylalanine transporter gene, e.g., pheP gene, is operably linked to a promoter that is inducible by isopropyl β-d-1-thiogalactopyranoside (IPTG), e.g., Ptac promoter. In some embodiments, the engineered microorganism, e.g., genetically engineered bacterium, comprises a gene encoding L-amino acid deaminase (LAAD), e.g., pma. In some embodiments, the LAAD gene is operably linked to an inducible promoter. In some embodiments, the LAAD gene is operably linked to a promoter that is inducible by arabinose, e.g., PBAD promoter. In some embodiments, the engineered microorganism, e.g., genetically engineered bacterium, comprises multiple copies of the genes encoding mPAL1, phenylalanine transporter, and/or LAAD. In some embodiments, the genes encoding mPAL1, phenylalanine transporter, and/or LAAD are chromosomally integrated.

In some embodiments, the engineered microorganism, e.g., genetically engineered bacterium, comprises a gene encoding methionine gamma lyase (MGL), MetNIQ, and/or methionine decarboxylase (MDC), e.g., a gene encoding MGL from *Brevibacterium aurantiacum, Citrobacter freundii, Porphyromonas gingivalis*, or *Porphyromonas gingivalis*; a gene encoding MetNIQ from *E. coli*; and/or a gene encoding MDC from *Streptomyces* sp590, respectively. In some embodiments, the MGL gene is operably linked to an inducible promoter. In some embodiments, the MGL gene, is operably linked to a promoter that is inducible under low oxygen conditions, e.g., a PfnrS promoter. In some embodiments, the MGL gene is operably linked to a promoter that is inducible by isopropyl β-d-1-thiogalactopyranoside (IPTG), e.g., a Ptac promoter.

In some embodiments, the metNIQ gene is operably linked to an inducible promoter. In some embodiments, the metNIQ gene is operably linked to a promoter that is inducible under low oxygen conditions, e.g., a PfnrS promoter. In some embodiments, the metNIQ gene is operably linked to a promoter that is inducible by isopropyl β-d-1-thiogalactopyranoside (IPTG), e.g., Ptac promoter.

In some embodiments, the MDC gene is operably linked to an inducible promoter. In some embodiments, the MDC gene is operably linked to a promoter that is inducible under low oxygen conditions, e.g., a PfnrS promoter. In some embodiments, the MDC gene is operably linked to a promoter that is inducible by isopropyl β-d-1-thiogalactopyranoside (IPTG), e.g., a Ptac promoter.

In some embodiments, the engineered microorganism, e.g., genetically engineered bacterium, comprises a gene encoding a methionine transporter, e.g., a gene encoding a methionine transporter from *Bacillus subtilis*, e.g., a metP gene. In some embodiments, the methionine transporter gene, e.g., metP gene, is operably linked to an inducible promoter. In some embodiments, the methionine transporter gene, e.g., metP gene, is operably linked to a promoter that is inducible under low oxygen conditions, e.g., a PfnrS promoter.

In some embodiments, the engineered microorganism, e.g., genetically engineered bacterium, comprises multiple copies of the gene(s) encoding MGL, MetNIQ, MDC, and/or MetP. In some embodiments, the engineered microorganism, e.g., genetically engineered bacterium, comprises genes encoding MGL, MetNIQ. MDC, and/or MetP are on a plasmid. In some embodiments, the gene encoding MGL, MetNIQ, MDC, and/or MetP are integrated into the bacterial chromosome.

In some embodiments, the genetically engineered bacterium is SYN7349 and comprises a gene encoding MDC and a gene encoding MetNIQ, each operably linked to a Ptet promoter, and a deletion of the yjeH gene. See, e.g., PCT/US2021/017775, which is incorporated by reference in its entirety herein.

In some embodiments, the engineered microorganism, e.g., genetically engineered bacterium, comprises a gene encoding oxalate catabolismenzyme(s) e.g., oxalate-CoA ligase, (e.g., ScAAE3 from *S. cerevisiae*), an oxalyl-CoA decarboxylase (Oxc, e.g., from *O. formigenes*), and a formyl-CoA transferase (e.g., Frc, e.g., from *O. formigenes*). In some embodiments, the scaaE3 gene is operably linked to an inducible promoter. In some embodiments, the scaaE3 gene is operably linked to a promoter that is inducible under low oxygen conditions, e.g., a PfnrS promoter. In some embodiments, the scaaE3 gene is operably linked to a promoter that is inducible by isopropyl β-d-1-thiogalactopyranoside (IPTG), e.g., a Ptac promoter.

In some embodiments, the oxc gene is operably linked to an inducible promoter. In some embodiments, the oxc gene is operably linked to a promoter that is inducible under low oxygen conditions, e.g., a PfnrS promoter. In some embodiments, the oxc gene is operably linked to a promoter that is inducible by isopropyl β-d-1-thiogalactopyranoside (IPTG), e.g., a Ptac promoter.

In some embodiments, the frc gene is operably linked to an inducible promoter. In some embodiments, the frc gene, is operably linked to a promoter that is inducible under low oxygen conditions, e.g., PfnrS promoter. In some embodiments, the frc gene is operably linked to a promoter that is inducible by isopropyl β-d-1-thiogalactopyranoside (IPTG), e.g., Ptac promoter.

In some embodiments, the engineered microorganism, e.g., genetically engineered bacterium, comprises a gene encoding a oxalate transporter, e.g., a gene encoding a methionine transporter from *O. formigenes*, e.g., an oxIT gene. In some embodiments, the oxalate transporter gene, e.g., oxIT gene, is operably linked to an inducible promoter. In some embodiments, the oxalate transporter gene, e.g., oxIT gene, is operably linked to a promoter that is inducible under low oxygen conditions, e.g., a PfnrS promoter.

In some embodiments, the engineered microorganism, e.g., genetically engineered bacterium, comprises multiple copies of the genes encoding scaaE3, frc, oxc, and/or oxIT. In some embodiments, the engineered microorganism, e.g., genetically engineered bacterium, comprises genes encoding scaaE3, frc, oxc, and/or oxIT are on a plasmid. In some embodiments, the gene encoding scaaE3, frc, oxc, and/or oxIT are integrated into the bacterial chromosome.

In some embodiments, the genetically engineered bacterium is SYN7169 or SYNB8802 and comprises a genes encoding scaaE3, oxc, fre and a gene encoding oxIT, each operably linked to a FNR promoter, and a deletion of phage 3. See, e.g., PCT/US2021/013401, which is incorporated by reference in its entirety herein.

Pharmaceutical Compositions

In some embodiments, the disclosure provides pharmaceutical compositions comprising an engineered microorganism, e.g., engineered bacterium, that comprises a modified pks island. In some embodiments, the disclosure provides pharmaceutical compositions comprising an engineered microorganism, e.g., engineered bacterium, that comprises a modified pks island and one or more gene(s) or gene cassette(s) for producing a therapeutic molecule. In some embodiments, the pharmaceutical composition may be used to treat, manage, ameliorate, and/or prevent a diseases or disorder, e.g., a cancer; or a disease associated with excess phenylalanine, e.g., PKU; or a disease associated with hyperammonemia, e.g., UCD; or a disease associated with excess oxalate, e.g., HOX, or a disease associated with other deleterious molecules described herein.

Pharmaceutical compositions comprising one or more engineered microorganisms, e.g., engineered bacteria, alone or in combination with prophylactic agents, therapeutic agents, and/or and pharmaceutically acceptable carriers are provided. In certain embodiments, the pharmaceutical composition comprises one species, strain, or subtype of microorganism, e.g., bacteria, that are engineered to comprise the genetic modifications, e.g., pks island modifications, described herein. In alternate embodiments, the pharmaceutical composition comprises two or more species, strains, and/or subtypes of microorganisms, e.g., bacteria, that are each engineered to comprise the genetic modifications, e.g., pks island modifications, described herein.

In some embodiments, the pharmaceutical compositions comprise an engineered microorganism, e.g., engineered bacterium, that comprises a modified clb sequence selected from one or more of the clbA, clbB, clbC, clbD, clbE, clbF, clbG, clbH, clbI, clbJ, clbK, clbL, clbM, clbN, clbO, clbP, clbQ, clbR, and clbS gene sequences and/or operably linked promoter sequences, as compared to a suitable control, e.g., the native pks island in an unmodified bacterium of the same strain and/or subtype. In some embodiments, the modified clb sequence is an insertion, a substitution, and/or a deletion as compared to the control.

In some embodiments, the pharmaceutical compositions comprise an engineered microorganism, e.g., engineered bacterium, that comprises a modification in one or more of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the pharmaceutical compositions comprise an engineered microorganism, e.g., engineered bacterium, that comprises a modification in one or more of the promoter sequences operably linked to the clbA, clbB, clbC, clbD, clbE, clbF, clbG, clbH, clbI, clbJ, clbK, clbL, clbM, clbN, clbO, clbP, clbQ, and clbR genes as compared to the suitable control.

In some embodiments, the pharmaceutical compositions comprise an engineered microorganism, e.g., engineered bacterium, that comprises a modification in each of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the pharmaceutical compositions comprise an engineered microorganism, e.g., engineered bacterium, that comprises a modification in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical compositions comprise an engineered microorganism, e.g., engineered bacterium, that comprises a modification in one or more of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the pharmaceutical compositions comprise an engineered microorganism, e.g., engineered bacterium, that comprises a modification in one or more of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical compositions comprise an engineered microorganism, e.g., engineered bacterium, that comprises a modification in each of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the pharmaceutical compositions comprise an engineered microorganism, e.g., engineered bacterium, that comprises a modification in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical compositions comprise an engineered microorganism, e.g., engineered bacterium, that comprises an unmodified clbS gene sequence, a modification in each of the clbA, clbB, clbC, clbD, clbE, clbF, clbG, clbH, clbI, clbJ, clbK, clbL, clbM, clbN, clbO, clbP, clbQ, and clbR gene sequences, and a modification in the clbS promoter sequence, as compared to the suitable control.

In some embodiments, the pharmaceutical compositions comprise an engineered microorganism, e.g., engineered bacterium, that comprises a full or partial deletion in the pks island, e.g., a full or deletion in a clb sequence, e.g., a clb gene or promoter sequence. In some embodiments, the pharmaceutical compositions comprise an engineered microorganism, e.g., engineered bacterium, that comprises a full or partial deletion in a clb sequence selected from one or more of the clbA, clbB, clbC, clbD, clbE, clbF, clbG, clbH, clbI, clbJ, clbK, clbL, clbM, clbN, clbO, clbP, clbQ, clbR, and clbS gene sequences and/or operably linked promoter sequences, as compared to a suitable control, e.g., the native pks island in an unmodified bacterium of the same strain and/or subtype. In some embodiments, the clb sequence, e.g., clb gene or promoter sequence, may be deleted by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared to the control, e.g., the corresponding clb sequence in the native pks island in an unmodified bacterium of the same strain and/or subtype. In some embodiments, the clb sequence, e.g., clb gene or promoter sequence, may be 100% deleted as compared to the control, e.g., the corresponding clb sequence in the native pks island in an unmodified bacterium of the same strain and/or subtype In some embodiments, the pharmaceutical compositions comprise an engineered microorganism, e.g., engineered bacterium, that comprises a partial or full deletion in one or more of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the pharmaceutical compositions comprise an engineered microorganism, e.g., engineered bacterium, that comprises a partial or full deletion in one or more of the promoter sequences operably linked to the clbA, clbB, clbC, clbD, clbE, clbF, clbG, clbH, clbI, clbJ, clbK, clbL, clbM, clbN, clbO, clbP, clbQ, and clbR genes as compared to the suitable control.

In some embodiments, the pharmaceutical compositions comprise an engineered microorganism, e.g., engineered bacterium, that comprises a partial or full deletion in each of the clbA, clbB, clbC, clbD, clbE, clbF, clbG, clbH, clbI, clbJ, clbK, clbL, clbM, clbN, clbO, clbP, clbQ, and clbR gene sequences as compared to the suitable control.

In some embodiments, the pharmaceutical compositions comprise an engineered microorganism, e.g., engineered bacterium, that comprises a partial or full deletion in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical compositions comprise an engineered microorganism, e.g., engineered bacterium, that comprises a partial or full deletion in one or more of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the pharmaceutical compositions comprise an engineered microorganism, e.g., engineered bacterium, that comprises a partial or full deletion in one or more of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical compositions comprise an engineered microorganism, e.g., engineered bacterium, that comprises a partial or full deletion in each of the clbA, clbB, clbC, clbD, clbE, clbF, clbG, clbH, clbI, clbJ, clbK, clbL, clbM, clbN, clbO, clbP, clbQ, clbR, and clbS gene sequences as compared to the suitable control.

In some embodiments, the pharmaceutical composition comprises an engineered microorganism, e.g., engineered bacterium, that comprises a partial or full deletion in each of the promoter sequences operably linked to the clbA, clbB, clbC, clbD, clbE, clbF, clbG, clbH, clbI, clbJ, clbK, clbL, clbM, clbN, clbO, clbP, clbQ, clbR, and clbS genes as compared to the suitable control.

In some embodiments, the pharmaceutical composition comprises an engineered microorganism, e.g., engineered bacterium, that comprises an unmodified clbS gene sequence, a partial or full deletion in each of the clbA, clbB, clbC, clbD, clbE, clbF, clbG, clbH, clbI, clbJ, clbK, clbL, clbM, clbN, clbO, clbP, clbQ, and clbR gene sequences, and a partial or full deletion in the clbS promoter sequence, as compared to the suitable control In some embodiments, the pharmaceutical composition comprises an engineered microorganism, e.g., engineered bacterium, that comprises a modified pks island and expresses less colibactin compared to a suitable control, e.g., an unmodified bacterium of the same strain and/or subtype comprising the native pks island. In some embodiments, the pharmaceutical composition comprises an engineered microorganism, e.g., engineered bacterium, that comprises a modified pks island and expresses less N-myristoyl-D-asparagine compared to control. In some embodiments, the pharmaceutical composition comprises an engineered microorganism, e.g., engineered bacterium, that comprises a modified pks island and exhibits decreased accessory protein activity as compared to control. In some embodiments, the pharmaceutical composition comprises an engineered microorganism, e.g., engineered bacterium, that comprises a modified pks island and exhibits decreased phosphopantetheinyl transferase activity as compared to control. In some embodiments, the pharmaceutical composition comprises an engineered microorganism, e.g., engineered bacterium, that comprises a modified pks island and exhibits decreased polyketide synthase activity as compared to control. In some embodiments, the pharmaceutical composition comprises an engineered microorganism, e.g., engineered bacterium, that comprises a modified pks island and exhibits decreased non-ribosomal peptide synthase activity as compared to control. In some embodiments, the pharmaceutical composition comprises an engineered microorganism, e.g., engineered bacterium, that comprises a modified pks island and exhibits decreased activity of hybrid non-ribosomal peptide/polyketide synthase as compared to control. In some embodiments, the pharmaceutical composition comprises an engineered microorganism, e.g., engineered bacterium, that comprises a modified pks island and exhibits decreased hydroxyl acyl coA dehydrogenase activity as compared to control. In some embodiments, the pharmaceutical composition comprises an engineered microorganism, e.g., engineered bacterium, that comprises a modified pks island and decreased acyl carrier protein activity as compared to control. In some embodiments, the pharmaceutical composition comprises an engineered microorganism, e.g., engineered bacterium, that comprises a modified pks island and decreased αβ dehydrogenase activity as compared to control. In some embodiments, the pharmaceutical composition comprises an engineered microorganism, e.g., engineered bacterium, that comprises a modified pks island and exhibits decreased acyl transferase activity as compared to control. In some embodiments, the pharmaceutical composition comprises an engineered microorganism, e.g., engineered bacterium, that comprises a modified pks island and exhibits decreased amidase activity as compared to control. In some embodiments, the pharmaceutical composition comprises an engineered microorganism, e.g., engineered bacterium, that comprises a modified pks island and exhibits decreased MATE transporter activity as compared to control. In some embodiments, the pharmaceutical composition comprises an engineered microorganism, e.g., engineered bacterium, that comprises a modified pks island and exhibits decreased fmtA peptidase activity as compared to control. In some embodiments, the pharmaceutical composition comprises an engineered microorganism, e.g., engineered bacterium, that comprises a modified pks island and exhibits decreased thioesterase activity as compared to control. In some embodiments, the pharmaceutical composition comprises an engineered microorganism, e.g., engineered bacterium, that comprises a modified pks island and exhibits decreased precolibactin transport across the cytoplasmic membrane as compared to control. In some embodiments, the pharmaceutical composition comprises an engineered microorganism, e.g., engineered bacterium, that comprises a modified pks island and exhibits decreased precolibactin transport across the periplasm as compared to control. In some embodiments, the pharmaceutical composition comprises an engineered microorganism, e.g., engineered bacterium, that comprises a modified pks island and exhibits decreased precolibactin cleavage into colibactin as compared to control.

In some embodiments, the pharmaceutical composition comprises an engineered microorganism, e.g., engineered bacterium, that comprises a modified pks island and further comprises one or more gene(s) for producing a desired therapeutic molecule as described herein. In some embodiments, the one or more gene(s) for producing a desired therapeutic molecule are operably linked to a promoter, e.g., an inducible promoter, as described herein.

In some embodiments, the pharmaceutical composition comprises an engineered microorganism, e.g., engineered bacterium, that comprises a modified pks island and further comprises one or more gene(s) or gene cassette(s) for producing at least one phenylalanine metabolizing enzyme, e.g., PAL and/or LAAD, as described herein.

In some embodiments, the pharmaceutical composition comprises an engineered microorganism, e.g., engineered bacterium, that comprises a modified pks island and further comprises one or more gene(s) encoding GOT1, GOT2, TAT, and/or DDC.

In some embodiments, the pharmaceutical composition comprises an engineered microorganism, e.g., engineered bacterium, that comprises a modified pks island and further comprises one or more gene(s) or gene cassette(s) encoding a modified arginine biosynthesis pathway, e.g., deleted arginine repressor, modified arginine repressor binding sites, and/or arginine feedback resistant N-acetylglutamate synthase mutation.

In some embodiments, the pharmaceutical composition comprises an engineered microorganism, e.g., engineered bacterium, that comprises a modified pks island and further comprises one or more gene(s) or gene cassette(s) for producing an anti-cancer molecule, e.g., a deadenylate cyclase gene or an enzyme capable of producing a stimulator of interferon gene agonist.

In some embodiments (e.g., wherein the microorganism, e.g., bacterium, is genetically engineered to comprise a PME) activity may be measured by conversion of phenylalanine to TCA, e.g., in vitro or in vivo, e.g., urinary HA. In some embodiments (e.g., wherein the microorganism, e.g., bacterium, is genetically engineered to comprise a PME), activity may be measured by conversion of phenylalanine to PPA, e.g., in vitro or in vivo. In some embodiments (e.g., wherein the microorganism, e.g., bacterium, is genetically engineered to comprise a modified arginine biosynthesis pathway, e.g., deleted arginine repressor, modified arginine repressor binding sites, and/or arginine feedback resistant N-acetylglutamate synthase mutation), the activity may be measured by assaying the levels of ammonia, arginine or citrulline, e.g., in vitro or in vivo. In some embodiments (e.g., wherein the microorganism, e.g., bacterium, is genetically engineered to comprise an anti-cancer molecule, e.g., dacA), the activity may be measured by assaying the levels of cyclic dinucleotide, e.g. cyclic di-AMP, e.g., in vitro or in vivo.

In some embodiments, the pharmaceutical composition comprises an engineered microorganism, e.g., engineered bacterium, that comprises a modified pks island and further comprises one or more gene(s) or gene cassette(s) for producing at least one oxalate metabolic enzyme, as described herein.

In some embodiments, the pharmaceutical compositions comprise engineered microorganisms that comprise a modified pks island and further comprise one or more gene(s) and/or gene cassette(s) encoding at least one oxalate catabolismenzyme and are capable of converting oxalate into oxalyl-CoA. In some embodiments, the pharmaceutical compositions comprise engineered microorganisms that comprise a modified pks island and further comprise one or more gene(s) and/or gene cassette(s) encoding at least one oxalate catabolismenzyme and are capable of converting oxalyl-CoA into formate and carbon dioxide. In some embodiments, the pharmaceutical compositions comprise engineered microorganisms that comprise a modified pks island and further comprise one or more gene(s) and/or gene cassette(s) encoding at least one oxalate catabolismenzyme and are capable of converting oxalate into oxalyl-CoA, and oxalyl-CoA into formate and carbon dioxide. In some embodiments, the pharmaceutical compositions comprise engineered microorganisms that comprise a modified pks island and further comprise one or more gene(s) and or gene cassette encoding one or more oxalate catabolismenzyme(s) which convert oxalate and formyl CoA into oxalyl-CoA and formate. In some embodiments, the pharmaceutical compositions comprise engineered microorganisms that comprise a modified pks island and further comprise one or more gene(s) and/or gene cassette(s) encoding one or more oxalate catabolismenzyme(s) which convert oxalate and acetyl-coA into oxalyl-CoA and acetate. In some embodiments, the pharmaceutical compositions comprise engineered microorganisms that comprise a modified pks island and further comprise one or more gene(s) and/or gene cassette(s) encoding one or more oxalate catabolismenzyme(s) which convert oxalate and CoA into oxalyl-CoA (e.g., by converting one ATP to AMP plus diphosphate). In some embodiments, the pharmaceutical compositions comprise engineered microorganisms that comprise a modified pks island and further comprise one or more gene(s) and/or gene cassette(s) encoding one or more oxalate catabolismenzyme(s) which convert oxalyl-CoA to carbon dioxide and formyl-CoA. In some embodiments, the pharmaceutical compositions comprise engineered microorganisms that comprise a modified pks island and further produce formate as a result of oxalate catabolismin some embodiments, the engineered bacteria comprise a modified pks island and further produce formate and carbon dioxide as a result of oxalate catabolism. In some embodiments, the pharmaceutical compositions comprise engineered microorganisms that comprise a modified pks island and further produce acetate as a result of oxalate catabolism. In some embodiments, the pharmaceutical compositions comprise engineered microorganisms that comprise a modified pks island and further produce acetate and carbon dioxide as a result of oxalate catabolismin some embodiments, the pharmaceutical compositions comprise engineered microorganisms that comprise a modified pks island and further produce formate, acetate, and carbon dioxide as a result of oxalate catabolism.

In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme and are capable of converting oxalyl-CoA into formate and carbon dioxide. In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme and are capable of converting oxalate into oxalyl-CoA, and oxalyl-CoA into formate and carbon dioxide. In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme(s) which convert oxalate and formyl CoA into oxalyl-CoA and formate. In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme(s) which convert oxalate and acetyl-coA into oxalyl-CoA and acetate. In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme(s) which convert oxalate and CoA into oxalyl-CoA (e.g., by converting one ATP to AMP plus diphosphate). In some embodiments, the pharmaceutical compositions comprise engineered microorganisms, e.g., engineered bacteria, comprising a modified pks island as disclosed herein, and one or more gene(s) and/or gene cassette(s) encoding at least one oxalate catabolismenzyme(s) which convert oxalyl-CoA to carbon dioxide and formyl-CoA. In some embodiments, the engineered bacteria, comprising a modified pks island as disclosed herein, produce formate as a result of oxalate catabolismin some embodiments, the pharmaceutical compositions comprise engineered microorganisms, e.g., engineered bacteria, comprising a modified pks island as disclosed herein, produce formate and carbon dioxide as a result of oxalate catabolismin some embodiments, the pharmaceutical compositions comprise engineered microorganisms, e.g., engineered bacteria, comprising a modified pks island as disclosed herein, produce acetate as a result of oxalate catabolism. In some embodiments, the pharmaceutical compositions comprise engineered microorganisms, e.g., engineered bacteria, comprising a modified pks island as disclosed herein, produce acetate and carbon dioxide as a result of oxalate catabolismin some embodiments, the pharmaceutical compositions comprise engineered microorganisms, e.g., engineered bacteria, comprising a modified pks island as disclosed herein, produce formate, acetate, and carbon dioxide as a result of oxalate catabolism.

In some embodiments, the pharmaceutical compositions comprise engineered microorganisms, e.g., engineered bacteria, comprising a modified pks island and one or more oxalate catabolismenzyme(s) that increases the rate of oxalate and/or oxalyl-CoA catabolismin the cell. In some embodiments, the pharmaceutical compositions comprise engineered microorganisms, e.g., engineered bacteria, comprising a modified pks island and one or more oxalate catabolismenzyme(s) that decreases the level of oxalate in the cell. In some embodiments, the pharmaceutical compositions comprise engineered microorganisms, e.g., engineered bacteria, comprising a modified pks island and one or more oxalate catabolism enzyme(s) that decreases the level of oxalyl-CoA in the cell. In some embodiments, the pharmaceutical compositions comprise engineered microorganisms, e.g., engineered bacteria, comprising a modified pks island and one or more oxalate catabolismenzyme(s) that decreases the level of oxalic acid in the cell.

In some embodiments, the pharmaceutical composition comprise engineered microorganisms, e.g., genetically engineered bacteria comprising a modified pks island, as disclosed herein, and one or more oxalate catabolismenzyme(s) that decreases the level of oxalate in the cell. In some embodiments, the pharmaceutical composition comprise engineered microorganisms, e.g., genetically engineered bacteria comprising a modified pks island, as disclosed herein, and one or more oxalate catabolismenzyme(s) that decreases the level of oxalyl-CoA in the cell. In some embodiments, the pharmaceutical composition comprise engineered microorganisms, e.g., genetically engineered bacteria comprising a modified pks island, as disclosed herein, and one or more oxalate catabolismenzyme(s) that decreases the level of oxalic acid in the cell.

In some embodiments, the pharmaceutical composition comprise engineered microorganisms, e.g., genetically engineered bacteria comprising a modified pks island, as disclosed herein, and one or more oxalate catabolismenzyme(s) that increases the level of oxalyl-CoA in the cell as compared to the level of its corresponding oxalate in the cell. In some embodiments, the pharmaceutical composition comprise engineered microorganisms, e.g., genetically engineered bacteria comprising a modified pks island, as disclosed herein, and one or more oxalate catabolismenzyme(s) that increases the level of formate and carbon dioxide in the cell as compared to the level of its corresponding oxalyl-CoA in the cell. In some embodiments, the pharmaceutical composition comprise engineered microorganisms, e.g., genetically engineered bacteria comprising a modified pks island, as disclosed herein and one or more oxalate catabolismenzyme(s) that decreases the level of the oxalate and/or oxalyl CoA as compared to the level of oxalate in the cell. In some embodiments, the pharmaceutical composition comprises engineered microorganisms, e.g., engineered bacteria, comprises a modified pks island and at least one heterologous gene encoding an importer of oxalate and at least one heterologous gene encoding at least one oxalate catabolismenzyme. In some embodiments, the pharmaceutical composition comprises engineered microorganisms, e.g., engineered bacteria, comprising at least one heterologous gene encoding an exporter of formate and at least one heterologous gene encoding at least one oxalate catabolismenzyme. In some embodiments, the pharmaceutical composition comprises engineered microorganisms, e.g., engineered bacteria, comprising at least one heterologous gene encoding an oxalate: formate antiporter and at least one heterologous gene encoding at least one oxalate catabolismenzyme.

In some embodiments, the pharmaceutical composition comprise engineered microorganisms, e.g., genetically engineered bacteria comprising a modified pks island as disclosed herein, comprising at least one heterologous gene encoding at least one oxalate catabolismenzyme. In some embodiments, the pharmaceutical composition comprise engineered microorganisms, e.g., genetically engineered bacteria comprising a modified pks island as disclosed herein, comprising at least one heterologous gene encoding an importer of oxalate and at least one heterologous gene encoding at least one oxalate catabolismenzyme. In some embodiments, the pharmaceutical composition comprise engineered microorganisms, e.g., genetically engineered bacteria comprising a modified pks island as disclosed herein, comprising at least one heterologous gene encoding an exporter of formate and at least one heterologous gene encoding at least one oxalate catabolismenzyme. In some embodiments, the pharmaceutical composition comprise engineered microorganisms, e.g., genetically engineered bacteria comprising a modified pks island as disclosed herein, comprising at least one heterologous gene encoding an oxalate: formate antiporter and at least one heterologous gene encoding at least one oxalate catabolismenzyme.

In some embodiments, the pharmaceutical composition comprise engineered microorganisms, e.g., engineered bacteria comprising the gene sequence(s) encoding the one or more oxalate catabolismenzyme(s) comprises a formyl-CoA:oxalate CoA-transferase sequence. In some embodiments, the pharmaceutical composition comprises engineered microorganisms, e.g., engineered bacteria, comprising the formyl-CoA:oxalate CoA-transferase frc, e.g., from *O. formigenes*. In some embodiments, the pharmaceutical composition comprise engineered microorganisms, e.g., engineered bacteria, comprising the frc gene that has at least about 80% identity with the entire sequence of SEQ ID NO: 1. In some embodiments, the pharmaceutical composition comprise engineered microorganisms, e.g., engineered bacteria, comprising the frc gene that has at least about 90% identity with the entire sequence of SEQ ID NO: 1. In some embodiments, the pharmaceutical composition comprise engineered microorganisms, e.g., engineered bacteria, comprising the frc gene that has at least about 95% identity with the entire sequence of SEQ ID NO: 1. In some embodiments, the pharmaceutical composition comprise engineered microorganisms, e.g., engineered bacteria, comprising the frc gene that has at least about 85%, 86%, 87%, 88%, 89%, 90%, 91%, 92%, 93%, 94%, 95%, 96%, 97%, 98%, or 99% identity with the entire sequence of SEQ ID NO: 1. In some embodiments, the pharmaceutical composition comprise engineered microorganisms, e.g., engineered bacteria, comprises the frc gene comprising the sequence of SEQ ID NO: 1. In some embodiments, the pharmaceutical composition comprise engineered microorganisms, e.g., engineered bacteria, comprising the frc gene that consists of the sequence of SEQ ID NO:1.

In some embodiments, the pharmaceutical composition comprise engineered microorganisms, e.g., genetically engineered bacteria comprising a modified pks island, as disclosed herein, and further comprising the gene sequence(s) encoding the one or more oxalate catabolismenzyme(s)

comprises a formyl-CoA:oxalate CoA-transferase sequence. In some embodiments, the pharmaceutical composition comprise engineered microorganisms, e.g., genetically engineered bacteria comprising a modified pks island, as disclosed herein, and further comprising the formyl-CoA:oxalate CoA-transferase frc, e.g., from *O. formigenes*. In some embodiments, the pharmaceutical composition comprise engineered microorganisms, e.g., genetically engineered bacteria comprising a modified pks island, as disclosed herein, and further comprising the frc gene that has at least about 80% identity with the entire sequence of SEQ ID NO: 1. In some embodiments, the pharmaceutical composition comprise engineered microorganisms, e.g., genetically engineered bacteria comprising a modified pks island, as disclosed herein, and further comprising the frc gene that has at least about 90% identity with the entire sequence of SEQ ID NO: 1. In some embodiments, the pharmaceutical composition comprise engineered microorganisms, e.g., genetically engineered bacteria comprising a modified pks island, as disclosed herein, and further comprising the frc gene that has at least about 95% identity with the entire sequence of SEQ ID NO: 1. In some embodiments, the pharmaceutical composition comprise engineered microorganisms, e.g., genetically engineered bacteria comprising a modified pks island, as disclosed herein, and further comprising the frc gene that has at least about 85%, 86%, 87%, 88%, 89%, 90%, 91%, 92%, 93%, 94%, 95%, 96%, 97%, 98%, or 99% identity with the entire sequence of SEQ ID NO: 1. In some embodiments, the pharmaceutical composition comprise engineered microorganisms, e.g., genetically engineered bacteria comprising a modified pks island, as disclosed herein, and further comprising the frc gene comprising the sequence of SEQ ID NO: 1. In some embodiments, the pharmaceutical composition comprise engineered microorganisms, e.g., genetically engineered bacteria comprising a modified pks island, as disclosed herein, and further comprising the frc gene that consists of the sequence of SEQ ID NO:1.

In some embodiments, the pharmaceutical composition comprises engineered microorganisms, e.g., engineered bacteria, comprising the gene sequence(s) encoding the one or more oxalate catabolismenzyme(s) comprising a oxalyl-CoA decarboxylase sequence. In some embodiments, the pharmaceutical composition comprises engineered microorganisms, e.g., engineered bacteria, comprising the oxalyl-CoA decarboxylase that is oxc, e.g., from *O. formigenes*. In some embodiments, the pharmaceutical composition comprises engineered microorganisms, e.g., engineered bacteria, comprising the oxc gene that has at least about 80% identity with the entire sequence of SEQ ID NO: 2. In some embodiments, the pharmaceutical composition comprise engineered microorganisms, e.g., engineered bacteria, further comprising the oxc gene that has at least about 90% identity with the entire sequence of SEQ ID NO: 2. In some embodiments, the pharmaceutical composition comprise engineered microorganisms, e.g., engineered bacteria, comprising the oxc gene that has at least about 95% identity with the entire sequence of SEQ ID NO: 2. In some embodiments, the pharmaceutical composition comprises engineered microorganisms, e.g., engineered bacteria, comprising the oxc gene that has at least about 85%, 86%, 87%, 88%, 89%, 90%, 91%, 92%, 93%, 94%, 95%, 96%, 97%, 98%, or 99% identity with the entire sequence of SEQ ID NO: 2. In some embodiments, the pharmaceutical composition comprises engineered microorganisms, e.g., engineered bacteria, comprising the oxc gene that comprises the sequence of SEQ ID NO: 2. In some embodiments, the pharmaceutical composition comprise engineered microorganisms, e.g., engineered bacteria, comprising the oxc gene that consists of the sequence of SEQ ID NO: 2. In some embodiments, the pharmaceutical composition comprises engineered microorganisms, e.g., engineered bacteria, comprising the oxc gene that consists of the sequence of SEQ ID NO: 2.

In some embodiments, the pharmaceutical composition comprises engineered microorganisms, e.g., genetically engineered bacteria comprising a modified pks island and further comprising the gene sequence(s) encoding the one or more oxalate catabolismenzyme(s) comprising an oxalyl-CoA decarboxylase sequence. In some embodiments, the pharmaceutical composition comprises engineered microorganisms, e.g., genetically engineered bacteria comprising a modified pks island as disclosed herein, and further comprising the oxalyl-CoA decarboxylase that is oxc, e.g., from *O. formigenes*. In some embodiments, the pharmaceutical composition comprises engineered microorganisms, e.g., genetically engineered bacteria comprising a modified pks island as disclosed herein and further comprising the oxc gene that has at least about 80% identity with the entire sequence of SEQ ID NO: 2. In some embodiments, the pharmaceutical composition comprises engineered microorganisms, e.g., genetically engineered bacteria comprising a modified pks island as disclosed herein, and further comprising the oxc gene that has at least about 90% identity with the entire sequence of SEQ ID NO: 2. In some embodiments, the pharmaceutical composition comprises engineered microorganisms, e.g., genetically engineered bacteria comprising a modified pks island as disclosed herein, and further comprising the oxc gene that has at least about 95% identity with the entire sequence of SEQ ID NO: 2. In some embodiments, the pharmaceutical composition comprises engineered microorganisms, e.g., genetically engineered bacteria comprising a modified pks island as disclosed herein, and further comprising the oxc gene that has at least about 85%, 86%, 87%, 88%, 89%, 90%, 91%, 92%, 93%, 94%, 95%, 96%, 97%, 98%, or 99% identity with the entire sequence of SEQ ID NO: 2. In some embodiments, the pharmaceutical composition comprise engineered microorganisms, e.g., genetically engineered bacteria comprising a modified pks island as disclosed herein, and further comprising the oxc gene comprising the sequence of SEQ ID NO: 2. In some embodiments, the pharmaceutical composition comprises engineered microorganisms, e.g., genetically engineered bacteria comprising a modified pks island as disclosed herein, and further comprising the oxc gene that consists of the sequence of SEQ ID NO: 2. In some embodiments, the pharmaceutical composition comprises engineered microorganisms, e.g., genetically engineered bacteria comprising a modified pks island as disclosed herein, and further comprising the oxc gene that consists of the sequence of SEQ ID NO: 2.

In some embodiments, the pharmaceutical composition comprises engineered microorganisms, e.g., engineered bacteria, comprising at least one gene encoding the at least one oxalate catabolismenzyme comprising an oxalate-CoA ligase sequence. In some embodiments, the pharmaceutical composition comprises engineered microorganisms, e.g., engineered bacteria, comprising the oxalate-CoA ligase that is ScAAE3 from *S. cerevisiae*. In some embodiments, the pharmaceutical composition comprises engineered microorganisms, e.g., engineered bacteria, comprising the ScAAE3 gene has at least about 80% identity with the entire sequence of SEQ ID NO: 3. In some embodiments, the pharmaceutical composition comprise engineered microorganisms, e.g., engineered bacteria, c comprising the ScAAE3 gene has at least about 90% identity with the entire sequence of SEQ ID NO: 3. In some embodiments, the pharmaceutical composition comprise engineered microorganisms, e.g., engineered bacteria, comprising the ScAAE3 gene that has at least about 95% identity with the entire sequence of SEQ ID NO: 3. In some embodiments, the pharmaceutical composition comprises engineered microorganisms, e.g., engineered bacteria, comprising the ScAAE3 gene that has at least about 85%, 86%, 87%, 88%, 89%, 90%, 91%, 92%, 93%, 94%, 95%, 96%, 97%, 98%, or 99% identity with the entire sequence of SEQ ID NO: 3. In some embodiments, the pharmaceutical composition comprise engineered microorganisms, e.g., engineered bacteria, further comprising the ScAAE3 gene comprising the sequence of SEQ ID NO: 3. In some embodiments, the pharmaceutical composition comprise engineered microorganisms, e.g., engineered bacteria, comprising the ScAAE3 gene that consists of the sequence of SEQ ID NO: 3.

In some embodiments, the pharmaceutical composition comprises engineered microorganisms, e.g., genetically engineered bacteria comprising a modified pks island as disclosed herein, and further comprising at least one gene encoding the at least one oxalate catabolismenzyme comprising an oxalate-CoA ligase sequence. In some embodiments, the pharmaceutical composition comprises engineered microorganisms, e.g., genetically engineered bacteria comprising a modified pks island, as disclosed herein, and further comprising the oxalate-CoA ligase that is ScAAE3 from *S. cerevisiae*. In some embodiments, the pharmaceutical composition comprise engineered microorganisms, e.g., genetically engineered bacteria comprising a modified pks island, as disclosed herein, and further comprising the ScAAE3 gene that has at least about 80% identity with the entire sequence of SEQ ID NO: 3. In some embodiments, the pharmaceutical composition comprise engineered microorganisms, e.g., genetically engineered bacteria comprising a modified pks island, as disclosed herein, and further comprising the ScAAE3 gene that has at least about 90% identity with the entire sequence of SEQ ID NO: 3. In some embodiments, the pharmaceutical composition comprise engineered microorganisms, e.g., genetically engineered bacteria comprising a modified pks island, as disclosed herein, and further comprising the ScAAE3 gene that has at least about 95% identity with the entire sequence of SEQ ID NO: 3. In some embodiments, the pharmaceutical composition comprise engineered microorganisms, e.g., genetically engineered bacteria comprising a modified pks island, as disclosed herein, and further comprising the ScAAE3 gene that has at least about 85%, 86%, 87%, 88%, 89%, 90%, 91%, 92%, 93%, 94%, 95%, 96%, 97%, 98%, or 99% identity with the entire sequence of SEQ ID NO: 3. In some embodiments, the pharmaceutical composition comprise engineered microorganisms, e.g., genetically engineered bacteria comprising a modified pks island, as disclosed herein, and further comprising the ScAAE3 gene comprising the sequence of SEQ ID NO: 3. In some embodiments, the pharmaceutical composition comprise engineered microorganisms, e.g., genetically engineered bacteria comprising a modified pks island, as disclosed herein, and further comprising the ScAAE3 gene that consists of the sequence of SEQ ID NO: 3.

In some embodiments, the pharmaceutical composition comprises engineered microorganisms, e.g., engineered bacteria, comprising at least one gene encoding the at least one oxalate catabolismenzyme comprises an acetyl-CoA:oxalate CoA-transferase sequence. In some embodiments, the pharmaceutical composition comprises engineered microorganisms, e.g., engineered bacteria, comprising the acetyl-CoA:oxalate CoA-transferase YfdE from *E. coli* from *S. cerevisiae*. In some embodiments, the pharmaceutical composition comprises engineered microorganisms, e.g., engineered bacteria, comprising the YfdE gene that has at least about 80% identity with the entire sequence of SEQ ID NO: 4. In some embodiments, the pharmaceutical composition comprise engineered microorganisms, e.g., engineered bacteria, comprising the YfdE gene that has at least about 90% identity with the entire sequence of SEQ ID NO: 4. In some embodiments, the pharmaceutical composition comprise engineered microorganisms, e.g., engineered bacteria, comprising the YfdE gene that has at least about 95% identity with the entire sequence of SEQ ID NO: 4. In some embodiments, the pharmaceutical composition comprise engineered microorganisms, e.g., engineered bacteria, comprising the YfdE gene that has at least about 85%, 86%, 87%, 88%, 89%, 90%, 91%, 92%, 93%, 94%, 95%, 96%, 97%, 98%, or 99% identity with the entire sequence of SEQ ID NO: 4. In some embodiments, the pharmaceutical composition comprise engineered microorganisms, e.g., engineered bacteria, comprising the YfdE gene comprising the sequence of SEQ ID NO: 4. In some embodiments, the pharmaceutical composition comprise engineered microorganisms, e.g., engineered bacteria, comprising the YfdE gene that consists of the sequence of SEQ ID NO: 4.

In some embodiments, the pharmaceutical composition comprise engineered microorganisms, e.g., genetically engineered bacteria comprising a modified pks island as disclosed herein, and further comprising at least one gene encoding an oxalate catabolism enzyme comprising an acetyl-CoA:oxalate CoA-transferase sequence. In some embodiments, the pharmaceutical composition comprises engineered microorganisms, e.g., genetically engineered bacteria comprising a modified pks island as disclosed herein, and further comprising the acetyl-CoA:oxalate CoA-transferase is YfdE from *E. coli* from *S. cerevisiae*. In some embodiments, the pharmaceutical composition comprise engineered microorganisms, e.g., genetically engineered bacteria comprising a modified pks island as disclosed herein, and further comprising the YfdE gene that has at least about 80% identity with the entire sequence of SEQ ID NO: 4. In some embodiments, the pharmaceutical composition comprise engineered microorganisms, e.g., genetically engineered bacteria comprising a modified pks island as disclosed herein, and further comprising the YfdE gene that has at least about 90% identity with the entire sequence of SEQ ID NO: 4. In some embodiments, the pharmaceutical composition comprise engineered microorganisms, e.g., genetically engineered bacteria comprising a modified pks island as disclosed herein, and further comprising the YfdE gene that has at least about 95% identity with the entire sequence of SEQ ID NO: 4. In some embodiments, the pharmaceutical composition comprise engineered microorganisms, e.g., genetically engineered bacteria comprising a modified pks island as disclosed herein, and further comprising the YfdE gene that has at least about 85%, 86%, 87%, 88%, 89%, 90%, 91%, 92%, 93%, 94%, 95%, 96%, 97%, 98%, or 99% identity with the entire sequence of SEQ ID NO: 4. In some embodiments, the pharmaceutical composition comprise engineered microorganisms, e.g., genetically engineered bacteria comprising a modified pks island as disclosed herein, and further comprising the YfdE gene comprising the sequence of SEQ ID NO: 4. In some embodiments, the pharmaceutical composition comprise engineered microorganisms, e.g., genetically engineered bacteria comprising a modified pks island as disclosed herein, and further comprising the YfdE gene that consists of the sequence of SEQ ID NO: 4.

In some embodiments, the pharmaceutical composition comprise engineered microorganisms, e.g., engineered bacteria, comprising one or more polypeptide(s) encoded by the oxalate catabolism cassette(s) and expressed by the genetically engineered bacteria comprising a formyl-CoA transferase, e.g. frc from *O. formigenes*. In some embodiments, the pharmaceutical composition comprise engineered microorganisms, e.g., engineered bacteria, comprising polypeptide(s) having at least about 80% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria have at least about 85% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria that have at least about 90% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria have at least about 95% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria have at least about 96%, 97%, 98%, or 99% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria that have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria comprising the sequence of SEQ ID NO: 5. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria consist of the sequence of SEQ ID NO: 5.

In some embodiments, the pharmaceutical composition comprise engineered microorganisms, e.g., engineered bacteria, comprising a modified pks island, as disclosed herein, and further comprising one or more polypeptide(s) encoded by the oxalate catabolism cassette(s) and expressed by the genetically engineered bacteria comprises a formyl-CoA transferase, e.g. frc from *O. formigenes*. In some embodiments, the pharmaceutical composition comprise engineered microorganisms, e.g., engineered bacteria, comprising a modified pks island, as disclosed herein, and further comprising polypeptide(s) that have at least about 80% identity with SEQ ID NO: 5. In some embodiments, the pharmaceutical composition comprise engineered microorganisms, e.g., engineered bacteria, comprising the modified pks island as disclosed herein, comprising one or more polypeptide(s) encoded by the oxalate catabolism gene(s) or gene cassette(s) and expressed by the genetically engineered bacteria have at least about 85% identity with SEQ ID NO: 5. In some embodiments, the pharmaceutical composition comprise engineered microorganisms, e.g., engineered bacteria, comprising a modified pks island as disclosed herein, and further comprising one or more polypeptide(s) encoded by the oxalate catabolism gene(s) or gene cassette(s) and expressed by the genetically engineered bacteria have at least about 90% identity with SEQ ID NO: 5. In some embodiments, the pharmaceutical composition comprise engineered microorganisms, e.g., engineered bacteria, comprising a modified pks island, as disclosed herein, and further comprising one or more polypeptide(s) encoded by the oxalate catabolism gene(s) or gene cassette(s) and expressed by the genetically engineered bacteria have at least about 95% identity with SEQ ID NO: 5. In some embodiments, the pharmaceutical composition comprise engineered microorganisms, e.g., engineered bacteria, comprising a modified pks island, as disclosed herein, and further comprising one or more polypeptide(s) encoded by the oxalate catabolism gene(s) or gene cassette(s) and expressed by the genetically engineered bacteria have at least about 96%, 97%, 98%, or 99% identity with SEQ ID NO: 5. In some embodiments, the pharmaceutical composition comprise engineered microorganisms, e.g., engineered bacteria, comprising a modified pks island, as disclosed herein, and further comprising one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 5. In some embodiments, the pharmaceutical composition comprise engineered microorganisms, e.g., engineered bacteria, comprising a modified pks island, as disclosed herein, and further comprising one or more polypeptide(s) encoded by the oxalate catabolism gene(s) or gene cassette(s) and expressed by the genetically engineered bacteria comprise the sequence of SEQ ID NO: 5. In some embodiments, the pharmaceutical composition comprise engineered microorganisms, e.g., engineered bacteria, comprising a modified pks island, as disclosed herein, and further comprising one or more polypeptide(s) encoded by the oxalate catabolism gene(s) or gene cassette(s) and expressed by the genetically engineered bacteria consist of the sequence of SEQ ID NO: 5.

In some embodiments, the pharmaceutical composition comprise engineered microorganisms, e.g., engineered bacteria, comprising one or more polypeptide(s) encoded by the oxalate catabolism cassette(s) and expressed by the engineered bacteria comprises a oxalyl-CoA decarboxylase, e.g. oxc from *O. formigenes*. In some embodiments, the pharmaceutical composition comprise engineered microorganisms, e.g., engineered bacteria, comprise polypeptide(s) having at least about 80% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette (s and expressed by the engineered bacteria have at least about 85% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette(s) and expressed by the engineered bacteria have at least about 90% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette(s) and expressed by the engineered bacteria have at least about 95% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette(s) and expressed by the engineered bacteria have at least about 96%, 97%, 98%, or 99% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 6. In some embodiments, the pharmaceutical composition comprise engineered microorganisms, e.g., engineered bacteria, comprise polypeptide(s) having one or more polypeptide(s) encoded by the oxalate catabolism gene(s) or gene cassette(s) and expressed by the engineered bacteria comprise the sequence of SEQ ID NO: 6. In some embodiments, the pharmaceutical composition comprise engineered microorganisms, e.g., genetically engineered bacteria comprise polypeptide(s) having one or more polypeptide(s) encoded by the oxalate catabolism gene(s) or gene cassette(s) and expressed by the genetically engineered bacteria consist of the sequence of SEQ ID NO: 6.

In some embodiments, the pharmaceutical composition comprise engineered microorganisms, e.g., genetically engineered bacteria comprising a modified pks island as disclosed herein, and further comprising one or more polypeptide(s) encoded by the oxalate catabolism cassette(s) and expressed by the engineered bacteria comprises a oxalyl-CoA decarboxylase, e.g. oxc from *O. formigenes*. In some embodiments, the pharmaceutical composition comprise engineered microorganisms, e.g., genetically engineered bacteria comprising a modified pks island as disclosed herein, and further comprising polypeptide(s) having least about 80% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette (s and expressed by the engineered bacteria have at least about 85% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the engineered bacteria have at least about 90% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the engineered bacteria have at least about 95% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the engineered bacteria have at least about 96%, 97%, 98%, or 99% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the engineered bacteria comprise the sequence of SEQ ID NO: 6. In some embodiments, the pharmaceutical composition comprise engineered microorganisms, e.g., genetically engineered bacteria comprising a modified pks island as disclosed herein, and further comprising polypeptide(s) having one or more polypeptide(s) encoded by the oxalate catabolism gene(s) or gene cassette(s) and expressed by the genetically engineered bacteria consist of the sequence of SEQ ID NO: 6.

In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria comprises an oxalate-CoA ligase, e.g. ScAAE3 from *S cerevisiae*. In some embodiments, the pharmaceutical composition comprise engineered microorganisms, e.g., engineered bacteria, comprising polypeptide(s) having at least about 80% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette (s and expressed by the engineered bacteria have at least about 85% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette(s) and expressed by the engineered bacteria have at least about 90% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette(s) and expressed by the engineered bacteria have at least about 95% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette(s) and expressed by the engineered bacteria have at least about 96%, 97%, 98%, or 99% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 7. In some embodiments, the pharmaceutical composition comprise engineered microorganisms, e.g., engineered bacteria, comprising polypeptide(s) having one or more polypeptide(s) encoded by the oxalate catabolism gene(s) or gene cassette(s) and expressed by the engineered bacteria comprise the sequence of SEQ ID NO: 7. In some embodiments, the pharmaceutical composition comprise engineered microorganisms, e.g., engineered bacteria, comprising polypeptide(s) having one or more polypeptide(s) encoded by the oxalate catabolism cassette(s) and expressed by the genetically engineered bacteria consist of the sequence of SEQ ID NO: 7.

In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria comprises an oxalate-CoA ligase, e.g. ScAAE3 from *S cerevisiae*. In some embodiments, the pharmaceutical composition comprise engineered microorganisms, e.g., genetically engineered bacteria comprising a modified pks island as disclosed herein, and further comprising polypeptide(s) having at least about 80% identity with SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette (s and expressed by the engineered bacteria have at least about 85% identity with SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 90% identity with SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 95% identity with SEQ ID NO: 7 In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 96%, 97%, 98%, or 99% identity with SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria comprise the sequence of SEQ ID NO: 7. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism cassette(s) and expressed by the genetically engineered bacteria consist of the sequence of SEQ ID NO: 7.

In some embodiments, the pharmaceutical composition comprise engineered microorganisms, e.g., engineered bacteria, comprising one or more polypeptide(s) encoded by the oxalate catabolism cassette(s) and expressed by the engineered bacteria comprises an Acetyl-CoA:oxalate CoA-transferase from, e.g. YfdE from *E. coli*. In some embodiments, the pharmaceutical composition comprise engineered microorganisms, e.g., engineered bacteria, comprising the polypeptide(s) having at least about 80% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette (s and expressed by the engineered bacteria have at least about 85% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 90% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 95% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 96%, 97%, 98%, or 99% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria comprise the sequence of SEQ ID NO: 8. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria consist of the sequence of with SEQ ID NO: 8.

In some embodiments, the pharmaceutical composition comprise engineered microorganisms, e.g., genetically engineered bacteria comprising a modified pks island as disclosed herein, and further comprising one or more polypeptide(s) encoded by the oxalate catabolism cassette(s) and expressed by the engineered bacteria comprises an Acetyl-CoA:oxalate CoA-transferase from, e.g. YfdE from *E. coli*. In some embodiments, the pharmaceutical composition comprise engineered microorganisms, e.g., genetically engineered bacteria comprising a modified pks island as disclosed herein, and further comprising polypeptide(s) having at least about 80% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette (s and expressed by the engineered bacteria have at least about 85% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 90% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 95% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 96%, 97%, 98%, or 99% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria comprise the sequence of SEQ ID NO: 8. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria consist of the sequence of with SEQ ID NO: 8.

In some embodiments, the pharmaceutical composition comprise engineered microorganisms, e.g., engineered bacteria, comprising one or more polypeptide(s) encoded by the oxalate catabolism gene(s) or gene cassette(s) and expressed by the genetically engineered bacteria comprises a formyl CoA transferase, e.g., yfdW from *E. coli*. In some embodiments, the pharmaceutical composition comprise engineered microorganisms, e.g., engineered bacteria, comprising polypeptide(s) having at least about 80% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette (s and expressed by the engineered bacteria have at least about 85% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 90% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 95% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 96%, 97%, 98%, or 99% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered comprise the sequence of SEQ ID NO: 9. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria consist of the sequence of SEQ ID NO: 9.

In some embodiments, the pharmaceutical composition comprise engineered microorganisms, e.g., genetically engineered bacteria comprising a modified pks island as disclosed herein, comprising one or more polypeptide(s) encoded by the oxalate catabolism gene(s) or gene cassette(s) and expressed by the genetically engineered bacteria comprises a formyl CoA transferase, e.g., yfdW from *E. coli*. In some embodiments, the pharmaceutical composition comprise engineered microorganisms, e.g., genetically engineered bacteria comprising a modified pks island as disclosed herein, and further comprising polypeptide(s) having at least about 80% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette (s and expressed by the engineered bacteria have at least about 85% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 90% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 95% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 96%, 97%, 98%, or 99% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 80%, 81%, 82%, 83%, 84%, 85%, 86%, 879%, 88%, 89%, 90%, 91%, 92%, 93%, 94%, 95%, 96%, 97%, 98%, or 99% identity with SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered comprise the sequence of SEQ ID NO: 9. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria consist of the sequence of SEQ ID NO: 9.

In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria comprises a oxalyl-CoA decarboxylase, e.g., ydfU from *E. coli*. In some embodiments, the pharmaceutical composition comprise engineered microorganisms, e.g., engineered bacteria, comprise the polypeptide(s) having at least about 80% identity with SEQ ID NO: 10. In another embodiment, one or more polypeptide(s) encoded by the oxalate catabolism gene(s) or gene cassette (s and expressed by the engineered bacteria have at least about 85% identity with SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 90% identity with SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 95% identity with SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 96%, 97%, 98%, or 99% identity with SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria comprise the sequence of SEQ ID NO: 10. In some embodiments, the pharmaceutical composition comprise engineered microorganisms, e.g., engineered bacteria, comprising one or more polypeptide(s) encoded by the oxalate catabolism gene(s) or gene cassette(s) and expressed by the engineered bacteria consist of the sequence of SEQ ID NO: 10.

In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria comprises a oxalyl-CoA decarboxylase, e.g., ydfU from *E. coli*. In some embodiments, the pharmaceutical composition comprise engineered microorganisms, e.g., genetically engineered bacteria comprising a modified pks island as disclosed herein, and further comprising the polypeptide(s) having at least about 80% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette (s and expressed by the engineered bacteria have at least about 85% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 90% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 95% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 96%, 97%, 98%, or 99% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria comprise the sequence of SEQ ID NO: 10. In some embodiments, the pharmaceutical composition comprise engineered microorganisms, e.g., genetically engineered bacteria comprising a modified pks island as disclosed herein, and further comprising one or more polypeptide(s) encoded by the oxalate catabolism gene(s) or gene cassette(s) and expressed by the engineered bacteria consist of the sequence of SEQ ID NO: 10.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The engineered microorganism, e.g., engineered bacterium, described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release).

The engineered microorganism, e.g., engineered bacterium, may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the engineered microorganism, e.g., engineered bacterium, of the invention may be formulated in a solution of sodium bicarbonate, e.g., 1 molar solution of sodium bicarbonate (to buffer an acidic cellular environment, such as the stomach, for example). In some embodiments, the engineered microorganism comprises a phenylalanine metabolizing enzyme such as phenylalanine ammonia lyase and is formulated in a solution of sodium bicarbonate or calcium bicarbonate optionally with PPI to buffer an acidic environment (e.g., less than a pH of 1, less than a pH of 2, less than a pH of 3, less than a pH of 4, less than a pH of 5, less than a pH of 6, or less than a pH of 7) and/or to reduce the acidity of the environment (e.g., resulting in a pH of greater than 5, a pH of greater than 6, a pH of greater than 7, a pH of greater than 8, a pH of greater than 9, or a pH of greater than 10), e.g., to modulate the acidity or acidic environment of the gut in a subject. In some embodiments, the engineered microorganism comprises a phenylalanine metabolizing enzyme such as phenylalanine ammonia lyase, is formulated in a solution of sodium bicarbonate or calcium bicarbonate, and further administered with (e.g., before, concurrently with, after) an antiemetic. Examples of antiemetics include but are not limited to promethazine, meclizine, hydroxyzine, droperidol, metoclopramide, ondansetron, dolasetron, maropitant, phenotyhiazines, famotidine, ranitidine, omeprazole, pantoprazole, misoprostol proton pump inhibitors, histamine-2 receptor antagonists, serotonin (5-HT3) antagonists, antihistamines, butyrophenones, or gastrokinetic agents. The engineered microorganism, e.g., engineered bacterium, may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The pharmaceutical compositions disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The pharmaceutical compositions disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the engineered microorganism, e.g., engineered bacterium, are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the engineered microorganism, e.g., engineered bacterium, described herein.

In one embodiment, the engineered microorganism, e.g., engineered bacterium, may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the engineered microorganism, e.g., engineered bacterium, may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The pharmaceutical composition may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The engineered microorganism, e.g., engineered bacterium, may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, LD50, ED50, EC50, and IC50 may be determined, and the dose ratio between toxic and therapeutic effects (LD50/ED50) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally trehalose. Other suitable cryoprotectants include other disaccharides (e.g., sucrose or lactose), amino acids, and polymers.

Uses and Methods of Treatment

In some embodiments, the disclosure provides methods for treating a subject suffering from a disease or disorder, where the methods comprise administering engineered microorganisms, e.g., engineered bacteria, comprising a modified pks island. In some embodiments, the disclosure provides methods for treating a subject suffering from a disease or disorder, where the methods comprise administering engineered microorganisms, e.g., engineered bacteria, comprising a modified pks island and one or more gene(s) or gene cassette(s) encoding a therapeutic molecule.

In some embodiments, the engineered microorganisms, e.g., engineered bacteria, comprise a modified pks island as disclosed herein and further comprises one or more gene(s) or gene cassette(s) for producing an anti-cancer molecule, e.g., a deadenylate cyclase gene or an enzyme capable of producing a stimulator of interferon gene agonist; or comprising gene(s) or gene cassette(s) encoding a modified arginine biosynthesis pathway, e.g., deleted arginine repressor, modified arginine repressor binding sites, and/or arginine feedback resistant N-acetylglutamate synthase mutation; or comprising gene(s) or gene cassette(s) for producing a phenylalanine metabolizing enzyme; or comprising gene(s) or gene cassette(s) for producing a oxalate metabolic enzyme.

In some embodiments, the disclosure provides methods for reducing hyperphenylalaninemia or treating a disease associated with hyperphenylalaninemia by administering to the subject a pharmaceutical composition comprising an engineered microorganism, e.g., engineered bacterium, comprising a modified pks island and a phenylalanine metabolizing enzyme. In some embodiments, the disclosure provides methods for reducing hyperphenylalaninemia or treating a disease associated with hyperphenylalaninemia by administering a pharmaceutical composition comprising an engineered microorganism, e.g., engineered bacterium comprising a modified pks island and a phenylalanine metabolizing enzyme. In some embodiments, the disclosure provides methods for reducing hyperphenylalaninemia or treating a disease associated with hyperphenylalaninemia by administering a pharmaceutical composition comprising an engineered microorganism, e.g., engineered bacterium comprising a modified pks island and a phenylalanine transporter. In some embodiments, the disease associated with hyperphenylalaninemia is selected from phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency. Segawa's disease, and liver disease.

In some embodiments, the method of treatment comprises administering engineered bacteria comprising a gene encoding at least one PME, e.g., PAL and/or LAAD, wherein the PME gene is operably linked to an inducible promoter. In some embodiments, the method of treatment comprises administering engineered bacteria that comprise a non-native PME gene, e.g., additional copies of a native PME gene. In some embodiments, the promoter is not associated with the PME gene in nature. In some embodiments, the method of treatment comprises administering engineered bacteria that further comprise a phenylalanine transporter, e.g., PheP. In some embodiments, the method of treatment comprises administering engineered bacteria that comprise a non-native phenylalanine transporter gene, e.g., additional copies of a native phenylalanine transporter gene. In some embodiments, the promoter is not associated with the phenylalanine transporter gene in nature. In some embodiments, the promoter is a thermoregulated promoter or a promoter induced under low-oxygen or anaerobic conditions. In some embodiments, the inducible promoters are induced prior to administration to the subject. In some embodiments, the inducible promoters are induced after administration to the subject. In some embodiments, the bacteria manufactured by the methods disclosed herein are auxotrophs for one or more essential genes, e.g., thyA or dapA In some embodiments, the disclosure provides a methods of treating inflammatory bowel disease (IBD), autoimmune disorders, diarrheal diseases, related diseases, and other diseases that benefit from reduced gut inflammation and/or enhanced gut barrier function by administering to the subject a pharmaceutical composition comprising an engineered microorganism, e.g., engineered bacterium, comprising a modified pks island and gene(s) or gene cassette(s) encoding an anti-inflammatory and/or gut barrier function enhancer molecule. In some embodiments, the diarrheal disease is selected from the group consisting of acute watery diarrhea, e.g., cholera, acute bloody diarrhea, e.g., dysentery, and persistent diarrhea. In some embodiments, the IBD or related disease is selected from the group consisting of Crohn's disease, ulcerative colitis, collagenous colitis, lymphocytic colitis, diversion colitis, Behcet's disease, intermediate colitis, short bowel syndrome, ulcerative proctitis, proctosigmoiditis, left-sided colitis, pancolitis, and fulminant colitis. In some embodiments, the disease or condition is an autoimmune disorder selected from the group consisting of acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenia purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenia purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenia purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis. In some embodiments, the invention provides methods for reducing, ameliorating, or eliminating one or more symptom(s) associated with these diseases, including but not limited to diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, and inflammation of the skin, eyes, joints, liver, and bile ducts. In some embodiments, the invention provides methods for reducing gut inflammation and/or enhancing gut barrier function, thereby ameliorating or preventing a systemic autoimmune disorder, e.g., asthma (Arrieta et al., 2015).

In some embodiments, the disclosure provides methods for treating a disease or disorder associated with hyperammonemia by administering engineered microorganisms, e.g., engineered bacteria, comprising a modified pks island and further comprising a modified arginine biosynthesis pathway, e.g., deleted arginine repressor, modified arginine repressor binding sites, and/or arginine feedback resistant N-acetylglutamate synthase mutation. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine, transcarbamylase deficiency. In alternate embodiments, the disorder is a liver disorder such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency: β-oxidation deficiency; lysinuric protein intolerance: pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the hyperammonemia is associated with Huntington's disease. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia. In some embodiments, the disorder is a cancer, e.g., wherein the cancer's tumor microenvironment is associated with increased ammonia.

In some embodiments, the disclosure provides methods for treating cancer by administering engineered microorganisms, e.g., engineered bacteria, comprising a modified pks island and at least one gene for producing an anti-cancer molecule, e.g., dacA or an enzyme capable of producing a STING agonist. In some embodiments, the cancer is selected from adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hogkin lymphoma, Non-Hogkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macrogloblulinemia, and Wilms tumor.

In some embodiments, the disclosure provides methods for reducing oxalate and/or oxalic acid levels associated with HOX by administering engineered microorganisms, e.g., engineered bacteria, comprising a modified pks island and gene(s) or gene cassette(s) encoding an oxalate metabolic or oxalate catabolismenzyme. The method may comprise preparing a pharmaceutical composition with at least one genetically engineered species, strain, or subtype of bacteria described herein, and administering the pharmaceutical composition to a subject in a therapeutically effective amount. In some embodiments, the method of treating a disease or disorder associated with elevated oxalate comprises administering to a subject in need thereof an engineered bacterium comprising gene sequence(s) encoding one or more oxalate catabolism enzyme(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate transporter(s) or a pharmaceutical composition thereof. In some embodiments, the method of treating a disease or disorder associated with elevated oxalate comprises administering to a subject in need thereof an engineered bacterium comprising gene sequence(s) encoding one or more formate importers(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate: formate antiporter(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate catabolismenzyme(s) and gene sequence(s) encoding one or more of the following: (i) one or more oxalate transporter(s); (ii) one or more formate exporter(s); (iii) one or more oxalate: formate antiporter(s); and (iv) combinations thereof or a pharmaceutical composition thereof. In some embodiments, the bacterial cells disclosed herein are administered orally, e.g., in a liquid suspension. In some embodiments, the bacterial cells disclosed herein are lyophilized in a gel cap and administered orally. In some embodiments, the bacterial cells disclosed herein are administered via a feeding tube or gastric shunt. In some embodiments, the bacterial cells disclosed herein are administered rectally, e.g., by enema. In some embodiments, the genetically engineered bacteria are administered topically, intraintestinally, intrajejunally, intraduodenally, intraileally, and/or intracolically.

In some embodiments, the disclosure provides methods for reducing oxalate and/or oxalic acid levels in a subject or treating a disease associated with hyperoxaluria by administering the pharmaceutical compositions disclosed herein, e.g., genetically engineered bacteria comprising a gene encoding an oxalate catabolismenzyme. In some embodiments, the disclosure provides methods for reducing oxalate and/or oxalic acid levels in a subject or treating a disease associated with hyperoxaluria by administering the pharmaceutical compositions disclosed herein, e.g., genetically engineered bacteria comprising a oxalate catabolismenzyme and a modified pks island. The method may comprise reducing the levels of oxalate in a subject, the method comprising administering to the subject a pharmaceutical composition comprising a engineered microorganism comprising one or more gene sequences encoding one or more oxalate catabolism enzymes operably linked to a directly or indirectly first inducible promoter that is not associated with the oxalate catabolismenzyme gene in nature, thereby reducing the levels of oxalate in the subject. The method may comprise reducing the levels of oxalate in a subject, the method comprising administering to the subject a pharmaceutical composition comprising a engineered microorganism comprising a modified pks island, as disclosed herein, and one or more gene sequences encoding one or more oxalate catabolism enzymes operably linked to a directly or indirectly first inducible promoter that is not associated with the oxalate catabolismenzyme gene in nature, thereby reducing the levels of oxalate in the subject.

In some embodiments, the method involves the administration of the pharmaceutical compositions, as described herein, to reduce oxalate and/or oxalic acid levels in a subject to normal levels. In another embodiment, the pharmaceutical composition described herein is administered to reduce oxalate and/or oxalic acid levels in a subject to below a normal level. In another embodiment, the pharmaceutical composition described herein is administered to reduce the daily urinary oxalate excretion of a subject to less than 40 mg per 24 hours.

In some embodiments, the method involves the administration of the pharmaceutical compositions, as described herein, to reduce acute levels of oxalate in the subject to about 25 mg/day, about 30 mg/day, about 40 mg/day, about 50 mg/day, about 60 mg/day, about 70 mg/day, about 80 mg/day, about 90 mg/day, or about 100 mg/day. In one embodiment, the method reduces chronic levels of oxalate in the subject to about 25 mg/day, about 30 mg/day, about 40 mg/day, about 50 mg/day, about 60 mg/day, about 70 mg/day, about 80 mg/day, about 90 mg/day, or about 100 mg/day.

In certain embodiments, the method involves the administration of the pharmaceutical composition, as described herein, to reduce oxalate and/or oxalic acid levels in a subject. In some embodiments, the methods of the present disclosure reduce the oxalate and/or oxalic acid levels in a subject by at least about 10%, 20%, 25%, 30%, 40%, 50%, 60%, 70%, 75%, 80%, 85%, 90%, 95%, or more. In another embodiment, the methods of the present invention reduce the oxalate and/or oxalic acid levels in a subject by at least two-fold, three-fold, four-fold, five-fold, six-fold, seven-fold, eight-fold, nine-fold, or ten-fold. In another embodiment, the methods of the present invention reduce the daily urinary oxalate excretion of a subject to less than 40 mg per 24 hours. In some embodiments, reduction is measured by comparing the oxalate and/or oxalic acid level in a subject before and after administration of the pharmaceutical composition. In one embodiment, the oxalate and/or oxalic acid level is reduced in the gut of the subject. In one embodiment, the oxalate and/or oxalic acid level is reduced in the urine of the subject. In another embodiment, the oxalate and/or oxalic acid level is reduced in the blood of the subject. In another embodiment, the oxalate and/or oxalic acid level is reduced in the plasma of the subject. In another embodiment, the oxalate and/or oxalic acid level is reduced in the fecal matter of the subject. In another embodiment, the oxalate and/or oxalic acid level is reduced in the brain of the subject.

In one embodiment, the pharmaceutical composition described herein is administered to reduce oxalate in a subject to a normal level.

In some embodiments, the method of treating the disorder in which oxalate is detrimental, e.g., hyperoxaluria, allows one or more symptoms of the condition or disorder to improve by at least about 10%, 20%, 30%, 40%, 50%, 60%, 70%, 80%, 90%, 95%, or more. In some embodiments, the method of treating the disorder in which oxalate is detrimental, e.g., hyperoxaluria, allows one or more symptoms of the condition or disorder to improve by at least about two-fold, three-fold, four-fold, five-fold, six-fold, seven-fold, eight-fold, nine-fold, or ten-fold.

Before, during, and after the administration of the pharmaceutical composition, oxalate and/or oxalic acid levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, kidney, liver, duodenum, jejunum, ileum, cecum, colon, rectum, and anal canal. In some embodiments, the methods may include administration of the compositions disclosed herein to reduce levels of the oxalate and/or oxalic acid. In some embodiments, the methods may include administration of the compositions of the invention to reduce the oxalate and/or oxalic acid to undetectable levels in a subject. In some embodiments, the methods may include administration of the compositions of the invention to reduce the oxalate and/or oxalic acid concentrations to undetectable levels, or to less than about 1%, 2%. 5%, 10%, 20%, 25%, 30%, 40%, 50%, 60%, 70%, 75%, 80%, 85%, 90%, or 95% of the subject's oxalate and/or oxalic acid levels prior to treatment.

In some embodiments, the method involves the administration of a pharmaceutical composition comprising engineered microorganisms, e.g., engineered bacterium, as disclosed herein. The engineered microorganisms produce an oxalate catabolismenzyme under exogenous environmental conditions, such as the low-oxygen environment of the mammalian gut, to reduce levels of oxalate and/or oxalic acid in the urine, blood or plasma by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions.

In some embodiments, the method involves the administration of pharmaceutical compositions disclosed herein reduce plasma levels of oxalate will be reduced to less than 4 mg/dL. In one embodiment, the pharmaceutical compositions disclosed herein reduce plasma levels of oxalate to less than 3.9 mg/dL. In one embodiment, the pharmaceutical compositions disclosed herein reduce plasma levels of oxalate, to less than 3.8 mg/dL, 3.7 mg/dl, 3.6 mg/dL, 3.5 mg/dL. 3.4 mg/dL. 3.3 mg/dL, 3.2 mg/dL, 3.1 mg/dL, 3.0 mg/dL, 2.9 mg/dL, 2.8 mg/dL, 2.7 mg/dL, 2.6 mg/dL, 2.5 mg/dL. 2.0 mg/dL, 1.75 mg/dL, 1.5 mg/dL. 1.0 mg/dL, or 0.5 mg/dL.

In one embodiment, the subject has plasma levels of at least 4 mg/dL oxalate prior to administration of the pharmaceutical composition disclosed herein. In another embodiment, the subject has plasma levels of at least 4.1 mg/dL, 4.2 mg/dL, 4.3 mg/dL, 4.4 mg/dL, 4.5 mg/dL, 4.75 mg/dL, 5.0 mg/dL. 5.5 mg/dL, 6 mg/dL, 7 mg/dL, 8 mg/dL, 9 mg/dL, or 10 mg/dL prior to administration of the pharmaceutical composition disclosed herein.

In some embodiments, the methods disclosed herein further comprise comparing the level of the oxalate and/or oxalic acid in the plasma sample from the subject after administration of a pharmaceutical composition disclosed herein to the plasma sample from the subject before administration of a pharmaceutical composition disclosed herein. In one embodiment, a reduced level of the oxalate and/or oxalic acid in the plasma sample from the subject after administration of a pharmaceutical composition disclosed herein indicates that the plasma levels of the oxalate and/or oxalic acid are decreased, thereby treating the disorder in which oxalate and/or oxalic acid is detrimental in the subject. In one embodiment, the plasma level of oxalate and/or oxalic acid is decreased at least 10%, 20%, 30%, 40%, 50%, 60%, 70%, 80%, 90%, or 100% in the sample after administration of the pharmaceutical composition as compared to the oxalate and/or oxalic acid level in the plasma sample before administration of the pharmaceutical composition. In another embodiment, the plasma level of the oxalate and/or oxalic acid is decreased at least two-fold, three-fold, four-fold, or five-fold in the plasma sample after administration of the pharmaceutical composition as compared to the oxalate and/or oxalic acid level in the plasma sample before administration of the pharmaceutical composition.

In some embodiments, the methods disclosed herein further comprise comparing the level of the oxalate and/or oxalic acid in the urine sample from the subject after administration of a pharmaceutical composition disclosed herein to the urine sample from the subject before administration of a pharmaceutical composition disclosed herein. In one embodiment, a reduced level of the oxalate and/or oxalic acid in the urine sample from the subject after administration of a pharmaceutical composition disclosed herein indicates that the urine levels of the oxalate and/or oxalic acid are decreased, thereby treating the disorder in which oxalate and/or oxalic acid is detrimental in the subject. In one embodiment, the urine level of oxalate and/or oxalic acid is decreased at least 10%, 20%, 30%, 40%, 50%, 60%, 70%, 80%, 90%, or 100% in the sample after administration of the pharmaceutical composition as compared to the oxalate and/or oxalic acid level in the urine sample before administration of the pharmaceutical composition. In another embodiment, the urine level of the oxalate and/or oxalic acid is decreased at least two-fold, three-fold, four-fold, or five-fold in the urine sample after administration of the pharmaceutical composition as compared to the oxalate and/or oxalic acid level in the urine sample before administration of the pharmaceutical composition.

In some embodiments, the method of treatment comprises administering engineered microorganisms, e.g., engineered bacteria comprising a modified pks island and optionally a therapeutic molecule as disclosed herein, compositions or formulations thereof, wherein the composition or formulation comprises 1-20% trehalose, 1-10% trehalose, 5-15% trehalose, 7-13% trehalose, 9-11% trehalose, or about 10% trehalose in a biological buffer covering a pH range of 6-8, where the biological buffer may be PIPES, MOPS, HEPES, and/or Tris buffer. In some embodiments, the composition or formulation comprises 1-400 mM Tris buffer. In some embodiments, the composition or formulation comprises 1-300 mM Tris buffer. In some embodiments, the composition or formulation comprises 1-200 mM Tris buffer. In some embodiments, the composition or formulation comprises 1-100 mM Tris buffer. In some embodiments, the composition or formulation comprises 1-50 mM Tris buffer. In some embodiments, the composition or formulation comprises 1-10 mM Tris buffer. In some embodiments, the pharmaceutical composition comprises lyophilized bacteria. In some embodiments, the percent water content of the lyophilized bacteria is approximately 1-10%. In some embodiments, the percent water content is approximately 3-8%. In some embodiments, the percent water content is approximately 3-6%. In some embodiments, the percent water content is approximately 3-5%. In some embodiments, the percent water content is approximately 3%, approximately 4%, or approximately 5%.

Exemplary diseases, disorders, and methods of treatment are provided in WO2016090343, WO2016200614, WO2017139697, WO2016183531, WO2017087580, WO2016141108, WO2017074566, WO2017136792, WO2017136795, WO2018129404, WO2019014391, WO2016210384, WO2017123418, WO2017123676, WO2016183531, WO2018237198, WO2016201380, US20170216370, and WO2017040719, the contents of which are hereby incorporated by reference in their entirety The disclosure also provides methods of assessing colibactin production and pks island activity, e.g., by measuring colibactin precursor(s) or metabolite(s). In some embodiments, the method of assessing colibactin levels comprises detecting N-myristoyl-D-asparagine. In some embodiments, N-myristoyl-D-asparagine is detected using mass spectrometry, e.g., quantitative LC-MS/MS.

EXAMPLES

Example 1

Pharmacokinetic Profile of Δpks Strain in Mouse

Figure 3A:
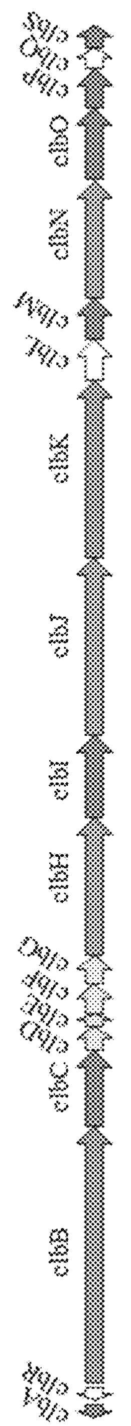
FIGS. 3A and B show schematics of an exemplary pks island.
Figure 3B:
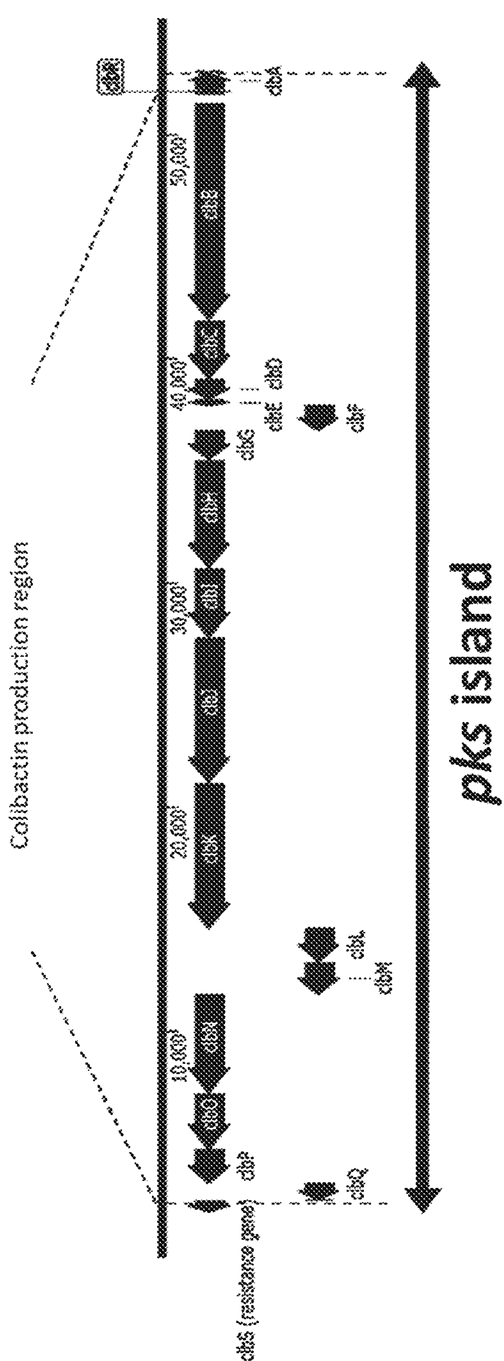
FIG. 3B depicts an exemplary deletion. The deletion is demarcated by dashed lines.
Figure 6:
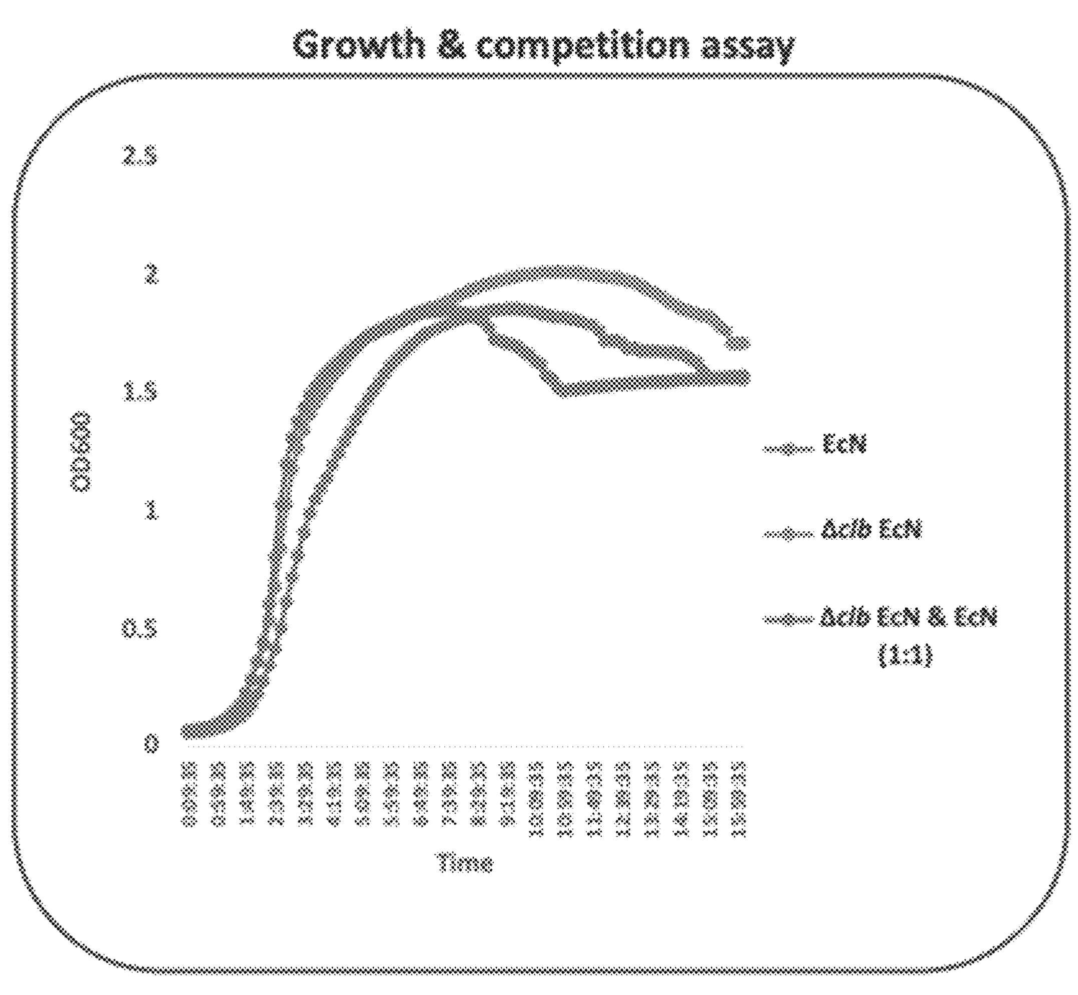
FIG. 6 shows in vitro growth and competition rates for an exemplary Δpks strain (deleted clbA-clbR gene and promoter sequences, intact clbS gene sequence with the operably linked promoter deleted; called Δclb here (Δclb in this figure refers to the deletion of all genes required for production of colibactin).

A Δpks *E. coli* Nissle (EcN) strain was generated by deleting the clb sequences of the clbA-R genes and operably linked promoters; the clbS gene sequence was unmodified (intact), but its operably linked promoter was deleted (FIG. 3B). The constructs were generated using lambda red methods as previously described. See, e.g., PCT/US2016/032562, the contents of which is herein incorporated by reference in its entirety. The pharmacokinetic profile of a Δpks strain was investigated in naïve healthy mice and in mice pre-treated with Streptomycin, an aminoglycoside antibiotic that binds to the bacterial 30S ribosomal subunit and impairs protein synthesis, hence abolishing mouse GI-resident flora survival and growth.

The day prior to strain dosing, female wild-type C57BL/6j mice were labelled and identified with tail markings, and separated into experimental groups (Table A) based on body weight. Strep-water was made by dissolving 5 g Streptomycin in 1 L of Reverse-Osmosis (RO) water, and provided ad-libitum in drinking bottles to mice in Group 2. The following day, subgroups of mice received an oral gavage (PO dose) of 1e+10 EcN cells (either WT, Δpks or combination of both) or vehicle (Table A).

TABLE A

Mouse Study Design

| Experimental groups | Treatment | No. Animals per group | PO dose volume | CFU dose |
|---|---|---|---|---|
| GROUP 1 | Vehicle | 5 | 150 uL | N/A |
| (Normal water) | WT EcN | 5 | 150 uL | 1e+10 |
| | Δpks EcN | 5 | 150 uL | 1e+10 |
| GROUP 2 | Vehicle | 5 | 150 uL | N/A |
| (Strep-water) | WT EcN + Δpks EcN (COMBO) | 5 | 300 uL total (150 uL per strain) | 1e+10 |

The mice were then placed into clean cages to avoid excremental cross-contamination. Fecal pellets were collected fresh by free-catch at different time points (1, 3, 6, 24, 48, 72 hours post-dose) by holding the animals over a pre-weighed Bead Beater collection tube. Pellets were then processed for CFU plating within one hour of collection, via homogenization in 500 μl of PBS with FastPrep 24 at the speed of 4 m/s for 10 seconds. Ten microliters of eight serial 1-to-10 dilutions of the homogenate were row-plated in triplicate on petri dishes of LB agar containing antibiotics selective for each strain. Specifically, fecal samples were plated on Strep-300, Kan-100 or Strep-300 & Kan-100 plates, according to whether they were obtained from mice in the WT EcN, Δpks EcN, or vehicle and combo WT+ Δpks EcN group, respectively. Plates were incubated overnight at 37° C. to allow clonogenic growth of antibiotic-resistant cells. CFUs were counted the following day and normalized to the weight (g) of the fecal pellets previously collected. In naïve healthy mice (GROUP 1), both non-engineered (WT) and Δpks EcN cells completed fecal transition and excretion by 72 hrs post-dose, as indicated by the absence of CFUs at the 72 hrs collection time point (FIG. 1A). Also, Δpks and WT EcN cells showed comparable viability, as measured by the number of CFUs retrieved in fecal samples from early time points (FIG. 1A). In mice with eradicated resident enteric bacteria (GROUP 2), where WT and Δpks strains were co-dosed, the CFU recovery of non-engineered versus Δpks cells was indistinguishable across all time points, pointing at a non-observable competitive disadvantage in viability for Δpks EcN (FIG. 1B).

Example 2

Pharmacokinetic Profile of Δpks Strain in Non-Human Primate (NHP).

The Δpks EcN strain described in Example 1 (deleted clbA-clbR gene and promoter sequences, intact clbS gene sequence with the operably linked promoter deleted) was administered to non-human primate. The pharmacokinetic profile of the Δpks strain described above was investigated in our colony of non-naïve male Cynomolgus Macaque, hosted at the Charles River Laboratories. Six monkeys with body weight not exceeding 5 Kg, received subsequent oral gavages of Sodium Bicarbonate (5 mL), a combination of equally numbered WT EcN and Δpks EcN cells in the total amount of 1e+12 (10 mL), and water to flush residues from the syringe.

The urine and fecal pans were cleaned and changed 3-hours prior to each fecal collection. Fecal collections occurred over a 3-hour period per time-point to allow time for the animals to defecate. Collections time points were: 6-hours (T3-6), 24-hours (T21-24), 48-hours (T45-48), 72-hours (T69-72), 96-hours (T93-96), and 120-hours (T117-120) post dose. Fecal samples were weighted, packaged in ice and shipped immediately to Synlogic. Samples were homogenized in Bead Beater containing 1 ml of PBS with FastPrep 24 at the speed of 4 m/s for 40 seconds and plated according to the methodology described above (Pharmacokinetic in mouse). CFUs were counted after the overnight incubation at 37° C. No significant difference in CFU recovery was observed across time points, and by day 5 no CFUs were retrieved in the fecal homogenates plated to selectively support the growth of each single strain (FIG. 2). Thus, we concluded that both non-engineered (WT) and Δpks EcN have a similar excretion and viability profile.

Example 3

In Vitro Activity Profile of Δpks Strains Expressing Phenylalanine Ammonia Lyase The Δpks EcN strain described in Example 1 (deleted clbA-clbR gene and promoter sequences, intact clbS gene sequence with the operably linked promoter deleted) and further comprising gene sequences encoding phenylalanine ammonia lyase (PAL), e.g., wild-type PAL from *Photorhabdus luminescens* (stlA) or mutant PAL (mPAL1) described herein. Exemplary PAL enzymes are also described in PCT/US2016/032562 filed May 13, 2016, the contents of which is herein incorporated by reference in its entirety. Degradation of phenylalanine by PAL results in the production of hippuric acid. Levels of hippurate production were measured to assess effects of Δpks on strain activity. SYNB 1618 and SYNB1618 are parental strains having intact clb sequences. SYN8260 and SYN8261 are clones derived from parental clone SYNB1618 and having Δpks. SYN8256 is a clone derived from parental clone SYNB 1934 and having Δpkspks.

To measure PAL activity from activated cells, frozen cell aliquots were thawed and diluted 1000× to measure cell density (OD) at absorbance of 600 nm. Using the OD values generated, cells were diluted to 10 OD in M9 buffer. For the assay, cells were further diluted to 1 OD in the assay buffer (M9 with 40 mM Phenylalanine) to a final volume of 1 mL and incubated without shaking at 37° C. for 2 hours in a 96-deep well plate. At 0, 30, 60, 90, and 120 minutes, 150 μL of the samples were collected in a v-bottom 96-well plate and centrifuged at 4000 rpm for 2 minutes. Aliquots of the supernatants (100 μL) were transferred to a clear flat-bottom 96-well plate for TCA measurement at 290 nm absorbance. A synergy neo microplate reader was used to measure absorbance at 600 and 290 nm.

Figure 7:
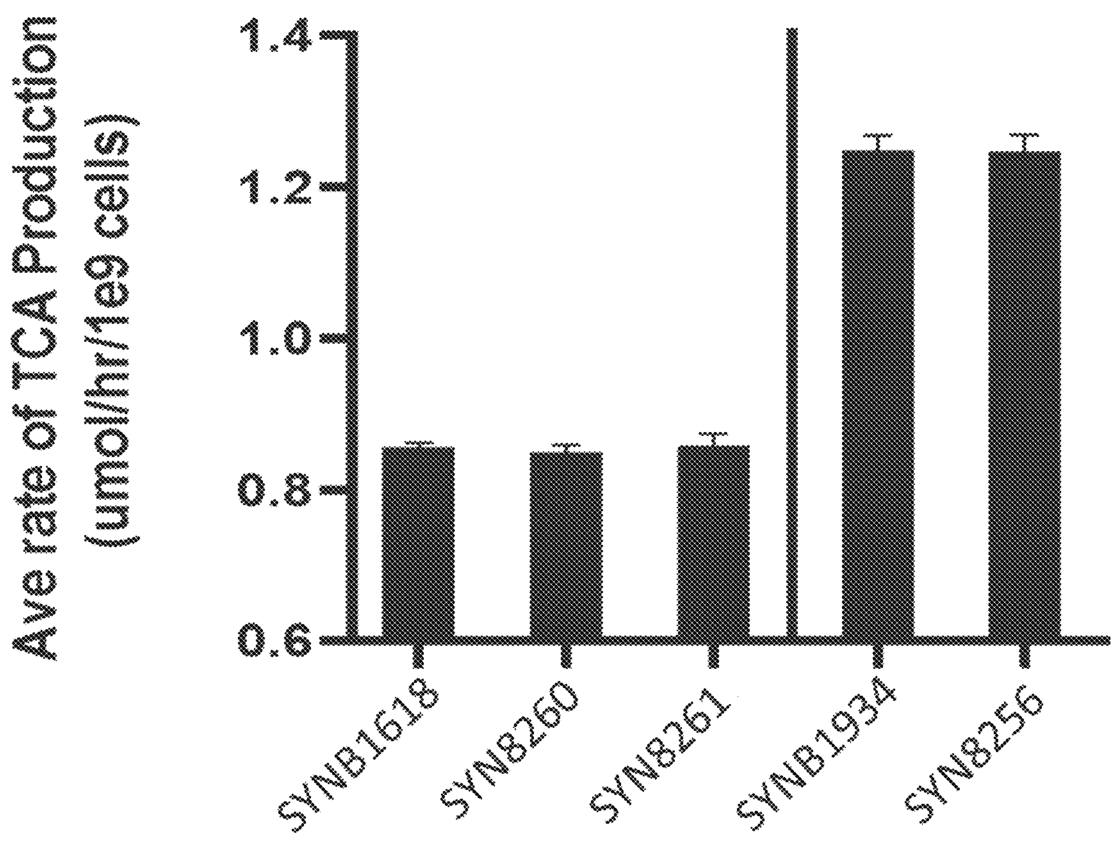
FIG. 7 depicts a bar graph showing the average rate of in vitro TCA production in bacterial supernatants of parental strains SYNB1618 and SYNB1934 having intact clb sequences and in SYNB1618- and SYNB 1934-derivative strains having a Δpks deletion. SYN8260 and SYN8261 are clones derived from parental clone SYNB1618 and having Δpks. SYN8256 is a clone derived from parental clone SYNB1934 and having Δpks.

TCA standards were prepared in the assay buffer with the following concentrations: 0.625, 0.313, 0.156, 0.078, 0.039, 0.02, and 0.01 mM. A standard curve was generated with absorbance values at 290 nm for each of the concentrations and was used to convert absorbance values to mM TCA produced during the assay. TCA production rates were calculated using the quantity of TCA calculated for each of the 0-, 30-, 60-, 90-, and 120-minutes time points, and normalized by 1E9 cells/mL (assuming 1 OD=1E9 cells) per hour. Final TCA production values were reported as μmol/hr/1E9 cells. Results are shown in FIG. 7 and indicate that colibactin knock-out strains exhibit no loss in TCA production as compared to their parental strains.

Example 4

In Vitro Production of Colibactin

To confirm that Δpks deletions abrogated colibactin production, ability of strains having the Δpks deletions to produce colibactin was assessed. Colibactin is volatile and cannot be directly detected. A surrogate assay to assess colibactin levels was conducted, in which levels of colibactin precursor are measured. Colibactin precursor is metabolized by ClbP to colibactin and N-myristoyl-D-asparagine in a 1:2 ratio and N-myristoyl-D-asparagine is measured in bacterial supernatant by LC-MS/MS.

Figure 8:
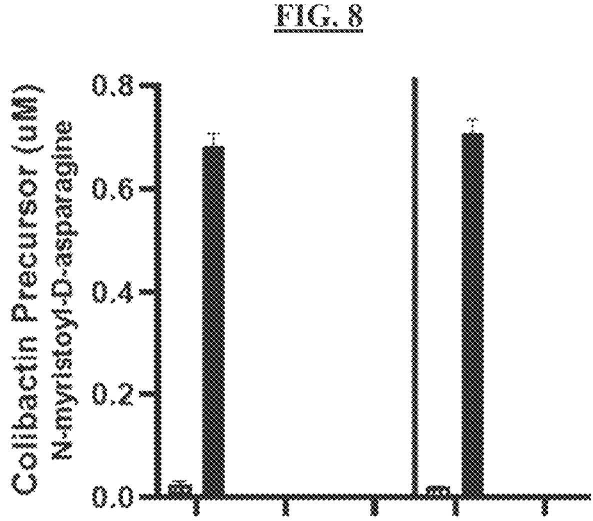
FIG. 8 depicts a graph showing levels of a precursor of colibactin present in supernatants from overnight cultures and shake flask cultures of parental strains SYNB1618 and SYNB1934, having intact clb sequences, and SYNB1618 and SYNB1618-derivative strains having a Δpks deletion.
Figure 10:
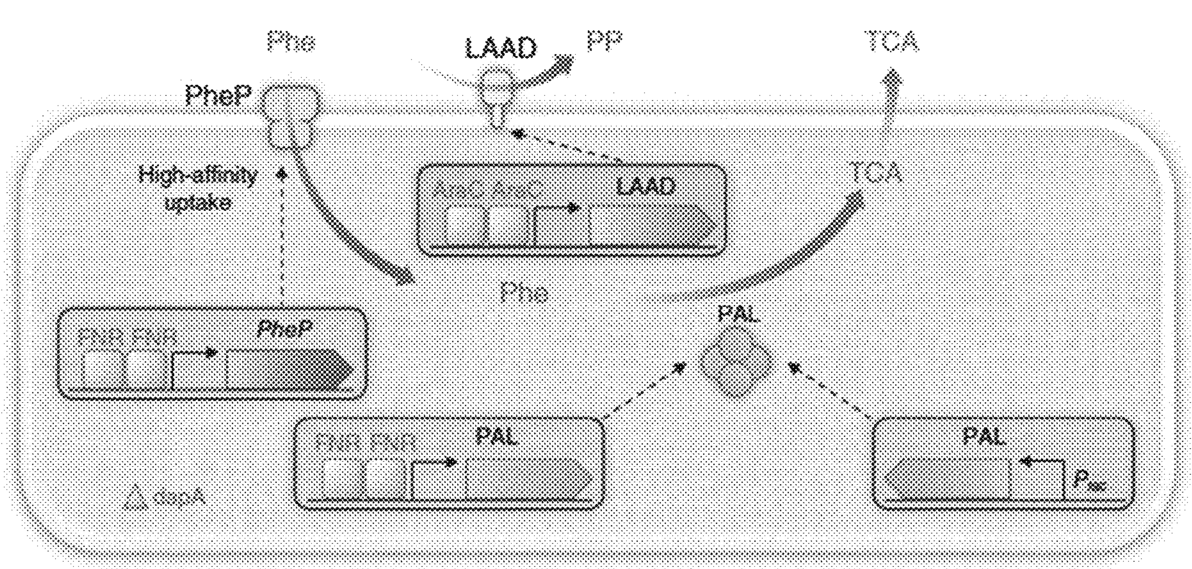
FIG. 10 depicts exemplary genetically engineered bacterium SYNB1618 for reducing hyperphenylalaninemia and treating disorders characterized by hyperphenylalaninemia.
Figure 11:
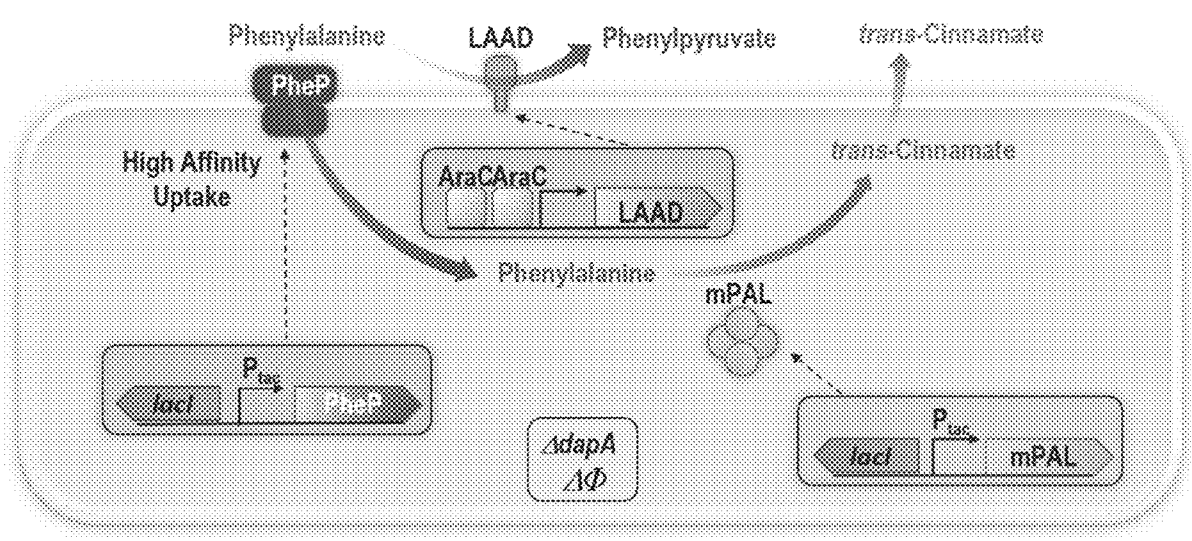
FIG. 11 depicts exemplary genetically engineered bacterium SYNB1934 for reducing hyperphenylalaninemia and treating disorders characterized by hyperphenylalaninemia.

In brief, N-myristoyl-D-Asparagine was quantitated in bacterial supernatant by LC-MS/MS using a Thermo Vanquish UHPLC-Altis TSQ MS system. Standard was prepared at concentrations from 0.032 to 20 μg/mL in 80% acetonitrile. Samples were extracted with acetonitrile to 80%. Two microliters were injected onto a Thermo Hypersil Gold 5 μM C18, 2.1×100 mm column using 0.1% formic acid (A) and acetonitrile with 0.1% formic acid (B) at 0.4 mL/min and 40° C. Analytes were separated using a gradient from 30 to 98% B over 2 minutes followed by wash and equilibration steps. Compounds were detected by tandem mass spectroscopy with selected reaction monitoring in electrospray negative ion mode using the N-myristoyl-D-asparagine specific collision induced mass transitions: 343/211, 343/326, 343/133. Peak areas of the 343/211 ion pair were used to calculate unknown concentrations against the standard calibration curve. Results are shown in FIG. 8 and demonstrate that colibactin precursor production was eliminated in SYNB1618Δclb and. SYNB1934Δclb strains.

Example 5

Activity of a Δpks Strain Following Administration to Non-Human Primates

The objective of this study was to evaluate the pharmacokinetics following oral administration innon-human primates. The experimental design is shown in Table 4.

TABLE 4

Experimental Design

| Group | No. Animals | Treatment | Dose Volume (mL) | Dose Regimen |
|---|---|---|---|---|
| 1 | 6 | Peptone | 6.1 | PO |
| | | Sodium bicarbonate | 5 | |
| | | D5-Phe | 7.7 | |
| | | SYN8256 | 3 | |
| 2 | 6 | Peptone | 6.1 | |
| | | Sodium bicarbonate | 5 | |
| | | D5-Phe | 7.7 | |
| | | SYNB1934 | 3 | |

Administration of Treatment

Test Articles were administered to the appropriate animals by oral gavage on Day 1. Dose formulations were administered by oral gavage using a disposable catheter attached to a plastic syringe. Following dosing, the gavage tube was rinsed with 5 mL of the animal drinking water, into the animal's stomach. Each group was dosed with a clean gavage tube. The first day of dosing was designated as Day 1. Animals were fasted overnight the day before dosing (Day-1). Peptone was provided at 3.05 grams and was chosen because it simulates a low-protein diet in humans and allows detection of Phe in the blood after feeding and metabolites of Phe in the urine. NHPs were dosed with 10e11 bacteria. D5-Phe (20 mg/mL) was dispensed for all animals on Day 1. The in-life procedures, observations, and measurements were performed for all animals, including alternates as applicable. Food was returned following the final blood collection.

Sample Collection and Processing

Blood was collected by venipuncture from an appropriate peripheral vein on Day 1 at 0 hr pre-dose, and at 30 min, 1 hr, 2 hr, 4 hr, and 6 hr post-dose for bioanalysis. After collection, samples were transferred to the appropriate laboratory for processing and stored at −80° C. Samples were collected according to the following table. On Day 1, prior to dosing, a clean collection pan was inserted to assist in urine collection at room temperature. At conclusion of 6 hours post-dose, the total amount of urine was measured and recorded. Urine samples were collected and immediately frozen on dry ice. Target volume was 1 mL and the anticoagulant was heparin (sodium). Samples were placed on crushed wet ice until centrifugation. The samples were centrifuged as per standard procedures. The resultant plasma was separated, transferred in two aliquots and immediately frozen on dry ice and stored at −80° C.

Phe, d5-phe, TCA, d5-TCA, HA, d5-HA, creatinine Quantitation in NHP plasma or urine by LC-MS/MS Phenylalanine, d5-phenylalanine, trans-cinnamic acid and d5-trans-cinnamic acid in NHP plasma as well as hippuric acid, d5-hippuric acid and creatinine in NHP urine were quantitated in nonhuman primate urine by LC-MS/MS using a Thermo Ultimate 3000 UHPLC-TSQ Quantum MS system. Standard solutions from 0.16 to 250 μg/mL were made in water. Neat plasma, 40 fold diluted urine, and standards in water were derivatized with 50 mM each of 2-hydrazinoquinoline, dipyridyl disulfide, and tripheylphospine in acetonitrile containing 1 μg/mL 13C915N-phenylalanine and d5-creatinine as internal standards and incubated at 60° C. for one hour. Following derivatization, 20 μL of standards and samples were diluted with 180 μL 0.1% formic acid/acetonitrile (140:40). Ten microliters were injected onto a Phenomenex Luna 5 μm C18 (2) 100A, 100×2 mm column using 0.1% formic acid (A) and acetonitrile with 0.1% formic acid at 0.5 mL/min after an initial 10% B hold for 0.5 minutes using a gradient from 10 to 97% B over 1.5 minutes followed by wash and equilibration steps. Compounds were detected by tandem mass spectroscopy with selected reaction monitoring in electrospray positive ion mode using the following ion pairs: Phenylalanine 307/186, d5-phenylalanine 312/186, trans-cinnamic acid 290/131, d5-trans-cinnamic acid 295/136, hippuric acid, 321/160, d5-hippuric acid 326/160, 13C9 15N-phenylalanine 317/187, creatinine 114/44, d5-creatinine 119/49. Chromatograms are integrated and analyte/internal standard peak area ratios were used to calculate unknown concentrations.

Example 6

In Vitro Activity Profile of Δpks Strains Comprising a Gene Expression System for the Degradation of Oxalate The Δpks EcN strain described in Example 1 (deleted clbA-clbR gene and promoter sequences, intact clbS gene sequence with the operably linked promoter deleted) is engineered to further comprise an expression systems for the degradation of oxalate, as described in PCT/US2016/049781 filed Aug. 31, 2016, the contents of which is herein incorporated by reference in its entirety, to assess the effect of Δpks on the ability of the strains to consume oxalate.

Strains are grown in shake flasks and subsequently activated in an anaerobic chamber followed by concentration and freezing at ≤−65° C. in glycerol-based formulation buffer (PBS+25% Glycerol). In assay media containing 10 mM oxalate, activated cells are resuspended to OD600=5 and incubated statically at 37° C. Supernatant samples are removed at 30 and 60 min to determine the concentrations of oxalate. Concentrations are determined by liquid chromatography-tandem mass spectrometry (LC-MS/MS).

Oxalate is quantitated in bacterial supernatant by LC-MS/MS using a Thermo Vanquish UHPLC-Altis TSQ MS system. Standards are prepared at 0.8 to 1000 μg/mL in water. Samples and standards are diluted ten-fold with 10 mM ammonium acetate that includes 1 μg/mL 13C2-oxalate as an internal standard. Ten microliters are injected onto a Waters Acquity HSS T3 1.8 μm 100A 2.1×100 mm column using 10 mM ammonium acetate (A) and methanol (B) at 0.4 mL/min and 50° C. Analytes are separated after an initial 100% A hold for 0.5 minutes using a gradient from 0 to 95% B over 1.5 minutes followed by wash and equilibration steps. Compounds are detected by tandem mass spectroscopy with selected reaction monitoring in electrospray negative ion mode using the following ion pairs: Oxalate 89/61, 13C2-oxalate 91/62. Chromatograms are integrated and oxalate/13C2-oxalate (analyte/internal standard) peak area ratios are used to calculate unknown concentrations.

Example 7

Pharmacodynamics of a Δpks Strain Capable of Catabolizing Oxalate Following Administration to Non-Human Primates The in vivo activity of a Δpks EcN strain, e.g., as described in Example 1, engineered to further comprise an expression system for the degradation of oxalate, as described in Example 6, was compared to a strain comprising the expression system for the degradation of oxalate but not the Δpks deletion.

In vivo activity single dose cross-over studies were performed to assess the ability of the strains to metabolize gastrointestinal and diet-derived oxalate and 13 C2-oxalate in a nonhuman primate model of acute hyperoxaluria. Urinary recovery of oxalate and 13 C2-oxalate was significantly decreased regardless of the presence of the pks deletion, as compared to vehicle control, indicating that both strains are capable of consuming oxalate in nonhuman primates with acute hyperoxaluria. Results are shown in Table 5 and Table 6.

TABLE 5

| Percent change in Urine Oxalate as compared to vehicle control | | |
|---|---|---|
| Strain | Timepoint | % change as compared to vehicle |
| SYNB8802 | 6 h | 73% |
| SYNB8802v1 (SYNB8802, further having Δpks) | 8 h | 65% |

TABLE 6

| Percent change in Urine 13 C2-oxalate as compared to vehicle control | | |
|---|---|---|
| Strain | Timepoint | % change as compared to vehicle |
| SYNB8802 | 6 h | 75% |
| SYNB8802v1 (SYNB8802 further having Δpks) | 8 h | 82% |

Exemplary Sequences

```
>Brevibacterium_aurantiacum_MGL-SEQ ID NO: 101
ATGACGAGCCTTCACCCCGAAACTTTAATGGTGCACGGGGGTATGAAGGGATTGACAGAGG
CGGGTGTTCACGTCCCGGCGATCGACCTGTCGACAACGAATCCTGTTAATGACGTAGCGACA
GGGGGTGATTCTTACGAATGGCTTGCAACGGGTCACACGTTGAAGGATGGTGATTCTGCTGT
TTACCAGCGTTTATGGCAGCCCGGTGTAGCTCGTTTCGAGACGGCTCTGGCTGGGCTGGAGC
ACGCGGAGGAGGCTGTAGCTTTCGCCACGGGTATGGCCGCCATGACCGCGGCCTTATTGGCA
GCAGTATCAGCTGGCACGCCTCATATCGTCGCAGTCCGCCCATTATACGGCGGTTCAGACCA
TCTTTTAGAGACTGGTTTACTGGGGACAACTGTCACGTGGGCGAAAGAAGCTGACATCGCCA
GTGCAATCCAAGACGATACAGGGTTAGTGATCGTGGAGACGCCAGCCAATCCTAGTCTTGAT
CTGGTAGACCTGGATTCTGTCGTGTCAGCGGCAGGGAACGTCCCTGTCCTTGTAGATAATAC
GTTTTGTACTCCTGTCCTTCAGCAACCTATCTCGCACGGCGCCGCACTTGTATTACATTCGGC
AACAAAGTATTTAGGGGGGCATGGGGACGCCATGGGCGGGATCATCGCGACTAATGCTGAT
TGGGCTATGCGCCTGCGTCAGGTCCGTGCGATCACTGGTGCATTACTGCATCCGATGGGCGC
GTACTTGTTACACCGCGGTTTGCGTACTCTGGCTGTTCGCATGCGTGCCGCTCAGACAACTGC
TGGTGAGCTTGCTGAGCGCTTAGACGCTCATCCCGCTATTTCAGTTGTGCACTACCCAGGATT
GAAGGGGCAAGATCCTCGTGGATTGTTAGGCCGTCAGATGAGTGGAGGTGGGGCAATGATT
GCTATGGAGCTGGCAGGGGGATTCGATGCGGCACGCTCCTTTGTTGAGCATTGTAACTTGGT
CGTGCATGCCGTATCACTTGGGGGAGCAGACACATTAATTCAACATCCGGCAAGTTTGACAC
```

-continued

| Exemplary Sequences |
|---|

ACCGCCCGGTCGCAGCAACCGCCAAGCCTGGTGATGGTTTGATCCGCTTGAGCGTGGGGCTT
GAGCACGTTGACGACTTGGCCGATGACTTGATCGCTGCTTTGGACGCCTCTCGCGCTGCTGC
ATGA

>Citrobacter_freundii_MGL-SEQ ID NO: 102
ATGTCTGATTGTCGTGCCTACGGCTTTAACACACAGATCGTCCACGCCGGACAACAACCGGA
CCCAAGCACTGGTGCATTGTCGACGCCAATCTTTCAGACTTCTACTTTCGTTTTCGATTCGGC
AGAACAGGGGGCCGCACGTTTCGCGTTGGAGGAACCGGGATACATCTATACGCGCTTGGGC
AATCCAACTACTGATGCGCTTGAAAAGAAACTTGCAGTGCTGGAACGTGGGGACGCGGCGT
TAGCCACAGCGAGCGGCATCTCCGCTATTACCACAAGTCTTCTTACTCTTTGCCAGCAAGGG
GACCATATCGTATCAGCTAGTGCAATCTACGGTTGCACTCACGCATTCTTAAGTCATTCGCTT
CCTAAATTTGGCATTAACGTTTCATTCGTCGACGCAGCGAAGCCCGAAGAAATCCGCGCCGC
CATGCGTCCAGAGACAAAAGTGGTATATATCGAGACGCCCGCGAACCCTACTTTATCCTTAG
TGGATATTGAGACTGTTGCTGGAATCGCGCACCAGCAAGGAGCCTTGTTAGTCGTGGACAAC
ACTTTTATGTCTCCGTATTGTCAACAACCATTACTGCTGGGTGCTGACATCGTGGTCCATAGT
GTTACCAAGTACATTAACGGGCATGGGGATGTTATTGGCGGTGTCATCGTAGGTAAACAGGA
GTTCATCGACCAAGCACGCTTTGTGGGATTAAAGGACATTACGGGCGGATGCATGAGCCCCT
TTAATGCATGGCTGACACTTCGCGGGGTAAAGACGTTAGGGATCCGTATGGAGCGTCATTGC
GAAAACGCATTGAAAATCGCGCGTTTTCTTGAGGGCCATCCTGCTATTACACGTGTCTATTAT
CCTGGATTGCCGTCACACCCCCAATACGAACTTGGGAAGCGCCAAATGTCGCTTCCTGGGGG
AATCATTTCGTTTGAAATTGCTGGTGGCCTTGAAGCAGGTCGCCGTATGATTAACAGCGTGG
AGTTATGTTTGCTGGCAGTTAGCTTAGGTGATACGGAGACGTTGATTCAGCATCCGGCGAGC
ATGACACATTCCCCTGTTGCTCCCGAGGAGCGTCTGAAGGCTGGCATCACTGATGGACTGAT
CCGTTTGTCCGTCGGCCTTGAAGATCCGGAAGACATCATTAACGACCTGGAGCACGCCATTC
GCAAGGCAACGTTTtaa >Porphyromonas_gingivalis_MGL-SEQ ID NO: 103
ATGAAGAAAGAGGACTTAATGCGTTCGGGGTTCGCAACTCGTGCTATTCATGGTGGAGCCAT
CGAAAATGCTTTTGGGTGCCTGGCCACCCCCATCTACCAAACTTCAACGTTTGTTTTCGATAC
GGCTGAACAGGGTGGACGTCGCTTTGCGGGTGAAGAAGATGGGTACATTTACACTCGCTTAG
GAAACCCGAACTGTACCCAGGTTGAGGAGAAGCTGGCGATGTTAGAAGGAGGGGAAGCAG
CGGCCTCCGCAAGTAGTGGTATCGGAGCGATCTCTTCAGCTATCTGGGTGTGCGTCAAGGCG
GGAGATCATATTGTAGCGGGAAAAACTTTGTACGGTTGCACGTTTGCGTTCTTGACCCACGG
ACTTTCTCGCTATGGAGTTGAGGTCACCTTGGTGGACACGCGCCATCCAGAAGAGGTTGAGG
CCGCTATTCGTCCAAACACTAAGTTGGTCTATTTGGAAACTCCCGCAAACCCTAACATGTAC
CTTACTGATATCAAAGCTGTGTGTGATATCGCGCACAAGCATGAGGGTGTTCGCGTCATGGT
GGATAATACCTACTGTACACCTTACATCTGTCGCCCACTGGAGTTAGGTGCTGATATTGTTGT
CCATTCCGCCACAAAATATCTGAACGGACATGGAGATGTTATCGCTGGGTTTGTAGTAGGGA
AAGAGGATTACATCAAGGAGGTCAAATTGGTTGGTGTTAAGGACTTGACAGGAGCCAATAT
GTCACCCTTCGACGCATACCTTATTAGTCGTGGTATGAAGACGTTACAAATCCGTATGGAAC
AACATTGCCGTAACGCACAAACAGTTGCTGAGTTTCTGGAGAAGCATCCTGCGGTTGAGGCG
GTGTACTTCCCGGGCTTGCCTTCATTCCCGCAATATGAGTTGGCCAAGAAGCAGATGGCACT
TCCGGGAGCGATGATTGCGTTTGAAGTTAAGGGAGGCTGCGAAGCCGGTAAGAAACTTATG
AACAATCTTCATCTGTGTTCCTTAGCCGTCTCCTTAGGCGATACCGAGACTTTAATCCAACAC
CCGGCCTCAATGACGCACTCGCCCTATACGCCCGAGGAACGCGCCGCAAGCGACATCTCGG
AGGGGCTTGTACGCCTTTCTGTTGGATTGGAAAATGTTGAGGATATTATCGCGGACCTGAAG
CATGGCCTGGATAGTCTTATCtaa >Streptomyces_sp590_MDC-SEQ ID NO: 104
ATGTCCCCGACGGCGTTTCCAGCGGCCGAAACAGCTACTGCCCCTGCAACTGCCGTCGAT
CCTGGGCCAGAACTGGACGGCGGAGATTTCGCCCTTCCAGAGGGCGGGCTGGATGACGATC
GTCGCTTACGTGCATTGGACGCAGTTGACGAGTATTTGACCCGCAAGCGCAAGCATTTGGTT
GGGTACCAAGCTACCCAGGATATGCAGGGAACGGCCTTGGATTTAGCCCGTTTCATGCCCAA
CAACATCAACAACCTGGGAGATCCTTTCCAGTCGGGTGGGTATAAACCAAATACGAAAGTC
GTTGAGCGTGCCGTACTGGACTACTATGCAAAATTGTGGCACGCAGAACGTCCACACGACCC
AGCTGACCCAGAAAGCTACTGGGGTTACATGTTATCGATGGGCTCAACTGAGGGCAACATGT
ACGCCCTGTGGAATGCACGTGACTACCTGTCGGGTAAGGCTTTGATTCAGCCTCCCACGGCA
CCATTTGACGCTGTTCGCTACGTGAAGGCTGACCCCGATCGCCGCAATCCTAACGCACACCA
CCCAGTCGCATTCTACTCGGAGGATACCCACTATTCTTTTGCTAAAGCCGTTGCGGTGCTGGG
TGTCGAAACTTTCCACGCTGTGGGTCTGGAGAAATACGCTGACGAGTGCCCCTTGGTGGATC
CAGTAACCGGCCTTCGTACCTGGCCGACCGAAGTTCCATCGCGCCCGGGGCCGTCGGGTTTA
AGCTGGGACGGCCCTGGTGAGATTGATGTTGATGCGCTTGCAGTACTGGTCGAGTTCTTCGC
AGCGAAGGGTCACCCCGTCTTCGTCAACCTTAACTTGGGGTCTACATTTAAAGGAGCACATG
ATGACGTACGTGCGGTATGTGAACGCTTATTACCAATCTTCGAGCGCCATGGCTTAGTACAA
CGTGAAGTTGTATATGGGAGCTGTCCCCAAACCGGCCGCCCTTTAGTGGATGTACGTCGCGG
ATTTTGGATCCACGTAGATGGGGCACTTGGGGCGGGGTATGCCCCTTTTCTGCGTCTTGCCGC
CGAAGACCCGGAAGGTTATGGTTGGACCCCTGAGGCAGAATTACCTGAGTTCGACTTCGGCT
TACGTTTGCCGACGGCGGGGCATGGAGAAGTTGATATGGTTAGCAGCATCGCCATGAGTGG
ACATAAGTGGGCAGGCGCGCCGTGGCCATGCGGCATCTATATGACGAAAGTGAAATATCAG
ATTAGTCCACCGTCACAGCCCGATTATATTGGTGCTCCTGACACAACATTTGCCGGTTCCCGT
AACGGCTTTTCGCCGTTAATTTTGTGGGATCATTTATCGCGCTACTCGTACCGCGACCAGGTA
GAGCGCATCCGCGAAGCACAGGAGCTTGCAGCATATTTGGAACGCCGCCTTACCGCTATGG
AGCGCGAGCTGGGAGTGGAACTTTGGCCAGCCCGCACACCGGGTGCTGTAACCGTACGTTTT
CGCAAACCCTCTGCTGAGCTGGTTGCGAAGTGGTCCTTGTCGTCGCAGGATGTTTTAATGGT
GCCGGGTGATGAAACTACGCGTCGTAGTTACGTTCATGTGTTCGTGATGCCTTCTGTTGATCG
TGCAAAGTTAGATGCGTTGCTGGCAGAATTGGCCGAAGATCCCGTCATCTTGGGTGCGCCTta
a Exemplary Sequences ABC transporter from EcN-MetNIQ
>MetN-SEQ ID NO: 105
Atgataaaactttcgaatatcaccaaagtgttccaccagggcacccgcaccatccaggcgttgaacaacgtcagcctgcatgtgccagctggacaaattt
atggcgttatcggtgcctcaggcgcgggtaagagtacgcttatacgttgtgtaaacctgctggagcgcccaaccgagggtagcgtgctggtcgatggcc
aggaactgaccacgctgtcagaatccgagttgaccaaagctcgtcgccagattggtatgatttttccagcattttaacctgctctcttcgcgtactgtttttggc
aacgtggctctgccgctggagctggacaacacaccgaaagacgagatcaaacgtcgcgtgacggaattgctgtcattggttggtcttggcgataagcat
gatagctacccgtcgaatctttccggtgggcagaaacaacgtgtggcgattgcccgtgcattagccagcaatcccaaagtattgctgtgtgatgaagccac
cagcgcgctggacccggcaacgacacgttctattctcgaactgctgaaagacatcaaccgccgtctgggtttgacgattctgttgatcactcacgaaatgg
acgttgtgaagcgcatttgtgattgcgtggcggtcatcagcaatggcgaactgatcgagcaggacacggtaagtgaagtgttctcgcatccgaaaacgcc
gctggcgcagaagtttattcagtcgaccctgcatctggatatcccggaagattaccaggaacgtctgcaagcggagccatttactgactgcgtgccgatg
ctgcgtctggagtttaccggtcaatcggtcgatgccccactgctttctgaaaccgcgcgtcgtttcaacgtcaacaacaacattattagcgcgcagatggat
tacgccggtggcgttaagttcggcatcatgctgactgaaatgcacggcacacaacaagatacgcaagccgccattgcctggctgcaggaacaccatgta
aaagtagaggtactgggttatgtctga >MetI-SEQ ID NO: 106
Atgtctgagccgatgatgtggctgctggttcgtggcgtatgggaaacgctggcaatgaccttcgtatccggttttttggctttgtgattggtctgccgg
ttggcgttctgctttatgtcacgcgtccggggcaaattattgctaacgcgaagttgtatcgtaccatttctgcgattgtgaacattttccgttccatcccgttc
attatcttgctggtatggatgattccgtttacccgcgttattgtcggtacatcgattggattgcaggcagcgattgttccgttaaccgttggtgcagcaccgtt
tattgcccgtatggtcgagaacgctctgctggagatcccaaccgggttaattgaagcttcccgcgcaatgggggccacgccaatgcagatcgtccgtaaagtgc
tgttaccggaagcgttgccgggtctggtgaatgcggcaactatcaccctgattaccctggttggttattccgcgatgggtggtgcagtcggtgccggtggtt
taggtcagattggctatcagtatggctacatcggctacaacgcgacggtgatgaatacggtactggtattgctggtcattctggtttatttaattcagttcgca
ggcgaccgcatcgtccgggctgtcactcgcaagtaa >MetQ-SEQ ID NO: 107
Atggcgttcaaattcaaaacctttgcggcagtgggagccctgattggatcactggcactggtaggctgcggtcaggatgaaaaagatccaaaccacatta
aagtcggcgtgattgttggtgccgaacagcaggttgcagaagtcgcgcagaaagttgcgaaagacaaatatggcctggacgttgagctggtaaccttca
acgactatgttctgccaaacgaagcattgagcaaaggcgatatcgacgccaacgccttccagcataaaccgtaccttgatcagcaactgaaagatcgtgg
ctacaaactggtcgcagtaggcaacacatttgtttatccgattgctggttactccaagaaaatcaaatcactggatgaactgcaggatggttcgcaggttgc
cgtgccaaacgacccaactaaccttggtcgttcactgctgctgctgcaaaaagtgggcttgatcaaactgaaagatggcgttggcctgctgccgaccgttc
ttgatgttgttgagaacccaaaaaatctgaaaattgttgaactggaagcaccgcagctaccgcgctctctggacgacgcgcaaatcgctctggcagttatc
aataccacctatgccagccagattggcctgactccagcgaaagacggtatctttgtcgaagataaagagtccccgtacgtaaacctgatcgtaacgcgtg
aagacaacaaagacgccgaaaacgtgaagaaattcgttcaggcttatcagtctgacgaagtttacgaagcagcaaacaaagtgtttaacggcggcgctg
ttaaaggctggtaa >Brevibacterium_aurantiacum_MGL-SEQ ID NO: 108
MTSLHPETLMVHGGMKGLTEAGVHVPAIDLSTTNPVNDVATGGDSYEWLATGHTLKDGDSAV
YQRLWQPGVARFETALAGLEHAEEAVAFATGMAAMTAALLAAVSAGTPHIVAVRPLYGGSDH
LLETGLLGTTVTWAKEADIASAIQDDTGLVIVETPANPSLDLVDLDSVVSAAGNVPVLVDNTFCT
PVLQQPISHGAALVLHSATKYLGGHGDAMGGIIATNADWAMRLRQVRAITGALLHPMGAYLLH
RGLRTLAVRMRAAQTTAGELAERLDAHPAISVVHYPGLKGQDPRGLLGRQMSGGGAMIAMEL
AGGFDAARSFVEHCNLVVHAVSLGGADTLIQHPASLTHRPVAATAKPGDGLIRLSVGLEHVDDL
ADDLIAALDASRAAA*

>Citrobacter_freundii_MGL-SEQ ID NO: 109
MSDCRAYGFNTQIVHAGQQPDPSTGALSTPIFQTSTFVFDSAEQGAARFALEEPGYIYTRLGN
PTTDALEKKLAVLERGDAALATASGISAITTSLLTLCQQGDHIVSASAIYGCTHAFLSHSLPKFGIN
VSFVDAAKPEEIRAAMRPETKVVYIETPANPTLSLVDIETVAGIAHQQGALLVVDNTFMSPYCQQ
PLLLGADIVVHSVTKYINGHGDVIGGVIVGKQEFIDQARFVGLKDITGGCMSPFNAWLTLRGVKT
LGIRMERHCENALKIARFLEGHPAITRVYYPGLPSHPQYELGKRQMSLPGGIISFEIAGGLEAGRR
MINSVELCLLAVSLGDTETLIQHPASMTHSPVAPEERLKAGITDGLIRLSVGLEDPEDIINDLEHAI
RKATF*

>Porphyromonas_gingivalis_MGL-SEQ ID NO: 110
MKKEDLMRSGFATRAIHGGAIENAFGCLATPIYQTSTFVFDTAEQGGRRFAGEEDGYIYTRLGNP
NCTQVEEKLAMLEGGEAAASASSGIGAISSAIWVCVKAGDHIVAGKTLYGCTFAFLTHGLSRYG
VEVTLVDTRHPEEVEAAIRPNTKLVYLETPANPNMYLTDIKAVCDIAHKHEGVRVMVDNTYCTP
YICRPLELGADIVVHSATKYLNGHGDVIAGFVVGKEDYIKEVKLVGVKDLTGANMSPFDAYLIS
RGMKTLQIRMEQHCRNAQTVAEFLEKHPAVEAVYFPGLPSFPQYELAKKQMALPGAMIAFEVK
GGCEAGKKLMNNLHLCSLAVSLGDTETLIQHPASMTHSPYTPEERAASDISEGLVRLSVGLENVE
DIIADLKHGLDSLI*

>Streptomyces_sp590_MDC-SEQ ID NO: 111
MSPTAFPAAETATAPATAVDPGPELDGGDFALPEGGLDDDRRLRALDAVDEYLTRKRKHLVGY
QATQDMQGTALDLARFMPNNINNLGDPFQSGGYKPNTKVVERAVLDYYAKLWHAERPHDPAD
PESYWGYMLSMGSTEGNMYALWNARDYLSGKALIQPPTAPFDAVRYVKADPDRRNPNAHHPV
AFYSEDTHYSFAKAVAVLGVETFHAVGLEKYADECPLVDPVTGLRTWPTEVPSRPGPSGLSWDG
PGEIDVDALAVLVEFFAAKGHPVFVNLNLGSTFKGAHDDVRAVCERLLPIFERHGLVQREVVYG
SCPQTGRPLVDVRRGFWIHVDGALGAGYAPFLRLAAEDPEGYGWTPEAELPEFDFGLRLPTAGH
GEVDMVSSIAMSGHKWAGAPWPCGIYMTKVKYQISPPSQPDYIGAPDTTFAGSRNGFSPLILWD
HLSRYSYRDQVERIREAQELAAYLERRLTAMERELGVELWPARTPGAVTVRFRKPSAELVAKW
SLSSQDVLMVPGDETTRRSYVHVFVMPSVDRAKLDALLAELAEDPVILGAP*

ABC transporter from EcN-MetNIQ
>MetN-SEQ ID NO: 112
MIKLSNITKVFHQGTRTIQALNNVSLHVPAGQIYGVIGASGAGKSTLIRCVNLLERPTEGSVLV
DGQELTTLSESELTKARRQIGMIFQHFNLLSSRTVFGNVALPLELDNTPKDEIKRRVTELLSLVGL -continued Exemplary Sequences GDKHDSYPSNLSGGQKQRVAIARALASNPKVLLCDEATSALDPATTRSILELLKDINRRLGLTILL
ITHEMDVVKRICDCVAVISNGELIEQDTVSEVFSHPKTPLAQKFIQSTLHLDIPEDYQERLQAEPFT
DCVPMLRLEFTGQSVDAPLLSETARRFNVNNNIISAQMDYAGGVKFGIMLTEMHGTQQDTQAAI
AWLQEHHVKVEVLGYV*

>MetI-SEQ ID NO: 113
MSEPMMWLLVRGVWETLAMTFVSGFFGFVIGLPVGVLLYVTRPGQIIANAKLYRTISAIVNIF
RSIPFIILLVWMIPFTRVIVGTSIGLQAAIVPLTVGAAPFIARMVENALLEIPTGLIEASRAMGATPM
QIVRKVLLPEALPGLVNAATITLITLVGYSAMGGAVGAGGLGQIGYQYGYIGYNATVMNTVLVL
LVILVYLIQFAGDRIVRAVTRK*

>MetQ-SEQ ID NO: 114
MAFKFKTFAAVGALIGSLALVGCGQDEKDPNHIKVGVIVGAEQQVAEVAQKVAKDKYGLD
VELVTFNDYVLPNEALSKGDIDANAFQHKPYLDQQLKDRGYKLVAVGNTFVYPIAGYSKKIKSL
DELQDGSQVAVPNDPTNLGRSLLLLQKVGLIKLKDGVGLLPTVLDVVENPKNLKIVELEAPQLPR
SLDDAQIALAVINTTYASQIGLTPAKDGIFVEDKESPYVNLIVTREDNKDAENVKKFVQAYQSDE
VYEAANKVFNGGAVKGW*

>yjeH-SEQ ID NO: 115
atgagtggactcaaacaagaactggggctggcccagggcatcggcctactatcgacgtcattattaggcactggcgtgtttgccgttcctgcgttag
ctgcgctagtagcaggcaataacagcctgtgggcgtggcccgttttgattatcttagtgttcccgattgcgattgtgtttgcgattctgggtegccactatccc
agcgcaggcggcgtcgcacacttcgtcggtatggcgtttggttcgcggcttgagcgagtcaccggctggttgtttttatcggtcattcccgtgggtttgcct
gccgcgctacaaattgctgccggattcggccaggcaatgtttggctggcatagcgggcaactgttgttggcagaactcggtacgctggcgctggtgtggt
atatcggtactcgaggtgccagttccagtgctaatctacaaacagttattgccgggcttatcgtcgcactgattgtcgctatctggtggggggcgatatcaa
acctgcgaatatccccttccctgcgccaggaaatatcgaacttaccgggttattcgctgcgttatcagtgatgttctggtgttttgtcggtctggaagcatttg
cccatcttgcctcggaatttaaaaatccagagcgtgattttcctcgtgctttgatgattggcctgctgctggcaggattagtctattggggctgtacggtagtc
gtcttacacttcgacgcctatggtgaacaaatggcggcggcagcatcgcttcccaaaattgtagtgcagttattcggtgtaggagcgttatggattgcctgcgt
aattggctatctggcctgctttgccagtctcaacatttatatacagagcttcgcccgcctggtctggtcgcaggcgcaacataatcctgaccattacctggca
cgcctctcttctcgccatattccgaataatgccctcaatgcggtgctcggctgctgcgtggtgagcacgttggtgattcatgctttagagatcaatctggacg
ctcttattatttatgccaatggcatctttattatgatttatctgttatgcatgctggcaggctgtaaattattgcaaggacgttatcgactactggcagtggtt
ggcgggctattatgcgttctgttactggcaatggtcggctggaaaagtctctacgcgctgatcatgctggcggggttatggctgtttctgccaaaacgaaaaac
gccggaaaatggcataaccacataa >Citrobacter_freundii_WT_MGL-SEQ ID NO: 116
atgtctgactgtcgtgcttacggattcaatacccagatcgttcatgcgggccaacaacccgacccttccactggegcgctcagtacgcctattttccagacg
tcaaccttcgtttttgacagtgccgaacagggcgccgcccgctttgcgcttgaagaacccggctacatctatacgcgccttggaaaccccaccaccgacg
cgctggagaaaaagctggctgtgctggaaagaggcgatgccgcgctggcaactgcatccggtatttcagccatcaccacctcgttgctgaccctttgcca
gcagggcgaccatatcgtttccgccagtgccatttacggctgcactcacgcttttctgtcacacagcctgccgaagttcggcattaacgtcagcttcgtcga
cgccgccaagccggaagaaatccgcgcggccatgcgcccggaaaccaaagtggtgtatatcgaaacaccagcaaacccaacgctctcgctggttgat
attgaaacggtcgccgggatcgcccatcagcaaggcgcattgctggtcgtggataacacctttatgtcaccctactgccagcaacctctgctgttaggtgc
cgacatcgtggtgcacagcgtgaccaagtacatcaacggccacggggacgtgattggcggtgtgattgttggcaagcaggaatttatcgaccaggcac
gattcgtcgggctgaaagatatcaccggcggctgcatgagtccgttcaacgcctggctgacgctgcgcggcgtgaaaacgctgggcatccgaatggag
cgccattgtgaaaacgcgttaaaaattgcccgcttcctggaagggcatccggccattacccgcgtgtattaccctggcttgccttcacatccgcagtatgag
ctgggtaaacgtcagatgagcctgccgggaggaattatcagcttcgaaatcgccggcggcctcgaggctggcagacggatgatcaattctgtagaattgt
gcctcctcgcggtcagtctcggtgacaccgaaaccctcattcagcacccagcgtctatgacacattcgcccgttgcgccagaggaacggcttaaagcag
gtattaccgacggacttatccgtctttctgttggtcttgaagatccagaagatattattaacgaccttgaacacgccatcagaaaggcaacattctga >Porphyromonas_gingivalis_WT_MGL-SEQ ID NO: 117
Atgaaaaaagaagaccttatgcgtagtggctttgccacacgtgccatccatggaggcgctatcgagaacgccttcggctgcttagccactcccatctacc
aaacatcgactttcgtttttgacactgccgaacagggaggccgccgctttgccggagaggaagacggatacatctatacccgtctgggcaaccccaactg
cacccaagtggaagagaaactggccatgctcgagggcggagaagccgccgcatcggcctcatccggtatcggagccatcagctctgccatctgggtat
gcgtgaaggccggcgaccatatcgtagccggcaagacgctctacggctgcaccttcgccttcctcacccacggactgagccgctacggtgtggaagtc
accctcgtggatacccgccatccggaagaggtggaggctgccattcgcccgaatacgaagctcgtctatctggagactccggccaaccccaatatgtac
ctgaccgacatcaaggcagtctgcgacatcgctcataagcacgaaggcgtacgcgtcatggtggacaatacctactgcacgccctatatctgccgtccg
ctggagctgggtgccgacatcgtggtacacagcgcgaccaagtacctgaacggacatggcgacgtcatcgccggattcgtcgttggtaaagaggacta
catcaaggaggtgaagctcgtcggcgtcaaggacctcacgggggccaatatgagtccgttcgatgcttatctgatcagccgcggcatgaagacgctgca
gatacgtatggagcagcactgccgcaatgctcagaccgtagccgaattcctcgaaaagcatccggccgtagaagcagtttatttccccggacttccgagc
ttcccccaatacgaattggccaagaagcagatggcactgcccggagccatgatcgccttcgaagtgaagggcggttgcgaagccggtaagaagctgat
gaacaacctgcacctctgctccctcgccgtgagcttggggatacggaaacccctcatccagcatccggccagcatgacccactegccctacacacccg
aagagcgtgctgccagcgacatatccgaaggactggtacgcctgtccgtgggtctggagaacgtggaggacatcatcgccgacctcaaacacggtctg
gacagcctgatctaa >Brevibacterium_aurantiacum_WT_MGL-SEQ ID NO: 118
atgacctcactgcacccagaaacgctcatggtccacggcggaatgaaaggcctcaccgaggcaggagtccacgtaccggccatcgacctctcgacca
ccaacccagtcaacgatgtcgccaccggcggtgactcctacgaatggctcgccaccggccatacgctcaaggacggcgactcggccgtctaccagcg
cctctggcagcccggtgtcgcacgcttcgagaccgcgctggccgggctcgaacacgctgaggaagcagtcgccttcgccacgggcatggccgcaat
gactgccgcacttctcgcggccgtcagcgcaggaacaccccacatcgtcgcagtgcgtcccctctatggcggaagcgaccacctcctcgaaaccgga
ctgctggggacaacagtcacatgggcaaaggaagccgacatcgcctcggcgatccaagatgacaccggactcgtcattgtcgagaccccggcaaacc
ccagcctggaccttgttgatctcgacagtgtcgtctcagccgccggcaacgtgcctgtgctggtggacaacacattctgcacacctgttctccagcagccc
atctcccacggagcggccctcgtactgcacagcgcgacaaaatacctcggcggtcatggcgatgccatggggcatcatcgccaccaacgccgact
gggcgatgcgcctgcgacaggtccgagccatcacaggagccctgctccaccccatgggcgcgtatctccttcatcggggcttgcgcactctggccgtg
cgcatgcgcgcggctcagaccaccgccggtgagctcgctgagcgcctggacgcgcaccctgccatctccgtcgtccactacccgggactgaaaggcc
aggacccacgcggactgctcggacgccaaatgtccggtggtggtgcgatgatcgcgatggagctcgccggtggattcgacgccgcccgcagcttcgt
cgaacactgcaacctcgtcgtccacgcggtgtccctgggcggcgctgacactctcatccagcatccggcgtcactgactcacaggccagttgcggcca
cggcgaagcccggcgatggtctcatccgactctctgtgggactcgaacacgtcgatgacctggcagacgatctcatcgctgccctcgacgcgagtcgg
gccgctgcctga -continued

| Exemplary Sequences |
| --- |
| >Streptomyces_sp590_WT_MetDC-SEQ ID NO: 119<br>atgagcccgaccgccttccccgccgccgagaccgcgaccgcgcccgcgaccgccgtcgatcccggtccggagctggacggcggtgacttcgccctc<br>cccgagggcggcctggacgacgaccggcggctgcgcgcgctcgacgccgtggacgagtacctgacccgcaagcgcaagcacctggtcggctacc<br>aggccacccaggacatgcagggcaccgcactggacctcgcccggttcatgccgaacaacatcaacaacctcggcgacccgttccagagcggcggat<br>acaagcccaacaccaaggtcgtcgagcgggccgtgctcgactactacgcgaagctctggcacgccgagcgcccgcacgacccggccgacccggag<br>tcgtactggggctacatgctgtccatgggctcgaccgagggcaacatgtacgccctctggaacgccagggactacctgagcggcaaggcgctgatcca<br>gccgccgaccgccccttcgacgcggtgcgctacgtcaaggccgaccccgaccgacggaacccgaacgcccaccacccggtggccttctactccga<br>ggacacccactactccttcgccaaggccgtggccgtcctcggcgtggagaccttccacgccgtcggcctggagaagtacgccgacgagtgcccgctg<br>gtcgacccggtgaccgggctgcgcacctggcccaccgaggtgccctcccgcccgggtccgtccggcctgtcctgggacggccccggcgagatagac<br>gtcgacgccctcgccgtactcgtcgagttcttcgccgccaagggtcacccggtcttcgtcaacctcaacctcggcagcaccttcaagggcgcccacgac<br>gacgtccgcgccgtctgcgagcgcttgctgccgatcttcgagcggcacgggctcgtccagcgcgaggtggtctacggcagctgcccgcagaccggcc<br>ggccgctggtggacgtgcgccgcggcttctggatccacgtggacggcgcgctcggcgccggctacgcgccgttcctgcggctggccgccgaggacc<br>cggaagggtacggctggacgcccgaggcggagctgcccgagttcgacttcggcctgcggctgcccaccgccgggcacggcgaggtggacatggtc<br>tcctcgatcgcgatgagcggccacaagtgggccggcgcgccgtggccgtgcggcatctacatgaccaaggtgaagtaccagatctcgccgccgtccc<br>agccggactacatcggcgccccggacaccaccttcgccggctcccgcaacggcttctccccgctgatcctctgggaccacctgtcccggtactctacc<br>gggaccaggtggagcggatccgcgaggcccaggagctggccgcctacctggagcggcggctgaccgccatggagcgcgaactcggcgtcgagct<br>ctggccggcccgtaccccgggcgccgtcaccgtacggttccgcaagccgagcgccgagctggtggccaagtggtcgctgtcctcccaggacgtgctg<br>atggtcccgggcgacgagaccacccggcgcagctacgtgcacgtcttcgtgatgccctcggtcgaccgggccaagctggacgcgctgctcgccgaac<br>tcgccgaggacccggtgatcctgggcgcaccgtag<br><br>OxIT coding region (oxalate:formate antiporter from *O. formigenes*)-SEQ ID NO: 120<br>ATGAATAATCCACAAACAGGACAATCAACAGGCCTCTTGGGCAATCGTTGGTTCTACTTGGT<br>ATTAGCAGTTTTGCTGATGTGTATGATCTCGGGTGTCCAATATTCCTGGACACTGTACGCTAA<br>CCCGGTTAAAGACAACCTTGGCGTTTCTTTGGCTGCGGTTCAGACGGCTTTCACACTCTCTCA<br>GGTCATTCAAGCTGGTTCTCAGCCTGGTGGTGGTTACTTCGTTGATAAATTCGGTCCAAGAAT<br>TCCATTGATGTTCGGTGGTGCGATGGTTCTCGCTGGCTGGACCTTCATGGGTATGGTTGACAG<br>TGTTCCTGCTCTGTATGCTCTTTATACTCTGGCCGGTGCAGGTGTTGGTATCGTTTACGGTAT<br>CGCGATGAACACGGCTAACAGATGGTTCCCGGACAAACGCGGTCTGGCTTCCGGTTTCACCG<br>CTGCCGGTTACGGTCTGGGTGTTCTGCCGTTCCTGCCACTGATCAGCTCCGTTCTGAAAGTTG<br>AAGGTGTTGGCGCAGCATTCATGTACACCGGTTTGATCATGGGTATCCTGATTATCCTGATC<br>GCTTTCGTTATCCGTTTCCCTGGCCAGCAAGGCGCCAAAAAACAAATCGTTGTTACCGACAA<br>GGATTTCAATTCTGGCGAAATGCTGAGAACACCACAATTCTGGGTTCTGTGGACCGCATTCT<br>TTTCCGTTAACTTTGGTGGTTTGCTGCTGGTTGCCAACAGCGTCCCTTACGGTCGCAGCCTCG<br>GTCTTGCCGCAGGTGTGCTGACGATCGGTGTTTCGATCCAGAACCTGTTCAATGGTGGTTGC<br>CGTCCTTTCTGGGGTTTCGTTTCCGATAAAATCGGCCGTTACAAAACCATGTCCGTCGTTTTC<br>GGTATCAATGCTGTTGTTCTCGCACTTTTCCCGACGATTGCTGCCTTGGGCGATGTAGCCTTT<br>ATCGCCATGTTGGCAATCGCATTCTTCACATGGGGTGGTAGCTACGCTCTGTTCCCATCGACC<br>AACAGCGATATTTTCGGTACGGCATACTCTGCCAGAAACTATGGTTTCTTCTGGGCTGCAAA<br>AGCAACTGCCTCGATCTTCGGTGGTGGTCTGGGTGCTGCAATTGCAACCAACTTCGGATGGA<br>ATACCGCTTTCCTGATTACTGCGATTACTTCTTTCATCGCATTTGCTCTGGCTACCTTCGTTAT<br>TCCAAGAATGGGCCGTCCAGTCAAGAAAATGGTCAAATTGTCTCCAGAAGAAAAAGCTGTA<br>CATTAA<br><br>OxIT (oxalate:formate antiporter from *O. formigenes*)-SEQ ID NO: 121<br>MNNPQTGQSTGLLGNRWFYLVLAVLLMCMISGVQYSWTLYANPVKDNLGVSLAAVQTAFTLS<br>QVIQAGSQPGGGYFVDKFGPRIPLMFGGAMVLAGWTFMGMVDSVPALYALYTLAGAGVGIVY<br>GIAMNTANRWFPDKRGLASGFTAAGYGLGVLPFLPLISSVLKVEGVGAAFMYTGLIMGILIILIAF<br>VIRFPGQQGAKKQIVVTDKDFNSGEMLRTPQFWVLWTAFFSVNFGGLLLVANSVPYGRSLGLAA<br>GVLTIGVSIQNLFNGGCRPFWGFVSDKIGRYKTMSVVFGINAVVLALFPTIAALGDVAFIAMLAIA<br>FFTWGGSYALFPSTNSDIFGTAYSARNYGFFWAAKATASIFGGGLGAAIATNFGWNTAFLITAITS<br>FIAFALATFVIPRMGRPVKKMVKLSPEEKAVH*<br><br>frc (formyl-CoA transferase from *O. formigenes*)-SEQ ID NO: 122<br>ATGACTAAACCATTAGATGGAATTAATGTGCTTGACTTTACCCACGTCCAGGCAGGTCCTGC<br>CTGTACACAGATGATGGGTTTCTTGGGCGCAAACGTCATCAAGATTGAAAGACGTGGTTCCG<br>GAGATATGACTCGTGGATGGCTGCAGGACAAACCAAATGTTGATTCCCTGTATTTCACGATG<br>TTCAACTGTAACAAACGTTCGATTGAACTGGACATGAAAACCCCGGAAGGCAAAGAGCTTC<br>TGGAACAGATGATCAAGAAAGCCGACGTCATGGTCGAAAACTTCGGACCAGGCGCACTGGA<br>CCGTATGGGCTTTACTTGGGAATACATTCAGGAACTGAATCCACGCGTCATTCTGGCTTCCGT<br>TAAAGGCTATGCAGAAGGCCACGCCAACGAACACCTGAAAGTTTATGAAAACGTTGCACAG<br>TGTTCCGGCGGTGCTGCAGCTACCACCGGTTTCTGGGATGGTCCTCCAACCGTTTCCGGCGCT<br>GCTCTGGGTGACTCCAACTCCGGTATGCACCTGATGATCGGTATTCTGGCCGCTCTGGAAAT<br>GCGTCACAAAACCGGCCGTGGTCAGAAAGTTGCCGTCGCTATGCAGGACGCTGTTCTGAATC<br>TGGTTCGTATCAAACTGCGTGACCAGCAACGTCTGGAAAGAACCGGCATTCTGGCTGAATAC<br>CCACAGGCTCAGCCTAACTTTGCCTTCGACAGAGACGGTAACCCACTGTCCTTCGACAACAT<br>CACTTCCGTTCCACGTGGTGGTAACGCAGGTGGCGGCGGCCAGCCAGGCTGGATGCTGAAAT<br>GTAAAGGTTGGGAAACCGATGCGGACTCCTACGTTTACTTCACCATCGCTGCAAACATGTGG<br>CCACAGATCTGCGACATGATCGACAAGCCAGAATGGAAAGACGACCCAGCCTACAACACAT<br>TCGAAGGTCGTGTTGACAAGCTGATGGACATCTTCTCCTTCATCGAAACCAAGTTCGCTGAC<br>AAGGACAAATTCGAAGTTACCGAATGGGCTGCCCAGTACGGCATTCCTTGCGGTCCGGTCAT<br>GTCCATGAAAGAACTGGCTCACGATCCTTCCCTGCAGAAAGTTGGTACCGTCGTTGAAGTTG<br>TCGACGAAATTCGTGGTAACCACCTGACCGTTGGCGCACCGTTCAAATTCTCCGGATTCCAG<br>CCGGAAATTACCCGTGCTCCGCTGTTGGGCGAACATACCGACGAAGTTCTGAAAGAACTGG<br>GTCTTGACGATGCCAAGATCAAGGAACTGCATGCAAAACAGGTAGTTTGA |

-continued

| Exemplary Sequences |
|---|
| Frc (Formyl-CoA transferase from *O. formigenes*)-SEQ ID NO: 123<br>MTKPLDGINVLDFTHVQAGPACTQMMGFLGANVIKIERRGSGDMTRGWLQDKPNVDSLYFTMF<br>NCNKRSIELDMKTPEGKELLEQMIKKADVMVENFGPGALDRMGFTWEYIQELNPRVILASVKGY<br>AEGHANEHLKVYENVAQCSGGAAATTGFWDGPPTVSGAALGDSNSGMHLMIGILAALEMRHK<br>TGRGQKVAVAMQDAVLNLVRIKLRDQQRLERTGILAEYPQAQPNFAFDRDGNPLSFDNITSVPR<br>GGNAGGGGQPGWMLKCKGWETDADSYVYFTIAANMWPQICDMIDKPEWKDDPAYNTFEGRV<br>DKLMDIFSFIETKFADKDKFEVTEWAAQYGIPCGPVMSMKELAHDPSLQKVGTVVEVVDEIRGN<br>HLTVGAPFKFSGFQPEITRAPLLGEHTDEVLKELGLDDAKIKELHAKQVV* |
| oxc (oxalylCoA decarboxylase from *O. formigenes*) also referred to as oxdc (oxalate decarboxylase)-SEQ ID NO: 124<br>ATGAGTAACGACGACAATGTAGAGTTGACTGATGGCTTTCATGTTTTGATCGATGCCCTGAA<br>AATGAATGACATCGATACCATGTATGGTGTTGTCGGCATTCCTATCACGAACCTGGCTCGTA<br>TGTGGCAAGATGACGGTCAGCGTTTTTACAGCTTCCGTCACGAACAACACGCAGGTTATGCA<br>GCTTCTATCGCCGGTTACATCGAAGGAAAACCTGGCGTTTGCTTGACCGTTTCCGCCCCTGGC<br>TTCCTGAACGGCGTGACTTCCCTGGCTCATGCAACCACCAACTGCTTCCCAATGATCCTGTTG<br>AGCGGTTCCAGTGAACGTGAAATCGTCGATTTGCAACAGGGCGATTACGAAGAAATGGATC<br>AGATGAATGTTGCACGTCCACACTGCAAAGCTTCTTTCCGTATCAACAGCATCAAAGACATT<br>CCAATCGGTATCGCTCGTGCAGTTCGCACCGCTGTATCCGGACGTCCAGGTGGTGTTTACGTT<br>GACTTGCCAGCAAAACTGTTCGGTCAGACCATTTCTGTAGAAGAAGCTAACAAACTGCTCTT<br>CAAACCAATCGATCCAGCTCCGGCACAGATTCCTGCTGAAGACGCTATCGCTCGCGCTGCTG<br>ACCTGATCAAGAACGCCAAACGTCCAGTTATCATGCTGGGTAAAGGCGCTGCATACGCACA<br>ATGCGACGACGAAATCCGCGCACTGGTTGAAGAAACCGGCATCCCATTCCTGCCAATGGGT<br>ATGGCTAAAGGCCTGCTGCCTGACAACCATCCACAATCCGCTGCTGCAACCCGTGCTTTCGC<br>ACTGGCACAGTGTGACGTTTGCGTACTGATCGGCGCTCGTCTGAACTGGCTGATGCAGCACG<br>GTAAAGGCAAAACCTGGGGCGACGAACTGAAGAAATACGTTCAGATCGACATCCAGGCTAA<br>CGAAATGGACAGCAACCAGCCTATCGCTGCACCAGTTGTTGGTGACATCAAGTCCGCCGTTT<br>CCCTGCTCCGCAAAGCACTGAAAGGCGCTCCAAAAGCTGACGCTGAATGGACCGGCGCTCT<br>GAAAGCCAAAGTTGACGGCAACAAAGCCAAACTGGCTGGCAAGATGACTGCCGAAACCCCA<br>TCCGGAATGATGAACTACTCCAATTCCCTGGGCGTTGTTCGTGACTTCATGCTGGCAAATCC<br>GGATATTTCCCTGGTTAACGAAGGCGCTAATGCACTCGACAACACTCGTATGATTGTTGACA<br>TGCTGAAACCACGCAAACGTCTTGACTCCGGTACCTGGGGTGTTATGGGTATTGGTATGGGC<br>TACTGCGTTGCTGCAGCTGCTGTTACCGGCAAACCGGTTATCGCTGTTGAAGGCGATAGCGC<br>ATTCGGTTTCTCCGGTATGGAACTGGAAACCATCTGCCGTTACAACCTGCCAGTTACCGTTAT<br>CATCATGAACAATGGTGGTATCTATAAAGGTAACGAAGCAGATCCACAACCAGGCGTTATCT<br>CCTGTACCCGTCTGACCCGTGGTCGTTACGACATGATGATGGAAGCATTTGGCGGTAAAGGT<br>TATGTTGCCAATACTCCAGCAGAACTGAAAGCTGCTCTGGAAGAAGCTGTTGCTTCCGGCAA<br>ACCATGCCTGATCAACGCGATGATCGATCCAGACGCTGGTGTCGAATCTGGCCGTATCAAGA<br>GCCTGAACGTTGTAAGTAAAGTTGGCAAGAAATAA |
| Oxc (oxalylCoA decarboxylase from *O. formigenes*) SEQ ID NO: 125<br>MSNDDNVELTDGFHVLIDALKMNDIDTMYGVVGIPITNLARMWQDDGQRFYSFRHEQHAGYA<br>ASIAGYIEGKPGVCLTVSAPGFLNGVTSLAHATTNCFPMILLSGSSEREIVDLQQGDYEEMDQMN<br>VARPHCKASFRINSIKDIPIGIARAVRTAVSGRPGGVYVDLPAKLFGQTISVEEANKLLFKPIDPAP<br>AQIPAEDAIARAADLIKNAKRPVIMLGKGAAYAQCDDEIRALVEETGIPFLPMGMAKGLLPDNHP<br>QSAAATRAFALAQCDVCVLIGARLNWLMQHGKGKTWGDELKKYVQIDIQANEMDSNQPIAAP<br>VVGDIKSAVSLLRKALKGAPKADAEWTGALKAKVDGNKAKLAGKMTAETPSGMMNYSNSLG<br>VVRDFMLANPDISLVNEGANALDNTRMIVDMLKPRKRLDSGTWGVMGIGMGYCVAAAAVTG<br>KPVIA VEGDSAFGFSGMELETICRYNLPVTVIIMNNGGIYKGNEADPQPGVISCTRLTRGRYDMM<br>MEAFGGKGYVANTPAELKAALEEAVASGKPCLINAMIDPDAGVESGRIKSLNVVSKVGKK* |
| ScAAE3 (oxalate-CoA ligase from *S. cerevisiae*)-SEQ ID NO: 126<br>ATGACCAGTGCAGCTACGGTGACCGCGAGCTTTAATGACACTTTTTCTGTGAGCGATAATGT<br>CGCGGTAATCGTACCGGAAACCGATACGCAGGTCACCTACCGTGATCTTTCCCACATGGTAG<br>GACACTTTCAAACAATGTTCACGAACCCGAATAGTCCTCTGTACGGGGCGGTCTTTCGTCAA<br>GACACGGTAGCGATTAGCATGCGTAACGGCCTTGAATTTATTGTGGCTTTCCTTGGAGCCAC<br>GATGGATGCGAAAATTGGTGCGCCACTGAATCCCAATTATAAAGAGAAGGAGTTTAATTTTT<br>ACCTGAATGACTTAAAGTCCAAAGCCATCTGCGTGCCGAAAGGCACCACCAAACTGCAAAG<br>TTCAGAAATTCTTAAGAGTGCGTCCACGTTCGGGTGCTTTATTGTGGAACTGGCGTTTGACGC<br>CACCCGTTTTCGTGTTGAATATGACATTTACTCCCCGGAGGACAATTATAAACGTGTGATCTA<br>CCGCAGCCTTAACAATGCTAAGTTTGTCAACACAAACCCTGTCAAGTTCCCGGGTTTCGCCC<br>GCAGCTCGGATGTTGCACTTATTTTGCATACCTCAGGCACCACTAGTACCCCAAAGACCGTA<br>CCCCTCTTGCATCTGAATATTGTCCGTTCAACCCTGAATATCGCCAACACTTACAAACTTACC<br>CCGCTGGATCGCTCCTATGTTGTAATGCCGCTGTTTCATGTACATGGATTAATCGGCGTCTTA<br>CTGAGTACGTTCCGCACCCAGGGCAGTGTAGTCGTCCCGGACGGCTTTCATCCGAAGCTCTT<br>CTGGGATCAGTTTGTTAAATATAACTGCAATTGGTTTAGTTGCGTCCCAACGATCTCTATGAT<br>TATGTTGAATATGCCCAAACCGAATCCGTTTCCGCACATTCGCTTTATCCGCTCATGTAGCAG<br>CGCGCTGGCGCCAGCAACGTTTCACAAGCTGGAAAAAGAATTTAATGCCCCAGTTCTGGAA<br>GCGTACGCGATGACAGAAGCATCTCATCAGATGACCAGTAACAATCTGCCTCCCGGTAAAC<br>GTAAACCGGGGACCGTGGGCCAACCTCAAGGTGTAACCGTAGTAATCCTGGATGACAACGA<br>TAACGTTCTGCCGCCCGGCAAAGTTGGCGAGGTGTCGATCCGTGGGGAGAACGTCACCCTGG<br>GCTACGCTAATAACCCGAAAGCTAACAAAGAAAACTTCACTAAACGTGAAAACTATTTCCGT<br>ACCGGGGATCAGGGCTACTTCGACCCGGAGGGCTTTCTCGTGCTGACCGGCCGCATTAAAGA<br>ATTGATCAATCGCGGTGGTGAAAAAATTAGTCCTATTGAACTGGACGGAATCATGCTCTCGC<br>ATCCTAAAATCGACGAGGCGGTGGCGTTCGGCGTTCCAGATGATATGTATGGCCAAGTCGTT |

-continued

| Exemplary Sequences |
| --- |
| CAGGCGGCAATCGTGTTGAAAAAGGGGGAAAAGATGACCTATGAAGAATTAGTGAATTTCC<br>TGAAAAAGCATTTAGCAAGCTTTAAAATCCCAACCAAAGTCTACTTTGTGGATAAGCTGCCT<br>AAAACGGCCACCGGGAAGATTCAACGTCGCGTAATCGCCGAAACCTTCGCGAAATCTAGTC<br>GCAACAAAAGCAAACTTtaa |
| ScAAE3 (Oxalate-CoA ligase from *S. cerevisiae*)-SEQ ID NO: 127<br>MTSAATVTASFNDTFSVSDNVAVIVPETDTQVTYRDLSHMVGHFQTMFTNPNSPLYGAVFRQDT<br>VAISMRNGLEFIVAFLGATMDAKIGAPLNPNYKEKEFNFYLNDLKSKAICVPKGTTKLQSSEILKS<br>ASTFGCFIVELAFDATRFRVEYDIYSPEDNYKRVIYRSLNNAKFVNTNPVKFPGFARSSDVALILH<br>TSGTTSTPKTVPLLHLNIVRSTLNIANTYKLTPLDRSYVVMPLFHVHGLIGVLLSTFRTQGSVVVP<br>DGFHPKLFWDQFVKYNCNWFSCVPTISMIMLNMPKPNPFPHIRFIRSCSSALAPATFHKLEKEFN<br>APVLEAYAMTEASHQMTSNNLPPGKRKPGTVGQPQGVTVVILDDNDNVLPPGKVGEVSIRGEN<br>VTLGYANNPKANKENFTKRENYFRTGDQGYFDPEGFLVLTGRIKELINRGGEKISPIELDGIMLSH<br>PKIDEAVAFGVPDDMYGQVVQAAIVLKKGEKMTYEELVNFLKKHLASFKIPTKVYFVDKLPKT<br>ATGKIQRRVIAETFAKSSRNKSKL* |
| yfdE (Acetyl-CoA:oxalate CoA-transferase from *E. coli*)-SEQ ID NO: 128<br>atgACAAATAATGAAAGCAAAGGGCCGTTTGAAGGCTTATTAGTTATCGATATGACACATGTC<br>CTTAATGGACCTTTCGGAACTCAACTTCTTTGTAATATGGGCGCAAGGGTAATTAAAGTTGA<br>GCCGCCGGGTCATGGTGATGATACCCGCACATTTGGTCCCTATGTGGATGGACAGTCACTCT<br>ATTACAGTTTTATTAATCATGGCAAAGAGAGTGTGGTTCTTGATTTAAAGAATGATCACGAT<br>AAAAGTATATTTATAAATATGCTCAAACAAGCTGATGTATTAGCTGAGAATTTTCGCCCAGG<br>TACAATGGAAAAACTGGGGTTTTCATGGGAAACGCTTCAAGAAATCAACCCGCGCCTCATAT<br>ATGCTTCATCGTCAGGTTTCGGACATACCGGTCCGCTAAAAGATGCTCCTGCCTACGATACC<br>ATCATTCAGGCAATGAGCGGGATAATGATGGAAACAGGATATCCTGATGCTCCGCCAGTGC<br>GCGTTGGTACATCTCTTGCGGATCTATGCGGCGGTGTCTATTTATTCAGCGGAATAGTGAGT<br>GCACTTTATGGCCGCGAAAAGAGCCAGAGAGGGGCGCATGTCGATATAGCGATGTTTGATG<br>CCACGCTGAGTTTTCTGGAGCATGGTCTGATGGCATATATCGCAACTGGGAAGTCACCACAA<br>CGTCTGGGAAATCGCCATCCCTACATGGCACCTTTTGATGTTTTCAATACTCAGGATAAGCC<br>GATTACGATTTGTTGTGGTAATGACAAGCTTTTTTCTGCGTTATGCCAGGCACTGGAGCTTAC<br>GGAACTGGTTAATGATCCCCGATTTAGCAGCAATATTTTACGCGTACAAAACCAGGCTATTC<br>TTAAACAATATATTGAGCGGACGTTAAAAACGCAGGCAGCTGAAGTTTGGTTAGCCAGAAT<br>ACATGAAGTTGGTGTACCCGTCGCGCCGTTATTAAGTGTGGCTGAGGCCATTAAATTGCCAC<br>AAACTCAGGCGAGAAATATGTTGATTGAAGCCGGGGGAATAATGATGCCGGGTAATCCGAT<br>AAAAATCAGCGGCTGCGCGGACCCGCATGTTATGCCGGGAGCGGCAACGCTCGACCAGCAT<br>GGGGAACAAATTCGCCAGGAGTTCTCATCAtaa |
| yfdE (Acetyl-CoA:oxalate CoA-transferase from *E. coli*)-SEQ ID NO: 129<br>MTNNESKGPFEGLLVIDMTHVLNGPFGTQLLCNMGARVIKVEPPGHGDDTRTFGPYVDGQSLY<br>YSFINHGKESVVLDLKNDHDKSIFINMLKQADVLAENFRPGTMEKLGFSWETLQEINPRLIYASSS<br>GFGHTGPLKDAPAYDTIIQAMSGIMMETGYPDAPPVRVGTSLADLCGGVYLFSGIVSALYGREKS<br>QRGAHVDIAMFDATLSFLEHGLMAYIATGKSPQRLGNRHPYMAPFDVFNTQDKPITICCGNDKL<br>FSALCQALELTELVNDPRESSNILRVQNQAILKQYIERTLKTQAAEVWLARIHEVGVPVAPLLSV<br>AEAIKLPQTQARNMLIEAGGIMMPGNPIKISGCADPHVMPGAATLDQHGEQIRQEFSS* |
| yfdW (formyl CoA transferase from *E. coli*)-SEQ ID NO: 130<br>SYYHHHHHHLESTSLYKKAGLMSTPLQGIKVLDFTGVQSGPSCTQMLAWFGADVIKIERPGVGD<br>VTRHQLRDIPDIDALYFTMLNSNKRSIELNTKTAEGKEVMEKLIREADILVENFHPGAIDHMGFT<br>WEHIQEINPRLIFGSIKGFDECSPYVNVKAYENVAQAAGGAASTTGFWDGPPLVSAAALGDSNT<br>GMHLLIGLLAALLHREKTGRGQRVTMSMQDAVLNLCRVKLRDQQRLDKLGYLEEYPQYPNGT<br>FGDAVPRGGNAGGGGQPGWILKCKGWETDPNAYIYFTIQEQNWENTCKAIGKPEWITDPAYST<br>AHARQPHIFDIFAEIEKYTVTIDKHEAVAYLTQFDIPCAPVLSMKEISLDPSLRQSGSVVEVEQPLR<br>GKYLTVGCPMKFSAFTPDIKAAPLLGEHTAAVLQELGYSDDEIAAMKQNHAI |
| yfdU (oxalyl-CoA decarboxylase *E. coli*)-SEQ ID NO: 131<br>MSDQLQMTDGMHIIVEALKQNNIDTIYGVVGIPVTDMARHAQAEGIRYIGFRHEQSAGYAAAAS<br>GFLTQKPGICLTVSAPGFLNGLTALANATVNGFPMIMISGSSDRAIVDLQQGDYEELDQMNAAKP<br>YAKAAFRVNQPQDLGIALARAIRVSVSGRPGGVYLDLPANVLAATMEKDEALTTIVKVENPSPA<br>LLPCPKSVTSAISLLAKAERPLIILGKGAAYSQADEQLREFIESAQIPFLPMSMAKGILEDTHPLSA<br>AAARSFALANADVVMLVGARLNWLLAHGKKGWAADTQFIQLDIEPQEIDSNRPIAVPVVGDIAS<br>SMQGMLAELKQNTFTTPLVWRDILNIHKQQNAQKMHEKLSTDTQPLNYFNALSAVRDVLRENQ<br>DIYLVNEGANTLDNARNIIDMYKPRRRLDCGTWGVMGIGMGYAIGASVTSGSPVVAIEGDSAFG<br>FSGMEIETICRYNLPVTIVIFNNGGIYRGDGVDLSGAGAPSPTDLLHHARYDKLMDAFRGVGYNV<br>TTTDELRHALTTGIQSRKPTIINVVIDPAAGTESGHITKLNPKQVAGN |
| Methionine import system permease protein MetP (*Bacillus subtilis*)-<br>SEQ ID NO: 132<br>atgtttgagaagtattttccaaatgttgacttgaccgagttatggaatgccacatatgaaactctgtat<br>atgacattgatttccttactgtttgccttcgtaatcggcgtcatcctgggattgctgttattcttaaca<br>tctaaggggtctctttggcaaaataaagcagtaaattccgttatcgcagccgttgtcaacatctttcgt<br>tcaattcccttccttattttaatcatcctgcttcttggtttcactaaattcttagtgggaacaattttg<br>ggaccaaatgcggctcttcccgcgttagtcatcggtagtgctcccttttatgctcgtctggtcgaaatc<br>gcacttcgtgaagtggacaaaggagtgattgaggcggcgaaatcgatgggggctaagacgagcactatt<br>atttttaaggttcttatccccgagtccatgcccgcgctgatttccggaattacagtgactgcgattgca<br>ttgatcgggtcaaccgccatcgcaggagctattggttctggtggattgggaaacttagcatacgttgaa<br>ggctatcaatcgaataatgcggatgtgaccttcgtggccacagttttcatcctgattattgttttcatc<br>attcagatcattggtgaccttattaccaacatcatcgataaacgc |

The invention claimed is:

1. An engineered bacterium comprising one or more gene(s) or gene cassette(s) encoding a therapeutic molecule and a modified pks island as compared to a corresponding bacterium comprising an unmodified pks island, wherein the modified pks island comprises 1) a full or partial deletion of the clbA, clbB, clbC, clbD, clbE, clbF, clbG, clbH, clbI, clbJ, clbK, clbL, clbM, clbN, clbO, clbP, clbQ, and clbR gene sequences; and
2) an intact or unmodified clbS gene sequence; and
3) a full or partial deletion of the promoter operably linked to clbS;

wherein the therapeutic molecule is a protein, and wherein the engineered bacterium is an engineered *Escherichia coli*.

2. The engineered bacterium of claim 1, wherein the therapeutic molecule is 1) a phenylalanine metabolizing enzyme; or
2) an oxalate metabolic enzyme; or
3) is a protein capable of reducing a deleterious molecule.

3. The engineered bacterium of claim 1, wherein the engineered bacterium is an engineered *Escherichia coli* Nissle.

4. The engineered bacterium of claim 1, wherein the engineered bacterium produces less colibactin compared to a corresponding bacterium comprising an unmodified pks island.

5. The engineered bacterium of claim 1, wherein the engineered bacterium produces less colibactin precursor or metabolite compared to a corresponding bacterium comprising an unmodified pks island.

6. The engineered bacterium of claim 1, wherein the engineered bacterium produces less N-myristoyl-D-asparagine compared to a corresponding bacterium comprising an unmodified pks island.

7. A pharmaceutical composition comprising the engineered bacterium of claim 1.

8. A method of treatment comprising administering the pharmaceutical composition of claim 7 to a subject in need thereof.

9. A method of reducing a deleterious molecule comprising administering the pharmaceutical composition of claim 7 to a subject in need thereof.

10. A method of reducing oxalate comprising administering the pharmaceutical composition of claim 7 to a subject in need thereof, wherein the therapeutic molecule is a oxalate metabolic enzyme.

11. A method of treating hyperoxaluria (HOX) comprising administering the pharmaceutical composition of claim 7 to a subject in need thereof, wherein the therapeutic molecule is a oxalate metabolic enzyme.

12. A method of reducing phenylalanine comprising administering the pharmaceutical composition of claim 7 to a subject in need thereof, wherein the therapeutic molecule is a phenylalanine metabolizing enzyme.

13. A method of treating hyperphenylalaninemia comprising administering the pharmaceutical composition of claim 7 to a subject in need thereof, wherein the therapeutic molecule is a phenylalanine metabolizing enzyme.

14. A method of treating phenylketonuria (PKU) comprising administering the pharmaceutical composition of claim 7 to a subject in need thereof, wherein the therapeutic molecule is a phenylalanine metabolizing enzyme.

15. A method of reducing methionine levels comprising administering the pharmaceutical composition of claim 7 to a subject in need thereof, wherein the therapeutic molecule is a phenylalanine metabolizing enzyme.

16. A method of treating homocysteinuria comprising administering the pharmaceutical composition of claim 7 to a subject in need thereof, wherein the therapeutic molecule is a methionine metabolizing enzyme.

* * * * *

SEQUENCE LISTING

<160> NUMBER OF SEQ ID NOS: 171

<210> SEQ ID NO 1
<211> LENGTH: 1287
<212> TYPE: DNA
<213> ORGANISM: Oxalobacter formigenes

<400> SEQUENCE: 1

```
atgactaaac cattagatgg aattaatgtg cttgacttta cccacgtcca ggcaggtcct     60
gcctgtacac agatgatggg tttcttgggc gcaaacgtca tcaagattga aagacgtggt    120
tccggagata tgactcgtgg atggctgcag gacaaaccaa atgttgattc cctgtatttc    180
acgatgttca actgtaacaa acgttcgatt gaactggaca tgaaaacccc ggaaggcaaa    240
gagcttctgg aacagatgat caagaaagcc gacgtcatgg tcgaaaactt cggaccaggc    300
gcactggacc gtatgggctt tacttgggaa tacattcagg aactgaatcc acgcgtcatt    360
ctggcttccg ttaaaggcta tgcagaaggc cacgccaacg aacacctgaa agtttatgaa    420
aacgttgcac agtgttccgg cggtgctgca gctaccaccg gtttctggga tggtcctcca    480
accgtttccg gcgctgctct gggtgactcc aactccggta tgcacctgat gatcggtatt    540
ctggccgctc tggaaatgcg tcacaaaacc ggccgtggtc agaaagttgc cgtcgctatg    600
caggacgctg ttctgaatct ggttcgtatc aaactgcgtg accagcaacg tctggaaaga    660
accggcattc tggctgaata cccacaggct cagcctaact ttgccttcga cagagacggt    720
aacccactgt ccttcgacaa catcacttcc gttccacgtg gtggtaacgc aggtggcggc    780
ggccagccag gctggatgct gaaatgtaaa ggttgggaaa ccgatgcgga ctcctacgtt    840
tacttcacca tcgctgcaaa catgtggcca cagatctgcg acatgatcga caagccagaa    900
tggaaagacg acccagccta caacacattc gaaggtcgtg ttgacaagct gatggacatc    960
ttctccttca tcgaaaccaa gttcgctgac aaggacaaat tcgaagttac cgaatgggct   1020
gcccagtacg gcattccttg cggtccggtc atgtccatga aagaactggc tcacgatcct   1080
tccctgcaga aagttggtac cgtcgttgaa gttgtcgacg aaattcgtgg taaccacctg   1140
accgttggcg caccgttcaa attctccgga ttccagccgg aaattacccg tgctccgctg   1200
ttgggcgaac ataccgacga agttctgaaa gaactgggtc ttgacgatgc caagatcaag   1260
gaactgcatg caaaacaggt agtttga                                       1287
```

<210> SEQ ID NO 2
<211> LENGTH: 1707
<212> TYPE: DNA
<213> ORGANISM: Oxalobacter formigenes

<400> SEQUENCE: 2

```
atgagtaacg acgacaatgt agagttgact gatggctttc atgttttgat cgatgccctg     60
aaaatgaatg acatcgatac catgtatggt gttgtcggca ttcctatcac gaacctggct    120
cgtatgtggc aagatgacgg tcagcgtttt tacagcttcc gtcacgaaca acacgcaggt    180
tatgcagctt ctatcgccgg ttacatcgaa ggaaaacctg gcgtttgctt gaccgtttcc    240
gcccctggct tcctgaacgg cgtgacttcc ctggctcatg caaccaccaa ctgcttccca    300
atgatcctgt tgagcggttc cagtgaacgt gaaatcgtcg atttgcaaca gggcgattac    360
gaagaaatgg atcagatgaa tgttgcacgt ccacactgca aagcttcttt ccgtatcaac    420
agcatcaaag acattccaat cggtatcgct cgtgcagttc gcaccgctgt atccggacgt    480
ccaggtggtg tttacgttga cttgccagca aaactgttcg gtcagaccat ttctgtagaa    540
```

```
gaagctaaca aactgctctt caaaccaatc gatccagctc cggcacagat tcctgctgaa    600
gacgctatcg ctcgcgctgc tgacctgatc aagaacgcca aacgtccagt tatcatgctg    660
ggtaaaggcg ctgcatacgc acaatgcgac gacgaaatcc gcgcactggt tgaagaaacc    720
ggcatcccat tcctgccaat gggtatggct aaaggcctgc tgcctgacaa ccatccacaa    780
tccgctgctg caacccgtgc tttcgcactg gcacagtgtg acgtttgcgt actgatcggc    840
gctcgtctga actggctgat gcagcacggt aaaggcaaaa cctggggcga cgaactgaag    900
aaatacgttc agatcgacat ccaggctaac gaaatggaca gcaaccagcc tatcgctgca    960
ccagttgttg gtgacatcaa gtccgccgtt tccctgctcc gcaaagcact gaaaggcgct   1020
ccaaaagctg acgctgaatg gaccggcgct ctgaaagcca aagttgacgg caacaaagcc   1080
aaactggctg gcaagatgac tgccgaaacc ccatccggaa tgatgaacta ctccaattcc   1140
ctgggcgttg ttcgtgactt catgctggca aatccggata tttccctggt taacgaaggc   1200
gctaatgcac tcgacaacac tcgtatgatt gttgacatgc tgaaaccacg caaacgtctt   1260
gactccggta cctggggtgt tatgggtatt ggtatgggct actgcgttgc tgcagctgct   1320
gttaccggca aaccggttat cgctgttgaa ggcgatagcg cattcggttt ctccggtatg   1380
gaactggaaa ccatctgccg ttacaacctg ccagttaccg ttatcatcat gaacaatggt   1440
ggtatctata aaggtaacga agcagatcca caaccaggcg ttatctcctg tacccgtctg   1500
acccgtggtc gttacgacat gatgatggaa gcatttggcg gtaaaggtta tgttgccaat   1560
actccagcag aactgaaagc tgctctggaa gaagctgttg cttccggcaa accatgcctg   1620
atcaacgcga tgatcgatcc agacgctggt gtcgaatctg gccgtatcaa gagcctgaac   1680
gttgtaagta aagttggcaa gaaataa                                       1707
```

```
<210> SEQ ID NO 3
<211> LENGTH: 1632
<212> TYPE: DNA
<213> ORGANISM: Saccharomyces cerevisiae

<400> SEQUENCE: 3

atgaccagtg cagctacggt gaccgcgagc tttaatgaca ctttttctgt gagcgataat     60
gtcgcggtaa tcgtaccgga aaccgatacg caggtcacct accgtgatct ttcccacatg    120
gtaggacact ttcaaacaat gttcacgaac ccgaatagtc ctctgtacgg ggcggtcttt    180
cgtcaagaca cggtagcgat tagcatgcgt aacggccttg aatttattgt ggctttcctt    240
ggagccacga tggatgcgaa aattggtgcg ccactgaatc ccaattataa agagaaggag    300
tttaattttt acctgaatga cttaaagtcc aaagccatct gcgtgccgaa aggcaccacc    360
aaactgcaaa gttcagaaat tcttaagagt gcgtccacgt tcgggtgctt tattgtggaa    420
ctggcgtttg acgccacccg ttttcgtgtt gaatatgaca tttactcccc ggaggacaat    480
tataaacgtg tgatctaccg cagccttaac aatgctaagt ttgtcaacac aaaccctgtc    540
aagttcccgg gtttcgcccg cagctcggat gttgcactta ttttgcatac ctcaggcacc    600
actagtaccc caaagaccgt acccctcttg catctgaata ttgtccgttc aaccctgaat    660
atcgccaaca cttacaaact taccccgctg gatcgctcct atgttgtaat gccgctgttt    720
catgtacatg gattaatcgg cgtcttactg agtacgttcc gcacccaggg cagtgtagtc    780
gtcccggacg gctttcatcc gaagctcttc tgggatcagt ttgttaaata taactgcaat    840
tggtttagtt gcgtcccaac gatctctatg attatgttga atatgcccaa accgaatccg    900
```

```
tttccgcaca ttcgctttat ccgctcatgt agcagcgcgc tggcgccagc aacgtttcac    960

aagctggaaa aagaatttaa tgccccagtt ctggaagcgt acgcgatgac agaagcatct   1020

catcagatga ccagtaacaa tctgcctccc ggtaaacgta aaccggggac cgtgggccaa   1080

cctcaaggtg taaccgtagt aatcctggat gacaacgata acgttctgcc gcccggcaaa   1140

gttggcgagg tgtcgatccg tggggagaac gtcaccctgg gctacgctaa taacccgaaa   1200

gctaacaaag aaaacttcac taaacgtgaa aactatttcc gtaccgggga tcagggctac   1260

ttcgacccgg agggctttct cgtgctgacc ggccgcatta aagaattgat caatcgcggt   1320

ggtgaaaaaa ttagtcctat tgaactggac ggaatcatgc tctcgcatcc taaaatcgac   1380

gaggcggtgg cgttcggcgt tccagatgat atgtatggcc aagtcgttca ggcggcaatc   1440

gtgttgaaaa aggggaaaaa gatgacctat gaagaattag tgaatttcct gaaaaagcat   1500

ttagcaagct ttaaaatccc aaccaaagtc tactttgtgg ataagctgcc taaaacggcc   1560

accgggaaga ttcaacgtcg cgtaatcgcc gaaaccttcg cgaaatctag tcgcaacaaa   1620

agcaaacttt aa                                                        1632
```

<210> SEQ ID NO 4
<211> LENGTH: 1146
<212> TYPE: DNA
<213> ORGANISM: Escherichia coli

<400> SEQUENCE: 4

```
atgacaaata atgaaagcaa agggccgttt gaaggcttat tagttatcga tatgacacat     60

gtccttaatg gacctttcgg aactcaactt ctttgtaata tgggcgcaag ggtaattaaa    120

gttgagccgc cgggtcatgg tgatgatacc cgcacatttg gtccctatgt ggatggacag    180

tcactctatt acagttttat taatcatggc aaagagagtg tggttcttga tttaaagaat    240

gatcacgata aaagtatatt tataaatatg ctcaaacaag ctgatgtatt agctgagaat    300

tttcgcccag gtacaatgga aaaactgggg ttttcatggg aaacgcttca agaaatcaac    360

ccgcgcctca tatatgcttc atcgtcaggt ttcggacata ccggtccgct aaaagatgct    420

cctgcctacg ataccatcat tcaggcaatg agcgggataa tgatggaaac aggatatcct    480

gatgctccgc cagtgcgcgt tggtacatct cttgcggatc tatgcggcgg tgtctattta    540

ttcagcggaa tagtgagtgc actttatggc cgcgaaaaga gccagagagg ggcgcatgtc    600

gatatagcga tgtttgatgc cacgctgagt tttctggagc atggtctgat ggcatatatc    660

gcaactggga agtcaccaca acgtctggga aatcgccatc cctacatggc acctttttgat    720

gttttcaata ctcaggataa gccgattacg atttgttgtg gtaatgacaa gcttttttct    780

gcgttatgcc aggcactgga gcttacggaa ctggttaatg atccccgatt tagcagcaat    840

attttacgcg tacaaaacca ggctattctt aaacaatata ttgagcggac gttaaaaacg    900

caggcagctg aagtttggtt agccagaata catgaagttg gtgtacccgt cgcgccgtta    960

ttaagtgtgg ctgaggccat taaattgcca caaactcagg cgagaaatat gttgattgaa   1020

gccgggggaa taatgatgcc gggtaatccg ataaaaatca gcggctgcgc ggacccgcat   1080

gttatgccgg gagcggcaac gctcgaccag catggggaac aaattcgcca ggagttctca   1140

tcataa                                                              1146
```

<210> SEQ ID NO 5
<211> LENGTH: 428
<212> TYPE: PRT
<213> ORGANISM: Oxalobacter formigenes

<400> SEQUENCE: 5

```
Met Thr Lys Pro Leu Asp Gly Ile Asn Val Leu Asp Phe Thr His Val
1               5                   10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asp Met Thr Arg Gly Trp
        35                  40                  45

Leu Gln Asp Lys Pro Asn Val Asp Ser Leu Tyr Phe Thr Met Phe Asn
    50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Met Arg His Lys Thr Gly Arg
            180                 185                 190

Gly Gln Lys Val Ala Val Ala Met Gln Asp Ala Val Leu Asn Leu Val
        195                 200                 205

Arg Ile Lys Leu Arg Asp Gln Gln Arg Leu Glu Arg Thr Gly Ile Leu
    210                 215                 220

Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
                245                 250                 255

Ala Gly Gly Gly Gly Gln Pro Gly Trp Met Leu Lys Cys Lys Gly Trp
            260                 265                 270

Glu Thr Asp Ala Asp Ser Tyr Val Tyr Phe Thr Ile Ala Ala Asn Met
        275                 280                 285

Trp Pro Gln Ile Cys Asp Met Ile Asp Lys Pro Glu Trp Lys Asp Asp
    290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
    370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
```

```
                405                 410                 415

Ala Lys Ile Lys Glu Leu His Ala Lys Gln Val Val
            420                 425


<210> SEQ ID NO 6
<211> LENGTH: 568
<212> TYPE: PRT
<213> ORGANISM: Oxalobacter formigenes

<400> SEQUENCE: 6

Met Ser Asn Asp Asp Asn Val Glu Leu Thr Asp Gly Phe His Val Leu
1               5                   10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Asp Gly Gln
        35                  40                  45

Arg Phe Tyr Ser Phe Arg His Glu Gln His Ala Gly Tyr Ala Ala Ser
    50                  55                  60

Ile Ala Gly Tyr Ile Glu Gly Lys Pro Gly Val Cys Leu Thr Val Ser
65                  70                  75                  80

Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
        115                 120                 125

Ala Arg Pro His Cys Lys Ala Ser Phe Arg Ile Asn Ser Ile Lys Asp
    130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
        195                 200                 205

Leu Ile Lys Asn Ala Lys Arg Pro Val Ile Met Leu Gly Lys Gly Ala
    210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255

Asn His Pro Gln Ser Ala Ala Ala Thr Arg Ala Phe Ala Leu Ala Gln
            260                 265                 270

Cys Asp Val Cys Val Leu Ile Gly Ala Arg Leu Asn Trp Leu Met Gln
        275                 280                 285

His Gly Lys Gly Lys Thr Trp Gly Asp Glu Leu Lys Lys Tyr Val Gln
    290                 295                 300

Ile Asp Ile Gln Ala Asn Glu Met Asp Ser Asn Gln Pro Ile Ala Ala
305                 310                 315                 320

Pro Val Val Gly Asp Ile Lys Ser Ala Val Ser Leu Leu Arg Lys Ala
                325                 330                 335

Leu Lys Gly Ala Pro Lys Ala Asp Ala Glu Trp Thr Gly Ala Leu Lys
            340                 345                 350
```

```
Ala Lys Val Asp Gly Asn Lys Ala Lys Leu Ala Gly Lys Met Thr Ala
        355                 360                 365

Glu Thr Pro Ser Gly Met Met Asn Tyr Ser Asn Ser Leu Gly Val Val
    370                 375                 380

Arg Asp Phe Met Leu Ala Asn Pro Asp Ile Ser Leu Val Asn Glu Gly
385                 390                 395                 400

Ala Asn Ala Leu Asp Asn Thr Arg Met Ile Val Asp Met Leu Lys Pro
                405                 410                 415

Arg Lys Arg Leu Asp Ser Gly Thr Trp Gly Val Met Gly Ile Gly Met
            420                 425                 430

Gly Tyr Cys Val Ala Ala Ala Ala Val Thr Gly Lys Pro Val Ile Ala
        435                 440                 445

Val Glu Gly Asp Ser Ala Phe Gly Phe Ser Gly Met Glu Leu Glu Thr
    450                 455                 460

Ile Cys Arg Tyr Asn Leu Pro Val Thr Val Ile Ile Met Asn Asn Gly
465                 470                 475                 480

Gly Ile Tyr Lys Gly Asn Glu Ala Asp Pro Gln Pro Gly Val Ile Ser
                485                 490                 495

Cys Thr Arg Leu Thr Arg Gly Arg Tyr Asp Met Met Met Glu Ala Phe
            500                 505                 510

Gly Gly Lys Gly Tyr Val Ala Asn Thr Pro Ala Glu Leu Lys Ala Ala
        515                 520                 525

Leu Glu Glu Ala Val Ala Ser Gly Lys Pro Cys Leu Ile Asn Ala Met
    530                 535                 540

Ile Asp Pro Asp Ala Gly Val Glu Ser Gly Arg Ile Lys Ser Leu Asn
545                 550                 555                 560

Val Val Ser Lys Val Gly Lys Lys
                565


<210> SEQ ID NO 7
<211> LENGTH: 543
<212> TYPE: PRT
<213> ORGANISM: Saccharomyces cerevisiae

<400> SEQUENCE: 7

Met Thr Ser Ala Ala Thr Val Thr Ala Ser Phe Asn Asp Thr Phe Ser
1               5                   10                  15

Val Ser Asp Asn Val Ala Val Ile Val Pro Glu Thr Asp Thr Gln Val
            20                  25                  30

Thr Tyr Arg Asp Leu Ser His Met Val Gly His Phe Gln Thr Met Phe
        35                  40                  45

Thr Asn Pro Asn Ser Pro Leu Tyr Gly Ala Val Phe Arg Gln Asp Thr
    50                  55                  60

Val Ala Ile Ser Met Arg Asn Gly Leu Glu Phe Ile Val Ala Phe Leu
65                  70                  75                  80

Gly Ala Thr Met Asp Ala Lys Ile Gly Ala Pro Leu Asn Pro Asn Tyr
                85                  90                  95

Lys Glu Lys Glu Phe Asn Phe Tyr Leu Asn Asp Leu Lys Ser Lys Ala
            100                 105                 110

Ile Cys Val Pro Lys Gly Thr Thr Lys Leu Gln Ser Ser Glu Ile Leu
        115                 120                 125

Lys Ser Ala Ser Thr Phe Gly Cys Phe Ile Val Glu Leu Ala Phe Asp
    130                 135                 140

Ala Thr Arg Phe Arg Val Glu Tyr Asp Ile Tyr Ser Pro Glu Asp Asn
145                 150                 155                 160
```

```
Tyr Lys Arg Val Ile Tyr Arg Ser Leu Asn Asn Ala Lys Phe Val Asn
                165                 170                 175

Thr Asn Pro Val Lys Phe Pro Gly Phe Ala Arg Ser Ser Asp Val Ala
            180                 185                 190

Leu Ile Leu His Thr Ser Gly Thr Thr Ser Thr Pro Lys Thr Val Pro
        195                 200                 205

Leu Leu His Leu Asn Ile Val Arg Ser Thr Leu Asn Ile Ala Asn Thr
    210                 215                 220

Tyr Lys Leu Thr Pro Leu Asp Arg Ser Tyr Val Val Met Pro Leu Phe
225                 230                 235                 240

His Val His Gly Leu Ile Gly Val Leu Leu Ser Thr Phe Arg Thr Gln
                245                 250                 255

Gly Ser Val Val Val Pro Asp Gly Phe His Pro Lys Leu Phe Trp Asp
            260                 265                 270

Gln Phe Val Lys Tyr Asn Cys Asn Trp Phe Ser Cys Val Pro Thr Ile
        275                 280                 285

Ser Met Ile Met Leu Asn Met Pro Lys Pro Asn Pro Phe Pro His Ile
    290                 295                 300

Arg Phe Ile Arg Ser Cys Ser Ser Ala Leu Ala Pro Ala Thr Phe His
305                 310                 315                 320

Lys Leu Glu Lys Glu Phe Asn Ala Pro Val Leu Glu Ala Tyr Ala Met
                325                 330                 335

Thr Glu Ala Ser His Gln Met Thr Ser Asn Asn Leu Pro Pro Gly Lys
            340                 345                 350

Arg Lys Pro Gly Thr Val Gly Gln Pro Gln Gly Val Thr Val Val Ile
        355                 360                 365

Leu Asp Asp Asn Asp Asn Val Leu Pro Pro Gly Lys Val Gly Glu Val
    370                 375                 380

Ser Ile Arg Gly Glu Asn Val Thr Leu Gly Tyr Ala Asn Asn Pro Lys
385                 390                 395                 400

Ala Asn Lys Glu Asn Phe Thr Lys Arg Glu Asn Tyr Phe Arg Thr Gly
                405                 410                 415

Asp Gln Gly Tyr Phe Asp Pro Glu Gly Phe Leu Val Leu Thr Gly Arg
            420                 425                 430

Ile Lys Glu Leu Ile Asn Arg Gly Gly Glu Lys Ile Ser Pro Ile Glu
        435                 440                 445

Leu Asp Gly Ile Met Leu Ser His Pro Lys Ile Asp Glu Ala Val Ala
    450                 455                 460

Phe Gly Val Pro Asp Asp Met Tyr Gly Gln Val Val Gln Ala Ala Ile
465                 470                 475                 480

Val Leu Lys Lys Gly Glu Lys Met Thr Tyr Glu Glu Leu Val Asn Phe
                485                 490                 495

Leu Lys Lys His Leu Ala Ser Phe Lys Ile Pro Thr Lys Val Tyr Phe
            500                 505                 510

Val Asp Lys Leu Pro Lys Thr Ala Thr Gly Lys Ile Gln Arg Arg Val
        515                 520                 525

Ile Ala Glu Thr Phe Ala Lys Ser Ser Arg Asn Lys Ser Lys Leu
    530                 535                 540
```

```
<210> SEQ ID NO 8
<211> LENGTH: 381
<212> TYPE: PRT
<213> ORGANISM: Escherichia coli
```

<400> SEQUENCE: 8

```
Met Thr Asn Asn Glu Ser Lys Gly Pro Phe Glu Gly Leu Leu Val Ile
1               5                   10                  15

Asp Met Thr His Val Leu Asn Gly Pro Phe Gly Thr Gln Leu Leu Cys
            20                  25                  30

Asn Met Gly Ala Arg Val Ile Lys Val Glu Pro Pro Gly His Gly Asp
        35                  40                  45

Asp Thr Arg Thr Phe Gly Pro Tyr Val Asp Gly Gln Ser Leu Tyr Tyr
    50                  55                  60

Ser Phe Ile Asn His Gly Lys Glu Ser Val Val Leu Asp Leu Lys Asn
65                  70                  75                  80

Asp His Asp Lys Ser Ile Phe Ile Asn Met Leu Lys Gln Ala Asp Val
                85                  90                  95

Leu Ala Glu Asn Phe Arg Pro Gly Thr Met Glu Lys Leu Gly Phe Ser
            100                 105                 110

Trp Glu Thr Leu Gln Glu Ile Asn Pro Arg Leu Ile Tyr Ala Ser Ser
        115                 120                 125

Ser Gly Phe Gly His Thr Gly Pro Leu Lys Asp Ala Pro Ala Tyr Asp
    130                 135                 140

Thr Ile Ile Gln Ala Met Ser Gly Ile Met Met Glu Thr Gly Tyr Pro
145                 150                 155                 160

Asp Ala Pro Pro Val Arg Val Gly Thr Ser Leu Ala Asp Leu Cys Gly
                165                 170                 175

Gly Val Tyr Leu Phe Ser Gly Ile Val Ser Ala Leu Tyr Gly Arg Glu
            180                 185                 190

Lys Ser Gln Arg Gly Ala His Val Asp Ile Ala Met Phe Asp Ala Thr
        195                 200                 205

Leu Ser Phe Leu Glu His Gly Leu Met Ala Tyr Ile Ala Thr Gly Lys
    210                 215                 220

Ser Pro Gln Arg Leu Gly Asn Arg His Pro Tyr Met Ala Pro Phe Asp
225                 230                 235                 240

Val Phe Asn Thr Gln Asp Lys Pro Ile Thr Ile Cys Cys Gly Asn Asp
                245                 250                 255

Lys Leu Phe Ser Ala Leu Cys Gln Ala Leu Glu Leu Thr Glu Leu Val
            260                 265                 270

Asn Asp Pro Arg Phe Ser Ser Asn Ile Leu Arg Val Gln Asn Gln Ala
        275                 280                 285

Ile Leu Lys Gln Tyr Ile Glu Arg Thr Leu Lys Thr Gln Ala Ala Glu
    290                 295                 300

Val Trp Leu Ala Arg Ile His Glu Val Gly Val Pro Val Ala Pro Leu
305                 310                 315                 320

Leu Ser Val Ala Glu Ala Ile Lys Leu Pro Gln Thr Gln Ala Arg Asn
                325                 330                 335

Met Leu Ile Glu Ala Gly Gly Ile Met Met Pro Gly Asn Pro Ile Lys
            340                 345                 350

Ile Ser Gly Cys Ala Asp Pro His Val Met Pro Gly Ala Ala Thr Leu
        355                 360                 365

Asp Gln His Gly Glu Gln Ile Arg Gln Glu Phe Ser Ser
    370                 375                 380
```

<210> SEQ ID NO 9
<211> LENGTH: 437
<212> TYPE: PRT
<213> ORGANISM: Escherichia coli

<400> SEQUENCE: 9

```
Ser Tyr Tyr His His His His His His Leu Glu Ser Thr Ser Leu Tyr
1               5                   10                  15

Lys Lys Ala Gly Leu Met Ser Thr Pro Leu Gln Gly Ile Lys Val Leu
            20                  25                  30

Asp Phe Thr Gly Val Gln Ser Gly Pro Ser Cys Thr Gln Met Leu Ala
        35                  40                  45

Trp Phe Gly Ala Asp Val Ile Lys Ile Glu Arg Pro Gly Val Gly Asp
    50                  55                  60

Val Thr Arg His Gln Leu Arg Asp Ile Pro Asp Ile Asp Ala Leu Tyr
65                  70                  75                  80

Phe Thr Met Leu Asn Ser Asn Lys Arg Ser Ile Glu Leu Asn Thr Lys
                85                  90                  95

Thr Ala Glu Gly Lys Glu Val Met Glu Lys Leu Ile Arg Glu Ala Asp
            100                 105                 110

Ile Leu Val Glu Asn Phe His Pro Gly Ala Ile Asp His Met Gly Phe
        115                 120                 125

Thr Trp Glu His Ile Gln Glu Ile Asn Pro Arg Leu Ile Phe Gly Ser
    130                 135                 140

Ile Lys Gly Phe Asp Glu Cys Ser Pro Tyr Val Asn Val Lys Ala Tyr
145                 150                 155                 160

Glu Asn Val Ala Gln Ala Ala Gly Gly Ala Ala Ser Thr Thr Gly Phe
                165                 170                 175

Trp Asp Gly Pro Pro Leu Val Ser Ala Ala Ala Leu Gly Asp Ser Asn
            180                 185                 190

Thr Gly Met His Leu Leu Ile Gly Leu Leu Ala Ala Leu Leu His Arg
        195                 200                 205

Glu Lys Thr Gly Arg Gly Gln Arg Val Thr Met Ser Met Gln Asp Ala
    210                 215                 220

Val Leu Asn Leu Cys Arg Val Lys Leu Arg Asp Gln Gln Arg Leu Asp
225                 230                 235                 240

Lys Leu Gly Tyr Leu Glu Glu Tyr Pro Gln Tyr Pro Asn Gly Thr Phe
                245                 250                 255

Gly Asp Ala Val Pro Arg Gly Gly Asn Ala Gly Gly Gly Gly Gln Pro
            260                 265                 270

Gly Trp Ile Leu Lys Cys Lys Gly Trp Glu Thr Asp Pro Asn Ala Tyr
        275                 280                 285

Ile Tyr Phe Thr Ile Gln Glu Gln Asn Trp Glu Asn Thr Cys Lys Ala
    290                 295                 300

Ile Gly Lys Pro Glu Trp Ile Thr Asp Pro Ala Tyr Ser Thr Ala His
305                 310                 315                 320

Ala Arg Gln Pro His Ile Phe Asp Ile Phe Ala Glu Ile Glu Lys Tyr
                325                 330                 335

Thr Val Thr Ile Asp Lys His Glu Ala Val Ala Tyr Leu Thr Gln Phe
            340                 345                 350

Asp Ile Pro Cys Ala Pro Val Leu Ser Met Lys Glu Ile Ser Leu Asp
        355                 360                 365

Pro Ser Leu Arg Gln Ser Gly Ser Val Val Glu Val Glu Gln Pro Leu
    370                 375                 380

Arg Gly Lys Tyr Leu Thr Val Gly Cys Pro Met Lys Phe Ser Ala Phe
385                 390                 395                 400

Thr Pro Asp Ile Lys Ala Ala Pro Leu Leu Gly Glu His Thr Ala Ala
```

```
                405                 410                 415

Val Leu Gln Glu Leu Gly Tyr Ser Asp Asp Glu Ile Ala Ala Met Lys
            420                 425                 430

Gln Asn His Ala Ile
        435


<210> SEQ ID NO 10
<211> LENGTH: 564
<212> TYPE: PRT
<213> ORGANISM: Escherichia coli

<400> SEQUENCE: 10

Met Ser Asp Gln Leu Gln Met Thr Asp Gly Met His Ile Ile Val Glu
1               5                   10                  15

Ala Leu Lys Gln Asn Asn Ile Asp Thr Ile Tyr Gly Val Val Gly Ile
            20                  25                  30

Pro Val Thr Asp Met Ala Arg His Ala Gln Ala Glu Gly Ile Arg Tyr
        35                  40                  45

Ile Gly Phe Arg His Glu Gln Ser Ala Gly Tyr Ala Ala Ala Ala Ser
    50                  55                  60

Gly Phe Leu Thr Gln Lys Pro Gly Ile Cys Leu Thr Val Ser Ala Pro
65                  70                  75                  80

Gly Phe Leu Asn Gly Leu Thr Ala Leu Ala Asn Ala Thr Val Asn Gly
                85                  90                  95

Phe Pro Met Ile Met Ile Ser Gly Ser Ser Asp Arg Ala Ile Val Asp
            100                 105                 110

Leu Gln Gln Gly Asp Tyr Glu Glu Leu Asp Gln Met Asn Ala Ala Lys
        115                 120                 125

Pro Tyr Ala Lys Ala Ala Phe Arg Val Asn Gln Pro Gln Asp Leu Gly
    130                 135                 140

Ile Ala Leu Ala Arg Ala Ile Arg Val Ser Val Ser Gly Arg Pro Gly
145                 150                 155                 160

Gly Val Tyr Leu Asp Leu Pro Ala Asn Val Leu Ala Ala Thr Met Glu
                165                 170                 175

Lys Asp Glu Ala Leu Thr Thr Ile Val Lys Val Glu Asn Pro Ser Pro
            180                 185                 190

Ala Leu Leu Pro Cys Pro Lys Ser Val Thr Ser Ala Ile Ser Leu Leu
        195                 200                 205

Ala Lys Ala Glu Arg Pro Leu Ile Ile Leu Gly Lys Gly Ala Ala Tyr
    210                 215                 220

Ser Gln Ala Asp Glu Gln Leu Arg Glu Phe Ile Glu Ser Ala Gln Ile
225                 230                 235                 240

Pro Phe Leu Pro Met Ser Met Ala Lys Gly Ile Leu Glu Asp Thr His
                245                 250                 255

Pro Leu Ser Ala Ala Ala Ala Arg Ser Phe Ala Leu Ala Asn Ala Asp
            260                 265                 270

Val Val Met Leu Val Gly Ala Arg Leu Asn Trp Leu Leu Ala His Gly
        275                 280                 285

Lys Lys Gly Trp Ala Ala Asp Thr Gln Phe Ile Gln Leu Asp Ile Glu
    290                 295                 300

Pro Gln Glu Ile Asp Ser Asn Arg Pro Ile Ala Val Pro Val Val Gly
305                 310                 315                 320

Asp Ile Ala Ser Ser Met Gln Gly Met Leu Ala Glu Leu Lys Gln Asn
                325                 330                 335
```

```
Thr Phe Thr Thr Pro Leu Val Trp Arg Asp Ile Leu Asn Ile His Lys
            340                 345                 350

Gln Gln Asn Ala Gln Lys Met His Glu Lys Leu Ser Thr Asp Thr Gln
        355                 360                 365

Pro Leu Asn Tyr Phe Asn Ala Leu Ser Ala Val Arg Asp Val Leu Arg
    370                 375                 380

Glu Asn Gln Asp Ile Tyr Leu Val Asn Glu Gly Ala Asn Thr Leu Asp
385                 390                 395                 400

Asn Ala Arg Asn Ile Ile Asp Met Tyr Lys Pro Arg Arg Arg Leu Asp
                405                 410                 415

Cys Gly Thr Trp Gly Val Met Gly Ile Gly Met Gly Tyr Ala Ile Gly
            420                 425                 430

Ala Ser Val Thr Ser Gly Ser Pro Val Val Ala Ile Glu Gly Asp Ser
        435                 440                 445

Ala Phe Gly Phe Ser Gly Met Glu Ile Glu Thr Ile Cys Arg Tyr Asn
    450                 455                 460

Leu Pro Val Thr Ile Val Ile Phe Asn Asn Gly Gly Ile Tyr Arg Gly
465                 470                 475                 480

Asp Gly Val Asp Leu Ser Gly Ala Gly Ala Pro Ser Pro Thr Asp Leu
                485                 490                 495

Leu His His Ala Arg Tyr Asp Lys Leu Met Asp Ala Phe Arg Gly Val
            500                 505                 510

Gly Tyr Asn Val Thr Thr Thr Asp Glu Leu Arg His Ala Leu Thr Thr
        515                 520                 525

Gly Ile Gln Ser Arg Lys Pro Thr Ile Ile Asn Val Val Ile Asp Pro
    530                 535                 540

Ala Ala Gly Thr Glu Ser Gly His Ile Thr Lys Leu Asn Pro Lys Gln
545                 550                 555                 560

Val Ala Gly Asn
```

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 1182
<212> TYPE: DNA
<213> ORGANISM: Brevibacterium aurantiacum

<400> SEQUENCE: 101
atgacgagcc ttcaccccga aactttaatg gtgcacgggg gtatgaaggg attgacagag 60
gcgggtgttc acgtcccggc gatcgacctg tcgacaacga atcctgttaa tgacgtagcg 120
acagggggtg attcttacga atggcttgca acgggtcaca cgttgaagga tggtgattct 180
gctgtttacc agcgtttatg gcagcccggt gtagctcgtt tcgagacggc tctggctggg 240
ctggagcacg cggaggaggc tgtagctttc gccacgggta tggccgccat gaccgcggcc 300
ttattggcag cagtatcagc tggcacgcct catatcgtcg cagtccgccc attatacggc 360
ggttcagacc atcttttaga gactggttta ctggggacaa ctgtcacgtg ggcgaaagaa 420
gctgacatcg ccagtgcaat ccaagacgat acagggttag tgatcgtgga gacgccagcc 480
aatcctagtc ttgatctggt agacctggat tctgtcgtgt cagcggcagg gaacgtccct 540
gtccttgtag ataatacgtt ttgtactcct gtccttcagc aacctatctc gcacggcgcc 600
gcacttgtat tacattcggc aacaaagtat ttagggggc atggggacgc catgggcggg 660
atcatcgcga ctaatgctga ttgggctatg cgcctgcgtc aggtccgtgc gatcactggt 720
gcattactgc atccgatggg cgcgtacttg ttacaccgcg gtttgcgtac tctggctgtt 780
cgcatgcgtg ccgctcagac aactgctggt gagcttgctg agcgcttaga cgctcatccc 840
gctatttcag ttgtgcacta cccaggattg aaggggcaag atcctcgtgg attgttaggc 900

```
cgtcagatga gtggaggtgg ggcaatgatt gctatggagc tggcaggggg attcgatgcg    960

gcacgctcct ttgttgagca ttgtaacttg gtcgtgcatg ccgtatcact tgggggagca   1020

gacacattaa ttcaacatcc ggcaagtttg acacaccgcc cggtcgcagc aaccgccaag   1080

cctggtgatg gtttgatccg cttgagcgtg gggcttgagc acgttgacga cttggccgat   1140

gacttgatcg ctgctttgga cgcctctcgc gctgctgcat ga                       1182
```

```
<210> SEQ ID NO 102
<211> LENGTH: 1197
<212> TYPE: DNA
<213> ORGANISM: Citrobacter freundii

<400> SEQUENCE: 102

atgtctgatt gtcgtgccta cggctttaac acacagatcg tccacgccgg acaacaaccg     60

gacccaagca ctggtgcatt gtcgacgcca atctttcaga cttctacttt cgttttcgat    120

tcggcagaac agggggccgc acgtttcgcg ttggaggaac cgggatacat ctatacgcgc    180

ttgggcaatc caactactga tgcgcttgaa aagaaacttg cagtgctgga acgtggggac    240

gcggcgttag ccacagcgag cggcatctcc gctattacca caagtcttct tactctttgc    300

cagcaagggg accatatcgt atcagctagt gcaatctacg gttgcactca cgcattctta    360

agtcattcgc ttcctaaatt tggcattaac gtttcattcg tcgacgcagc gaagcccgaa    420

gaaatccgcg ccgccatgcg tccagagaca aaagtggtat atatcgagac gcccgcgaac    480

cctactttat ccttagtgga tattgagact gttgctggaa tcgcgcacca gcaaggagcc    540

ttgttagtcg tggacaacac ttttatgtct ccgtattgtc aacaaccatt actgctgggt    600

gctgacatcg tggtccatag tgttaccaag tacattaacg ggcatgggga tgttattggc    660

ggtgtcatcg taggtaaaca ggagttcatc gaccaagcac gctttgtggg attaaaggac    720

attacgggcg gatgcatgag cccctttaat gcatggctga cacttcgcgg ggtaaagacg    780

ttagggatcc gtatggagcg tcattgcgaa aacgcattga aaatcgcgcg ttttcttgag    840

ggccatcctg ctattacacg tgtctattat cctggattgc cgtcacaccc ccaatacgaa    900

cttgggaagc gccaaatgtc gcttcctggg ggaatcattt cgtttgaaat tgctggtggc    960

cttgaagcag gtcgccgtat gattaacagc gtggagttat gtttgctggc agttagctta   1020

ggtgatacgg agacgttgat tcagcatccg gcgagcatga cacattcccc tgttgctccc   1080

gaggagcgtc tgaaggctgg catcactgat ggactgatcc gtttgtccgt cggccttgaa   1140

gatccggaag acatcattaa cgacctggag cacgccattc gcaaggcaac gttttaa      1197
```

```
<210> SEQ ID NO 103
<211> LENGTH: 1200
<212> TYPE: DNA
<213> ORGANISM: Porphyromonas gingivalis

<400> SEQUENCE: 103

atgaagaaag aggacttaat gcgttcgggg ttcgcaactc gtgctattca tggtggagcc     60

atcgaaaatg cttttgggtg cctggccacc cccatctacc aaacttcaac gtttgttttc    120

gatacggctg aacagggtgg acgtcgcttt gcgggtgaag aagatgggta catttacact    180

cgcttaggaa acccgaactg tacccaggtt gaggagaagc tggcgatgtt agaaggaggg    240

gaagcagcgg cctccgcaag tagtggtatc ggagcgatct cttcagctat ctgggtgtgc    300

gtcaaggcgg gagatcatat tgtagcggga aaaactttgt acggttgcac gtttgcgttc    360
```

```
ttgacccacg gactttctcg ctatggagtt gaggtcacct tggtggacac gcgccatcca    420

gaagaggttg aggccgctat tcgtccaaac actaagttgg tctatttgga aactcccgca    480

aaccctaaca tgtaccttac tgatatcaaa gctgtgtgtg atatcgcgca caagcatgag    540

ggtgttcgcg tcatggtgga taatacctac tgtacacctt acatctgtcg cccactggag    600

ttaggtgctg atattgttgt ccattccgcc acaaaatatc tgaacggaca tggagatgtt    660

atcgctgggt ttgtagtagg gaaagaggat tacatcaagg aggtcaaatt ggttggtgtt    720

aaggacttga caggagccaa tatgtcaccc ttcgacgcat accttattag tcgtggtatg    780

aagacgttac aaatccgtat ggaacaacat tgccgtaacg cacaaacagt tgctgagttt    840

ctggagaagc atcctgcggt tgaggcggtg tacttcccgg gcttgccttc attcccgcaa    900

tatgagttgg ccaagaagca gatggcactt ccgggagcga tgattgcgtt tgaagttaag    960

ggaggctgcg aagccggtaa gaaacttatg aacaatcttc atctgtgttc cttagccgtc   1020

tccttaggcg ataccgagac tttaatccaa cacccggcct caatgacgca ctcgccctat   1080

acgcccgagg aacgcgccgc aagcgacatc tcggaggggc ttgtacgcct ttctgttgga   1140

ttggaaaatg ttgaggatat tatcgcggac ctgaagcatg gcctggatag tcttatctaa   1200
```

<210> SEQ ID NO 104
<211> LENGTH: 1674
<212> TYPE: DNA
<213> ORGANISM: Streptomyces sp.

<400> SEQUENCE: 104

```
atgtccccga cggcgtttcc agcggccgaa acagctactg cccctgcaac tgccgtcgat     60

cctgggccag aactggacgg cggagatttc gcccttccag agggcgggct ggatgacgat    120

cgtcgcttac gtgcattgga cgcagttgac gagtatttga cccgcaagcg caagcatttg    180

gttgggtacc aagctaccca ggatatgcag ggaacggcct tggatttagc ccgtttcatg    240

cccaacaaca tcaacaacct gggagatcct ttccagtcgg gtgggtataa accaaatacg    300

aaagtcgttg agcgtgccgt actggactac tatgcaaaat tgtggcacgc agaacgtcca    360

cacgacccag ctgacccaga aagctactgg ggttacatgt tatcgatggg ctcaactgag    420

ggcaacatgt acgccctgtg gaatgcacgt gactacctgt cgggtaaggc tttgattcag    480

cctcccacgg caccatttga cgctgttcgc tacgtgaagg ctgaccccga tcgccgcaat    540

cctaacgcac accacccagt cgcattctac tcggaggata cccactattc ttttgctaaa    600

gccgttgcgg tgctgggtgt cgaaactttc cacgctgtgg gtctggagaa atacgctgac    660

gagtgcccct tggtggatcc agtaaccggc cttcgtacct ggccgaccga agttccatcg    720

cgcccggggc cgtcgggttt aagctgggac ggccctggtg agattgatgt tgatgcgctt    780

gcagtactgg tcgagttctt cgcagcgaag ggtcaccccg tcttcgtcaa ccttaacttg    840

gggtctacat ttaaaggagc acatgatgac gtacgtgcgg tatgtgaacg cttattacca    900

atcttcgagc gccatggctt agtacaacgt gaagttgtat atgggagctg tccccaaacc    960

ggccgccctt tagtggatgt acgtcgcgga ttttggatcc acgtagatgg ggcacttggg   1020

gcggggtatg cccctttttct gcgtcttgcc gccgaagacc cggaaggtta tggttggacc   1080

cctgaggcag aattacctga gttcgacttc ggcttacgtt tgccgacggc ggggcatgga   1140

gaagttgata tggttagcag catcgccatg agtggacata agtgggcagg cgcgccgtgg   1200

ccatgcggca tctatatgac gaaagtgaaa tatcagatta gtccaccgtc acagcccgat   1260

tatattggtg ctcctgacac aacatttgcc ggttcccgta acggcttttc gccgttaatt   1320
```

```
ttgtgggatc atttatcgcg ctactcgtac cgcgaccagg tagagcgcat ccgcgaagca   1380

caggagcttg cagcatattt ggaacgccgc cttaccgcta tggagcgcga gctgggagtg   1440

gaactttggc cagcccgcac accgggtgct gtaaccgtac gttttcgcaa accctctgct   1500

gagctggttg cgaagtggtc cttgtcgtcg caggatgttt taatggtgcc gggtgatgaa   1560

actacgcgtc gtagttacgt tcatgtgttc gtgatgcctt ctgttgatcg tgcaaagtta   1620

gatgcgttgc tggcagaatt ggccgaagat cccgtcatct tgggtgcgcc ttaa         1674
```

<210> SEQ ID NO 105
<211> LENGTH: 1032
<212> TYPE: DNA
<213> ORGANISM: Escherichia coli

<400> SEQUENCE: 105

```
atgataaaac tttcgaatat caccaaagtg ttccaccagg gcacccgcac catccaggcg     60

ttgaacaacg tcagcctgca tgtgccagct ggacaaattt atggcgttat cggtgcctca    120

ggcgcgggta agagtacgct tatacgttgt gtaaacctgc tggagcgccc aaccgagggt    180

agcgtgctgg tcgatggcca ggaactgacc acgctgtcag aatccgagtt gaccaaagct    240

cgtcgccaga ttggtatgat tttccagcat tttaacctgc tctcttcgcg tactgttttt    300

ggcaacgtgg ctctgccgct ggagctggac aacacaccga aagacgagat caaacgtcgc    360

gtgacggaat tgctgtcatt ggttggtctt ggcgataagc atgatagcta cccgtcgaat    420

ctttccggtg ggcagaaaca acgtgtggcg attgcccgtg cattagccag caatcccaaa    480

gtattgctgt gtgatgaagc caccagcgcg ctggacccgg caacgacacg ttctattctc    540

gaactgctga aagacatcaa ccgccgtctg ggtttgacga ttctgttgat cactcacgaa    600

atggacgttg tgaagcgcat ttgtgattgc gtggcggtca tcagcaatgg cgaactgatc    660

gagcaggaca cggtaagtga agtgttctcg catccgaaaa cgccgctggc gcagaagttt    720

attcagtcga ccctgcatct ggatatcccg gaagattacc aggaacgtct gcaagcggag    780

ccatttactg actgcgtgcc gatgctgcgt ctggagttta ccggtcaatc ggtcgatgcc    840

ccactgcttt ctgaaaccgc gcgtcgtttc aacgtcaaca acaacattat tagcgcgcag    900

atggattacg ccggtggcgt taagttcggc atcatgctga ctgaaatgca cggcacacaa    960

caagatacgc aagccgccat tgcctggctg caggaacacc atgtaaaagt agaggtactg   1020

ggttatgtct ga                                                       1032
```

<210> SEQ ID NO 106
<211> LENGTH: 654
<212> TYPE: DNA
<213> ORGANISM: Escherichia coli

<400> SEQUENCE: 106

```
atgtctgagc cgatgatgtg gctgctggtt cgtggcgtat gggaaacgct ggcaatgacc     60

ttcgtatccg gtttttttgg ctttgtgatt ggtctgccgg ttggcgttct gctttatgtc    120

acgcgtccgg ggcaaattat tgctaacgcg aagttgtatc gtaccatttc tgcgattgtg    180

aacattttcc gttccatccc gttcattatc ttgctggtat ggatgattcc gtttacccgc    240

gttattgtcg gtacatcgat tggattgcag gcagcgattg ttccgttaac cgttggtgca    300

gcaccgttta ttgcccgtat ggtcgagaac gctctgctgg agatcccaac cgggttaatt    360

gaagcttccc gcgcaatggg ggccacgcca atgcagatcg tccgtaaagt gctgttaccg    420
```

gaagcgttgc cgggtctggt gaatgcggca actatcaccc tgattaccct ggttggttat 480
tccgcgatgg gtggtgcagt cggtgccggt ggtttaggtc agattggcta tcagtatggc 540
tacatcggct acaacgcgac ggtgatgaat acggtactgg tattgctggt cattctggtt 600
tatttaattc agttcgcagg cgaccgcatc gtccgggctg tcactcgcaa gtaa 654

<210> SEQ ID NO 107
<211> LENGTH: 816
<212> TYPE: DNA
<213> ORGANISM: Escherichia coli

<400> SEQUENCE: 107
atggcgttca aattcaaaac ctttgcggca gtgggagccc tgattggatc actggcactg 60
gtaggctgcg gtcaggatga aaaagatcca aaccacatta aagtcggcgt gattgttggt 120
gccgaacagc aggttgcaga agtcgcgcag aaagttgcga aagacaaata tggcctggac 180
gttgagctgg taaccttcaa cgactatgtt ctgccaaacg aagcattgag caaaggcgat 240
atcgacgcca acgccttcca gcataaaccg taccttgatc agcaactgaa agatcgtggc 300
tacaaactgg tcgcagtagg caacacattt gtttatccga ttgctggtta ctccaagaaa 360
atcaaatcac tggatgaact gcaggatggt tcgcaggttg ccgtgccaaa cgacccaact 420
aaccttggtc gttcactgct gctgctgcaa aaagtgggct tgatcaaact gaaagatggc 480
gttggcctgc tgccgaccgt tcttgatgtt gttgagaacc caaaaaatct gaaaattgtt 540
gaactggaag caccgcagct accgcgctct ctggacgacg cgcaaatcgc tctggcagtt 600
atcaatacca cctatgccag ccagattggc ctgactccag cgaaagacgg tatctttgtc 660
gaagataaag agtccccgta cgtaaacctg atcgtaacgc gtgaagacaa caaagacgcc 720
gaaaacgtga agaaattcgt tcaggcttat cagtctgacg aagtttacga agcagcaaac 780
aaagtgttta acggcggcgc tgttaaaggc tggtaa 816

<210> SEQ ID NO 108
<211> LENGTH: 393
<212> TYPE: PRT
<213> ORGANISM: Brevibacterium aurantiacum

<400> SEQUENCE: 108

```
Met Thr Ser Leu His Pro Glu Thr Leu Met Val His Gly Gly Met Lys
1               5                   10                  15

Gly Leu Thr Glu Ala Gly Val His Val Pro Ala Ile Asp Leu Ser Thr
            20                  25                  30

Thr Asn Pro Val Asn Asp Val Ala Thr Gly Gly Asp Ser Tyr Glu Trp
        35                  40                  45

Leu Ala Thr Gly His Thr Leu Lys Asp Gly Asp Ser Ala Val Tyr Gln
    50                  55                  60

Arg Leu Trp Gln Pro Gly Val Ala Arg Phe Glu Thr Ala Leu Ala Gly
65                  70                  75                  80

Leu Glu His Ala Glu Glu Ala Val Ala Phe Ala Thr Gly Met Ala Ala
                85                  90                  95

Met Thr Ala Ala Leu Leu Ala Ala Val Ser Ala Gly Thr Pro His Ile
            100                 105                 110

Val Ala Val Arg Pro Leu Tyr Gly Gly Ser Asp His Leu Leu Glu Thr
        115                 120                 125

Gly Leu Leu Gly Thr Thr Val Thr Trp Ala Lys Glu Ala Asp Ile Ala
    130                 135                 140
```

```
Ser Ala Ile Gln Asp Asp Thr Gly Leu Val Ile Val Glu Thr Pro Ala
145                 150                 155                 160

Asn Pro Ser Leu Asp Leu Val Asp Leu Asp Ser Val Val Ser Ala Ala
                165                 170                 175

Gly Asn Val Pro Val Leu Val Asp Asn Thr Phe Cys Thr Pro Val Leu
            180                 185                 190

Gln Gln Pro Ile Ser His Gly Ala Ala Leu Val Leu His Ser Ala Thr
        195                 200                 205

Lys Tyr Leu Gly Gly His Gly Asp Ala Met Gly Gly Ile Ile Ala Thr
    210                 215                 220

Asn Ala Asp Trp Ala Met Arg Leu Arg Gln Val Arg Ala Ile Thr Gly
225                 230                 235                 240

Ala Leu Leu His Pro Met Gly Ala Tyr Leu Leu His Arg Gly Leu Arg
                245                 250                 255

Thr Leu Ala Val Arg Met Arg Ala Ala Gln Thr Thr Ala Gly Glu Leu
            260                 265                 270

Ala Glu Arg Leu Asp Ala His Pro Ala Ile Ser Val Val His Tyr Pro
        275                 280                 285

Gly Leu Lys Gly Gln Asp Pro Arg Gly Leu Leu Gly Arg Gln Met Ser
    290                 295                 300

Gly Gly Gly Ala Met Ile Ala Met Glu Leu Ala Gly Gly Phe Asp Ala
305                 310                 315                 320

Ala Arg Ser Phe Val Glu His Cys Asn Leu Val Val His Ala Val Ser
                325                 330                 335

Leu Gly Gly Ala Asp Thr Leu Ile Gln His Pro Ala Ser Leu Thr His
            340                 345                 350

Arg Pro Val Ala Ala Thr Ala Lys Pro Gly Asp Gly Leu Ile Arg Leu
        355                 360                 365

Ser Val Gly Leu Glu His Val Asp Asp Leu Ala Asp Asp Leu Ile Ala
    370                 375                 380

Ala Leu Asp Ala Ser Arg Ala Ala Ala
385                 390


<210> SEQ ID NO 109
<211> LENGTH: 398
<212> TYPE: PRT
<213> ORGANISM: Citrobacter freundii

<400> SEQUENCE: 109

Met Ser Asp Cys Arg Ala Tyr Gly Phe Asn Thr Gln Ile Val His Ala
1               5                   10                  15

Gly Gln Gln Pro Asp Pro Ser Thr Gly Ala Leu Ser Thr Pro Ile Phe
            20                  25                  30

Gln Thr Ser Thr Phe Val Phe Asp Ser Ala Glu Gln Gly Ala Ala Arg
        35                  40                  45

Phe Ala Leu Glu Glu Pro Gly Tyr Ile Tyr Thr Arg Leu Gly Asn Pro
    50                  55                  60

Thr Thr Asp Ala Leu Glu Lys Lys Leu Ala Val Leu Glu Arg Gly Asp
65                  70                  75                  80

Ala Ala Leu Ala Thr Ala Ser Gly Ile Ser Ala Ile Thr Thr Ser Leu
                85                  90                  95

Leu Thr Leu Cys Gln Gln Gly Asp His Ile Val Ser Ala Ser Ala Ile
            100                 105                 110

Tyr Gly Cys Thr His Ala Phe Leu Ser His Ser Leu Pro Lys Phe Gly
        115                 120                 125
```

```
Ile Asn Val Ser Phe Val Asp Ala Ala Lys Pro Glu Glu Ile Arg Ala
    130                 135                 140

Ala Met Arg Pro Glu Thr Lys Val Val Tyr Ile Glu Thr Pro Ala Asn
145                 150                 155                 160

Pro Thr Leu Ser Leu Val Asp Ile Glu Thr Val Ala Gly Ile Ala His
                165                 170                 175

Gln Gln Gly Ala Leu Leu Val Val Asp Asn Thr Phe Met Ser Pro Tyr
            180                 185                 190

Cys Gln Gln Pro Leu Leu Leu Gly Ala Asp Ile Val Val His Ser Val
        195                 200                 205

Thr Lys Tyr Ile Asn Gly His Gly Asp Val Ile Gly Gly Val Ile Val
    210                 215                 220

Gly Lys Gln Glu Phe Ile Asp Gln Ala Arg Phe Val Gly Leu Lys Asp
225                 230                 235                 240

Ile Thr Gly Gly Cys Met Ser Pro Phe Asn Ala Trp Leu Thr Leu Arg
                245                 250                 255

Gly Val Lys Thr Leu Gly Ile Arg Met Glu Arg His Cys Glu Asn Ala
            260                 265                 270

Leu Lys Ile Ala Arg Phe Leu Glu Gly His Pro Ala Ile Thr Arg Val
        275                 280                 285

Tyr Tyr Pro Gly Leu Pro Ser His Pro Gln Tyr Glu Leu Gly Lys Arg
    290                 295                 300

Gln Met Ser Leu Pro Gly Gly Ile Ile Ser Phe Glu Ile Ala Gly Gly
305                 310                 315                 320

Leu Glu Ala Gly Arg Arg Met Ile Asn Ser Val Glu Leu Cys Leu Leu
                325                 330                 335

Ala Val Ser Leu Gly Asp Thr Glu Thr Leu Ile Gln His Pro Ala Ser
            340                 345                 350

Met Thr His Ser Pro Val Ala Pro Glu Glu Arg Leu Lys Ala Gly Ile
        355                 360                 365

Thr Asp Gly Leu Ile Arg Leu Ser Val Gly Leu Glu Asp Pro Glu Asp
    370                 375                 380

Ile Ile Asn Asp Leu Glu His Ala Ile Arg Lys Ala Thr Phe
385                 390                 395


<210> SEQ ID NO 110
<211> LENGTH: 399
<212> TYPE: PRT
<213> ORGANISM: Porphyromonas gingivalis

<400> SEQUENCE: 110

Met Lys Lys Glu Asp Leu Met Arg Ser Gly Phe Ala Thr Arg Ala Ile
1               5                   10                  15

His Gly Gly Ala Ile Glu Asn Ala Phe Gly Cys Leu Ala Thr Pro Ile
            20                  25                  30

Tyr Gln Thr Ser Thr Phe Val Phe Asp Thr Ala Glu Gln Gly Gly Arg
        35                  40                  45

Arg Phe Ala Gly Glu Glu Asp Gly Tyr Ile Tyr Thr Arg Leu Gly Asn
    50                  55                  60

Pro Asn Cys Thr Gln Val Glu Glu Lys Leu Ala Met Leu Glu Gly Gly
65                  70                  75                  80

Glu Ala Ala Ala Ser Ala Ser Ser Gly Ile Gly Ala Ile Ser Ser Ala
                85                  90                  95

Ile Trp Val Cys Val Lys Ala Gly Asp His Ile Val Ala Gly Lys Thr
```

```
            100                 105                 110

Leu Tyr Gly Cys Thr Phe Ala Phe Leu Thr His Gly Leu Ser Arg Tyr
        115                 120                 125

Gly Val Glu Val Thr Leu Val Asp Thr Arg His Pro Glu Glu Val Glu
    130                 135                 140

Ala Ala Ile Arg Pro Asn Thr Lys Leu Val Tyr Leu Glu Thr Pro Ala
145                 150                 155                 160

Asn Pro Asn Met Tyr Leu Thr Asp Ile Lys Ala Val Cys Asp Ile Ala
                165                 170                 175

His Lys His Glu Gly Val Arg Val Met Val Asp Asn Thr Tyr Cys Thr
            180                 185                 190

Pro Tyr Ile Cys Arg Pro Leu Glu Leu Gly Ala Asp Ile Val Val His
        195                 200                 205

Ser Ala Thr Lys Tyr Leu Asn Gly His Gly Asp Val Ile Ala Gly Phe
    210                 215                 220

Val Val Gly Lys Glu Asp Tyr Ile Lys Glu Val Lys Leu Val Gly Val
225                 230                 235                 240

Lys Asp Leu Thr Gly Ala Asn Met Ser Pro Phe Asp Ala Tyr Leu Ile
                245                 250                 255

Ser Arg Gly Met Lys Thr Leu Gln Ile Arg Met Glu Gln His Cys Arg
            260                 265                 270

Asn Ala Gln Thr Val Ala Glu Phe Leu Glu Lys His Pro Ala Val Glu
        275                 280                 285

Ala Val Tyr Phe Pro Gly Leu Pro Ser Phe Pro Gln Tyr Glu Leu Ala
    290                 295                 300

Lys Lys Gln Met Ala Leu Pro Gly Ala Met Ile Ala Phe Glu Val Lys
305                 310                 315                 320

Gly Gly Cys Glu Ala Gly Lys Lys Leu Met Asn Asn Leu His Leu Cys
                325                 330                 335

Ser Leu Ala Val Ser Leu Gly Asp Thr Glu Thr Leu Ile Gln His Pro
            340                 345                 350

Ala Ser Met Thr His Ser Pro Tyr Thr Pro Glu Glu Arg Ala Ala Ser
        355                 360                 365

Asp Ile Ser Glu Gly Leu Val Arg Leu Ser Val Gly Leu Glu Asn Val
    370                 375                 380

Glu Asp Ile Ile Ala Asp Leu Lys His Gly Leu Asp Ser Leu Ile
385                 390                 395


<210> SEQ ID NO 111
<211> LENGTH: 557
<212> TYPE: PRT
<213> ORGANISM: Streptomyces sp.

<400> SEQUENCE: 111

Met Ser Pro Thr Ala Phe Pro Ala Ala Glu Thr Ala Thr Ala Pro Ala
1               5                   10                  15

Thr Ala Val Asp Pro Gly Pro Glu Leu Asp Gly Gly Asp Phe Ala Leu
            20                  25                  30

Pro Glu Gly Gly Leu Asp Asp Asp Arg Arg Leu Arg Ala Leu Asp Ala
        35                  40                  45

Val Asp Glu Tyr Leu Thr Arg Lys Arg Lys His Leu Val Gly Tyr Gln
    50                  55                  60

Ala Thr Gln Asp Met Gln Gly Thr Ala Leu Asp Leu Ala Arg Phe Met
65                  70                  75                  80
```

-continued

```
Pro Asn Asn Ile Asn Asn Leu Gly Asp Pro Phe Gln Ser Gly Gly Tyr
                85                  90                  95

Lys Pro Asn Thr Lys Val Val Glu Arg Ala Val Leu Asp Tyr Tyr Ala
            100                 105                 110

Lys Leu Trp His Ala Glu Arg Pro His Asp Pro Ala Asp Pro Glu Ser
        115                 120                 125

Tyr Trp Gly Tyr Met Leu Ser Met Gly Ser Thr Glu Gly Asn Met Tyr
    130                 135                 140

Ala Leu Trp Asn Ala Arg Asp Tyr Leu Ser Gly Lys Ala Leu Ile Gln
145                 150                 155                 160

Pro Pro Thr Ala Pro Phe Asp Ala Val Arg Tyr Val Lys Ala Asp Pro
                165                 170                 175

Asp Arg Arg Asn Pro Asn Ala His His Pro Val Ala Phe Tyr Ser Glu
            180                 185                 190

Asp Thr His Tyr Ser Phe Ala Lys Ala Val Ala Val Leu Gly Val Glu
        195                 200                 205

Thr Phe His Ala Val Gly Leu Glu Lys Tyr Ala Asp Glu Cys Pro Leu
    210                 215                 220

Val Asp Pro Val Thr Gly Leu Arg Thr Trp Pro Thr Glu Val Pro Ser
225                 230                 235                 240

Arg Pro Gly Pro Ser Gly Leu Ser Trp Asp Gly Pro Gly Glu Ile Asp
                245                 250                 255

Val Asp Ala Leu Ala Val Leu Val Glu Phe Phe Ala Ala Lys Gly His
            260                 265                 270

Pro Val Phe Val Asn Leu Asn Leu Gly Ser Thr Phe Lys Gly Ala His
        275                 280                 285

Asp Asp Val Arg Ala Val Cys Glu Arg Leu Leu Pro Ile Phe Glu Arg
    290                 295                 300

His Gly Leu Val Gln Arg Glu Val Val Tyr Gly Ser Cys Pro Gln Thr
305                 310                 315                 320

Gly Arg Pro Leu Val Asp Val Arg Arg Gly Phe Trp Ile His Val Asp
                325                 330                 335

Gly Ala Leu Gly Ala Gly Tyr Ala Pro Phe Leu Arg Leu Ala Ala Glu
            340                 345                 350

Asp Pro Glu Gly Tyr Gly Trp Thr Pro Glu Ala Glu Leu Pro Glu Phe
        355                 360                 365

Asp Phe Gly Leu Arg Leu Pro Thr Ala Gly His Gly Glu Val Asp Met
    370                 375                 380

Val Ser Ser Ile Ala Met Ser Gly His Lys Trp Ala Gly Ala Pro Trp
385                 390                 395                 400

Pro Cys Gly Ile Tyr Met Thr Lys Val Lys Tyr Gln Ile Ser Pro Pro
                405                 410                 415

Ser Gln Pro Asp Tyr Ile Gly Ala Pro Asp Thr Thr Phe Ala Gly Ser
            420                 425                 430

Arg Asn Gly Phe Ser Pro Leu Ile Leu Trp Asp His Leu Ser Arg Tyr
        435                 440                 445

Ser Tyr Arg Asp Gln Val Glu Arg Ile Arg Glu Ala Gln Glu Leu Ala
    450                 455                 460

Ala Tyr Leu Glu Arg Arg Leu Thr Ala Met Glu Arg Glu Leu Gly Val
465                 470                 475                 480

Glu Leu Trp Pro Ala Arg Thr Pro Gly Ala Val Thr Val Arg Phe Arg
                485                 490                 495

Lys Pro Ser Ala Glu Leu Val Ala Lys Trp Ser Leu Ser Ser Gln Asp
```

```
            500                 505                 510

Val Leu Met Val Pro Gly Asp Glu Thr Thr Arg Arg Ser Tyr Val His
        515                 520                 525

Val Phe Val Met Pro Ser Val Asp Arg Ala Lys Leu Asp Ala Leu Leu
    530                 535                 540

Ala Glu Leu Ala Glu Asp Pro Val Ile Leu Gly Ala Pro
545                 550                 555


<210> SEQ ID NO 112
<211> LENGTH: 343
<212> TYPE: PRT
<213> ORGANISM: Escherichia coli

<400> SEQUENCE: 112

Met Ile Lys Leu Ser Asn Ile Thr Lys Val Phe His Gln Gly Thr Arg
1               5                   10                  15

Thr Ile Gln Ala Leu Asn Asn Val Ser Leu His Val Pro Ala Gly Gln
            20                  25                  30

Ile Tyr Gly Val Ile Gly Ala Ser Gly Ala Gly Lys Ser Thr Leu Ile
        35                  40                  45

Arg Cys Val Asn Leu Leu Glu Arg Pro Thr Glu Gly Ser Val Leu Val
    50                  55                  60

Asp Gly Gln Glu Leu Thr Thr Leu Ser Glu Ser Glu Leu Thr Lys Ala
65                  70                  75                  80

Arg Arg Gln Ile Gly Met Ile Phe Gln His Phe Asn Leu Leu Ser Ser
                85                  90                  95

Arg Thr Val Phe Gly Asn Val Ala Leu Pro Leu Glu Leu Asp Asn Thr
            100                 105                 110

Pro Lys Asp Glu Ile Lys Arg Arg Val Thr Glu Leu Leu Ser Leu Val
        115                 120                 125

Gly Leu Gly Asp Lys His Asp Ser Tyr Pro Ser Asn Leu Ser Gly Gly
    130                 135                 140

Gln Lys Gln Arg Val Ala Ile Ala Arg Ala Leu Ala Ser Asn Pro Lys
145                 150                 155                 160

Val Leu Leu Cys Asp Glu Ala Thr Ser Ala Leu Asp Pro Ala Thr Thr
                165                 170                 175

Arg Ser Ile Leu Glu Leu Leu Lys Asp Ile Asn Arg Arg Leu Gly Leu
            180                 185                 190

Thr Ile Leu Leu Ile Thr His Glu Met Asp Val Val Lys Arg Ile Cys
        195                 200                 205

Asp Cys Val Ala Val Ile Ser Asn Gly Glu Leu Ile Glu Gln Asp Thr
    210                 215                 220

Val Ser Glu Val Phe Ser His Pro Lys Thr Pro Leu Ala Gln Lys Phe
225                 230                 235                 240

Ile Gln Ser Thr Leu His Leu Asp Ile Pro Glu Asp Tyr Gln Glu Arg
                245                 250                 255

Leu Gln Ala Glu Pro Phe Thr Asp Cys Val Pro Met Leu Arg Leu Glu
            260                 265                 270

Phe Thr Gly Gln Ser Val Asp Ala Pro Leu Leu Ser Glu Thr Ala Arg
        275                 280                 285

Arg Phe Asn Val Asn Asn Asn Ile Ile Ser Ala Gln Met Asp Tyr Ala
    290                 295                 300

Gly Gly Val Lys Phe Gly Ile Met Leu Thr Glu Met His Gly Thr Gln
305                 310                 315                 320
```

```
Gln Asp Thr Gln Ala Ala Ile Ala Trp Leu Gln Glu His His Val Lys
            325                 330                 335

Val Glu Val Leu Gly Tyr Val
            340


<210> SEQ ID NO 113
<211> LENGTH: 217
<212> TYPE: PRT
<213> ORGANISM: Escherichia coli

<400> SEQUENCE: 113

Met Ser Glu Pro Met Met Trp Leu Leu Val Arg Gly Val Trp Glu Thr
1               5                   10                  15

Leu Ala Met Thr Phe Val Ser Gly Phe Phe Gly Phe Val Ile Gly Leu
            20                  25                  30

Pro Val Gly Val Leu Leu Tyr Val Thr Arg Pro Gly Gln Ile Ile Ala
        35                  40                  45

Asn Ala Lys Leu Tyr Arg Thr Ile Ser Ala Ile Val Asn Ile Phe Arg
    50                  55                  60

Ser Ile Pro Phe Ile Ile Leu Leu Val Trp Met Ile Pro Phe Thr Arg
65                  70                  75                  80

Val Ile Val Gly Thr Ser Ile Gly Leu Gln Ala Ala Ile Val Pro Leu
            85                  90                  95

Thr Val Gly Ala Ala Pro Phe Ile Ala Arg Met Val Glu Asn Ala Leu
            100                 105                 110

Leu Glu Ile Pro Thr Gly Leu Ile Glu Ala Ser Arg Ala Met Gly Ala
        115                 120                 125

Thr Pro Met Gln Ile Val Arg Lys Val Leu Leu Pro Glu Ala Leu Pro
    130                 135                 140

Gly Leu Val Asn Ala Ala Thr Ile Thr Leu Ile Thr Leu Val Gly Tyr
145                 150                 155                 160

Ser Ala Met Gly Gly Ala Val Gly Ala Gly Gly Leu Gly Gln Ile Gly
            165                 170                 175

Tyr Gln Tyr Gly Tyr Ile Gly Tyr Asn Ala Thr Val Met Asn Thr Val
            180                 185                 190

Leu Val Leu Leu Val Ile Leu Val Tyr Leu Ile Gln Phe Ala Gly Asp
        195                 200                 205

Arg Ile Val Arg Ala Val Thr Arg Lys
    210                 215


<210> SEQ ID NO 114
<211> LENGTH: 271
<212> TYPE: PRT
<213> ORGANISM: Escherichia coli

<400> SEQUENCE: 114

Met Ala Phe Lys Phe Lys Thr Phe Ala Ala Val Gly Ala Leu Ile Gly
1               5                   10                  15

Ser Leu Ala Leu Val Gly Cys Gly Gln Asp Glu Lys Asp Pro Asn His
            20                  25                  30

Ile Lys Val Gly Val Ile Val Gly Ala Glu Gln Gln Val Ala Glu Val
        35                  40                  45

Ala Gln Lys Val Ala Lys Asp Lys Tyr Gly Leu Asp Val Glu Leu Val
    50                  55                  60

Thr Phe Asn Asp Tyr Val Leu Pro Asn Glu Ala Leu Ser Lys Gly Asp
65                  70                  75                  80
```

```
Ile Asp Ala Asn Ala Phe Gln His Lys Pro Tyr Leu Asp Gln Gln Leu
                85                  90                  95

Lys Asp Arg Gly Tyr Lys Leu Val Ala Val Gly Asn Thr Phe Val Tyr
            100                 105                 110

Pro Ile Ala Gly Tyr Ser Lys Lys Ile Lys Ser Leu Asp Glu Leu Gln
        115                 120                 125

Asp Gly Ser Gln Val Ala Val Pro Asn Asp Pro Thr Asn Leu Gly Arg
    130                 135                 140

Ser Leu Leu Leu Leu Gln Lys Val Gly Leu Ile Lys Leu Lys Asp Gly
145                 150                 155                 160

Val Gly Leu Leu Pro Thr Val Leu Asp Val Val Glu Asn Pro Lys Asn
                165                 170                 175

Leu Lys Ile Val Glu Leu Glu Ala Pro Gln Leu Pro Arg Ser Leu Asp
            180                 185                 190

Asp Ala Gln Ile Ala Leu Ala Val Ile Asn Thr Thr Tyr Ala Ser Gln
        195                 200                 205

Ile Gly Leu Thr Pro Ala Lys Asp Gly Ile Phe Val Glu Asp Lys Glu
    210                 215                 220

Ser Pro Tyr Val Asn Leu Ile Val Thr Arg Glu Asp Asn Lys Asp Ala
225                 230                 235                 240

Glu Asn Val Lys Lys Phe Val Gln Ala Tyr Gln Ser Asp Glu Val Tyr
                245                 250                 255

Glu Ala Ala Asn Lys Val Phe Asn Gly Gly Ala Val Lys Gly Trp
            260                 265                 270
```

<210> SEQ ID NO 115
<211> LENGTH: 1257
<212> TYPE: DNA
<213> ORGANISM: Unknown
<220> FEATURE:
<221> NAME/KEY: source
<223> OTHER INFORMATION: /note="Description of Unknown: yjeH sequence"

<400> SEQUENCE: 115

```
atgagtggac tcaaacaaga actggggctg gcccagggca tcggcctact atcgacgtca     60

ttattaggca ctggcgtgtt tgccgttcct gcgttagctg cgctagtagc aggcaataac    120

agcctgtggg cgtggcccgt tttgattatc ttagtgttcc cgattgcgat tgtgtttgcg    180

attctgggtc gccactatcc cagcgcaggc ggcgtcgcac acttcgtcgg tatggcgttt    240

ggttcgcggc ttgagcgagt caccggctgg ttgtttttat cggtcattcc cgtgggtttg    300

cctgccgcgc tacaaattgc tgccggattc ggccaggcaa tgtttggctg gcatagcggg    360

caactgttgt tggcagaact cggtacgctg gcgctggtgt ggtatatcgg tactcgaggt    420

gccagttcca gtgctaatct acaaacagtt attgccgggc ttatcgtcgc actgattgtc    480

gctatctggt gggcgggcga tatcaaacct gcgaatatcc ccttccctgc gccaggaaat    540

atcgaactta ccgggttatt cgctgcgtta tcagtgatgt tctggtgttt tgtcggtctg    600

gaagcatttg cccatcttgc ctcggaattt aaaaatccag agcgtgattt tcctcgtgct    660

ttgatgattg gcctgctgct ggcaggatta gtctattggg gctgtacggt agtcgtctta    720

cacttcgacg cctatggtga acaaatggcg gcggcagcat cgcttcccaa aattgtagtg    780

cagttattcg gtgtaggagc gttatggatt gcctgcgtaa ttggctatct ggcctgcttt    840

gccagtctca acatttatat acagagcttc gcccgcctgg tctggtcgca ggcgcaacat    900

aatcctgacc attacctggc acgcctctct tctcgccata ttccgaataa tgccctcaat    960
```

```
gcggtgctcg gctgctgcgt ggtgagcacg ttggtgattc atgctttaga gatcaatctg   1020

gacgctctta ttatttatgc caatggcatc tttattatga tttatctgtt atgcatgctg   1080

gcaggctgta aattattgca aggacgttat cgactactgg cagtggttgg cgggctatta   1140

tgcgttctgt tactggcaat ggtcggctgg aaaagtctct acgcgctgat catgctggcg   1200

gggttatggc tgtttctgcc aaaacgaaaa acgccggaaa atggcataac cacataa      1257
```

<210> SEQ ID NO 116
<211> LENGTH: 1197
<212> TYPE: DNA
<213> ORGANISM: Citrobacter freundii

<400> SEQUENCE: 116

```
atgtctgact gtcgtgctta cggattcaat acccagatcg ttcatgcggg ccaacaaccc     60

gacccttcca ctggcgcgct cagtacgcct attttccaga cgtcaacctt cgtttttgac    120

agtgccgaac agggcgccgc ccgctttgcg cttgaagaac ccggctacat ctatacgcgc    180

cttggaaacc ccaccaccga cgcgctggag aaaaagctgg ctgtgctgga aagaggcgat    240

gccgcgctgg caactgcatc cggtatttca gccatcacca cctcgttgct gaccctttgc    300

cagcagggcg accatatcgt ttccgccagt gccatttacg gctgcactca cgcttttctg    360

tcacacagcc tgccgaagtt cggcattaac gtcagcttcg tcgacgccgc caagccggaa    420

gaaatccgcg cggccatgcg cccggaaacc aaagtggtgt atatcgaaac accagcaaac    480

ccaacgctct cgctggttga tattgaaacg gtcgccggga tcgcccatca gcaaggcgca    540

ttgctggtcg tggataacac ctttatgtca ccctactgcc agcaacctct gctgttaggt    600

gccgacatcg tggtgcacag cgtgaccaag tacatcaacg gccacgggga cgtgattggc    660

ggtgtgattg ttggcaagca ggaatttatc gaccaggcac gattcgtcgg gctgaaagat    720

atcaccggcg gctgcatgag tccgttcaac gcctggctga cgctgcgcgg cgtgaaaacg    780

ctgggcatcc gaatggagcg ccattgtgaa aacgcgttaa aaattgcccg cttcctggaa    840

gggcatccgg ccattacccg cgtgtattac cctggcttgc cttcacatcc gcagtatgag    900

ctgggtaaac gtcagatgag cctgccggga ggaattatca gcttcgaaat cgccggcggc    960

ctcgaggctg gcagacggat gatcaattct gtagaattgt gcctcctcgc ggtcagtctc   1020

ggtgacaccg aaaccctcat tcagcaccca gcgtctatga cacattcgcc cgttgcgcca   1080

gaggaacggc ttaaagcagg tattaccgac ggacttatcc gtctttctgt tggtcttgaa   1140

gatccagaag atattattaa cgaccttgaa cacgccatca gaaaggcaac attctga      1197
```

<210> SEQ ID NO 117
<211> LENGTH: 1200
<212> TYPE: DNA
<213> ORGANISM: Porphyromonas gingivalis

<400> SEQUENCE: 117

```
atgaaaaaag aagaccttat gcgtagtggc tttgccacac gtgccatcca tggaggcgct     60

atcgagaacg ccttcggctg cttagccact cccatctacc aaacatcgac tttcgttttt    120

gacactgccg aacagggagg ccgccgcttt gccggagagg aagacggata catctatacc    180

cgtctgggca accccaactg cacccaagtg gaagagaaac tggccatgct cgagggcgga    240

gaagccgccg catcggcctc atccggtatc ggagccatca gctctgccat ctgggtatgc    300

gtgaaggccg gcgaccatat cgtagccggc aagacgctct acggctgcac cttcgccttc    360
```

ctcacccacg gactgagccg ctacggtgtg gaagtcaccc tcgtggatac ccgccatccg 420
gaagaggtgg aggctgccat tcgcccgaat acgaagctcg tctatctgga gactccggcc 480
aaccccaata tgtacctgac cgacatcaag gcagtctgcg acatcgctca taagcacgaa 540
ggcgtacgcg tcatggtgga caatacctac tgcacgccct atatctgccg tccgctggag 600
ctgggtgccg acatcgtggt acacagcgcg accaagtacc tgaacggaca tggcgacgtc 660
atcgccggat tcgtcgttgg taaagaggac tacatcaagg aggtgaagct cgtcggcgtc 720
aaggacctca cgggggccaa tatgagtccg ttcgatgctt atctgatcag ccgcggcatg 780
aagacgctgc agatacgtat ggagcagcac tgccgcaatg ctcagaccgt agccgaattc 840
ctcgaaaagc atccggccgt agaagcagtt tatttccccg gacttccgag cttcccccaa 900
tacgaattgg ccaagaagca gatggcactg cccggagcca tgatcgcctt cgaagtgaag 960
ggcggttgcg aagccggtaa gaagctgatg aacaacctgc acctctgctc cctcgccgtg 1020
agcttgggcg atacggaaac cctcatccag catccggcca gcatgaccca ctcgccctac 1080
acacccgaag agcgtgctgc cagcgacata tccgaaggac tggtacgcct gtccgtgggt 1140
ctggagaacg tggaggacat catcgccgac ctcaaacacg gtctggacag cctgatctaa 1200

<210> SEQ ID NO 118
<211> LENGTH: 1182
<212> TYPE: DNA
<213> ORGANISM: Brevibacterium aurantiacum

<400> SEQUENCE: 118
atgacctcac tgcacccaga aacgctcatg gtccacggcg gaatgaaagg cctcaccgag 60
gcaggagtcc acgtaccggc catcgacctc tcgaccacca acccagtcaa cgatgtcgcc 120
accggcggtg actcctacga atggctcgcc accggccata cgctcaagga cggcgactcg 180
gccgtctacc agcgcctctg gcagcccggt gtcgcacgct tcgagaccgc gctggccggg 240
ctcgaacacg ctgaggaagc agtcgccttc gccacgggca tggccgcaat gactgccgca 300
cttctcgcgg ccgtcagcgc aggaacaccc cacatcgtcg cagtgcgtcc cctctatggc 360
ggaagcgacc acctcctcga aaccggactg ctggggacaa cagtcacatg ggcaaaggaa 420
gccgacatcg cctcggcgat ccaagatgac accggactcg tcattgtcga gaccccggca 480
aaccccagcc tggaccttgt tgatctcgac agtgtcgtct cagccgccgg caacgtgcct 540
gtgctggtgg acaacacatt ctgcacacct gttctccagc agcccatctc ccacggagcg 600
gccctcgtac tgcacagcgc gacaaaatac ctcggcggtc atggcgatgc catgggcggc 660
atcatcgcca ccaacgccga ctgggcgatg cgcctgcgac aggtccgagc catcacagga 720
gccctgctcc accccatggg cgcgtatctc cttcatcggg gcttgcgcac tctggccgtg 780
cgcatgcgcg cggctcagac caccgccggt gagctcgctg agcgcctgga cgcgcaccct 840
gccatctccg tcgtccacta cccgggactg aaaggccagg acccacgcgg actgctcgga 900
cgccaaatgt ccggtggtgg tgcgatgatc gcgatggagc tcgccggtgg attcgacgcc 960
gcccgcagct tcgtcgaaca ctgcaacctc gtcgtccacg cggtgtccct gggcggcgct 1020
gacactctca tccagcatcc ggcgtcactg actcacaggc cagttgcggc cacggcgaag 1080
cccggcgatg gtctcatccg actctctgtg ggactcgaac acgtcgatga cctggcagac 1140
gatctcatcg ctgccctcga cgcgagtcgg gccgctgcct ga 1182

<210> SEQ ID NO 119
<211> LENGTH: 1674

```
<212> TYPE: DNA
<213> ORGANISM: Streptomyces sp.

<400> SEQUENCE: 119

atgagcccga ccgccttccc cgccgccgag accgcgaccg cgcccgcgac cgccgtcgat      60
cccggtccgg agctggacgg cggtgacttc gccctccccg agggcggcct ggacgacgac     120
cggcggctgc gcgcgctcga cgccgtggac gagtacctga cccgcaagcg caagcacctg     180
gtcggctacc aggccaccca ggacatgcag ggcaccgcac tggacctcgc ccggttcatg     240
ccgaacaaca tcaacaacct cggcgacccg ttccagagcg gcggatacaa gcccaacacc     300
aaggtcgtcg agcgggccgt gctcgactac tacgcgaagc tctggcacgc cgagcgcccg     360
cacgacccgg ccgacccgga gtcgtactgg ggctacatgc tgtccatggg ctcgaccgag     420
ggcaacatgt acgccctctg gaacgccagg gactacctga gcggcaaggc gctgatccag     480
ccgccgaccg ccccccttcga cgcggtgcgc tacgtcaagg ccgaccccga ccgacggaac     540
ccgaacgccc accacccggt ggccttctac tccgaggaca cccactactc cttcgccaag     600
gccgtggccg tcctcggcgt ggagaccttc cacgccgtcg gcctggagaa gtacgccgac     660
gagtgcccgc tggtcgaccc ggtgaccggg ctgcgcacct ggcccaccga ggtgccctcc     720
cgcccgggtc cgtccggcct gtcctgggac ggccccggcg agatagacgt cgacgccctc     780
gccgtactcg tcgagttctt cgccgccaag ggtcacccgg tcttcgtcaa cctcaacctc     840
ggcagcacct tcaagggcgc ccacgacgac gtccgcgccg tctgcgagcg cttgctgccg     900
atcttcgagc ggcacgggct cgtccagcgc gaggtggtct acggcagctg cccgcagacc     960
ggccggccgc tggtggacgt gcgccgcggc ttctggatcc acgtggacgg cgcgctcggc    1020
gccggctacg cgccgttcct gcggctggcc gccgaggacc cggaagggta cggctggacg    1080
cccgaggcgg agctgcccga gttcgacttc ggcctgcggc tgcccaccgc cgggcacggc    1140
gaggtggaca tggtctcctc gatcgcgatg agcggccaca agtgggccgg cgcgccgtgg    1200
ccgtgcggca tctacatgac caaggtgaag taccagatct cgccgccgtc ccagccggac    1260
tacatcggcg ccccggacac caccttcgcc ggctcccgca acggcttctc cccgctgatc    1320
ctctgggacc acctgtcccg gtactcctac cgggaccagg tggagcggat ccgcgaggcc    1380
caggagctgg ccgcctacct ggagcggcgg ctgaccgcca tggagcgcga actcggcgtc    1440
gagctctggc cggcccgtac cccgggcgcc gtcaccgtac ggttccgcaa gccgagcgcc    1500
gagctggtgg ccaagtggtc gctgtcctcc caggacgtgc tgatggtccc gggcgacgag    1560
accacccggc gcagctacgt gcacgtcttc gtgatgccct cggtcgaccg ggccaagctg    1620
gacgcgctgc tcgccgaact cgccgaggac ccggtgatcc tgggcgcacc gtag          1674

<210> SEQ ID NO 120
<211> LENGTH: 1257
<212> TYPE: DNA
<213> ORGANISM: Oxalobacter formigenes

<400> SEQUENCE: 120

atgaataatc cacaaacagg acaatcaaca ggcctcttgg gcaatcgttg gttctacttg      60
gtattagcag ttttgctgat gtgtatgatc tcgggtgtcc aatattcctg gacactgtac     120
gctaacccgg ttaaagacaa ccttggcgtt tctttggctg cggttcagac ggctttcaca     180
ctctctcagg tcattcaagc tggttctcag cctggtggtg gttacttcgt tgataaattc     240
ggtccaagaa ttccattgat gttcggtggt gcgatggttc tcgctggctg gaccttcatg     300
```

```
ggtatggttg acagtgttcc tgctctgtat gctctttata ctctggccgg tgcaggtgtt    360

ggtatcgttt acggtatcgc gatgaacacg gctaacagat ggttcccgga caaacgcggt    420

ctggcttccg gtttcaccgc tgccggttac ggtctgggtg ttctgccgtt cctgccactg    480

atcagctccg ttctgaaagt tgaaggtgtt ggcgcagcat tcatgtacac cggtttgatc    540

atgggtatcc tgattatcct gatcgctttc gttatccgtt tccctggcca gcaaggcgcc    600

aaaaaacaaa tcgttgttac cgacaaggat ttcaattctg gcgaaatgct gagaacacca    660

caattctggg ttctgtggac cgcattcttt tccgttaact ttggtggttt gctgctggtt    720

gccaacagcg tcccttacgg tcgcagcctc ggtcttgccg caggtgtgct gacgatcggt    780

gtttcgatcc agaacctgtt caatggtggt tgccgtcctt tctggggttt cgtttccgat    840

aaaatcggcc gttacaaaac catgtccgtc gttttcggta tcaatgctgt tgttctcgca    900

cttttcccga cgattgctgc cttgggcgat gtagccttta tcgccatgtt ggcaatcgca    960

ttcttcacat ggggtggtag ctacgctctg ttcccatcga ccaacagcga tattttcggt   1020

acggcatact ctgccagaaa ctatggtttc ttctgggctg caaaagcaac tgcctcgatc   1080

ttcggtggtg gtctgggtgc tgcaattgca accaacttcg gatggaatac cgctttcctg   1140

attactgcga ttacttcttt catcgcattt gctctggcta ccttcgttat tccaagaatg   1200

ggccgtccag tcaagaaaat ggtcaaattg tctccagaag aaaaagctgt acattaa      1257
```

<210> SEQ ID NO 121
<211> LENGTH: 418
<212> TYPE: PRT
<213> ORGANISM: Oxalobacter formigenes

<400> SEQUENCE: 121

```
Met Asn Asn Pro Gln Thr Gly Gln Ser Thr Gly Leu Leu Gly Asn Arg
1               5                   10                  15

Trp Phe Tyr Leu Val Leu Ala Val Leu Leu Met Cys Met Ile Ser Gly
            20                  25                  30

Val Gln Tyr Ser Trp Thr Leu Tyr Ala Asn Pro Val Lys Asp Asn Leu
        35                  40                  45

Gly Val Ser Leu Ala Ala Val Gln Thr Ala Phe Thr Leu Ser Gln Val
    50                  55                  60

Ile Gln Ala Gly Ser Gln Pro Gly Gly Gly Tyr Phe Val Asp Lys Phe
65                  70                  75                  80

Gly Pro Arg Ile Pro Leu Met Phe Gly Gly Ala Met Val Leu Ala Gly
                85                  90                  95

Trp Thr Phe Met Gly Met Val Asp Ser Val Pro Ala Leu Tyr Ala Leu
            100                 105                 110

Tyr Thr Leu Ala Gly Ala Gly Val Gly Ile Val Tyr Gly Ile Ala Met
        115                 120                 125

Asn Thr Ala Asn Arg Trp Phe Pro Asp Lys Arg Gly Leu Ala Ser Gly
    130                 135                 140

Phe Thr Ala Ala Gly Tyr Gly Leu Gly Val Leu Pro Phe Leu Pro Leu
145                 150                 155                 160

Ile Ser Ser Val Leu Lys Val Glu Gly Val Gly Ala Ala Phe Met Tyr
                165                 170                 175

Thr Gly Leu Ile Met Gly Ile Leu Ile Ile Leu Ile Ala Phe Val Ile
            180                 185                 190

Arg Phe Pro Gly Gln Gln Gly Ala Lys Lys Gln Ile Val Val Thr Asp
        195                 200                 205
```

```
Lys Asp Phe Asn Ser Gly Glu Met Leu Arg Thr Pro Gln Phe Trp Val
    210                 215                 220

Leu Trp Thr Ala Phe Phe Ser Val Asn Phe Gly Gly Leu Leu Leu Val
225                 230                 235                 240

Ala Asn Ser Val Pro Tyr Gly Arg Ser Leu Gly Leu Ala Ala Gly Val
                245                 250                 255

Leu Thr Ile Gly Val Ser Ile Gln Asn Leu Phe Asn Gly Gly Cys Arg
            260                 265                 270

Pro Phe Trp Gly Phe Val Ser Asp Lys Ile Gly Arg Tyr Lys Thr Met
        275                 280                 285

Ser Val Val Phe Gly Ile Asn Ala Val Val Leu Ala Leu Phe Pro Thr
    290                 295                 300

Ile Ala Ala Leu Gly Asp Val Ala Phe Ile Ala Met Leu Ala Ile Ala
305                 310                 315                 320

Phe Phe Thr Trp Gly Gly Ser Tyr Ala Leu Phe Pro Ser Thr Asn Ser
                325                 330                 335

Asp Ile Phe Gly Thr Ala Tyr Ser Ala Arg Asn Tyr Gly Phe Phe Trp
            340                 345                 350

Ala Ala Lys Ala Thr Ala Ser Ile Phe Gly Gly Gly Leu Gly Ala Ala
        355                 360                 365

Ile Ala Thr Asn Phe Gly Trp Asn Thr Ala Phe Leu Ile Thr Ala Ile
    370                 375                 380

Thr Ser Phe Ile Ala Phe Ala Leu Ala Thr Phe Val Ile Pro Arg Met
385                 390                 395                 400

Gly Arg Pro Val Lys Lys Met Val Lys Leu Ser Pro Glu Glu Lys Ala
                405                 410                 415

Val His
```

<210> SEQ ID NO 122
<211> LENGTH: 1287
<212> TYPE: DNA
<213> ORGANISM: Oxalobacter formigenes

<400> SEQUENCE: 122

```
atgactaaac cattagatgg aattaatgtg cttgacttta cccacgtcca ggcaggtcct     60

gcctgtacac agatgatggg tttcttgggc gcaaacgtca tcaagattga aagacgtggt    120

tccggagata tgactcgtgg atggctgcag gacaaaccaa atgttgattc cctgtatttc    180

acgatgttca actgtaacaa acgttcgatt gaactggaca tgaaaacccc ggaaggcaaa    240

gagcttctgg aacagatgat caagaaagcc gacgtcatgg tcgaaaactt cggaccaggc    300

gcactggacc gtatgggctt tacttgggaa tacattcagg aactgaatcc acgcgtcatt    360

ctggcttccg ttaaaggcta tgcagaaggc cacgccaacg aacacctgaa agtttatgaa    420

aacgttgcac agtgttccgg cggtgctgca gctaccaccg gtttctggga tggtcctcca    480

accgtttccg gcgctgctct gggtgactcc aactccggta tgcacctgat gatcggtatt    540

ctggccgctc tggaaatgcg tcacaaaacc ggccgtggtc agaaagttgc cgtcgctatg    600

caggacgctg ttctgaatct ggttcgtatc aaactgcgtg accagcaacg tctggaaaga    660

accggcattc tggctgaata cccacaggct cagcctaact ttgccttcga cagagacggt    720

aacccactgt ccttcgacaa catcacttcc gttccacgtg gtggtaacgc aggtggcggc    780

ggccagccag gctggatgct gaaatgtaaa ggttgggaaa ccgatgcgga ctcctacgtt    840

tacttcacca tcgctgcaaa catgtggcca cagatctgcg acatgatcga caagccagaa    900
```

```
tggaaagacg acccagccta caacacattc gaaggtcgtg ttgacaagct gatggacatc    960

ttctccttca tcgaaaccaa gttcgctgac aaggacaaat tcgaagttac cgaatgggct   1020

gcccagtacg gcattccttg cggtccggtc atgtccatga aagaactggc tcacgatcct   1080

tccctgcaga aagttggtac cgtcgttgaa gttgtcgacg aaattcgtgg taaccacctg   1140

accgttggcg caccgttcaa attctccgga ttccagccgg aaattacccg tgctccgctg   1200

ttgggcgaac ataccgacga agttctgaaa gaactgggtc ttgacgatgc caagatcaag   1260

gaactgcatg caaaacaggt agtttga                                       1287
```

```
<210> SEQ ID NO 123
<211> LENGTH: 428
<212> TYPE: PRT
<213> ORGANISM: Oxalobacter formigenes

<400> SEQUENCE: 123

Met Thr Lys Pro Leu Asp Gly Ile Asn Val Leu Asp Phe Thr His Val
1               5                   10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asp Met Thr Arg Gly Trp
        35                  40                  45

Leu Gln Asp Lys Pro Asn Val Asp Ser Leu Tyr Phe Thr Met Phe Asn
    50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Met Arg His Lys Thr Gly Arg
            180                 185                 190

Gly Gln Lys Val Ala Val Ala Met Gln Asp Ala Val Leu Asn Leu Val
        195                 200                 205

Arg Ile Lys Leu Arg Asp Gln Gln Arg Leu Glu Arg Thr Gly Ile Leu
    210                 215                 220

Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
                245                 250                 255

Ala Gly Gly Gly Gly Gln Pro Gly Trp Met Leu Lys Cys Lys Gly Trp
            260                 265                 270

Glu Thr Asp Ala Asp Ser Tyr Val Tyr Phe Thr Ile Ala Ala Asn Met
        275                 280                 285

Trp Pro Gln Ile Cys Asp Met Ile Asp Lys Pro Glu Trp Lys Asp Asp
    290                 295                 300
```

```
Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
    370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
                405                 410                 415

Ala Lys Ile Lys Glu Leu His Ala Lys Gln Val Val
            420                 425


<210> SEQ ID NO 124
<211> LENGTH: 1707
<212> TYPE: DNA
<213> ORGANISM: Oxalobacter formigenes

<400> SEQUENCE: 124

atgagtaacg acgacaatgt agagttgact gatggctttc atgttttgat cgatgccctg      60

aaaatgaatg acatcgatac catgtatggt gttgtcggca ttcctatcac gaacctggct     120

cgtatgtggc aagatgacgg tcagcgtttt tacagcttcc gtcacgaaca acacgcaggt     180

tatgcagctt ctatcgccgg ttacatcgaa ggaaaacctg gcgtttgctt gaccgtttcc     240

gcccctggct tcctgaacgg cgtgacttcc ctggctcatg caaccaccaa ctgcttccca     300

atgatcctgt tgagcggttc cagtgaacgt gaaatcgtcg atttgcaaca gggcgattac     360

gaagaaatgg atcagatgaa tgttgcacgt ccacactgca aagcttcttt ccgtatcaac     420

agcatcaaag acattccaat cggtatcgct cgtgcagttc gcaccgctgt atccggacgt     480

ccaggtggtg tttacgttga cttgccagca aaactgttcg gtcagaccat ttctgtagaa     540

gaagctaaca aactgctctt caaaccaatc gatccagctc cggcacagat tcctgctgaa     600

gacgctatcg ctcgcgctgc tgacctgatc aagaacgcca aacgtccagt tatcatgctg     660

ggtaaaggcg ctgcatacgc acaatgcgac gacgaaatcc gcgcactggt tgaagaaacc     720

ggcatcccat tcctgccaat gggtatggct aaaggcctgc tgcctgacaa ccatccacaa     780

tccgctgctg caacccgtgc tttcgcactg gcacagtgtg acgtttgcgt actgatcggc     840

gctcgtctga actggctgat gcagcacggt aaaggcaaaa cctggggcga cgaactgaag     900

aaatacgttc agatcgacat ccaggctaac gaaatggaca gcaaccagcc tatcgctgca     960

ccagttgttg gtgacatcaa gtccgccgtt tccctgctcc gcaaagcact gaaaggcgct    1020

ccaaaagctg acgctgaatg gaccggcgct ctgaaagcca aagttgacgg caacaaagcc    1080

aaactggctg gcaagatgac tgccgaaacc ccatccggaa tgatgaacta ctccaattcc    1140

ctgggcgttg ttcgtgactt catgctggca aatccggata tttccctggt taacgaaggc    1200

gctaatgcac tcgacaacac tcgtatgatt gttgacatgc tgaaaccacg caaacgtctt    1260

gactccggta cctggggtgt tatgggtatt ggtatgggct actgcgttgc tgcagctgct    1320

gttaccggca aaccggttat cgctgttgaa ggcgatagcg cattcggttt ctccggtatg    1380

gaactggaaa ccatctgccg ttacaacctg ccagttaccg ttatcatcat gaacaatggt    1440
```

```
ggtatctata aaggtaacga agcagatcca caaccaggcg ttatctcctg tacccgtctg   1500

acccgtggtc gttacgacat gatgatggaa gcatttggcg gtaaaggtta tgttgccaat   1560

actccagcag aactgaaagc tgctctggaa gaagctgttg cttccggcaa accatgcctg   1620

atcaacgcga tgatcgatcc agacgctggt gtcgaatctg gccgtatcaa gagcctgaac   1680

gttgtaagta aagttggcaa gaaataa                                       1707


<210> SEQ ID NO 125
<211> LENGTH: 568
<212> TYPE: PRT
<213> ORGANISM: Oxalobacter formigenes

<400> SEQUENCE: 125

Met Ser Asn Asp Asp Asn Val Glu Leu Thr Asp Gly Phe His Val Leu
1               5                   10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Asp Gly Gln
        35                  40                  45

Arg Phe Tyr Ser Phe Arg His Glu Gln His Ala Gly Tyr Ala Ala Ser
    50                  55                  60

Ile Ala Gly Tyr Ile Glu Gly Lys Pro Gly Val Cys Leu Thr Val Ser
65                  70                  75                  80

Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
        115                 120                 125

Ala Arg Pro His Cys Lys Ala Ser Phe Arg Ile Asn Ser Ile Lys Asp
    130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
        195                 200                 205

Leu Ile Lys Asn Ala Lys Arg Pro Val Ile Met Leu Gly Lys Gly Ala
    210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255

Asn His Pro Gln Ser Ala Ala Ala Thr Arg Ala Phe Ala Leu Ala Gln
            260                 265                 270

Cys Asp Val Cys Val Leu Ile Gly Ala Arg Leu Asn Trp Leu Met Gln
        275                 280                 285

His Gly Lys Gly Lys Thr Trp Gly Asp Glu Leu Lys Lys Tyr Val Gln
    290                 295                 300

Ile Asp Ile Gln Ala Asn Glu Met Asp Ser Asn Gln Pro Ile Ala Ala
305                 310                 315                 320
```

```
Pro Val Val Gly Asp Ile Lys Ser Ala Val Ser Leu Leu Arg Lys Ala
                325                 330                 335

Leu Lys Gly Ala Pro Lys Ala Asp Ala Glu Trp Thr Gly Ala Leu Lys
            340                 345                 350

Ala Lys Val Asp Gly Asn Lys Ala Lys Leu Ala Gly Lys Met Thr Ala
        355                 360                 365

Glu Thr Pro Ser Gly Met Met Asn Tyr Ser Asn Ser Leu Gly Val Val
    370                 375                 380

Arg Asp Phe Met Leu Ala Asn Pro Asp Ile Ser Leu Val Asn Glu Gly
385                 390                 395                 400

Ala Asn Ala Leu Asp Asn Thr Arg Met Ile Val Asp Met Leu Lys Pro
                405                 410                 415

Arg Lys Arg Leu Asp Ser Gly Thr Trp Gly Val Met Gly Ile Gly Met
            420                 425                 430

Gly Tyr Cys Val Ala Ala Ala Ala Val Thr Gly Lys Pro Val Ile Ala
        435                 440                 445

Val Glu Gly Asp Ser Ala Phe Gly Phe Ser Gly Met Glu Leu Glu Thr
    450                 455                 460

Ile Cys Arg Tyr Asn Leu Pro Val Thr Val Ile Ile Met Asn Asn Gly
465                 470                 475                 480

Gly Ile Tyr Lys Gly Asn Glu Ala Asp Pro Gln Pro Gly Val Ile Ser
                485                 490                 495

Cys Thr Arg Leu Thr Arg Gly Arg Tyr Asp Met Met Met Glu Ala Phe
            500                 505                 510

Gly Gly Lys Gly Tyr Val Ala Asn Thr Pro Ala Glu Leu Lys Ala Ala
        515                 520                 525

Leu Glu Glu Ala Val Ala Ser Gly Lys Pro Cys Leu Ile Asn Ala Met
    530                 535                 540

Ile Asp Pro Asp Ala Gly Val Glu Ser Gly Arg Ile Lys Ser Leu Asn
545                 550                 555                 560

Val Val Ser Lys Val Gly Lys Lys
                565
```

<210> SEQ ID NO 126
<211> LENGTH: 1632
<212> TYPE: DNA
<213> ORGANISM: Saccharomyces cerevisiae

<400> SEQUENCE: 126

```
atgaccagtg cagctacggt gaccgcgagc tttaatgaca ctttttctgt gagcgataat      60

gtcgcggtaa tcgtaccgga aaccgatacg caggtcacct accgtgatct ttcccacatg     120

gtaggacact ttcaaacaat gttcacgaac ccgaatagtc ctctgtacgg ggcggtcttt     180

cgtcaagaca cggtagcgat tagcatgcgt aacggccttg aatttattgt ggctttcctt     240

ggagccacga tggatgcgaa aattggtgcg ccactgaatc ccaattataa agagaaggag     300

tttaattttt acctgaatga cttaaagtcc aaagccatct gcgtgccgaa aggcaccacc     360

aaactgcaaa gttcagaaat tcttaagagt gcgtccacgt tcgggtgctt tattgtggaa     420

ctggcgtttg acgccacccg ttttcgtgtt gaatatgaca tttactcccc ggaggacaat     480

tataaacgtg tgatctaccg cagccttaac aatgctaagt ttgtcaacac aaaccctgtc     540

aagttcccgg gtttcgcccg cagctcggat gttgcactta ttttgcatac ctcaggcacc     600

actagtaccc caaagaccgt acccctcttg catctgaata ttgtccgttc aaccctgaat     660

atcgccaaca cttacaaact taccccgctg gatcgctcct atgttgtaat gccgctgttt     720
```

```
catgtacatg gattaatcgg cgtcttactg agtacgttcc gcacccaggg cagtgtagtc    780

gtcccggacg gctttcatcc gaagctcttc tgggatcagt ttgttaaata taactgcaat    840

tggtttagtt gcgtcccaac gatctctatg attatgttga atatgcccaa accgaatccg    900

tttccgcaca ttcgctttat ccgctcatgt agcagcgcgc tggcgccagc aacgtttcac    960

aagctggaaa aagaatttaa tgccccagtt ctggaagcgt acgcgatgac agaagcatct   1020

catcagatga ccagtaacaa tctgcctccc ggtaaacgta aaccggggac cgtgggccaa   1080

cctcaaggtg taaccgtagt aatcctggat gacaacgata acgttctgcc gcccggcaaa   1140

gttggcgagg tgtcgatccg tggggagaac gtcaccctgg gctacgctaa taacccgaaa   1200

gctaacaaag aaaacttcac taaacgtgaa aactatttcc gtaccgggga tcagggctac   1260

ttcgacccgg agggctttct cgtgctgacc ggccgcatta aagaattgat caatcgcggt   1320

ggtgaaaaaa ttagtcctat tgaactggac ggaatcatgc tctcgcatcc taaaatcgac   1380

gaggcggtgg cgttcggcgt tccagatgat atgtatggcc aagtcgttca ggcggcaatc   1440

gtgttgaaaa agggggaaaa gatgacctat gaagaattag tgaatttcct gaaaaagcat   1500

ttagcaagct ttaaaatccc aaccaaagtc tactttgtgg ataagctgcc taaaacggcc   1560

accgggaaga ttcaacgtcg cgtaatcgcc gaaaccttcg cgaaatctag tcgcaacaaa   1620

agcaaacttt aa                                                       1632
```

<210> SEQ ID NO 127
<211> LENGTH: 543
<212> TYPE: PRT
<213> ORGANISM: Saccharomyces cerevisiae

<400> SEQUENCE: 127

```
Met Thr Ser Ala Ala Thr Val Thr Ala Ser Phe Asn Asp Thr Phe Ser
1               5                   10                  15

Val Ser Asp Asn Val Ala Val Ile Val Pro Glu Thr Asp Thr Gln Val
            20                  25                  30

Thr Tyr Arg Asp Leu Ser His Met Val Gly His Phe Gln Thr Met Phe
        35                  40                  45

Thr Asn Pro Asn Ser Pro Leu Tyr Gly Ala Val Phe Arg Gln Asp Thr
    50                  55                  60

Val Ala Ile Ser Met Arg Asn Gly Leu Glu Phe Ile Val Ala Phe Leu
65                  70                  75                  80

Gly Ala Thr Met Asp Ala Lys Ile Gly Ala Pro Leu Asn Pro Asn Tyr
                85                  90                  95

Lys Glu Lys Glu Phe Asn Phe Tyr Leu Asn Asp Leu Lys Ser Lys Ala
            100                 105                 110

Ile Cys Val Pro Lys Gly Thr Thr Lys Leu Gln Ser Ser Glu Ile Leu
        115                 120                 125

Lys Ser Ala Ser Thr Phe Gly Cys Phe Ile Val Glu Leu Ala Phe Asp
    130                 135                 140

Ala Thr Arg Phe Arg Val Glu Tyr Asp Ile Tyr Ser Pro Glu Asp Asn
145                 150                 155                 160

Tyr Lys Arg Val Ile Tyr Arg Ser Leu Asn Asn Ala Lys Phe Val Asn
                165                 170                 175

Thr Asn Pro Val Lys Phe Pro Gly Phe Ala Arg Ser Ser Asp Val Ala
            180                 185                 190

Leu Ile Leu His Thr Ser Gly Thr Thr Ser Thr Pro Lys Thr Val Pro
        195                 200                 205
```

```
Leu Leu His Leu Asn Ile Val Arg Ser Thr Leu Asn Ile Ala Asn Thr
    210                 215                 220

Tyr Lys Leu Thr Pro Leu Asp Arg Ser Tyr Val Val Met Pro Leu Phe
225                 230                 235                 240

His Val His Gly Leu Ile Gly Val Leu Leu Ser Thr Phe Arg Thr Gln
                245                 250                 255

Gly Ser Val Val Val Pro Asp Gly Phe His Pro Lys Leu Phe Trp Asp
            260                 265                 270

Gln Phe Val Lys Tyr Asn Cys Asn Trp Phe Ser Cys Val Pro Thr Ile
        275                 280                 285

Ser Met Ile Met Leu Asn Met Pro Lys Pro Asn Pro Phe Pro His Ile
    290                 295                 300

Arg Phe Ile Arg Ser Cys Ser Ser Ala Leu Ala Pro Ala Thr Phe His
305                 310                 315                 320

Lys Leu Glu Lys Glu Phe Asn Ala Pro Val Leu Glu Ala Tyr Ala Met
                325                 330                 335

Thr Glu Ala Ser His Gln Met Thr Ser Asn Asn Leu Pro Pro Gly Lys
            340                 345                 350

Arg Lys Pro Gly Thr Val Gly Gln Pro Gln Gly Val Thr Val Val Ile
        355                 360                 365

Leu Asp Asp Asn Asp Asn Val Leu Pro Pro Gly Lys Val Gly Glu Val
    370                 375                 380

Ser Ile Arg Gly Glu Asn Val Thr Leu Gly Tyr Ala Asn Asn Pro Lys
385                 390                 395                 400

Ala Asn Lys Glu Asn Phe Thr Lys Arg Glu Asn Tyr Phe Arg Thr Gly
                405                 410                 415

Asp Gln Gly Tyr Phe Asp Pro Glu Gly Phe Leu Val Leu Thr Gly Arg
            420                 425                 430

Ile Lys Glu Leu Ile Asn Arg Gly Gly Glu Lys Ile Ser Pro Ile Glu
        435                 440                 445

Leu Asp Gly Ile Met Leu Ser His Pro Lys Ile Asp Glu Ala Val Ala
    450                 455                 460

Phe Gly Val Pro Asp Asp Met Tyr Gly Gln Val Val Gln Ala Ala Ile
465                 470                 475                 480

Val Leu Lys Lys Gly Glu Lys Met Thr Tyr Glu Glu Leu Val Asn Phe
                485                 490                 495

Leu Lys Lys His Leu Ala Ser Phe Lys Ile Pro Thr Lys Val Tyr Phe
            500                 505                 510

Val Asp Lys Leu Pro Lys Thr Ala Thr Gly Lys Ile Gln Arg Arg Val
        515                 520                 525

Ile Ala Glu Thr Phe Ala Lys Ser Ser Arg Asn Lys Ser Lys Leu
    530                 535                 540
```

<210> SEQ ID NO 128
<211> LENGTH: 1146
<212> TYPE: DNA
<213> ORGANISM: Escherichia coli

<400> SEQUENCE: 128

```
atgacaaata atgaaagcaa agggccgttt gaaggcttat tagttatcga tatgacacat     60

gtccttaatg gacctttcgg aactcaactt ctttgtaata tgggcgcaag ggtaattaaa    120

gttgagccgc cgggtcatgg tgatgatacc cgcacatttg gtccctatgt ggatggacag    180

tcactctatt acagttttat taatcatggc aaagagagtg tggttcttga tttaaagaat    240
```

```
gatcacgata aaagtatatt tataaatatg ctcaaacaag ctgatgtatt agctgagaat    300

tttcgcccag gtacaatgga aaaactgggg ttttcatggg aaacgcttca agaaatcaac    360

ccgcgcctca tatatgcttc atcgtcaggt ttcggacata ccggtccgct aaaagatgct    420

cctgcctacg ataccatcat tcaggcaatg agcgggataa tgatggaaac aggatatcct    480

gatgctccgc cagtgcgcgt tggtacatct cttgcggatc tatgcggcgg tgtctattta    540

ttcagcggaa tagtgagtgc actttatggc cgcgaaaaga gccagagagg ggcgcatgtc    600

gatatagcga tgtttgatgc cacgctgagt tttctggagc atggtctgat ggcatatatc    660

gcaactggga agtcaccaca acgtctggga aatcgccatc cctacatggc accttttgat    720

gttttcaata ctcaggataa gccgattacg atttgttgtg gtaatgacaa gctttttttct    780

gcgttatgcc aggcactgga gcttacggaa ctggttaatg atccccgatt tagcagcaat    840

attttacgcg tacaaaacca ggctattctt aaacaatata ttgagcggac gttaaaaacg    900

caggcagctg aagtttggtt agccagaata catgaagttg gtgtacccgt cgcgccgtta    960

ttaagtgtgg ctgaggccat taaattgcca caaactcagg cgagaaatat gttgattgaa   1020

gccgggggaa taatgatgcc gggtaatccg ataaaaatca gcggctgcgc ggacccgcat   1080

gttatgccgg gagcggcaac gctcgaccag catggggaac aaattcgcca ggagttctca   1140

tcataa                                                              1146
```

```
<210> SEQ ID NO 129
<211> LENGTH: 381
<212> TYPE: PRT
<213> ORGANISM: Escherichia coli

<400> SEQUENCE: 129

Met Thr Asn Asn Glu Ser Lys Gly Pro Phe Glu Gly Leu Leu Val Ile
1               5                   10                  15

Asp Met Thr His Val Leu Asn Gly Pro Phe Gly Thr Gln Leu Leu Cys
            20                  25                  30

Asn Met Gly Ala Arg Val Ile Lys Val Glu Pro Pro Gly His Gly Asp
        35                  40                  45

Asp Thr Arg Thr Phe Gly Pro Tyr Val Asp Gly Gln Ser Leu Tyr Tyr
    50                  55                  60

Ser Phe Ile Asn His Gly Lys Glu Ser Val Val Leu Asp Leu Lys Asn
65                  70                  75                  80

Asp His Asp Lys Ser Ile Phe Ile Asn Met Leu Lys Gln Ala Asp Val
                85                  90                  95

Leu Ala Glu Asn Phe Arg Pro Gly Thr Met Glu Lys Leu Gly Phe Ser
            100                 105                 110

Trp Glu Thr Leu Gln Glu Ile Asn Pro Arg Leu Ile Tyr Ala Ser Ser
        115                 120                 125

Ser Gly Phe Gly His Thr Gly Pro Leu Lys Asp Ala Pro Ala Tyr Asp
    130                 135                 140

Thr Ile Ile Gln Ala Met Ser Gly Ile Met Met Glu Thr Gly Tyr Pro
145                 150                 155                 160

Asp Ala Pro Pro Val Arg Val Gly Thr Ser Leu Ala Asp Leu Cys Gly
                165                 170                 175

Gly Val Tyr Leu Phe Ser Gly Ile Val Ser Ala Leu Tyr Gly Arg Glu
            180                 185                 190

Lys Ser Gln Arg Gly Ala His Val Asp Ile Ala Met Phe Asp Ala Thr
        195                 200                 205
```

```
Leu Ser Phe Leu Glu His Gly Leu Met Ala Tyr Ile Ala Thr Gly Lys
    210                 215                 220

Ser Pro Gln Arg Leu Gly Asn Arg His Pro Tyr Met Ala Pro Phe Asp
225                 230                 235                 240

Val Phe Asn Thr Gln Asp Lys Pro Ile Thr Ile Cys Cys Gly Asn Asp
                245                 250                 255

Lys Leu Phe Ser Ala Leu Cys Gln Ala Leu Glu Leu Thr Glu Leu Val
            260                 265                 270

Asn Asp Pro Arg Phe Ser Ser Asn Ile Leu Arg Val Gln Asn Gln Ala
        275                 280                 285

Ile Leu Lys Gln Tyr Ile Glu Arg Thr Leu Lys Thr Gln Ala Ala Glu
    290                 295                 300

Val Trp Leu Ala Arg Ile His Glu Val Gly Val Pro Val Ala Pro Leu
305                 310                 315                 320

Leu Ser Val Ala Glu Ala Ile Lys Leu Pro Gln Thr Gln Ala Arg Asn
                325                 330                 335

Met Leu Ile Glu Ala Gly Gly Ile Met Met Pro Gly Asn Pro Ile Lys
            340                 345                 350

Ile Ser Gly Cys Ala Asp Pro His Val Met Pro Gly Ala Ala Thr Leu
        355                 360                 365

Asp Gln His Gly Glu Gln Ile Arg Gln Glu Phe Ser Ser
    370                 375                 380


<210> SEQ ID NO 130
<211> LENGTH: 437
<212> TYPE: PRT
<213> ORGANISM: Escherichia coli

<400> SEQUENCE: 130

Ser Tyr Tyr His His His His His His Leu Glu Ser Thr Ser Leu Tyr
1               5                   10                  15

Lys Lys Ala Gly Leu Met Ser Thr Pro Leu Gln Gly Ile Lys Val Leu
            20                  25                  30

Asp Phe Thr Gly Val Gln Ser Gly Pro Ser Cys Thr Gln Met Leu Ala
        35                  40                  45

Trp Phe Gly Ala Asp Val Ile Lys Ile Glu Arg Pro Gly Val Gly Asp
    50                  55                  60

Val Thr Arg His Gln Leu Arg Asp Ile Pro Asp Ile Asp Ala Leu Tyr
65                  70                  75                  80

Phe Thr Met Leu Asn Ser Asn Lys Arg Ser Ile Glu Leu Asn Thr Lys
                85                  90                  95

Thr Ala Glu Gly Lys Glu Val Met Glu Lys Leu Ile Arg Glu Ala Asp
            100                 105                 110

Ile Leu Val Glu Asn Phe His Pro Gly Ala Ile Asp His Met Gly Phe
        115                 120                 125

Thr Trp Glu His Ile Gln Glu Ile Asn Pro Arg Leu Ile Phe Gly Ser
    130                 135                 140

Ile Lys Gly Phe Asp Glu Cys Ser Pro Tyr Val Asn Val Lys Ala Tyr
145                 150                 155                 160

Glu Asn Val Ala Gln Ala Ala Gly Gly Ala Ala Ser Thr Thr Gly Phe
                165                 170                 175

Trp Asp Gly Pro Pro Leu Val Ser Ala Ala Ala Leu Gly Asp Ser Asn
            180                 185                 190

Thr Gly Met His Leu Leu Ile Gly Leu Leu Ala Ala Leu Leu His Arg
```

```
        195                 200                 205

Glu Lys Thr Gly Arg Gly Gln Arg Val Thr Met Ser Met Gln Asp Ala
    210                 215                 220

Val Leu Asn Leu Cys Arg Val Lys Leu Arg Asp Gln Gln Arg Leu Asp
225                 230                 235                 240

Lys Leu Gly Tyr Leu Glu Glu Tyr Pro Gln Tyr Pro Asn Gly Thr Phe
                245                 250                 255

Gly Asp Ala Val Pro Arg Gly Gly Asn Ala Gly Gly Gly Gly Gln Pro
            260                 265                 270

Gly Trp Ile Leu Lys Cys Lys Gly Trp Glu Thr Asp Pro Asn Ala Tyr
        275                 280                 285

Ile Tyr Phe Thr Ile Gln Glu Gln Asn Trp Glu Asn Thr Cys Lys Ala
    290                 295                 300

Ile Gly Lys Pro Glu Trp Ile Thr Asp Pro Ala Tyr Ser Thr Ala His
305                 310                 315                 320

Ala Arg Gln Pro His Ile Phe Asp Ile Phe Ala Glu Ile Glu Lys Tyr
                325                 330                 335

Thr Val Thr Ile Asp Lys His Glu Ala Val Ala Tyr Leu Thr Gln Phe
            340                 345                 350

Asp Ile Pro Cys Ala Pro Val Leu Ser Met Lys Glu Ile Ser Leu Asp
        355                 360                 365

Pro Ser Leu Arg Gln Ser Gly Ser Val Val Glu Val Glu Gln Pro Leu
    370                 375                 380

Arg Gly Lys Tyr Leu Thr Val Gly Cys Pro Met Lys Phe Ser Ala Phe
385                 390                 395                 400

Thr Pro Asp Ile Lys Ala Ala Pro Leu Leu Gly Glu His Thr Ala Ala
                405                 410                 415

Val Leu Gln Glu Leu Gly Tyr Ser Asp Asp Glu Ile Ala Ala Met Lys
            420                 425                 430

Gln Asn His Ala Ile
        435


<210> SEQ ID NO 131
<211> LENGTH: 564
<212> TYPE: PRT
<213> ORGANISM: Escherichia coli

<400> SEQUENCE: 131

Met Ser Asp Gln Leu Gln Met Thr Asp Gly Met His Ile Ile Val Glu
1               5                   10                  15

Ala Leu Lys Gln Asn Asn Ile Asp Thr Ile Tyr Gly Val Val Gly Ile
            20                  25                  30

Pro Val Thr Asp Met Ala Arg His Ala Gln Ala Glu Gly Ile Arg Tyr
        35                  40                  45

Ile Gly Phe Arg His Glu Gln Ser Ala Gly Tyr Ala Ala Ala Ala Ser
    50                  55                  60

Gly Phe Leu Thr Gln Lys Pro Gly Ile Cys Leu Thr Val Ser Ala Pro
65                  70                  75                  80

Gly Phe Leu Asn Gly Leu Thr Ala Leu Ala Asn Ala Thr Val Asn Gly
                85                  90                  95

Phe Pro Met Ile Met Ile Ser Gly Ser Ser Asp Arg Ala Ile Val Asp
            100                 105                 110

Leu Gln Gln Gly Asp Tyr Glu Glu Leu Asp Gln Met Asn Ala Ala Lys
        115                 120                 125
```

```
Pro Tyr Ala Lys Ala Ala Phe Arg Val Asn Gln Pro Gln Asp Leu Gly
    130                 135                 140

Ile Ala Leu Ala Arg Ala Ile Arg Val Ser Val Ser Gly Arg Pro Gly
145                 150                 155                 160

Gly Val Tyr Leu Asp Leu Pro Ala Asn Val Leu Ala Ala Thr Met Glu
                165                 170                 175

Lys Asp Glu Ala Leu Thr Thr Ile Val Lys Val Glu Asn Pro Ser Pro
            180                 185                 190

Ala Leu Leu Pro Cys Pro Lys Ser Val Thr Ser Ala Ile Ser Leu Leu
        195                 200                 205

Ala Lys Ala Glu Arg Pro Leu Ile Ile Leu Gly Lys Gly Ala Ala Tyr
    210                 215                 220

Ser Gln Ala Asp Glu Gln Leu Arg Glu Phe Ile Glu Ser Ala Gln Ile
225                 230                 235                 240

Pro Phe Leu Pro Met Ser Met Ala Lys Gly Ile Leu Glu Asp Thr His
                245                 250                 255

Pro Leu Ser Ala Ala Ala Ala Arg Ser Phe Ala Leu Ala Asn Ala Asp
            260                 265                 270

Val Val Met Leu Val Gly Ala Arg Leu Asn Trp Leu Leu Ala His Gly
        275                 280                 285

Lys Lys Gly Trp Ala Ala Asp Thr Gln Phe Ile Gln Leu Asp Ile Glu
    290                 295                 300

Pro Gln Glu Ile Asp Ser Asn Arg Pro Ile Ala Val Pro Val Val Gly
305                 310                 315                 320

Asp Ile Ala Ser Ser Met Gln Gly Met Leu Ala Glu Leu Lys Gln Asn
                325                 330                 335

Thr Phe Thr Thr Pro Leu Val Trp Arg Asp Ile Leu Asn Ile His Lys
            340                 345                 350

Gln Gln Asn Ala Gln Lys Met His Glu Lys Leu Ser Thr Asp Thr Gln
        355                 360                 365

Pro Leu Asn Tyr Phe Asn Ala Leu Ser Ala Val Arg Asp Val Leu Arg
    370                 375                 380

Glu Asn Gln Asp Ile Tyr Leu Val Asn Glu Gly Ala Asn Thr Leu Asp
385                 390                 395                 400

Asn Ala Arg Asn Ile Ile Asp Met Tyr Lys Pro Arg Arg Arg Leu Asp
                405                 410                 415

Cys Gly Thr Trp Gly Val Met Gly Ile Gly Met Gly Tyr Ala Ile Gly
            420                 425                 430

Ala Ser Val Thr Ser Gly Ser Pro Val Val Ala Ile Glu Gly Asp Ser
        435                 440                 445

Ala Phe Gly Phe Ser Gly Met Glu Ile Glu Thr Ile Cys Arg Tyr Asn
    450                 455                 460

Leu Pro Val Thr Ile Val Ile Phe Asn Asn Gly Gly Ile Tyr Arg Gly
465                 470                 475                 480

Asp Gly Val Asp Leu Ser Gly Ala Gly Ala Pro Ser Pro Thr Asp Leu
                485                 490                 495

Leu His His Ala Arg Tyr Asp Lys Leu Met Asp Ala Phe Arg Gly Val
            500                 505                 510

Gly Tyr Asn Val Thr Thr Thr Asp Glu Leu Arg His Ala Leu Thr Thr
        515                 520                 525

Gly Ile Gln Ser Arg Lys Pro Thr Ile Ile Asn Val Val Ile Asp Pro
    530                 535                 540

Ala Ala Gly Thr Glu Ser Gly His Ile Thr Lys Leu Asn Pro Lys Gln
```

545 550 555 560

Val Ala Gly Asn

<210> SEQ ID NO 132
<211> LENGTH: 666
<212> TYPE: DNA
<213> ORGANISM: Bacillus subtilis

<400> SEQUENCE: 132
atgtttgaga agtattttcc aaatgttgac ttgaccgagt tatggaatgc cacatatgaa 60
actctgtata tgacattgat ttccttactg tttgccttcg taatcggcgt catcctggga 120
ttgctgttat tcttaacatc taaggggtct ctttggcaaa ataaagcagt aaattccgtt 180
atcgcagccg ttgtcaacat ctttcgttca attcccttcc ttattttaat catcctgctt 240
cttggtttca ctaaattctt agtgggaaca attttgggac caaatgcggc tcttcccgcg 300
ttagtcatcg gtagtgctcc cttttatgct cgtctggtcg aaatcgcact tcgtgaagtg 360
gacaaaggag tgattgaggc ggcgaaatcg atgggggcta agacgagcac tattattttt 420
aaggttctta tccccgagtc catgcccgcg ctgatttccg gaattacagt gactgcgatt 480
gcattgatcg ggtcaaccgc catcgcagga gctattggtt ctggtggatt gggaaactta 540
gcatacgttg aaggctatca atcgaataat gcggatgtga ccttcgtggc cacagttttc 600
atcctgatta ttgttttcat cattcagatc attggtgacc ttattaccaa catcatcgat 660
aaacgc 666

<210> SEQ ID NO 133
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133
atgagtaata tcagtttgta ttgtttgcca tattcaggtg gttctgccgc catgtattat 60
aaatggcgta gcgtgctgtc ggacaatatt actttgcggc ctttagaacc tgcggggagg 120
ggaactagaa tacgccagcc gctgtgtctt acgatggtgg atgccgtcgc tgacctttat 180
caacaatttg tgaaacacta cacaggtgga gactacgcca tttttgggca tagtctcgga 240
gggatcatgg ccttcgaact ggtgcattat attctcgatc atggacatga catgccatgc 300
gcgctgtttt tttccggctg tcgcccaccc gatcgggcct ctcatgaagt aatactgcat 360
accttgcccg atcaggcgtt tatggaagag atcgtcaagc tgggcggaac tccggttgat 420
gtctttcgta ataaagagtt aatgacaatt ttcacccccca tcattaaaaa cgattatcgg 480
ctctatgagc agtatgtatt tcaggccaag gcgcgcacat taacctgtcc gatcgtgcta 540
tttcatggcg atgctgacaa tctggtaatg caggatgaat tacttgcatg ggaaaaattc 600
accacacgaa agacgcggac tattatattt cctgctgccg atcatttttt tgtcgataag 660
cattttgaac aggtggtagg ttatgtgaac cagacgattg aatcactcga aatagtaggg 720
tag 723

<210> SEQ ID NO 134
<211> LENGTH: 1515
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134
atgacaataa tggaacacgt tagcattaaa acattatatc atctcctgtg ctgtatgctg 60
ctctttattt ccgctatgtg cgctttggcg caagaacatg agcctatcgg ggcgcaagat 120
gagcgcctgt cgacattaat tcaccaacgg atgcaggagg ccaaggtccc agccctttcc 180
gtaagtgtga ccattaaggg ggtacgtcag cgatttgtct acggtgttgc cgatgtggct 240
agtcagaaag cgaatactct agacacagtt tacgagctgg gatcgatgag taaggcgttt 300
accggacttg tggtgcaaat actgattcag gaaggcagac tccggcaagg ggatgatatc 360
attacctatc tgccggaaat gcgcttgaat tatcagggaa aacctgcttc cctgaccgtg 420
gctgatttcc tttatcatac atcaggattg cctttttcaa cactggctcg gctggaaaac 480
cctatgcctg ggagcgctgt ggcacagcaa ctgcgcaacg agaatctgct gtttgcgccg 540
ggtgcgaagt ttagctatgc ctccgccaat tatgatgtgt tgggcgcggt gattgaaaat 600
gtgacgggaa aaacctttac agaggtcatt gcggaacgac tcacgcagcc gctgggcatg 660
tcggcgactg tggcagttaa gggggatgag attattgtca acaaggcaag cggctataaa 720
ctgggattcg gcaaacccgt tctgtttcat gcgcctctgg cccggaacca tgttcctgcc 780
gcctatatcc atagcactct gcctgatatg gaaatatgga tagacgcctg gttgcacaga 840
aaggctttgc cggcaacgct gcgtgaggcg atgagtaaca gttggcgtgg taatagtgat 900
gttccgcttg ccgcagacaa tcgtatcctc tatgccagcg gttggtttat cgaccagaat 960
caaggccctt acatcagtca cggtgggcag aatccaaact ttcttcttg cattgcgttg 1020 cgaccggatc agcagattgg cattgttgcg ctggcaaata tgaattcgaa tctgatacta 1080
cagctttgcg cggatatcga taattatctg cgcattggca aatatgctga cggcgctggt 1140
gatgcaatta cagccaccga taccctttc gtctacctca cgttgttgct gtgtttttgg 1200
ggggcggtgg ttgtagtgcg cggtgctttc cgtgtttatc gcgcaacggc gcatggccct 1260
ggaaaacagc agaggttacg tttacgcgta cgtgactata tcatcgcctt ggcggttcct 1320
gggctcgtgg ccgccatgct ctatgtcgca ccgggtatac tatctccagg acttgactgg 1380
cgttttatct tggtatgggg tccatcgagc gtgttggcga taccgttcgg aattatcctg 1440
ttagctttcg ttctgacatt aaatcatcaa attaaacgaa ttctattaca caacaaggag 1500
tgggacgatg agtaa 1515

<210> SEQ ID NO 135
<211> LENGTH: 2460
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 135
atggcaaagg atgattttac ctgtggctca ctggatattg ccattattgg catgagcggg 60
cgtttttccg gtgcggaatc ggtgcccgag tggtgggata agttgctggc gggtgaggag 120
ttcactcaac cgacatgcac agaagacgat aatgggaacc cttggattag gctgcgcaat 180
ataatcaccg ctccctatga cttcgatgct gcatttttca atattccgcc tggcgaagcc 240

```
ctgttgatgg atccgcaaca acgaatattt cttgaatgct gctacaacgc tcttgagcat    300

gcgggctata ttcccacgca acttaagcga gtcggcgtct atggggcgac ctacgccaat    360

aactatttta tcgatcgcgt ctatccatac ctgaagatga gcggcgatca ccattatctt    420

caggcgcaga ttggtaacga aaaggattac ttgtgtgctc aggttgccta caagttgggg    480

tttaccggac ccgctgtgag tgtacagacc gcctgttcca gttcgttggt ggcagcatat    540

ttagcatgcg aggggttatt gacttttcaa gccgatgttg cgttggcagg tggggtcacc    600

ttgggttttt tacaggcgca cggctacagt ccgcaaggtg ataagctggt atcgcaagac    660

ggacactgcg ccccgtttag cgctgaggcg accggcacgg tatacagcag cggtgcggga    720

gttgtggtgc taaaacgtct tgaggatgca ctacgcgacc aagacagagt gtatgcggtg    780

attaaaggag gtgcggtaaa taacgacggc gggcgtcggc tggggtttgt cgcccccagc    840

gtagaaggac aggtagaagc gatcaatacg gcgcttgccg ccgcagaagt cgtaccgact    900

gatatcgcac tgatcgaaac gcacggtacc ggtaccccgt tgggtgatga gattgagctt    960

gaagctctgc accgggtttt cgcaccggca tgtgcgccgc acagcattca attgggtgcg   1020

gtaaaagcca acttgggtca cctgggagtc gcttccggta tcgtcagctt aatgaaaacc   1080

gcactgacgc tatatactgg tttagttccc ccgcagatca acctagtaaa taaacataaa   1140

aaactgttgc agccagcctc gccattttat ctcagtgatg tagtgacttc tgtcccacaa   1200

acgaaaagga tccatgccac cgttagttcg tttgggctgg gagggaccaa tgctcatttg   1260

gttctgcaaa actggtgcga gacgcctgcg caagcggtgc aagaaaatga gcgccgcctg   1320

tttttcttca gcgccaaaac gccattagcc cttagacaac agttggatgc tcattatcac   1380

gctctggcga cctatgcgga agcagataaa gatcgtatcg cctatactct cgcgcaacgc   1440

cgggcacatt tcccgtatcg ctgtgcgctg gcggcagaca gtgtggtagc gttgcgtgca   1500

agtttggcga aactgcggga tgctgacatg tcttttaccc ctatcaatat ggaaactacc   1560

ttggtgttcc tatatccgga ccgggacgat aagctggaga gtgccctgac gcatttgctg   1620

gcttgtcaac ctaacttgcg ccagcggcac cagcgcctgt ctcaggatgt tgcacaaatc   1680

tgcgaaccag ccgattggac gccagcattg cgtcagttta tccagcaggt gagtcttagt   1740

gaatggctga tcgaacaaag tatctcgcct gtgcagcaca tcggttacct gacgggggct   1800

gcagcagcgc agtatgttgc gcgcatcatc tcactggaaa acgctgttca gcaggtgatt   1860

gtggctgaaa cgacaccgga gcagacgctg gccggcaaca gtgaactgag cgaaatattg   1920

gctaatctgg cggtgacgga gggaacgctg atgctggaaa tcggtcgcgc ggggacgttt   1980

tccatattgt atcaccagca tgcgcagtgg gttgggcaaa cagtattttc ccccatgctg   2040

aatacggata cgcctgagga catcctgccg ctgttgggca ctctttggca acgaggagtg   2100

actatttgtt taccggaaat gccagccgtg cagactatag gcttacccgg ttattcgttt   2160

gatcgcgtcc ggtatgaaat tcagtccagt gatgcgagag agaacgctat gttaccagtg   2220

agttatttgt cggtcagcga ctttgtggag aaaacctggc gttcattgtt atgcatcgat   2280

cattatgacg aacacgcggt tattttcgaa tacggagcga cctcgatgca cgttatctct   2340

ttcgtcgaca gctgtaacca catttataaa atcggactga ctgccgccga tatttatgcc   2400

agacccgcta tccgtgagca cagtgaattt atctccgaat gtgttgatgg tattttatga   2460
```

<210> SEQ ID NO 136
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 136

```
atgatgtcgg gcaatccgtt gtcgtggcca caggaacagt gccacatcat tgatcaactg     60
tatccttaca gtgccgtaaa catcattggt ggtgtggtca ccattgaggg aattgtcgat    120
ctgccccgac tacacgcggc catccagtcc gccattcggc aatttgatgc gttgcgtatg    180
tggtttgtga tgggagagga gagtgaagtg gtcagccaag tgcagcctta tcactggcgc    240
gatatccgcc atttgacttt ttccccagat tatgacaagg agaacctacg cccagcggcg    300
atcgaaacat ttgttgatga gtggttccgg cagcccttta ccctgctggc gcacgatttg    360
ttcgagtttg tcacctttac gtgcggtgaa caatacagcg gttatttatt taaagcccat    420
cacggcattg ctgatggttg gtcaatggcg ttgttgtcaa accatgtcaa gcgagcatac    480
gaacagcagg acgtaccaga tgatgcgtca ccagcctata gcgcatttct ggcgcagcag    540
caatcttatc aggcgtcaac gcgctttgcc gttgatcgtg gctggtggcg tgactatatc    600
gacgaatacc gcgactgctt tccagacagt tcccccatcg ttactactga gggcatcagt    660
tgttccactt ggcttgagcc agccatgatt aaccgtctct acaggttgtg taatcgttat    720
ggctgtacgc ttaatacgct gtttattgca ctcttcgctc tctatcgcgc cagagtatgg    780
ggggaggaaa aaggcgtaat aggcgtgccg ttagccaatc ggcatactcg cgaggcgcgg    840
cgttgctttg gcatgtttac taatcaattg ccgctggcct atcgactggt gcgcacggaa    900
cgattctgtg aacgggtggc ctttttccag cgcgaactga aacgcggttt taaacacagc    960
aaatatccca ttaccttatt caaccaggat ttggcggaac aggggggagg gaagttgcgg   1020
gcgttcgatt attgcgttaa ttattataac tttacctatg aacgccacat tgcaggtgcc   1080
gcgcaacgcg tggagagtta ctacagcggc gagcagtcct ataagctaca gattgttttg   1140
caaactgtta ataatcataa agaaagcctt aggttgagtc tggaggcgct gcgtagcgct   1200
ttcactccgc accaactgac agcgatgaaa aatgggctgt tggatttagt cactgcattg   1260
gatcggcaac ctgacgctcg tctaggcgat ctcgaagtct atcctgcgcc gcacgtcgca   1320
ttggcatgtg gctcactcaa accctcattt acttcccgat ttgcagcgca agttgtggag   1380
catggtgatc gcacagcact aattgataat gaacagtctt tgacttatcg gcagttggat   1440
gacgctgttg agcgggttgc gcgttatctg cgccaacagg ggatcggacg cggtcaagtg   1500
gttgggatta tcgctgagca tagcgctcaa acggtgatgg ttatttatgg tattttgcgc   1560
tgcggcgcgg catttctgcc gctaaatccc gcgttgccaa cgacccgcct ttacgccatg   1620
tgtcgtaaag cgcaggtagc gcatatcctt tacgatccgg cgatgcatga attgacgcag   1680
gcgctggcgt ttcccgcgtc cagcttgctc caggccttag ccacttcggc gcttgctaga   1740
gaaccttggc cagctattga accgcaggat ctggcatatg tgctgtttac ctccggatcg   1800
accggcgagc ctaagggcgt gcaagtctct catggcaatc tggctaacta tctccatttc   1860
gccgccgaac gttactttac agcgcaggac cgggctgcgc tctactcttc gctgtccttc   1920
gatttgacca tcactacgct gttcgccccc ttatgtgtgg gcgctagcat cagcgtttgt   1980
cggcacgccg agagcgaaac attgctgcgc atggccgtgg ttgatcagcc caacacagtg   2040
atcaaactga cgcctgcaca cctgcggttg ttgtgtgcgg ctggcataag cagtgagcag   2100
attcgtacct tggtggttgg cggggaggat ttcaagcggg atctggcgcg taaggcggct   2160
```

```
gctctctttc ctcaggccgt gatctataac gaatatgggc cgacagaggc caccgttggt   2220
tgcatgatct atcgctacac cgggcaagaa acgctgcctt cattgcccat cggtatggcg   2280
atcgacggtt gccaggtagc aatttgctcc ccttggggct gtccggtacc ggaaggcgaa   2340
actggtgaat tggtgattta tggcgcgtca gtgacgcagg gctatatcga tgcgccgcaa   2400
caaacggccg ccgcctacct taaagatacc aatggggtga tgattggcta tcgcagcggt   2460
gatattggct acgccatcgc tcctaatacg ctggtttatc agggacgtaa agacgatcag   2520
gtcaaaatta atggctatcg tattgagctg tgcgaaatcg aacaagcgtt gttgagcgca   2580
cctcaggtag aaagtgcggc ggtggcggtg attgatgatg tgcaggggca gcacagcggg   2640
ttgctagcct gcgtgacacc gtcatctgtt gatgtagcta ccgtaatgca acatctgcgt   2700
cagcaattac ccacctacat gcaacccaag cagtgctgtg ctatcgccca actgccgcta   2760
tcgcacaatg gcaaggtgga cgtgcgtcag atggtcgcaa cggtccgaaa caccgcgcct   2820
gcatcgggta gcgagcggct gggagatgcg gcgataaggc attcagttcg ggtatgtgtg   2880
gaaggggcgc tggagcaaac tgagtttgat gataacgaaa atctttatgt cttggggttg   2940
gactccatca agagtatcca gattgcagcg cagctcaggc accacggctg gacgatgtca   3000
gcggtgcagg tgatggagtg tggaacagtg aacgccatct gtgagtttct cgctagtcat   3060
acaacggtgt cacagctcgc gcagtatgct cataacaccc gtatcgatct acccgcattg   3120
cgttggttta cgcagttggc gttgccagtg cccaatgttt ataaccatgt cattgtgctg   3180
aaagtgttgc cggctgccc gctcgagcag ttacacaaca ggctgcatac attaatccag   3240
cagcagccag ctttgcacag tgcgctggac gctgaggggc ggttgctagt atgcgaccct   3300
aatgtgtgtt atcccaacga ggtgctcacg gaatattcga cggcgcagtg gacgttggca   3360
gaggtgatcg ctcagtgcaa tagcatgctt gacgtgacaa atggtcgagt ctttacggca   3420
gctctgttac acgccccgca gcctgcgtct agcacgctgg tactctgtgc ccatcacttg   3480
tgcgtcgata tgcactcttg gtatttaatc ctcagcacgc tggacgccgt cagcactgtc   3540
aatggcacca gcaacagcgg actgcatcgc tggaatgact atctggcgag caaaacggta   3600
gattccgcca cacacgaaag ctggcgcaca gtatgtcaaa cgctaccgct gcatttccca   3660
cccgtgtcat tgccagatga ctcattacct cgtacgcgcg cttggcgtga agactttcgc   3720
catccttgcg tcaggaggtt gtttgaatcc agtggtaata ccgcgtacag cgccgaaacc   3780
tatgtgctaa cggcattggc gctggtgctg cgttactaca gcgaagagcc ttggtgtcgc   3840
atcgagatgg aaggcatggg acgcggctgc tggcccgatg agcctgacgt tgcggatacg   3900
gtcgggtggt ttactctatt ttatccttgg gcgatccctc tgcatggcga tatggcgaca   3960
ctgttatctg cgatcgcttc cgatttggca aaacgcacgc atggtggggg agattacggt   4020
ctgctgcaaa tgcggcatgc accggaagac tctcttgcgc aagggatccg aatgaattac   4080
atcggtgtgc aggcgcaacc ttcactccgc tattttcata ttgatcactt taatagtgat   4140
atctataccg cgcctgaaaa cgcgctcggc tgcgtgctgg agtttaatat tgcgcgctcg   4200
gcagctgatg gtctctcctt ccactgccgt ttcgatccca cgcgcattgc gctgaatgat   4260
gtgcaactcc tgctggcgcg ctacaagaac agcctcactg atctggatgc ctggctgtgc   4320
caacacagcg ccacgctgac gggcgcgccg actttgtgga cactataa                 4368
```

<210> SEQ ID NO 137
<211> LENGTH: 1440
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 137

```
atgacggtga ataagcttga gccagacaac ggcacgccga acgatgagct gttcacggtg     60
gcgggtatgt ttgacggctc gctgtataaa ttactcctgc gcatggcgtt gccgatgttt    120
gtcggtatgt taacgcaggt gacctatgcc atcgccgata ttttttggct gagccacatt    180
gatgtcacca acagcggcat cattgccggt gtggggctgg ttttccccgt tggaatgggg    240
ttatttgcca tcgccaacgg cattcaaatc ggtatgggat ctttgctgtc ccgcgccatc    300
ggcatgcagc ggttggatcg tgcacagcgg attttgtcgg tcggtatcat catcgcgcta    360
ttctttgcga tcgtgatcac cgtacttggc tatgtttatg cccagccgct attgcgctca    420
ctgggggcca cgaagagcat catcggctac gcaacggagt tctattatta ttcgctgctg    480
accgtgttca gcatcatgtt gattggcgtc atgatggggc tgtttcaagg cgcgggtaag    540
atcatggtca tcatgaaggc ctcattgttg gggcgttgg taaatattat gctcgatcca    600
atcatgatct ttgtattcga ttttggtgtg aaaggggtgg cattggcgtc gtttctggcg    660
caactgagta tggtcgccta tttcatctac acattgatgg gattacatat cgggttgagt    720
atacgcatcg cgttacgccc attctcctgg aaaatctacc gagagtttct ctccgtcggc    780
atggcgcaga tgctgatgca actgatcatt gcggtcggca tagtgattta taattttttt    840
atcgtcaggc tggacgtaaa cgcgatggca gcgtttacgc tcactggtcg catcgactat    900
ttcatcatca cgccgatgct ggctatcgcg accgcgttgc tgactgtggt ggggcaaaac    960
tggggacacg gaaatgtcac ccgcacgctg aatgcctatt gggccgccgt cgcgctggcc   1020
ttctctattg tgctggtgtt agccgttatg catattgtac tggcaccctg gatgtatccc   1080
ctgtttactc gtgttgttgc cgtgagtgac tatgcggtac tgcaaacccg tatcatggca   1140
ctggcactac cctttgtcgc tatcagcctg ttagcaagtg aatattatca ggccattggt   1200
aagccttggt attcggtgtt gttgacgctg atgcgtcacg tgtttatatc tgtccctgtc   1260
gtatacctgc tggcgattgt gttagagatg cgtattaccg gcgtctattt tggggcgatg   1320
agcggcactt ttgtggctgc gttgttggcg tggcgtctgc tgcgtctttc acctcgtctg   1380
ctgcgatgga atcaggaggc ggtgcgctcc caacacttgg atatggaggt ggcaccatga   1440
```

<210> SEQ ID NO 138
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
atgagtgagc agagctatcg tagcgcaggg acactgttgg cacagttggc gtccggagaa     60
accacctcag tggcgttggt gaatcactat ttttcacgta tggcgcagtt taacaagccg    120
ttgaatgcgg tggtgcagca gcactatgcg ttggcgttgg aggccgccgc gcgcgccgat    180
cgtgagcgac tggaggggcg cgcaaggggc gtgttgcacg gattaccttg tactgttaag    240
gagtcgtttg acgtgcaagg gtggttaacc acgtccggtg cccattatct gaaagataac    300
cgggcgacgc aggatgctcc ttccatcgca cgcttacgcg ctgccggggc gatcctgatg    360
```

```
ggaaaaacca atgtgccgat gatgactgcc gattggcaaa cctataacga tctgtatggc    420

accacccata acctgtggga taggcaacgt tcacccggcg gatcgtccgg aggagcggcg    480

gtggcggtgg cggcggattt caccccgtg gaatttggca gcgatttgtt tggctcactg     540

cgcattcccg cacactacac aggtgtctat gcccatcgtt gtagcttggg gttgatgtcg    600

gtcagaggac atgtgcccgg tggtggtccg caagcgactg atgagccgga tctctcgacg    660

gcgggcccca tggcgcgcag cgcggcggat ctgcgtctga tgatgcgcgc attgagcaca    720

ttctgggtgg aaccgccgcg tattcccgat tttagccgtt atcaggccaa agcaaactac    780

cgcgtgtgca cgtggtttag tgcgccccac catgagatag atcaacagat cgcacagcgt    840

tttcaatcgt ttatcgacaa gttacgcgca cagcctggcg tggaggttga tgatgctatg    900

cccgccgata tcgatcccga cgcactgttt gatatagcag tcaaactcag tggtcggctg    960

gtaagtacgg cgctcaatgg acgccagcgt cttacagccg ggctggctgc gctgggcttc   1020

aggcttgtgg gcaagctggc ggatgtgcct gaggggataa cgagctatta ccagggcatg   1080

ctgaaagaca gtggcgaaca gcggaataca gacaaactcc gccacgaata cagccgggtg   1140

atagaaaccc ttttcgcgcg ttatgacgtg ttgttgacac ctgtcagccc ggtgctggcg   1200

tttgcgcaca tgcagcagcc ggtgcgtaag cgcaagctta tcgtcaatgg cgaaccgcaa   1260

gattacaacg aacatttgtt ctggaacatg ttagcaacgg tttttggttt gcctgccacc   1320

gtttacccat tggcgaaaac gatggatgag cttccgtgcg gcatacagat catttccggg   1380

cattttcacg atgatgtgac gattaacttt gctgagttct gcgaaagcat cagtggcgga   1440

ttcacggtac cggaagggta ctag                                          1464
```

<210> SEQ ID NO 139
<211> LENGTH: 6465
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
atgacttaca gtgaaagcga tattgccatt gttggcatga actgccggta ccccggcgtg     60

cacagcgttg cggcattcga aacggtgctt cgcaccggat gcaacatttt ggaccccaaa    120

gtgaccccga gcaacggcca caatcacatt acgctgaaca acgtctatga gcacatggcg    180

gagttcgatg ccaacttttt tggctacagc cgtgcagaag cagaaatcat ggatccacag    240

cagcgcgtat ttctgacctg tgcttgggag atgtttgaac aaagcggtta caacccgaag    300

cagcacgatg cgcgcgtcgg cctatatgcg ggcgtgagta ccagcttcta tttgcttact    360

cacctgatga acaacccaga caagcttgca caactcggtg gtctccaaat catggtcggc    420

aatgacaaag atcatttgac gtcccaactg gcttaccgcc tgaatattac cggccccttgc   480

gtgacggttc aggccagttg tgccacctcg ctggtggcag tgcatctggc ctgcgaaggg    540

ctgctgagcg gtcagtgcga tatggcgcta gcgggtggcg tcacgtttcg catggaggag    600

cagcgcagct atgaatcgca cggtgatggg ctgcaagcag aggatggcct gattcatact    660

tttgatgcgc aggcgagcgg tacggtctac agcagtggtt tgggcatggt gctgctcaaa    720

cgggctacag acgcgcaggt gcaaggggat aacatccttg ccgtcatcaa gggaagcgcc    780

atcaacaatg atggcggtgc gcgcagtggt tataccgtgc cgggtgttga tggtcaggaa    840

gctgtgatga ttgaggcgca tagcttggcg gaggtgacgc cgcagcaaat tcagtatcta    900
```

```
gaactgcatg gcagcggcac gccgttgggt gacgctatcg aattcgcggc catcaaacgt    960
gtgtttggga cgccagcgcc gaatgcgaca ccgtggcgtc tgggggctgt gaaacctaac   1020
gtgggtcacg tagaaatggc atctggcatc accagtctca taaaaacggt gctgagtctt   1080
actaaccggg tgttttaccc tacgctgaat tttcaacggg ctaatccgca actggggttg   1140
gaggacagcc cgtttgaagt ggtgtcccgt ttaacgcctt ggccggaggg caccacgcca   1200
cgcaccgctg gtgtgagtgc gttcggattg ggcggcacca acgcacatct ggtggtacaa   1260
gcgccgttat cgacgccgca ggcgagggcg cagcagatgg ggccttgtgt cgttgtactc   1320
tcggcaaaaa accacaatgc cctggaacag atgcaaaacg ccctgctggc gaaactggcc   1380
gcacatccag agatacgctt acaggacgtg gcttacaccc tgcgtcacgg gcgtttctcc   1440
gccccggtac gtaagtgtgt catcgcagag aattgcaccc agctagcccg acaactccgc   1500
gacgcaccga tggtggaggc aaccacgggt tgcacgatct actggagatt ggggcaccgt   1560
ttcgttgttg cactcgagac gcttagtgac tggctggcgt gctctgaggt gttgtcacag   1620
gcggtgggac aactgctcga gcattttccg ctcgaaccag cctgtctgca agatctctcc   1680
cctgcgcaac ggacgtttat cagccagtat gcgctgatcg cgttgattga cgaacgggaa   1740
acgttgaatg tggtgctatg cggcgacggt gatggtggct atgctgccgc cgtactacga   1800
ggagactgca cactagagca agcatggcac aggttgaatg cgggccaacc gtttgatgat   1860
gtgccgacga atcccctctt gcagcccgat gtctgctctt tgatgctgga cgacgcggcg   1920
agtgatgcca atcgcaccgc gctagaggcg ttagggcagt tatggttggc tggcgtcagc   1980
ctagattggc gctgggtgga tgcggcggag cgtatgttgg gcagtcaacg catcgccctg   2040
ccggggaccg tttttacacc gcagcgctat tgggtcgagg ccgtacggcc tgccacgttc   2100
tcccacgaat cgtcgaataa tctcttatcc cgcgcaacaa aatccgatat tattgcagtg   2160
gtgacggaga tatgggaacg cacgcttggt gtcagcattg atgatcacca cgccagcttc   2220
ttcgaactgg gtgggcattc gctgttagcg tcaaccattt tatatgatat tcagcaacgt   2280
tacggcatca cctgtacgct aagcgcattc tttgccgatc ccaccatcga gggattaagt   2340
tgctatctgc tcgaacaagg cggcagtgag acagcggttt cagcattgcc tgatacggtc   2400
tttgcccctg accagcagca cctacctttt ccgctgactg acgtgcaaca ggcctattgg   2460
gttgggcggc gaaaatcctt gggattgggc aatatttcca cccatatcta tgtggaatat   2520
gaactacagg ggctagatga aacagcgttc aaccgcgcgc tcaatgcggt gattgcgcgg   2580
cacagcatgt tgcgtgcaat tgtcaacgat gacggtatgc agcagatatt gccaaacgtg   2640
ccggaatacc acgttgcctt ctataccacc cagtgcgagg atgcgtttca acagcgttgc   2700
cgtgagctgc gtgacaccct ctcacatcag atgattgatt gtagtcgctg gcctctgttt   2760
cagatggagg tcgtggttga tccgcagcaa aaagcccggc tacatgtatc tatcgacctg   2820
ctgatagccg atgcatggag tctggagttg ttcattcggg aactagctta tcactaccgc   2880
catccgcagg cggcattgcc tacattgacg tacagtttcc gcgactatgt gctgacctta   2940
aaatcctacg agaaaacgcc gcagtttgaa cgggcacgtg actactggcg cgcccgcatc   3000
gaaactctgc cgccggggcc acgattgccg ctgcgtaccg accccacgaa gctggaaaac   3060
cccacattcg tgcgccgtag ctattgtcta tctcgtgcta tctggcagcg cttgaaaacg   3120
caggcgggtc agatgagtat cacgcctact acactgctgc tcacggggtt tgctcaggtg   3180
ttggcgcgct ttagttcctc gccgcacttt agccttaacc tgacgctgtt taatcgtctg   3240
```

-continued

```
ccgttgcacg cagatatcaa tcacttaatt ggcgatttta ctgcactgac gttgctggag   3300
attgatatgt cgcagggaga aaccttgcag gcgcgggcaa acgtgatcca ctctcaactg   3360
tggcgcgatt tggataaccg cttgtttggc ggtatccagg tctctcgact gctggtacaa   3420
actcaccgcg atccggcgaa atcggtgatt cctatcgtgt tcaccagctt gctcaatcaa   3480
tatgaggcga gctgggaaac ggatgatacg ctgttcaacc aaccgcagga tgatctgtac   3540
agtatttcac agacaccgca ggtgtggctc gatcatcagg taatggagcg taacggggaa   3600
ttgcacttta attgggacgt ggtggaacaa ttgtttgaac cggcgctaat ggatcagatg   3660
ttccagtgtt attgccaact cctgcacgcc ctagcccagc gaccacagct ctggcatgag   3720
actcaagatg tgctggcgct gcccaccgtt agtgcaccgg tcacgcaggc tcctgcacct   3780
acggccttgt tgcaccatgg gttactgcgt caggcagcac tgacgccaca ggaaactgcg   3840
ctgatcagtc ctatccgtga attgacctat cgccaactgt cgacggcggc ggatcatgtg   3900
gcccgcgccc tgttagcgct gggcgtgcag catggcgacc gcgtggcggt ggtgatggaa   3960
aaaggctggc agcagattgc cgccgtacac ggcattttac gactgggtgc ggtctatctg   4020
ccagtggatc cggtgctacc gccacagcgt cgccagcttt tgctgacggt gggcgaggtg   4080
cgggtacaag taacgcagcc gggtctcacg caattggagc cgtcgctgcc cgtgctgatc   4140
atcgacgacg gaatgctgga cacgcctgct gcgccgttgc ctgaagtggc tggggatgtc   4200
acggatctgg cctatatcat tttcacttcc ggctccaccg gtaccccgaa aggagtgatg   4260
atcgaccacc gtgcggccat gaacacactg gaagacatca acgaacgctt tggcctcaat   4320
gcgcaggata gggtgttcgg gctgtcatca ttgagctttg acctgtcggt ttacgatgcc   4380
tttgcgcctt ttatggtggg tgcagcgctg gtactgccgg aagcaggacg ggaaaaagat   4440
ccgcgtcatt ggcagacagt tatggcacac ggtcatgtaa gcgtctggaa tgcagtgccc   4500
gcactgatgc agatgctgtg cgaataccac agcggcgatc ggatgagtta tccgacgttg   4560
cgtctggcac tgttgagcgg cgactggatc ccgctaacgt taccggagca gatgcgcgag   4620
cggctcaatg aaacgatgga catcatcagt ctgggtggag cgaccgagtg cgccatctgg   4680
tcggtctact acccgatagg tgaggtggaa tcgacgtgga ccagtattcc ctacggtcgg   4740
ggcctgcgca accagccagt atacgtgcta aatgcgcaac tggaggaatg tccggtcggg   4800
gtggaaggag agatttgcat tggcgggatg gggctggcac aaggctacct gaacgacgca   4860
gagaaaacgg cggcgagctt tgtctggcgc gaagcgagtg gtgagcgaat ttaccgcact   4920
ggggatcgcg ggcgctactt tgctgacggg caagtcgcct tttggggcgc caacgatacc   4980
caagtgaagg tgaatggtta ccgtatcgaa ctgggggaaa tcgagcgctg cattgcgcga   5040
catcccgatg tggagcagtc agtggtggtg gcagtgggta attctcaaca tcgtcggctg   5100
gtcgcttttg ccaaactgca cgatcgccac caggcgcagg cattgcaagc taaggaagcg   5160
gaggcggcgg cactggcgca gggtattatt gtgaatccgg cacagcgtct agcgttcaaa   5220
ctcaaggagc cacatattcg cgcgctggat ggtctgggca ttgcactgac ggcaccggcg   5280
gatagcacac gttacatcaa acgccgcagc tatcgtcatt tcagcgcgca aaaaaccacg   5340
ctggcacagt tggggcaatt gctgtcgggc ttggggcaga tgcgtctacc cggtctacct   5400
tttgccaagt atgcctatgc gtccgccggg ggctataccc cggtgcaaac ctacgtgtac   5460
ctgcatccag acaagatcga agagggagta tccggtattt actacttcga cccgcgacag   5520
agctgtctta tgccggtagc accagaagtc gagctgaaca gtggttttca tgccggacct   5580
aatcagtcta ttgccgatcg ggcggcattc acgctgttta tggtggctga tatggcggtg   5640
```

```
atctcgccat tctatgggca agaggcagct tggcacttct cggtgatgga agcaggtact   5700

ctctgccatt tactggaaga agatgcgccg cgctacggat tggggctgtg ccaacttggg   5760

atggcagact tttccgctgt ggcatcgcat tttcaattgt cgccacatca tcgctatgtc   5820

cattgcaccg tgggggggcgc gatagggcaa gaggcggcaa gtgctgcagc attgctgcgc   5880

gatttctcca cctatgagaa accgaaggaa accgctgcgc cgctggacat gcagagctac   5940

aaagatgcca tgctgcgcgg cctgcgtcag caactgcctg actatatggt gccgagtgat   6000

ctgatgttag cgaccgattt tccgttaacc gctaacggca agctagatcg gcaaaaatta   6060

cagctgcagg gcgaacaaat tgcccaccag cgtgacggcg tgggtccaat ccaggtggac   6120

agtgcgttac aacagcggct ggtggcgctc tggcaggagg tactcggcgt gagccacgtg   6180

tcggccgaag acgatttctt ctcgctgggg ggcagttcta tagaattggt gcgtattcag   6240

caggcacttg aggcgattat cgggcaggag attcccattg tcgatctgtt ccgtctgcca   6300

accatcgcgg atgtggcgcg ttaccttgat gagcaactgc acaatctacc cgccgcccac   6360

gatatcgtat tagcgcaggc tgaggtttcg caggtcagcg ctgcgcgcga gaatctggcg   6420

ttgcggcgta aacgtgccca acagggagaa aagggcgatg agtga                   6465
```

<210> SEQ ID NO 140
<211> LENGTH: 6501
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 140

```
atgacgatac atcatgccgc attggcgcga atgttaccgg cggaaaaaaa ggaaaagcta     60

ttacgacagt tggcgcaatc aggcgtgtcg cccagccgca ttcccatcat caaagcggat    120

ccggcgcagg caatcccgct gtcgtttaat caggagcggt tgtggttttt gcaaaaatac    180

gacagtaccg ccactaacta caacctttat gtggtgtatc gtttgcatgg cgtggtggat    240

atgccgatgc tcacggaggc attgcgccat gtgcaagcac gccacgccat cttgcgtacc    300

cgtatcatag tacgtaacga tcggccttgc caggtgatag atgatgcgtc ttcgttagtt    360

ctcgatacgg tcacgctggc agcgcaggcc ccaacttcag cgctagatgc ggtaattcag    420

caggtgataa acacccggtt cgatctggca cgcggtcctc tgtggggggt aactcagatt    480

attcaacccg atcaaggttg tcatttggtg ttttgcgcgc accatatcat catcgacggt    540

atctcgttac ggctattgtt cgatgagtta cagcagcagt atgctcgatt gcatgctggt    600

aatgaaacgt cgctgcctcc gccgccgctg caatatgccg attatgcctt ctggcagcgc    660

gaatggttcc aggatacctt gctggcgaac gaacttgcct actggcgtgc gcgtttgcaa    720

gacgcgcctc tgctgtcgac atttccatcg ctgcacccgc gcccggcaca accctctaca    780

catggttccc ggttcagcat caccctggat gaaacattaa gcctcgcgtt gaaacacgta    840

gcccgcacgc aggaaacaac gccgttcgtg ctgatgctga ctgccttcca actggtgctg    900

atgcgttacg ctcagcaaca gcgattggtg ataggcatgc cagtatcggg gcgcattcgc    960

ccggaattgc agagtagcat tggttattat gccagcactg cggttatcta caccgatttt   1020

aatggggttg aggtagggcg cgaggcgctc cagcgtgtga aggccagcgt gaaagagacg   1080

caggggcgcc agcaactgcc gtttgaaaac ttggtgaata tgctggatct ccctcgcagc   1140
```

```
ctttcccatt caccgttgtt ccagatcctc tatatctacc ataaccacgt gaccccacgc   1200
gcttttacct tggctggtgc gtattgggag caggtgacgt atcacaatca gaccgtcaaa   1260
tacgacatga cagtcgaggt gttccaaaac gacgccacgt tcgacgtctc ctttgagtac   1320
gatttggggt tatacgatgc tgatgtggtg aagcagattg ccgaggcgct gcgtcagcac   1380
tgcttatcgt tgacatcatc actggagacc ccgatagggg cgatccctct gcatgcaccg   1440
gagaccgcaa cgccgcggcg tgatccgctc aacgccacta acgtcccgtg gctcgggccg   1500
caggatgtgc tgcgtatcat tgaacagcgc tgtgtgcagc acccaaagca actggcaata   1560
cagcagcatg acggcacact gacctacgct gagctctggg cgcgtgtgca gttcatcgcg   1620
atgcgttttc gagcgcatgg catacaaccg ggcgatcgta ttggcgtgct gttgccacgt   1680
cacagggatg tgattgcaac catgttggcg acgtggtttg tgggggcgtg ctacgtgccg   1740
ttcgatattc atcagcctgc cgcgcgtttg caacgcctta tgcaacgcgc gcgtttggtc   1800
tgtctggtgg tccgtcagcc gggagagtgg ggtgaaattg tacaactgtc gttgccggaa   1860
ttgatgcagg acatgtcgaa tgcgatccgg tattctacac cttgcgcgct gttgccggat   1920
atgcaggcct acctgttgtt tacctccggc agtaccggtg aacctaaagg cgtgtgcgtt   1980
gttcaccgcg ggttgctgaa cttgttgttg gatatgcagc gtacctttgc ggttggctcg   2040
caagaccggc tgctctcggt gacgacgcca acatttgata tctcattctt ggagtatctg   2100
ttgccgctga tctccggtgc gagtctctat ctgacagagg cggaacgcgc cgcagacagc   2160
ttccgtatga ttccgctgat tgccgactat cgaccaacgc tgatgcaggc gacgccctcg   2220
ttctggcacg ggctgttgat ggcgggttgg cgtggcgacc cggaactatg tgtgctggca   2280
ggcggtgaag cgctgccaac gaaagtggcg gaagaactgt tgcgctgttg tggttcattg   2340
tggaacctct acggtcccac cgaaacaacc atttggtcgc tgaaatcgca gataacccaa   2400
gcggaaaaca tcaccctcgg cgctcccatt gccaataccc gtatatacat tctggacaat   2460
gagggccatc cagtgccgca aggcgttgac ggcgagcttt acatcgccgg ggatggtgtg   2520
gcgcaagggt atgatgggca gcctgagttg aacgcacagt tcttcttgtc agaaccaggg   2580
gtccccggtg gcaggatgtt ccgcactggc gatctggtca ggagtgatgc gcaggggcag   2640
ttgtttttg ttgggcgcaa agatagccag atcaaactgc gcggttatcg tattgagtta   2700
ggcgaaattg aacggacgtt ggcacggcat ccgcatgtgg acgccgcggt ggtggcctgt   2760
attgaaagag caccgttaca caaagcactg gcagcattca tcatcaccag tgagcctccc   2820
tcgctattcg agcaactgaa aaacgagctt cggcagcaac tgccagacta tatggtgcca   2880
acgctgtggc agagggtggc cgacttcccg aacactgaca acggtaaaat cgatcgtaag   2940
cggttagcgg aaaatttcgt tgccgatagc tcccttgtgt cgccgcagac gcaagcgctg   3000
agcgacacgg aacagatgtt gctggcgctg tggatgcgct atttgccgat aaaaaacgtc   3060
gatcctgagt gcgatttctt tcgcttgggg ggacattcgc tgttggcggt aacgttggta   3120
gcagagatca accgcacttt tcactgcgcc ttgaccctga aggacatttt ccactactcc   3180
acactacggg cactgagtgc gcgtattgca cagcaatcta tcacggacgc tgccgcgtct   3240
caggatgact gggtgatagt gcacgaccct gagcatcgtc atcaaccgtt cccattgacg   3300
gatgttcagc gcgcctactg gcttggacga cagacgggtg ctacctcgat cgcgacccac   3360
atctaccatg aatttgacgt agaacacttt aatgttacgc gttttaccca tgcggtgaat   3420
gcgctgatcg ctcgccatga aatgctacgt gcgcgggtac tccccgacgg tactcagcag   3480
attctggcgc aagtgccggc gtatcagtta gagcagcgcg atctgagtgc tttgtcccct   3540
```

```
aacgcacgaa acgatgcctt gatggcgatc cgcgatcggc tgtcgcatca tgtgcatccc   3600
gcagatcgtt ggccgctgtt tgatttcagt tattcggctt gcacggcgca acatggccgc   3660
ttgcatttca gtctcgatct gctgattgcc gatgctctga gtatgcgcac gctacagcag   3720
gagttgatga tgctgtaccg tgagccccat gtgtcactgc cgttgctacc gttctctttt   3780
cgtgactacg tgcaggcgct gttggtagag caggcgagtg aagcctatgc acgcgatcag   3840
gcctattggc aacgggcgct gccgcagctg tatggcccac caacgctgcc cgtacagggc   3900
gatttggcgc aactgtctgc gatcaggttc gtacgtcgcc gtcatcggct gtcagcccac   3960
aactggggag tgctgagcgc gctggcccaa cgcacacgta tcaccaagac ggcattgttg   4020
ttgacagtct ttagccaagt gctggcacgt tggagcctta gcccgacgtt tacgctcaat   4080
ctgacgttgt tcaaccgccc gcagggttac cccaacgcag aggcagttat tggtgatttt   4140
accgctgtca gcttgctgaa tgtttgttac gacagccagc actcttatgc ccacaacgct   4200
cagcgtattc aggtgcaact gtgggaagat ctcgaacatc gtcgtttcag tgggatccgc   4260
gccagcgagg cgctgatcca tagcggtcgt ttccatgcgc cgatgccggt ggtattcact   4320
agtatgttgg atatcgacgg ggagacgact gcgcaagacc ctcgggacac aacccgtttt   4380
actctgtgtc cggacgccaa tattacccaa acaccgcagg tgtggctcga tcaccaggtg   4440
atcgagttgg ctggggagtt gcatttcaac tgggacgcgg tcgagcaact gtttgatacc   4500
acgctgctgg atcagatgtt tggtgcttat tgtcatgcgc tgcaggcgct ggttgccatg   4560
ccgcaaagtt ggtgggggt aaatagttct ctggcgctgc ccaccgttag tgcaccggtc   4620
acgcaggctc ctgcacctac ggccttgttg caccatggat tactgcgtca ggcagcactg   4680
acgccacagg aaactgcgct gatcagtcct atccgtgaat tgacctatcg ccaactgtcg   4740
acggcggcgg atcatgtggc ccgcgccctg ttagcgctgg gcgtgcagca tggcgaccgc   4800
gtggcggtgg tgatggaaaa aggctggcag cagattgccg ccgtacacgg cattttacga   4860
ctgggtgcgg tctatctgcc agtggatccg gtgctaccgc cacagcgtcg ccagcttttg   4920
ctgacggtgg gcgaggtgcg ggtacaagta acgcagccgg gtctcacgca attggagccg   4980
tcgctgcccg tgctgatcat cgacgacgga atgctggaca cgcctgctgc gccgttgcct   5040
gaagtggctg gggatgtcac ggatctggcc tatatcattt tcacttccgg ctccaccggt   5100
accccgaaag gagtgatgat cgaccaccgt gcggccatga acacgctgga agacatcaac   5160
gaacgctttg gcctcaatgc gcaggatagg gtgttcgggc tgtcatcatt gagctttgac   5220
ctgtcggttt acgatgcctt tgcgcctttt atggtgggtg cagcgctggt actgccggaa   5280
gcaggacggg aaaaagatcc gcgtcattgg cagacagtta tggcacacgg tcatgtaagc   5340
gtctggaatg cagtgcccgc actgatgcag atgctgtgcg aataccacag cggcgatcgg   5400
atgagttatc cgacgttgcg tctggcactg ttgagcggcg actggatccc gctaacgtta   5460
ccggagcaga tgcgcgagcg gctcaatgaa acgatggaca tcatcagtct gggtggagcg   5520
accgagtgcg ccatctggtc ggtctactac ccgataggtg aggtggaatc gacgtggacc   5580
agtattccct acggtcgggg cctgcgcaac cagccagtat acgtgctaaa tgcgcaactg   5640
gaggaatgtc cggtcggggt ggaaggagag atttgcattg gcgggatggg gctggcacaa   5700
ggctacctga acgacgcaga gaaaacggcg gcgagctttg tctggcgcga agcgagtggt   5760
gagcgaattt accgcactgg ggatcgcggg cgctactttg ctgacgggca agtcgccttt   5820
ttggggcgca acgataccca agtgaaggtg aatggttacc gtatcgaact gggggaagtc   5880
```

```
aaaagccacc ttgaacagct cgacagcgta gggagtgccg ccgtggtgtg ccaccaggga   5940

cagctgtatg cctttatcac tgccgcagaa aacctgcatc ctgacgatac tgacgccctg   6000

ttagcgcgtg ttcgtgctca gttagccgtg cagttgccgt attacctgct gccccaacat   6060

ttctttcttc tcaaggtgct gccgatgaca ggcaacggca aaattgatca ggcggcaatg   6120

gttcaagagg ttatccaacg tatgtcgcaa tctacatcac agaagtcgag ggccctcgcg   6180

cacgcctcgc cctatgaaca gcaggtggcc gctctctggt gcgaggtact acaacgagaa   6240

cagatcggac tgaatgacaa ctttttttgaa gcgggggggcg gctcaatcca gatcgtgctg   6300

ttgcatcgcc gtattgagga gatttttaag gttacggtac ctattgctga gctatttcgc   6360

ttaaccaccg tgaaaagaat tgccggttat ttgcaggcta tgcaggacaa tgcacgggcg   6420

gtgaatcaaa cacagcagcg tgatgcttcc cgatcccgcg cccagcaacg acttgtacgt   6480

cgtcaccagc gtcagcgtta a                                             6501
```

<210> SEQ ID NO 141
<211> LENGTH: 3033
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 141

```
atggcagaga atgattttgg tatagctatc attgggatgg cggggcgttt ccctcaagcc     60

gatacggtac aggcgttttg ggaaaatctt ctggcaagcc gagagtgcat ttcctttttac   120

agcgatgagg aactgctggc gatgggaatc agtcctgaat ttgttcagca cccagattac    180

gtcaaggcca aaggggaggt agctgacatc gataaatttg atgctgcttt cttcggtatc    240

gcaccccgag aggcggagct gatggatcct cagcaccgtg tcctgttgga aaccgcgtgg    300

gcagccttcg aagatgcggg ctatgtggct gccgattatc cgggggatgt gggtattttt    360

gctggcaaaa gcatggattc ctatttgatg ctgaacttga tgccgcactt taaacgcgtt    420

ttctcttctg gcagtttgca ggcggccatt ggtaacgaca aagacagtat cactactacc    480

atcgcctatc acctcaacct gcgcggcccg gcgatcacgg tgcagacttc ctcatcgaca    540

tccttggtgg cggtgtgcgt ggcatgccaa agtctgttga cttggcagtg tgacatggcg    600

attgctggcg gagtaacgct ggggccacca gcaaaaaccg gctacttgtc gcaggaaggt    660

gggatcaccg ccgccgatgg ccactgtcgg gcgttttccg ataacagcag cggatttgtg    720

cccggcaccg gcgcggggct ggtggtgtta aagcgtgttg atgaagcgct gcgtgatggc    780

gataacatct atgcggtcat caaaggattt gccgtcaaca acgacggttc ggagaagatc    840

agttataccg cgccgagcgt ggatgcccaa gcgcgcgcca ttgctcaggc acagcggttg    900

gcaggtttga caccgcagga tatcacttat gtggaagccc acggtaccgg tacgcgtttg    960

ggcgatccgg ttgagttttc tgcgctaagc caagcctttg cgggcgcgtc acaaaagcag   1020

tactgtgcgc tggggtcggt aaaaaccaat atcggccatt tggatacggc agcgggcgtc   1080

gcagggttga taaaaaccgc gctggcagtg cagcagggaa taattcccgc aacattgcac   1140

tttgaacggc ccaatgcaca gatcgatctg accaatagtc cgttttacat caacactacc   1200

tgtcaaccgt ggcaaccgga aagcggcatc cgtcgcgcgg gcgtcacctc gcttggcatg   1260

ggcggcacca atgcccatgt tgtgctggaa caagcgccag ccgttgactt gcaagcgcga   1320

gcgcctgtac ctgcctacag tattttgccg ttttctgcca agaccgacag tgccttatcc   1380
```

```
tcggggctgg cgcgttttgc cgattttctg caacatgaat cgctgccgga taggcgggat   1440

ctggcgtgga cactctcaca gggacgtaaa gccttcgcac atcgcgccgc gctcgtaacc   1500

agagatctac atgctgccgg gacgctgttg cagcaggccg cgacagcgcc gtttgctcgt   1560

ggtgtagcgc agacacagct cgggctgggg ctgttgtttt ccgggcaggg tagccaatat   1620

cagcgcatgg gccatcagct ctatcaggtt tggccggcct acgccgatgc cttcgaccgt   1680

tgcgcgacgt tactcgagcg tgaataccaa ctggatatcc gccatgagtt gttcagagca   1740

gaagtctcgt tagcccaagg cgaacgcctt gcgcaaacct gcctcacaca accgctgctg   1800

ttcagcgtcg agtatgcctt agcccaattg tggctcagtt ggggaatcac gccaacggta   1860

atgattggtc attcgctggg cgaatgggtg gcagcgacgt tggcaggcgt gttctcttta   1920

gaggatgcgt tgcgcttggt ggcgcgtcga gcagagctga tgcatcaggc accaagcggt   1980

gccatgttga tggtggcgct gcccgaagca cagattcgcg cactgattac cgccccgctg   2040

gcgattgccg ctgttaacgc ccctgactat tcggttatcg ccgggcctac gtcggagatc   2100

ctcgccgtca gccagcgtct gacggagcag aacatcatca acaaacgatt gcatacctct   2160

catgccttcc actctagcat gatgcaagat gcggcgcagg cgctacgtca ggcatttgag   2220

aatgtacgac tgaacccgcc gacgctcacc atcatctcta ccgtaaccgg cgcgcacgtc   2280

agtgccgaca ctctcaccac accggactac tggattgaac agatgctgat gcctgtgcag   2340

ttctccgctg cactgcaaga ggcgcaagct acatttgatg tcgattttct ggaaatcggg   2400

ccaggtgcca ccctgaccca gctgaccaac ggtcatgcat taggtgatcg tctcgcgttc   2460

agctcgctgc cagcaggtgc ccgcagcagc gatgagcaca aacatatctt agataccgtg   2520

gcagcgcttt gggtgcgagg gcataacatc gatttgtctg cgtttgcagg tgagcaaccg   2580

cgccgtgtct ctctaccgac ctacgccttt gacaaaatcc gttactgggt cgacagtcca   2640

gaagaacaga ggagcgccgt aacgccggtg gcggacgcgg gaagtgtcat ccctagcgaa   2700

ccgtcggtgc gccgtcagcc gcgtccggcg ttttcggtgc cttacgcggc tccagagagc   2760

aaaacgcagc gcggcttagt ggcgatttgt gaagcattgc tgggaattga cggcttgggc   2820

attgacgaca acttcttcga agctggcgga cattcattga tgctgggcat gttgctggcg   2880

caggtacagg aacggttcgc cgtcactctt tcctttttcg acgtgatgga ggatgccagc   2940

gtgcgcgcgt tagcgcagtt ggtcgagcag gagcagcagg atgatggagg gtccgcactt   3000

gccgtgctag ttaacgacat gattaatgag tga                                3033
```

<210> SEQ ID NO 142
<211> LENGTH: 4797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 142

```
atggaacagc aagggattat gagacagttg cctaccgacg accaaacgat agtcgactat     60

ttgtatcgta tcgccggaga atatggggaa aaagccgctg tattgatggg ggacgcggcg    120

ctgagctatc acgatcttaa tgcacgctct aaccaactgg cgcattatct gcgtgggctg    180

gggatcggcg aggatcgtgt ggtagctatc cgcctgccgc gcggcatggc aatgctgatt    240

gccattttcg ctattgtaaa agctggtggt gcctatttac cgctggcgta caatgcaccg    300
```

```
cgcagccgca ttgaaaatat actgagcaac agcggcgctg tttgtctgat cggtactgac    360
gatggtgatc gctggccgat tcctcgcgtc gaaatcgaca gcgcggcggt cagtgccatg    420
ccaacgacgg atctgcgtta ccgaccacat gcgcggcaac tggcgtatat tatttacacc    480
tccggttcca ccggtgtccc taaaggggtg gcgacggaac atgcagcgct gctaaaccga    540
attgtctgga tgcagaacgc ttatcctatc agttctcagg acgtgctgtt tcagaagacg    600
gtgtacacct ttgacgtctc tgtctgggag atgttctggt gggcgatgta cggcgcatct    660
gtagtgctgt taccgtccgg actggagagc gatccgcgaa ccttggctcg actgattcag    720
cgtcaccgcg tgtcggttgt gcactttgtc ccttcgatgc tgaacctgtt tgtcgagtat    780
ctggagatga aacaggatcc tcgtttgacc gcctcattgc gattagtgtt ttccagcggt    840
gagaaactca cggtccacag tgtggctcgc ttttatcaat cggtggcgca gggtgatctt    900
ataaatctct atggcccgac cgaagcagca atcgatgtca gtcatcaccg ctgcctgcgc    960
gggtacgact acgacgatat ccctatcggt caagcgattg acggttgccg actctatgtg   1020
ctggatgacc atggtaatcc ggtagcagac ggcgaagagg gcgaactgta tctcgctggt   1080
atcgggctgg cacgtggcta tctcaacaac gtggcgttaa ctgatcgctg ttttactata   1140
catccaactt tgcgccattt agggaaaccg gagcggctgt ataaaactgg agatctggtg   1200
tggcgcgacg ggaaagccaa acaaattcat tacattggcc gtaatgattt tcagattaaa   1260
attagagggt tgcgcgttga attgggagaa atcgaagccc atgcgatgcg tttcccgggg   1320
gtacagcagg cagtcgtggt ggcggatcag gatgatcccg acaatcagtt gatttacgct   1380
tttgtcgtca gtagcgtgcc gctcaatttg gcggccttaa tggacgcact gtccaaaaac   1440
ttgcctgcct acatgctgcc gaaccgtttg ttggcaatgt cagagttacc actctccgac   1500
aatggcaagt gctgtcgtaa aacgttgctc gacttggcgc gggcgtactc agccagtcgc   1560
gtcgatttac gtgaaactcc cgccgtgcgc tacctaccgt tgtcatcggc tcaatcgtcg   1620
atgtggttta tgcaacaatt ggcgccgcat actgcactat acaataaccc caccgccttg   1680
ctgcttgaag gagaactgga tcgcacgcgg atggacggcg cgattcgtca attgatgagt   1740
cggcatactc tgttacgtgc tatggcggaa acccacaatg gacaaccagt attggcggtg   1800
cctcagtgcg tatcgtcgca ggcgttgctg accatagtgc cactcccctc ggtgagtgat   1860
gataacgcgc tacaggcgat gatcaaccag cgtgcggcac accccatgcc cttaacgtca   1920
ggcacaccgc tgtgccggtt tgaactgttg acgctcgatg acgatcgtag cgtattgttg   1980
attcatctgc accacatcat cagtgatggc tggtcgaaag gcgttttgtt acgcgaattg   2040
caggccgcat ataacggtga atcgctgacg ccagaaccgt tgttggagta tgccgactac   2100
atggagtacc aagaagagtg gcgtcagagt gacgcctatc aggacgcgat gcgttactgg   2160
caaaataccc tggcggggac gttgccgatt cttgatatcc ccaccgatca accgcgtcag   2220
aaggtggcac gttaccaagg cgcgtttgtt gccttcgcat tgtctgccaa cacatgcgag   2280
cgagtgttgg cggcggcgcg tgcgcagcgc gtgtcgttgt ataactatct gctgaccgcc   2340
ttcgtcctcc tgctgcatcg taatgcgcgt caacaggaat acatcgtcgg tatgccgatt   2400
gctgcgcggc tgacgaaaga acaggagcat atgatcgcgc cgctggtcaa cgtactaccg   2460
ctgcgcttac ctcttgacga agcggcatcg ttttccgagt tagtacagac gatcagaggt   2520
attctgtttg ccgctttcag gcaccagcgt ctcgaattta ccgacatagt gcgcgcagtg   2580
aatgtggatc gcagcgccgg acatttccca atatatcagt gcatgttcca actcgacaat   2640
atgcctctgg cgagcccgac actaaacggt gtcaacgtta caccattatt gttggatacc   2700
```

agtgcatctc aggtggatat ttcgctaagt atgcagcata tcgatgggcg catcaccggc 2760
actttcgaat acgacgctgg gttatacagt gcggatcgta ttcagcacct ggtggcgcag 2820
tggagagaac tgctagatga ggccagcagc caacccacgc agttagtccg cgatttgatt 2880
cgtttcaccc ctcgagagca cgcttggctg gcgcggcaca acgccactga agttgctctg 2940
ccgcccgtag ataacctgct ggcgctagtg ttaccgcact gccagcagcg ccctacacag 3000
gtggctttgc gccacgctga cgacgccatg acctatggcg aattgcaaca ggccacgatg 3060
cagatgtgta cttggctgcg tgcgcaaggc gtaaaacgcg gagaatctgt cgcactgcaa 3120
ctgccttttt gtttcgaatt gattatcgca caattggcga tcctctcttt gggggcgagc 3180
tatgtgccgc tggatggtaa cgcgccagcg gcccgcaatg ccctgatctt ggcgcaggca 3240
acgccgtgca tgctgctggt ggcgcaaccg ctggaatccc ctcatgggct gacgatacct 3300
tgggtgctag tgcctgactg gcgtagcctg ctgacagaaa taccgaacct gccagttagt 3360
gttgcgccag atgctttaga ttgcgatgcg gtggtgatct ttacctccgg tactaccggg 3420
cagcccaaag gcgtccgact cagccaacgt aatctggtca acttaaccgc atcctttata 3480
tccagctatc aagtgacgca tcaggatgtt ttgctaccca ttacctcagt cgcgtctgct 3540
agctttgtcg gggaggtact gccgctgctc gccgctggcg gtaccttagt attggcgcaa 3600
aaagcgcaga gtttggatag tgatgcgctc attgcgctgc tggcatctca gcgggtgact 3660
atcctgagca ccaccccatc gctttctgcc agcctctctg tgctggctca gtcgatggga 3720
tcgctgcgct tgtttctgtg cggtggtgaa gcgttagagt atgagcagat agcgccgctt 3780
ctgccgcaca tggcagtggt taacggttat ggcctgaccg aaagcggtat ctgctcgacc 3840
tactttcctg tcgcaaagcg tagggagcaa gaaacgggag cattgcccat tggccgcccg 3900
attcagaaca cccaagctta tgtggtggat gcatataatc gtttggtacc gccaggtgcc 3960
tgtggagaac tctgtttctc tggtctgggc atttcgcccg gctaccttga tgcacgacag 4020
gatcccgagc gctttgtcga gttgccggaa taccctggcg ttcgggtgct gaaaactggc 4080
gatcgtgctc gttgggcaac cgacgggatg ttgttctatc tcggcagaca agatcgccaa 4140
gtgcagatcc gtggataccg agttgaactg ggcgacatcg aaagcctact gaaacagcat 4200
ccggatattg ctgatgcgtg ggtcgatgtg cgacgcaatg cggcggcaac gccgctacta 4260
gtggccttct attgcagcgt caacggcgtt gcgctggatg ctcagcaatt gcgcgtatgg 4320
ctcagcctgc ggcttccgtt gcatatgctg ccgttgctct acgtgccgct gagcgccatg 4380
ccgctaggtg taaacggcaa aatcgatccc cagtgcctgc cgctggtcga tctgcggcag 4440
ttggaagggc cgggcgagta tgtccctccg gcaaccgaac tggaacagcg tctggcggag 4500
atctggcagc agttgcttgg cctggagcgt gtcggcacca ccacaaattt cttcgatctc 4560
ggtggacact cacttctgct agtacagatg cagcaataca tcgggcagca gtgcggtcag 4620
cacgtggcgt tggttgacct gctgcgcttc actaccatca aacgcttggc ggaatttctg 4680
ctggccccgg acgcagcgca agggaccaca ggagatcaga cacaactgcg tgcggcgaag 4740
cagcgtttgg cctttggtca cacgcgctgg gcagccacaa ccgacagtca tcactga 4797

<210> SEQ ID NO 143
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 143
atgacgaagg atgtcgcact gatgttccct ggctccggtt cgcaatatgt aggcatggca 60
cggtggctgt atgagcgtta tccgcaggtg cgtactctgt ttgatgaagc tagccagatc 120
acggaacggg acatggcagc gctgtgcctg tcgggtactt tggtacaact tgctgagccg 180
acggcaatgg cgctggctat ctataccacc agcgtggccc actttgtcgc gtggcagcag 240
tttttggcgc aaaccggtgt ccatgtcaac ctacgttata tgttgggtca tagtttgggc 300
gaatatgctg cgctgacctg tagtggtgcg ctgagctttt cccaagcact ggcgctggtg 360
gcgatgcgta gccgtttagc cagtgagatc gcccgcgaaa tggacgcgag taccactatc 420
atcaagcaag ggaatcaggc actggtggca gcggcgtgcg aggtggcgga gcgtgaaacc 480
cgacagcagg tcggtattgc ctgcttcaat tcgccgcaac agtttatgtt atccggacaa 540
aactcggcca ttatcgccgc cgagcaatac ctgctggatc atgatcgcca agtcgaagta 600
gtgccgctga ttggtggtgt tccttaccac agcccactat tgaaaccttg cggacagcaa 660
ttgcgcaagg cgctggatcg ctgcgaatgg cgacgtccgt gctgcccagt gatctccaat 720
gtcaacgctc aaccctatcc cgatacggtc acgccagtcc agtggctaga acaacagctc 780
tctcagccag tgcagtggca gcgctctctc acctacctga caggacactt gtcaccgatc 840
gcgatagaga tcggtccgca aagtgtgctg aaaaacctgc tgctggagaa tcgctatcca 900
gcaccagttt acgcatttga caatcgtcat gatcgtgcgc aactagcatt ggtgctgggg 960
gataacatgg cggtgaagac cgatccggaa gccgtgcgcc gccaacgcat cacgctgctc 1020
actaacgccc tgacagccac acgccatcac cgcgccgccg atgtggctgc cagtgcgcaa 1080
ttgaaagaat tgctcagtcg tttttttgag cgcatccagc agattgagca gcgcggcaca 1140
tccagcgaag aggacattgc ttttttgcat gagcttcttg aacagggatt tcaactcaaa 1200
ggcagtagtc aggcagaaat cgacgcctgc cacgcgcggt tggcttccga caacggcgga 1260
caggcgtaa 1269

<210> SEQ ID NO 144
<211> LENGTH: 1131
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144
atgtgcactg aaaattatga gctggctcag caagaggcag tcctgtttgc caaacaacat 60
ctcgccctgg ctgcacagaa tattgaacgt cagcagttta ttgtgccaga cattatttct 120
tgcgtggcgc aggccgggta cttaggtgcg tcaatccccc aaaaatatgg cggacgaggt 180
tacgattctt atcaactgtg cgctttgcat gaagtgatgg ctggggttca cggttcgtta 240
gaaaatctca taacagtgac tggcatggtc agcacgctgc tgcaacgcgt gggcagcgca 300
gcgcaaaaag cccattattt gccaaagctg gcaacggggg aattgatcgg cgcgattgcc 360
ctcacagagc cgaatatcgg cagtgactta gtgaacgtgg aaacagaatt acagcaggat 420
ggcgacggtt ggcggctgaa cgggaaaaag aaatggatca cgctagggca gattgctgat 480
ttttttattg ttttaatcca ctgtggtaat caattagcga cagtgcttat cgatcgcaat 540
accgacggct ttactatcac tccactcaac gacatgttgg ggttacgcgg caatatgttg 600

```
gcagagctgc attttaatga ctgccgcctg aaggaggatg cattgctcgg tccgctcacc    660

cctggggtac cgctggcggt gaattttgcg ctcaatgaag ggcggttcac caccgcttgt    720

ggcagcctag gattatgtcg ggccgctgtg gatgtggcag cgcgctacat ccgccagcgt    780

aaacagttca agcggcggtt attttctcat ggcattgttc agcacttgtt tgccacaatg    840

ctgacccaaa cgcgcagtgc gcaactaatg tgcttcagcg cggcggaata ccgcgaaacg    900

ctgcacccgg ccatgataaa ccaaatcctg atggcgaagt atgtcgcttc caaagctgcg    960

gtggacgtgg ccgggaaggc ggtgcaactg ctcggtgcga atggttgcca tgccgattat   1020

gccgtcgaac gttactaccg cgacgccaaa atcatggaaa tcatcgaagg gacatcgcaa   1080

attcatgaaa tccaaattgc gatgaattac atgatgggga gtgaagcatg a            1131
```

<210> SEQ ID NO 145
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145

```
atgaaaaagc aagatatgaa agccgccatt cgggaatttc tttcacgctc attacgtggg     60

catacgttga acgatgatga cgatattttt tctctcgggc ttgtccattc gttatttact    120

gtgcaaatca tactgtttat agaaaaaaat tttcaggttg agctggaagt gagtgagttg    180

aaaacagaac agattgctac cgtcaataaa atagtggagc tcattcagcg acaaacaggc    240

ctggagtaa                                                            249
```

<210> SEQ ID NO 146
<211> LENGTH: 870
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 146

```
atgatgaacg tggcggtaat aggtgcagga gtaatgggaa ctggcgtcgc tcataacatg     60

gcgcaatacg gcatatcaac taacgttgtg gatatttctc aatctcagtt ggataaatgc    120

cgacagatga tcgaagcgaa cttacgctta tataattttc acccgcagca taaaaaaaag    180

acgcatagca cagcggagat aatggaaaat atccgtttca caactgagtt ggacgacatt    240

gtagaatgtg atttggtgat tgagaatatt actgaggata tagagaaaaa aaatgcacta    300

tacacacgga tgaatacgat ctgcggcgcg tcgacagtgt ttggtgttaa tacgtccgcc    360

atatctatca ctgcgttgtc aaaattaatg cgacatccgg agaatgtagt cggcgtccat    420

tttatgaacc cggtaccgct gatgcacacc gtcgaattaa tccgtggtgt acatactgca    480

gagcgtacac tgaacatatt tcaccactta tttgctcagt tgaataaaac cggcatcgtg    540

gtcaatgatt ctccgggctt tgtcactaat cgtgccatga tgatttttgt taacgaagcc    600

atatttatgg tgcaggagca gatcgcccgt gctgaggata tcgatacgtt gtttaaaacc    660

tgcttcgggc acaagatggg gccactacaa actgccgatt tgattggctt ggatacgatt    720

ttgcaatcgt tgcaggtgct atatgaaagt tttaatgatg ataagtatcg ccccagcttt    780
```

```
ttattaaaga aaatggtcga tgcagggtat ttgggcgtga aatcagggca ggggttttat    840

cgctatcaac agacgtacgc cgagcagtga                                     870


<210> SEQ ID NO 147
<211> LENGTH: 2601
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 147

atggaatacg caagcgaaat gaacggcatg gaaatcgcca ttattggtat ggcggtccgt     60

ttcccgcagt cccggacgtt acacgaattc tggcataaca tcgttcaggg taaagagtgc    120

gtcaccttct ttagcgagga ggagttgctg gccgaaggcg tcgaacagag tactctggac    180

aacccggcct atgtacgggc caagccctat atcgagggca tatgcgactt tgatgctgca    240

tttttcggtt acagtcacaa agaggcgcag actctggatc cgaaatcccg cgtattacat    300

gaagttgcct accatgcgct ggaagatgca ggctatgccc aacgtaccag cgatctgatc    360

accggggtat tcgtgggggc gtcagaagat gtggattggc tacggcgttc gctgtcacag    420

attggcggcg atgcgctgaa tcgttttgag tctggcatct atggtcataa ggatctgctc    480

gcacatctca ttgcctacag tctcaatctc aacggtccgg tgtatagtct ctacaccagt    540

tgttcgactt ctctgagtgc aacgcatatc gcttgccgca gcttgttgtt tggcgaatgt    600

gatctggcgt tggcgggtgg aattactatc gatttaccgc agaagtcagg ctacttctgt    660

caacagggca tgatccactc caccgatggc cactgccgtc cttttgacag tcaggcttct    720

ggcaccctgt ttggcgatgg cgcgggtgtg gttgtgcttc ggcgtttgga agatgctctg    780

gcagcgggcg atcgcatcta tgcggtgatc cggggtagcg cggtcaacaa tgacggtaaa    840

caaaaaatcg gttttgtcgc gcctggtcat gagggacaga aggcggtcat ttgtgcggcc    900

tgtcatctgg cagaagtaag cccagaaagc atcggctacg ttgaaaccca cggtaccggc    960

acccgtattg gcgatcctat cgagttcgct gcgttgacgg aggcgttcga tacttcacac   1020

cgccaatact gtgcactagg ggctgtaaag gcgaatattg gccacaccca cgcggcggcg   1080

ggcgtggctg ggttaatcaa gacggcgctg gtacttcatc accggaccat tccgccgctc   1140

gccaactatc aaatgcctaa ctcgaagctg gatctggcgc attcaccgtt ttatatcccg   1200

atacagccgc aggagtggcc cgcatcgcgg atgccgcccc gcgctggcgt cagttctttt   1260

ggcattggcg gtactaatgt gcatatgatt ttggaagggc tgaatcctgc ggtgcgcgat   1320

gaccatgacc aagtgcgagc accggtgttt atccctctct ccgcgccgtc tttcgagcag   1380

ttggatgagc tgacgcaaca gcttaccccg ttgctggcta cccttgatgc gtcaacgcta   1440

gcctacacac aacaagtggc gcgccccgtg tttgattgcc gccgagtgat acaagtggaa   1500

aacgatggta cgcaagcgat gctggcatcg ctggataacc taatgcccga cgctccttgg   1560

ggcctacact gtccagatct acgtactacg aacgattgta cttacgcaca gtggctggcg   1620

cattcggcac attatcaacg cgaagcgact gctctgacgg cattactcga cggcatgaat   1680

attccacccg cttattgcca cgctgaaacg tgggcggcac aagcgaacag cagcctgcta   1740

atcagaggct gccagactat cgccgcgcta aaaacctgga tgaacctgct accgacatta   1800

acactgctgt cgggtgctgg aacaggcctt ttgcctgccg ctgcagccag tggcatgatt   1860

gcgacgcaag acgtgttgca tttgctgtgg gaaatggagc aaaaggcgct tcatctctgg   1920
```

```
cttcctgagc gccatgaacc tatccccggc tacgtgctgg cttggcaagg aaatcccatc   1980

accgatgcac agcgtaacga cagagggttt tggagtgaag cgctgttggc agatacccga   2040

gaactggggg agggcgttca cagtatcaac tgggttaggc tgccgccgga aataagagaa   2100

gacgttgatg tattgcgcta cgtggcgcaa ctgtggtgtg caggtatcaa tgtggattgg   2160

gccgtgtggt acggcactcc gctgccgcaa cgcgggagcg catcagcata tcccttcgca   2220

cacaaccact acccattgcc tggacgggta atgggtagtg tggagaccca acccgaagca   2280

ggacccgaaa cgcaccaccc ttatcaggca cgtcccgtgt taagcgtacc tttcgtagcc   2340

gcacactcgc ggggtatgca gtatatcaca ggtctgatgg aactgttgct ggaaatatcg   2400

ccggtcgggg tggacgacga ctttttgaa ttaggcgggc attcgctgct ggtgacgcaa   2460

ttgacctccc gtttagaacg cgatttcaac gtacatatcg atcttttgac cctgatggaa   2520

aaccccaatc cgcgcaatat ctacgcgcat atcgcggcgc aactgggggg cgaagacaac   2580

ctcgaaatag cctgtcagta a                                             2601
```

<210> SEQ ID NO 148
<211> LENGTH: 9621
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148

```
atggataata cctctggaga ttttccatgt aataagatgg acacgcgtaa gcagttaccg     60

ctaacaccaa gtcaacaggg gtttttattc cattccttaa aggataagaa aaggagtaac    120

taccatgagc attttacatg catttttttct cagcatgtag atagcgccca cttcaagtgg   180

gcgctggaaa cgttatttcg aaagcatgag tgttttcgca ctgattataa ctgggagatt    240

gatgagcgcc cttgtcaggt ggtgaagacc gatgtgttgc cggatatata tgtgttagac    300

tgtgagcaag aggaaatacg ttttctacta gctaatgatg acattatcat tcctgtcccg    360

caggatgacg gtattgatgc tataattcct caactgctac aggctgattt aaaataccca    420

ttttccttga aaacgatccc agtccgggcc taccttattc agtcaacgaa agaaaagtgct   480

tttatactat cataccatca tattgtgatg gatggctgga gcttatccct tttcattaaa    540

cagttgctcc aactctatgg agcggctgtg gtcagtggtg tgagggatga tagcgccatt    600

atcccctcat ctctgaaacc ccttgtagac acactgtcgg cccgacgtca cacctttcag    660

cacgactatt gggctgcata tcttcgggag ggaacaccaa cttgtatcgt gccgctgtca    720

caatatcaca cagatactga agccgagaac aattcttacg ttaatcaaac aaatcatgtg    780

gagatcaatt tgtctccgga tgtgtgtcag aaaatacaga cgctatgcag cgattatcgt    840

atcacccccg cagtaatctt ctatgtggcc tggggcatcc tgctacaacg ttggtgctat    900

gctgacgatg tgttattcgg cgcgacaata tcagggcgaa atataccaat tgatggtata    960

gaagaaacac tagggctatt tattaacacg ttgccgctgc gtctgcgtga tgatggggcg   1020

acactgttgc aacacttaca acgtatgcac caaacactaa tagctcacta cagcaatgaa   1080

catgatgcct tagccagcat acaacggttg gtacataaag aaggtcatgc tggggatctt   1140

tttaatacct tagtggtgtt ggagaattat cccgttgata tgacattatt gtcatgcgcg   1200

tcgcccgtgg caattcgcca tctcagtgta catgaacaaa cgcactatcc gctgaccttg   1260
```

-continued

```
accatcactc aacagaaggg attccgtttc agtattgcat atgcccttaa ctacctgacc   1320
aacaacatgg cgcaagcgtt gctgatgcac ctgagttatc tgcttgaaca actggtggac   1380
aatccgcagc gccccattgc tgcgttggta aacttgtccc catgccagca ggcgcaggta   1440
cttcaaccct atctggaacg catggcatgc cgggattggg atagtcaatc caacgtcatc   1500
gaacaatttc atcaagttgc tgcgacttcg ccagcacagg tcgcagtggt tgatgaattg   1560
tgcgcgttga cctattcgga gttggcagca caagctgagc agctcgcggc ttatttggta   1620
cagcagggtg ttatggttgg cgatactgta ggcataatta gcgaacgccg ggtaaacacc   1680
gtggttgcca tcatcgccat catgttgatc ggggctgctt atgtgcccat cagccccgac   1740
tacccagtgg gtaggatgca ggaaattatt gatgacagcg gcttggcgct gttgctggta   1800
catggcaaac cgctagatgc attaaacgtt gcgcagagtg acctctgtgc atttcccgtc   1860
gcgccctcgg tggtatttcc ggttatcaca ccagattctc gcgcttatgt gatttattca   1920
tcggggtcga cgggtaagcc aaaaggtatc gcggtggcgc accgcggttt attgcgcctg   1980
atacaaggcg acagcccgct gaaggtggag agcggtgaga caacgctgct gacctgccca   2040
tttgagtttg atgtttcggt gtttgagatg tggtctacct tgctcaacca cggcaaacta   2100
gtattactca gcaaacaggc attacttgat atcaatcaca ttcgccgcac gatcgctgat   2160
gaacaggtgg cgcgcgcctg gtttacctca tccttgttta actcctatgt ggcagaaggt   2220
gccgatttct tcggtatgtt acaacacatt acggtgggcg gcgaagcagt atctgcgtgg   2280
catgtcaacg acgtgatgca aaaatacccg catctggtgg tgacaaacgg ttatgggccg   2340
acggaaaaca ctatttttac caccgcatat cgtttcaacg ggttgcaacc cgcccgagtc   2400
ccgataggat acgcggtacc gggcacctcg ctctacatta ccgatctcca tgggcatttg   2460
ttgcctatcg gtgccaccgg tgaactagtg gcgggtggag tgggggtcgc catcggctat   2520
cagaacaacc cggcgctaag tgcgacggtt tttgtccctg atccttttat tcccggcggt   2580
atgatgtaca aaactggcga ttatgcccgg ttgctggatg atggctgtgt tgactgtttt   2640
gggcgtaaag acggtcaaat taagatcaat ggacaacgaa ttgaaaccgg agagatcgag   2700
cagcgcctgc tggagtgctc cggcattatc gaggcggtag tggttcctta ccgcgtacgt   2760
gaaacgctgc atattgcggc agtggtctgc gtcaatgata gctatgatga ggtggaagtt   2820
cgagggcaat tggctgacag attgccgcca ttcgctattc cggaatcctt ggtggtggtg   2880
acggagattg caaaaagcca tagtggcaag gccgacttgg cgcagttgcg gtatctcctg   2940
cccgcaactc agtgcaacgc cgtgtccacc acgatatcag aggtgcatag tgacatggaa   3000
catgcgctgc atgctatctg gcaacgcgta cttgatagac aagacattga tagcaatgcc   3060
tcctttttcg ccctcggtgg cacctcattg gataccatca gggttaaagg ggatattaag   3120
cggcaacttg gcttggagat tgatattacc gatctcttta agtacccaac gctcacggcg   3180
ttagcacatt ttctcgatac tgccgtatcg ccggaggatg caattccaac gcgtgctgtt   3240
gtctacagcg acatgccggt ggcgattgtc ggtatggcgg gacgtttccc cggtgcggcg   3300
aatattgcag cgttgtggac gctggttgta ggaggggaat cgggattaac actgttcagt   3360
gatgaagagt tgcgcgcgca tggtgtgaca cctgacacgc ttaaacaagc gaattatata   3420
aaaaccaaag ggattgttga tgatcacgaa tggtttgatg cggatttctt tggttatact   3480
cccaacgagg cggaatgtat ggatccgcaa attcgcttat tgcatcagtg ctgctggcaa   3540
actctggaac acgctgggtg cgatcctgcc acctttactg gtgcgattgg catttatgcc   3600
ggactgctga catcccccca ctggcttaat gcggtaatgc aagacactac cgactctacc   3660
```

```
gccctgtaca aggccagtat cctgaatatc cattccgtca cagcattgat tgcccatgcg   3720
cttaacctca ccggccctgc cgtgacgctt gacaccgcct gctccacttc ggcagtggct   3780
atccaccagg cctgcatcgc actacgtaac cgggattgcg atgcggcatt ggcgggcggc   3840
gtttctatcg agatgcctgc gtaccggggc tatgaatatc atgaaggcat gatcaatgcg   3900
cgagatggtg tctgtcgtcc tttcgatagc caagcctctg gcacagtcac cggtgatggc   3960
ttaggaatgc tgctgctaaa acgtctggac gacgcgctgg cggatcggga ctgcatctat   4020
ggtgtgatca aaggttcggc ggtcaataat gatggcaata acaaaatcgg ctataccgcg   4080
ccgagtgtga tcgggcaatc aacggtaatc cgcaccagtt tgcgccgtgc cggttttgat   4140
agcgacagta tcggattggt ggaagcgcac ggcaccggta cggtgctggg tgatcctatt   4200
gagttacgtg cgcttaatga ggtgtttggc ccaacacctg ttccgttttg tgtggtttca   4260
gcgctgaaaa gtaatattgg ccacctcaac tccgctgcgg gagtggcggg cgtcatcaaa   4320
acaacgctcg ccctgcatca tcaagtgttg ccaccaacag cgcactttcg ccaactcaat   4380
cctgctatag atctatcgcg ttctgcattg tacgttaacc agcaagtcca accgtggccg   4440
tcgacgcgtc ctcgtcgtgc actggtgagc tccttcggca tcggcggcac caatgccagc   4500
atcgcactag aagcacatca acatgaggac gacccttcag cgacgggggt acgcgacagc   4560
tatctgttgt tgttctccgc taaaacaccc gctgcgttag agttgcgcgt ggcctccaca   4620
ctggaatatg tcaagcatgg agtagggggtg cgcctgccgg atgtggctta tacattgcaa   4680
actggacgca cagcctttga ccatcggcgg gcttatttgg tgagtcgtgg gtcgaaaatc   4740
gatctctcct gtgccacgat attgcaagcg gaaatcttca atggtcagcg cacgacagcg   4800
gagatctgct tcatgtttcc tggtcaaggt agccaatatc acggcatggc cagcgcgctc   4860
tatgctcatc aacccatgtt tcgccagcac atggatcgct gctttgctgc attccaacgc   4920
tattcgacgg tcgatctcaa ggcgttgttg tttgacgatg aggatacgcg ggatattgat   4980
caaacgcagt tcacacaacc ggcgttgttc tgtgtcgaat acagcctagc gcgcaccttg   5040
attgatctgg ggattacgcc ggacagtatg atcgggcaca gtctgggcga gtatgttgcg   5100
gcctgtattg ctggcgtatt tactcttgag gatgcgctgc acgtcattga ggcgcgcgga   5160
cgtttgatgc agtccatgcg tcccggtagc atgatggcgg tctaccttag tcgcgaacag   5220
ttgaccccat ggctagctgc agaacggggt attgaactgg cagctaataa tagcgcgcat   5280
ttttgcgtag tcgcgggcga gcaggcggcc atttcccgtt tgagcacacg cttagtcgag   5340
ggcgggatac agcacaggcg cctgaaaacc tctcacgcat tccactcggc catgatgacg   5400
ccgatgctgc acgattttgc acagttgctg ggcaaatcc cgatgcacgc gccgcacaag    5460
cgctttatat ctaatgtaag cggtacatgg attactgagg agcaagctac ctcgccggat   5520
tactgggtgc agcaagtgcg caacgcggtg ctgtttagcg aaggtgcggc gcaactgttg   5580
gtacaaccca cgctgtttat cgaatgtggg ccgggtaata cgctctctac ctttattcaa   5640
ggacataacc aatacagcga tcagccgacc ctgttgacgc tacgcaaagc caacgcggcg   5700
atcgatgatg agcacatgtt gcatcgtacg ctggcggcgc tgtgggtcag gggggagaat   5760
attgattgga gacgctttaa ccagacggca ctcggcaagc acattccatt gccggattac   5820
cccttcgaac agacttatta ctatcgctat ggtgctgcac tttccggtta tcgccagtat   5880
ccaaatcctc tgcgccgtcc gcaagatgag tggctccagc gtgtgctgtg gcggatgcac   5940
gacacatcct tgcgggaggc gttctatgcg ccgggcgaat tgatcatcat tattagtgct   6000
```

```
gacggcgaca agttacagca gacgctgatg agtagtggtg tcgacagcat cacaatgccg   6060
ctgccgatat cgtcagagga cgacgtgtgg gataatgacc gtattctgac gcatttccac   6120
gacatctgcg cacttttagc acacaaaacc taccgacagt tacattgctt gtatgctccc   6180
ggtgcggagg caggatcatc gttgacacag tcgctctcgg gactttatcg tgttgctcgc   6240
tggtgtatgc acagcaccac gccgctggcg tccttaacag tattgaccca tggtgcgttt   6300
cgcgtacagg aagaggataa tcccgaaccg acgctggcag cgttgtcggg cgcagtaaac   6360
gtgtttgccc aagagctgca cccgaccgaa gtacgattga tcgatatcga tgcgcagagc   6420
agtgatgaga atctgaactt gctaacccag cgtctggccc cgaaacaaga aacggtaatg   6480
gcgctcaggc aggggatgct ttacctgcga cgctttatcc cgacacggct gttggcgcac   6540
ttaccccctc aaacagggtg tataccgggc aacgtactgt ggattatcgg cggtgaaaag   6600
gggattggcc gcatgatcgg cgaagcgctt gctcagcgtg agggagtccg tgtggtactg   6660
agcagccgca caggttatca ccatgaagcg gtgcagcagg acgcattaga cgttatccac   6720
tgcgacgtga cgcaggcgga ggcggttaga gcttgtctgg caactctgct cgaacgctat   6780
ggacggttgg atggcgtgat ttttgctgcc gacgctacca ccacattgac actgcatcaa   6840
ttgagcgaat ctgcgctacg cgacacgcta acggtgaaag aacggggtac tgctaatgtg   6900
ctgcatgcgt tagcgcaacg gaatctgctg gatgagcgtc tgctactgct gttctgtaac   6960
tcgttggctg ccgtgaatgc ggagattggc cagacaggct atgctaccgc cagcgcctat   7020
ttggatgcac tggcacagca actgcgtacc cgctacaagg tgaatgcgct cagtatcggg   7080
ttggatgcat tgcgtgagca gggcatgttg ttggatgcta taaacggcag tgaatacgat   7140
gtcttgcgtg gactgcgccc attgatgacg ggaacgttgc tacaggctta taaacaacaa   7200
ggggctgaca ccagctacta cgcgcgatta tcccccgagt ccgattggct gctggatgag   7260
caccggatat ccggtatcgc cacgctgccg ggaaccggct atctggcgct ggcgtatgaa   7320
gctctgcgcc attactttgt gcaagaccaa atctgcattg atgaattggt ctttttggca   7380
ccgttgactg tgatggacaa ctgcagtgtt gacgtttttg ttgacatttc acctaacggg   7440
caaggagtta gtgtcgaggt gaaatcaatg acggagcgct ttagtggcac gttaacaacc   7500
catgccagag gcagggcgac gcgtctgatg gtagacgata atgttgtgtg cgatctcacg   7560
gggctgatgc gcgagatgca cactatcact cctccaacaa aggaattatc gagcacgcac   7620
ttccactatg ggccgcgctg gcacagcgta caacaactgt atggcaatac cgcccagact   7680
caggttttcg caacgctggc cctgcccacc gttgccgcta atgatacgat cgcactgcac   7740
cctgcgctgt tggacatcgc cagcagtgtt gtcgaacaac tgcctggttt tcatactgat   7800
tcggtacctt tcctttatca ggatttacgc ctgtaccgcc cgttgccgaa caccttacat   7860
gtggcgctga ctgtcaatcg gcacgatgag gagggtgaca gctacgcttt cacgctctac   7920
gacatggcag gcgagatggt tgcccgctgt gcggcaatgg tgaagcgcaa ggtacagctc   7980
cacatacaag atgtcgatga cgacacgcga ctgcgcgtgc ccagtgccga taactaccaa   8040
ctgcggctgg ccgctgaggg ggagggggca ggaaagctag cgttgtgccc tacgccgcgc   8100
ttagcgctgg gggattcaca agtagagatt gaggtactgg ccaccggact gaactttaag   8160
gatgtgctgt tcaccacggg attgctccgg cagcagccgg gtgaggctcc gctgcaattg   8220
ggactggagt gcgccggacg cattactcgc gtgggtaaaa atgtcactga atttgccccg   8280
ggagaggatg ttatggcggt gctaaacggt ggttttgtcc agtacgcacg ggtagaaagc   8340
gattgcgtag tgagaaaacc agcccattgt cgcatcgaac aggcggctgc gctgcctatc   8400
```

gcatacctca ccgcctatta cgcactggtg gtgcgcgcta atttgcaacc cggagaacga 8460
gtattgatcc acagtgcggc ggggggcgtt ggcttggctg cgctacatat tgccaaacgc 8520
tgcggagcac agattttcgc cacagcaggt agcgagcaga aacgcgatta cttgctttcg 8580
ctaggcgtac atgccgtagc tgattcacac gacgaacagt tcgctgccac tctgctgacc 8640
gcatcggacg gacaggggat ggatgtgatc cttaactccc tcacaggccg tctgcttgac 8700
gctagcctcg cgctgctggc accgctgggc cgttttcttg agctgggcag caaggacatt 8760
gtggaagaca aagcgctacc gatgcgtttc ttcgcccaag gcggcacctt tattccgatt 8820
aattttcacg cggcgcatgg tgcgtttagt cgctacctgc aacagattgt cgcttggata 8880
gatgataaca cgctaccgct ccttccatgc aaatccgtac cattgcccga ggttgcacgc 8940
gccttcgcca ccctgaccac gccgcagcat attggcaagg tggtggtaac gcatcgcact 9000
gcggcaggca tggaccggct gaacgccatg atagcagaaa ggcgcctcgg cggctatgcg 9060
ctcagcatga gcaatgccga ggtgatgcgc caattgtggc cgatactgaa cactcgcagt 9120
ccgtgggcgc aactgctgct ctcacctcgg gcgatcgata gattagcgcg gggcaaccgg 9180
gtggatcgcg gtgtaccgtc tgccgctaac gatacgatta ctcagcagac agtgaaaaag 9240
cggccccgtc cggaaattgg cgtgccttac agccccgcga cacgtgaagt ggaacgcgtg 9300
ctctgccaaa tcctggaaga gtatctgggt ctggatagag taggcattga cgacaactat 9360
gccgaattag gggcaacctc actcgatatg gtgcaactga gtgggcaaat ggcgcgtcac 9420
tatccgcaag tgagcgtggt gtcgctgtac aaccacgcca ccgtgcgcca gctggcgacg 9480
ttttgccagc ccccggaggg cgagtcaaat gcgccatcac cacagcctgc agtacagacg 9540
aatacgcgcg cgaatcagat agcaaaacgt gctttgcaaa ttgcgaaaaa tactgcgcgc 9600
agtcacacgt ctttgcatta a 9621

<210> SEQ ID NO 149
<211> LENGTH: 213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 149
atggataagt tcaaagaaaa aaacccgtta tctctgcgtg aaagacaagt attgcgcatg 60
ctggcacaag gtgatgagta ctctcaaata tcacataatc ttaacatatc aataaacaca 120
gtaaagtttc atgtgaaaaa catcaaacat aaaatacaag ctcggaatac gaatcacgct 180
atacacattg ctaacaggaa tgagattatc taa 213

<210> SEQ ID NO 150
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 150
atgaggattg atatattaat tggacatact agtttttttc atcaaaccag tagagataac 60
ttccttcact atctcaatga ggaagaaata aaacgctatg atcagtttca ttttgtgagt 120

```
gataaagaac tctatatttt aagccgtatc ctgctcaaaa cagcactaaa aagatatcaa    180

cctgatgtct cattacaatc atggcaattt agtacgtgca aatatggcaa accatttata    240

gtttttcctc agttggcaaa aaagattttt tttaaccttt cccatactat agatacagta    300

gccgttgcta ttagttctca ctgcgagctt ggtgtcgata ttgaacaaat aagagattta    360

gacaactctt atctgaatat cagtcagcat ttttttactc cacaggaagc tactaacata    420

gtttcacttc ctcgttatga aggtcaatta ctttttttgga aaatgtggac gctcaaagaa    480

gcttacatca aatatcgagg taaaggccta tctttaggac tggattgtat tgaatttcat    540

ttaacaaata aaaaactaac ttcaaaatat agaggttcac ctgtttattt ctctcaatgg    600

aaaatatgta actcatttct cgcattagcc tctccactca tcacccctaa aataactatt    660

gagctatttc ctatgcagtc ccaactttat caccacgact atcagctaat tcattcgtca    720

aatgggcaga attga                                                      735
```

<210> SEQ ID NO 151
<211> LENGTH: 513
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 151

```
atggctgttc catcatcaaa agaagagtta attaaagcta ttaatagtaa tttttcttta     60

ttaaataaga agctagaatc tattacgccc caactcgcct ttgaacctct attggaaggg    120

cacgcgaagg ggactacgat tagcgtagcg aatctggttt cctatctgat tggctgggga    180

gagctggtgt tacactggca tgaccaagag gcaaaaggaa aaactattat ttttcctgag    240

gaaggattta aatggaatga attggggcgt ttagcacaga aattctaccg tgactatgag    300

gatattacag agtacgaagt tttattggca cggttaaagg aaaataagca gcaactcgtg    360

gctttgattg aacgattcag taacgacgag ctttacggta aaccttggta taataaatgg    420

acccgaggtc gtatgattca atttaatacc gcctcgcctt ataaaaatgc ttcggggagg    480

ttaaataaac tgcagaaatg tcttgcagaa tag                                 513
```

<210> SEQ ID NO 152
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 152

```
Met Ser Asn Ile Ser Leu Tyr Cys Leu Pro Tyr Ser Gly Gly Ser Ala
1               5                   10                  15

Ala Met Tyr Tyr Lys Trp Arg Ser Val Leu Ser Asp Asn Ile Thr Leu
            20                  25                  30

Arg Pro Leu Glu Pro Ala Gly Arg Gly Thr Arg Ile Arg Gln Pro Leu
        35                  40                  45

Cys Leu Thr Met Val Asp Ala Val Ala Asp Leu Tyr Gln Gln Phe Val
    50                  55                  60

Lys His Tyr Thr Gly Gly Asp Tyr Ala Ile Phe Gly His Ser Leu Gly
65                  70                  75                  80
```

```
Gly Ile Met Ala Phe Glu Leu Val His Tyr Ile Leu Asp His Gly His
                85                  90                  95

Asp Met Pro Cys Ala Leu Phe Phe Ser Gly Cys Arg Pro Pro Asp Arg
            100                 105                 110

Ala Ser His Glu Val Ile Leu His Thr Leu Pro Asp Gln Ala Phe Met
        115                 120                 125

Glu Glu Ile Val Lys Leu Gly Gly Thr Pro Val Asp Val Phe Arg Asn
    130                 135                 140

Lys Glu Leu Met Thr Ile Phe Thr Pro Ile Ile Lys Asn Asp Tyr Arg
145                 150                 155                 160

Leu Tyr Glu Gln Tyr Val Phe Gln Ala Lys Ala Arg Thr Leu Thr Cys
                165                 170                 175

Pro Ile Val Leu Phe His Gly Asp Ala Asp Asn Leu Val Met Gln Asp
            180                 185                 190

Glu Leu Leu Ala Trp Glu Lys Phe Thr Thr Arg Lys Thr Arg Thr Ile
        195                 200                 205

Ile Phe Pro Ala Ala Asp His Phe Phe Val Asp Lys His Phe Glu Gln
    210                 215                 220

Val Val Gly Tyr Val Asn Gln Thr Ile Glu Ser Leu Glu Ile Val Gly
225                 230                 235                 240


<210> SEQ ID NO 153
<211> LENGTH: 504
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
            20                  25                  30

His Glu Pro Ile Gly Ala Gln Asp Glu Arg Leu Ser Thr Leu Ile His
        35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ser Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
```

```
        195                 200                 205

Val Ile Ala Glu Arg Leu Thr Gln Pro Leu Gly Met Ser Ala Thr Val
    210                 215                 220

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270

Trp Ile Asp Ala Trp Leu His Arg Lys Ala Leu Pro Ala Thr Leu Arg
        275                 280                 285

Glu Ala Met Ser Asn Ser Trp Arg Gly Asn Ser Asp Val Pro Leu Ala
    290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
                325                 330                 335

Cys Ile Ala Leu Arg Pro Asp Gln Gln Ile Gly Ile Val Ala Leu Ala
            340                 345                 350

Asn Met Asn Ser Asn Leu Ile Leu Gln Leu Cys Ala Asp Ile Asp Asn
        355                 360                 365

Tyr Leu Arg Ile Gly Lys Tyr Ala Asp Gly Ala Gly Asp Ala Ile Thr
    370                 375                 380

Ala Thr Asp Thr Leu Phe Val Tyr Leu Thr Leu Leu Leu Cys Phe Trp
385                 390                 395                 400

Gly Ala Val Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
            420                 425                 430

Tyr Ile Ile Ala Leu Ala Val Pro Gly Leu Val Ala Ala Met Leu Tyr
        435                 440                 445

Val Ala Pro Gly Ile Leu Ser Pro Gly Leu Asp Trp Arg Phe Ile Leu
    450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500


<210> SEQ ID NO 154
<211> LENGTH: 819
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Met Ala Lys Asp Asp Phe Thr Cys Gly Ser Leu Asp Ile Ala Ile Ile
1               5                   10                  15

Gly Met Ser Gly Arg Phe Ser Gly Ala Glu Ser Val Pro Glu Trp Trp
            20                  25                  30

Asp Lys Leu Leu Ala Gly Glu Glu Phe Thr Gln Pro Thr Cys Thr Glu
        35                  40                  45
```

```
Asp Asp Asn Gly Asn Pro Trp Ile Arg Leu Arg Asn Ile Ile Thr Ala
    50                  55                  60

Pro Tyr Asp Phe Asp Ala Ala Phe Phe Asn Ile Pro Pro Gly Glu Ala
65                  70                  75                  80

Leu Leu Met Asp Pro Gln Gln Arg Ile Phe Leu Glu Cys Cys Tyr Asn
                85                  90                  95

Ala Leu Glu His Ala Gly Tyr Ile Pro Thr Gln Leu Lys Arg Val Gly
            100                 105                 110

Val Tyr Gly Ala Thr Tyr Ala Asn Asn Tyr Phe Ile Asp Arg Val Tyr
        115                 120                 125

Pro Tyr Leu Lys Met Ser Gly Asp His His Tyr Leu Gln Ala Gln Ile
    130                 135                 140

Gly Asn Glu Lys Asp Tyr Leu Cys Ala Gln Val Ala Tyr Lys Leu Gly
145                 150                 155                 160

Phe Thr Gly Pro Ala Val Ser Val Gln Thr Ala Cys Ser Ser Ser Leu
                165                 170                 175

Val Ala Ala Tyr Leu Ala Cys Glu Gly Leu Leu Thr Phe Gln Ala Asp
            180                 185                 190

Val Ala Leu Ala Gly Gly Val Thr Leu Gly Phe Leu Gln Ala His Gly
        195                 200                 205

Tyr Ser Pro Gln Gly Asp Lys Leu Val Ser Gln Asp Gly His Cys Ala
    210                 215                 220

Pro Phe Ser Ala Glu Ala Thr Gly Thr Val Tyr Ser Ser Gly Ala Gly
225                 230                 235                 240

Val Val Val Leu Lys Arg Leu Glu Asp Ala Leu Arg Asp Gln Asp Arg
                245                 250                 255

Val Tyr Ala Val Ile Lys Gly Gly Ala Val Asn Asn Asp Gly Gly Arg
            260                 265                 270

Arg Leu Gly Phe Val Ala Pro Ser Val Glu Gly Gln Val Glu Ala Ile
        275                 280                 285

Asn Thr Ala Leu Ala Ala Ala Glu Val Val Pro Thr Asp Ile Ala Leu
    290                 295                 300

Ile Glu Thr His Gly Thr Gly Thr Pro Leu Gly Asp Glu Ile Glu Leu
305                 310                 315                 320

Glu Ala Leu His Arg Val Phe Ala Pro Ala Cys Ala Pro His Ser Ile
                325                 330                 335

Gln Leu Gly Ala Val Lys Ala Asn Leu Gly His Leu Gly Val Ala Ser
            340                 345                 350

Gly Ile Val Ser Leu Met Lys Thr Ala Leu Thr Leu Tyr Thr Gly Leu
        355                 360                 365

Val Pro Pro Gln Ile Asn Leu Val Asn Lys His Lys Lys Leu Leu Gln
    370                 375                 380

Pro Ala Ser Pro Phe Tyr Leu Ser Asp Val Val Thr Ser Val Pro Gln
385                 390                 395                 400

Thr Lys Arg Ile His Ala Thr Val Ser Ser Phe Gly Leu Gly Gly Thr
                405                 410                 415

Asn Ala His Leu Val Leu Gln Asn Trp Cys Glu Thr Pro Ala Gln Ala
            420                 425                 430

Val Gln Glu Asn Glu Arg Arg Leu Phe Phe Phe Ser Ala Lys Thr Pro
        435                 440                 445

Leu Ala Leu Arg Gln Gln Leu Asp Ala His Tyr His Ala Leu Ala Thr
    450                 455                 460
```

```
Tyr Ala Glu Ala Asp Lys Asp Arg Ile Ala Tyr Thr Leu Ala Gln Arg
465                 470                 475                 480

Arg Ala His Phe Pro Tyr Arg Cys Ala Leu Ala Ala Asp Ser Val Val
                485                 490                 495

Ala Leu Arg Ala Ser Leu Ala Lys Leu Arg Asp Ala Asp Met Ser Phe
            500                 505                 510

Thr Pro Ile Asn Met Glu Thr Thr Leu Val Phe Leu Tyr Pro Asp Arg
        515                 520                 525

Asp Asp Lys Leu Glu Ser Ala Leu Thr His Leu Leu Ala Cys Gln Pro
    530                 535                 540

Asn Leu Arg Gln Arg His Gln Arg Leu Ser Gln Asp Val Ala Gln Ile
545                 550                 555                 560

Cys Glu Pro Ala Asp Trp Thr Pro Ala Leu Arg Gln Phe Ile Gln Gln
                565                 570                 575

Val Ser Leu Ser Glu Trp Leu Ile Glu Gln Ser Ile Ser Pro Val Gln
            580                 585                 590

His Ile Gly Tyr Leu Thr Gly Ala Ala Ala Ala Gln Tyr Val Ala Arg
        595                 600                 605

Ile Ile Ser Leu Glu Asn Ala Val Gln Gln Val Ile Val Ala Glu Thr
    610                 615                 620

Thr Pro Glu Gln Thr Leu Ala Gly Asn Ser Glu Leu Ser Glu Ile Leu
625                 630                 635                 640

Ala Asn Leu Ala Val Thr Glu Gly Thr Leu Met Leu Glu Ile Gly Arg
                645                 650                 655

Ala Gly Thr Phe Ser Ile Leu Tyr His Gln His Ala Gln Trp Val Gly
            660                 665                 670

Gln Thr Val Phe Ser Pro Met Leu Asn Thr Asp Thr Pro Glu Asp Ile
        675                 680                 685

Leu Pro Leu Leu Gly Thr Leu Trp Gln Arg Gly Val Thr Ile Cys Leu
    690                 695                 700

Pro Glu Met Pro Ala Val Gln Thr Ile Gly Leu Pro Gly Tyr Ser Phe
705                 710                 715                 720

Asp Arg Val Arg Tyr Glu Ile Gln Ser Ser Asp Ala Arg Glu Asn Ala
                725                 730                 735

Met Leu Pro Val Ser Tyr Leu Ser Val Ser Asp Phe Val Glu Lys Thr
            740                 745                 750

Trp Arg Ser Leu Leu Cys Ile Asp His Tyr Asp Glu His Ala Val Ile
        755                 760                 765

Phe Glu Tyr Gly Ala Thr Ser Met His Val Ile Ser Phe Val Asp Ser
    770                 775                 780

Cys Asn His Ile Tyr Lys Ile Gly Leu Thr Ala Ala Asp Ile Tyr Ala
785                 790                 795                 800

Arg Pro Ala Ile Arg Glu His Ser Glu Phe Ile Ser Glu Cys Val Asp
                805                 810                 815

Gly Ile Leu
```

<210> SEQ ID NO 155
<211> LENGTH: 1455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 155

```
Met Met Ser Gly Asn Pro Leu Ser Trp Pro Gln Glu Gln Cys His Ile
1               5                   10                  15

Ile Asp Gln Leu Tyr Pro Tyr Ser Ala Val Asn Ile Ile Gly Gly Val
            20                  25                  30

Val Thr Ile Glu Gly Ile Val Asp Leu Pro Arg Leu His Ala Ala Ile
        35                  40                  45

Gln Ser Ala Ile Arg Gln Phe Asp Ala Leu Arg Met Trp Phe Val Met
    50                  55                  60

Gly Glu Glu Ser Glu Val Val Ser Gln Val Gln Pro Tyr His Trp Arg
65                  70                  75                  80

Asp Ile Arg His Leu Thr Phe Ser Pro Asp Tyr Asp Lys Glu Asn Leu
                85                  90                  95

Arg Pro Ala Ala Ile Glu Thr Phe Val Asp Glu Trp Phe Arg Gln Pro
            100                 105                 110

Phe Thr Leu Leu Ala His Asp Leu Phe Glu Phe Val Thr Phe Thr Cys
        115                 120                 125

Gly Glu Gln Tyr Ser Gly Tyr Leu Phe Lys Ala His His Gly Ile Ala
    130                 135                 140

Asp Gly Trp Ser Met Ala Leu Leu Ser Asn His Val Lys Arg Ala Tyr
145                 150                 155                 160

Glu Gln Gln Asp Val Pro Asp Asp Ala Ser Pro Ala Tyr Ser Ala Phe
                165                 170                 175

Leu Ala Gln Gln Gln Ser Tyr Gln Ala Ser Thr Arg Phe Ala Val Asp
            180                 185                 190

Arg Gly Trp Trp Arg Asp Tyr Ile Asp Glu Tyr Arg Asp Cys Phe Pro
        195                 200                 205

Asp Ser Ser Pro Ile Val Thr Thr Glu Gly Ile Ser Cys Ser Thr Trp
    210                 215                 220

Leu Glu Pro Ala Met Ile Asn Arg Leu Tyr Arg Leu Cys Asn Arg Tyr
225                 230                 235                 240

Gly Cys Thr Leu Asn Thr Leu Phe Ile Ala Leu Phe Ala Leu Tyr Arg
                245                 250                 255

Ala Arg Val Trp Gly Glu Glu Lys Gly Val Ile Gly Val Pro Leu Ala
            260                 265                 270

Asn Arg His Thr Arg Glu Ala Arg Arg Cys Phe Gly Met Phe Thr Asn
        275                 280                 285

Gln Leu Pro Leu Ala Tyr Arg Leu Val Arg Thr Glu Arg Phe Cys Glu
    290                 295                 300

Arg Val Ala Phe Phe Gln Arg Glu Leu Lys Arg Gly Phe Lys His Ser
305                 310                 315                 320

Lys Tyr Pro Ile Thr Leu Phe Asn Gln Asp Leu Ala Glu Gln Gly Gly
                325                 330                 335

Gly Lys Leu Arg Ala Phe Asp Tyr Cys Val Asn Tyr Tyr Asn Phe Thr
            340                 345                 350

Tyr Glu Arg His Ile Ala Gly Ala Ala Gln Arg Val Glu Ser Tyr Tyr
        355                 360                 365

Ser Gly Glu Gln Ser Tyr Lys Leu Gln Ile Val Leu Gln Thr Val Asn
    370                 375                 380

Asn His Lys Glu Ser Leu Arg Leu Ser Leu Glu Ala Leu Arg Ser Ala
385                 390                 395                 400

Phe Thr Pro His Gln Leu Thr Ala Met Lys Asn Gly Leu Leu Asp Leu
                405                 410                 415
```

```
Val Thr Ala Leu Asp Arg Gln Pro Asp Ala Arg Leu Gly Asp Leu Glu
            420                 425                 430

Val Tyr Pro Ala Pro His Val Ala Leu Ala Cys Gly Ser Leu Lys Pro
        435                 440                 445

Ser Phe Thr Ser Arg Phe Ala Ala Gln Val Val Glu His Gly Asp Arg
    450                 455                 460

Thr Ala Leu Ile Asp Asn Glu Gln Ser Leu Thr Tyr Arg Gln Leu Asp
465                 470                 475                 480

Asp Ala Val Glu Arg Val Ala Arg Tyr Leu Arg Gln Gln Gly Ile Gly
                485                 490                 495

Arg Gly Gln Val Val Gly Ile Ile Ala Glu His Ser Ala Gln Thr Val
            500                 505                 510

Met Val Ile Tyr Gly Ile Leu Arg Cys Gly Ala Ala Phe Leu Pro Leu
        515                 520                 525

Asn Pro Ala Leu Pro Thr Thr Arg Leu Tyr Ala Met Cys Arg Lys Ala
    530                 535                 540

Gln Val Ala His Ile Leu Tyr Asp Pro Ala Met His Glu Leu Thr Gln
545                 550                 555                 560

Ala Leu Ala Phe Pro Ala Ser Ser Leu Leu Gln Ala Leu Ala Thr Ser
                565                 570                 575

Ala Leu Ala Arg Glu Pro Trp Pro Ala Ile Glu Pro Gln Asp Leu Ala
            580                 585                 590

Tyr Val Leu Phe Thr Ser Gly Ser Thr Gly Glu Pro Lys Gly Val Gln
        595                 600                 605

Val Ser His Gly Asn Leu Ala Asn Tyr Leu His Phe Ala Ala Glu Arg
    610                 615                 620

Tyr Phe Thr Ala Gln Asp Arg Ala Ala Leu Tyr Ser Ser Leu Ser Phe
625                 630                 635                 640

Asp Leu Thr Ile Thr Thr Leu Phe Ala Pro Leu Cys Val Gly Ala Ser
                645                 650                 655

Ile Ser Val Cys Arg His Ala Glu Ser Glu Thr Leu Leu Arg Met Ala
            660                 665                 670

Val Val Asp Gln Pro Asn Thr Val Ile Lys Leu Thr Pro Ala His Leu
        675                 680                 685

Arg Leu Leu Cys Ala Ala Gly Ile Ser Ser Glu Gln Ile Arg Thr Leu
    690                 695                 700

Val Val Gly Gly Glu Asp Phe Lys Arg Asp Leu Ala Arg Lys Ala Ala
705                 710                 715                 720

Ala Leu Phe Pro Gln Ala Val Ile Tyr Asn Glu Tyr Gly Pro Thr Glu
                725                 730                 735

Ala Thr Val Gly Cys Met Ile Tyr Arg Tyr Thr Gly Gln Glu Thr Leu
            740                 745                 750

Pro Ser Leu Pro Ile Gly Met Ala Ile Asp Gly Cys Gln Val Ala Ile
        755                 760                 765

Cys Ser Pro Trp Gly Cys Pro Val Pro Glu Gly Glu Thr Gly Glu Leu
    770                 775                 780

Val Ile Tyr Gly Ala Ser Val Thr Gln Gly Tyr Ile Asp Ala Pro Gln
785                 790                 795                 800

Gln Thr Ala Ala Ala Tyr Leu Lys Asp Thr Asn Gly Val Met Ile Gly
                805                 810                 815

Tyr Arg Ser Gly Asp Ile Gly Tyr Ala Ile Ala Pro Asn Thr Leu Val
            820                 825                 830

Tyr Gln Gly Arg Lys Asp Asp Gln Val Lys Ile Asn Gly Tyr Arg Ile
```

```
        835                 840                 845

Glu Leu Cys Glu Ile Glu Gln Ala Leu Leu Ser Ala Pro Gln Val Glu
    850                 855                 860

Ser Ala Ala Val Ala Val Ile Asp Asp Val Gln Gly Gln His Ser Gly
865                 870                 875                 880

Leu Leu Ala Cys Val Thr Pro Ser Ser Val Asp Val Ala Thr Val Met
                885                 890                 895

Gln His Leu Arg Gln Gln Leu Pro Thr Tyr Met Gln Pro Lys Gln Cys
            900                 905                 910

Cys Ala Ile Ala Gln Leu Pro Leu Ser His Asn Gly Lys Val Asp Val
        915                 920                 925

Arg Gln Met Val Ala Thr Val Arg Asn Thr Ala Pro Ala Ser Gly Ser
    930                 935                 940

Glu Arg Leu Gly Asp Ala Ala Ile Arg His Ser Val Arg Val Cys Val
945                 950                 955                 960

Glu Gly Ala Leu Glu Gln Thr Glu Phe Asp Asp Asn Glu Asn Leu Tyr
                965                 970                 975

Val Leu Gly Leu Asp Ser Ile Lys Ser Ile Gln Ile Ala Ala Gln Leu
            980                 985                 990

Arg His His Gly Trp Thr Met Ser  Ala Val Gln Val Met  Glu Cys Gly
        995                 1000                1005

Thr Val  Asn Ala Ile Cys Glu  Phe Leu Ala Ser His  Thr Thr Val
    1010                1015                1020

Ser Gln  Leu Ala Gln Tyr Ala  His Asn Thr Arg Ile  Asp Leu Pro
    1025                1030                1035

Ala Leu  Arg Trp Phe Thr Gln  Leu Ala Leu Pro Val  Pro Asn Val
    1040                1045                1050

Tyr Asn  His Val Ile Val Leu  Lys Val Leu Pro Gly  Cys Pro Leu
    1055                1060                1065

Glu Gln  Leu His Asn Arg Leu  His Thr Leu Ile Gln  Gln Gln Pro
    1070                1075                1080

Ala Leu  His Ser Ala Leu Asp  Ala Glu Gly Arg Leu  Leu Val Cys
    1085                1090                1095

Asp Pro  Asn Val Cys Tyr Pro  Asn Glu Val Leu Thr  Glu Tyr Ser
    1100                1105                1110

Thr Ala  Gln Trp Thr Leu Ala  Glu Val Ile Ala Gln  Cys Asn Ser
    1115                1120                1125

Met Leu  Asp Val Thr Asn Gly  Arg Val Phe Thr Ala  Ala Leu Leu
    1130                1135                1140

His Ala  Pro Gln Pro Ala Ser  Ser Thr Leu Val Leu  Cys Ala His
    1145                1150                1155

His Leu  Cys Val Asp Met His  Ser Trp Tyr Leu Ile  Leu Ser Thr
    1160                1165                1170

Leu Asp  Ala Val Ser Thr Val  Asn Gly Thr Ser Asn  Ser Gly Leu
    1175                1180                1185

His Arg  Trp Asn Asp Tyr Leu  Ala Ser Lys Thr Val  Asp Ser Ala
    1190                1195                1200

Thr His  Glu Ser Trp Arg Thr  Val Cys Gln Thr Leu  Pro Leu His
    1205                1210                1215

Phe Pro  Pro Val Ser Leu Pro  Asp Asp Ser Leu Pro  Arg Thr Arg
    1220                1225                1230

Ala Trp  Arg Glu Asp Phe Arg  His Pro Cys Val Arg  Arg Leu Phe
    1235                1240                1245
```

```
Glu Ser  Ser Gly Asn Thr Ala  Tyr Ser Ala Glu Thr  Tyr Val Leu
    1250                 1255                 1260

Thr Ala  Leu Ala Leu Val Leu  Arg Tyr Tyr Ser Glu  Glu Pro Trp
    1265                 1270                 1275

Cys Arg  Ile Glu Met Glu Gly  Met Gly Arg Gly Cys  Trp Pro Asp
    1280                 1285                 1290

Glu Pro  Asp Val Ala Asp Thr  Val Gly Trp Phe Thr  Leu Phe Tyr
    1295                 1300                 1305

Pro Trp  Ala Ile Pro Leu His  Gly Asp Met Ala Thr  Leu Leu Ser
    1310                 1315                 1320

Ala Ile  Ala Ser Asp Leu Ala  Lys Arg Thr His Gly  Gly Gly Asp
    1325                 1330                 1335

Tyr Gly  Leu Leu Gln Met Arg  His Ala Pro Glu Asp  Ser Leu Ala
    1340                 1345                 1350

Gln Gly  Ile Arg Met Asn Tyr  Ile Gly Val Gln Ala  Gln Pro Ser
    1355                 1360                 1365

Leu Arg  Tyr Phe His Ile Asp  His Phe Asn Ser Asp  Ile Tyr Thr
    1370                 1375                 1380

Ala Pro  Glu Asn Ala Leu Gly  Cys Val Leu Glu Phe  Asn Ile Ala
    1385                 1390                 1395

Arg Ser  Ala Ala Asp Gly Leu  Ser Phe His Cys Arg  Phe Asp Pro
    1400                 1405                 1410

Thr Arg  Ile Ala Leu Asn Asp  Val Gln Leu Leu Leu  Ala Arg Tyr
    1415                 1420                 1425

Lys Asn  Ser Leu Thr Asp Leu  Asp Ala Trp Leu Cys  Gln His Ser
    1430                 1435                 1440

Ala Thr  Leu Thr Gly Ala Pro  Thr Leu Trp Thr Leu
    1445                 1450                 1455
```

<210> SEQ ID NO 156
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 156

```
Met Thr Val Asn Lys Leu Glu Pro Asp Asn Gly Thr Pro Asn Asp Glu
1               5                   10                  15

Leu Phe Thr Val Ala Gly Met Phe Asp Gly Ser Leu Tyr Lys Leu Leu
            20                  25                  30

Leu Arg Met Ala Leu Pro Met Phe Val Gly Met Leu Thr Gln Val Thr
        35                  40                  45

Tyr Ala Ile Ala Asp Ile Phe Trp Leu Ser His Ile Asp Val Thr Asn
    50                  55                  60

Ser Gly Ile Ile Ala Gly Val Gly Leu Val Phe Pro Val Gly Met Gly
65                  70                  75                  80

Leu Phe Ala Ile Ala Asn Gly Ile Gln Ile Gly Met Gly Ser Leu Leu
                85                  90                  95

Ser Arg Ala Ile Gly Met Gln Arg Leu Asp Arg Ala Gln Arg Ile Leu
            100                 105                 110

Ser Val Gly Ile Ile Ile Ala Leu Phe Phe Ala Ile Val Ile Thr Val
        115                 120                 125
```

```
Leu Gly Tyr Val Tyr Ala Gln Pro Leu Leu Arg Ser Leu Gly Ala Thr
    130                 135                 140

Lys Ser Ile Ile Gly Tyr Ala Thr Glu Phe Tyr Tyr Tyr Ser Leu Leu
145                 150                 155                 160

Thr Val Phe Ser Ile Met Leu Ile Gly Val Met Met Gly Leu Phe Gln
                165                 170                 175

Gly Ala Gly Lys Ile Met Val Ile Met Lys Ala Ser Leu Leu Gly Ala
            180                 185                 190

Leu Val Asn Ile Met Leu Asp Pro Ile Met Ile Phe Val Phe Asp Phe
        195                 200                 205

Gly Val Lys Gly Val Ala Leu Ala Ser Phe Leu Ala Gln Leu Ser Met
    210                 215                 220

Val Ala Tyr Phe Ile Tyr Thr Leu Met Gly Leu His Ile Gly Leu Ser
225                 230                 235                 240

Ile Arg Ile Ala Leu Arg Pro Phe Ser Trp Lys Ile Tyr Arg Glu Phe
                245                 250                 255

Leu Ser Val Gly Met Ala Gln Met Leu Met Gln Leu Ile Ile Ala Val
            260                 265                 270

Gly Ile Val Ile Tyr Asn Phe Phe Ile Val Arg Leu Asp Val Asn Ala
        275                 280                 285

Met Ala Ala Phe Thr Leu Thr Gly Arg Ile Asp Tyr Phe Ile Ile Thr
    290                 295                 300

Pro Met Leu Ala Ile Ala Thr Ala Leu Leu Thr Val Val Gly Gln Asn
305                 310                 315                 320

Trp Gly His Gly Asn Val Thr Arg Thr Leu Asn Ala Tyr Trp Ala Ala
                325                 330                 335

Val Ala Leu Ala Phe Ser Ile Val Leu Val Leu Ala Val Met His Ile
            340                 345                 350

Val Leu Ala Pro Trp Met Tyr Pro Leu Phe Thr Arg Val Val Ala Val
        355                 360                 365

Ser Asp Tyr Ala Val Leu Gln Thr Arg Ile Met Ala Leu Ala Leu Pro
    370                 375                 380

Phe Val Ala Ile Ser Leu Leu Ala Ser Glu Tyr Tyr Gln Ala Ile Gly
385                 390                 395                 400

Lys Pro Trp Tyr Ser Val Leu Leu Thr Leu Met Arg His Val Phe Ile
                405                 410                 415

Ser Val Pro Val Val Tyr Leu Leu Ala Ile Val Leu Glu Met Arg Ile
            420                 425                 430

Thr Gly Val Tyr Phe Gly Ala Met Ser Gly Thr Phe Val Ala Ala Leu
        435                 440                 445

Leu Ala Trp Arg Leu Leu Arg Leu Ser Pro Arg Leu Leu Arg Trp Asn
    450                 455                 460

Gln Glu Ala Val Arg Ser Gln His Leu Asp Met Glu Val Ala Pro
465                 470                 475
```

<210> SEQ ID NO 157
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

```
Met Ser Glu Gln Ser Tyr Arg Ser Ala Gly Thr Leu Leu Ala Gln Leu
```

-continued

```
1               5                   10                  15

Ala Ser Gly Glu Thr Thr Ser Val Ala Leu Val Asn His Tyr Phe Ser
            20                  25                  30

Arg Met Ala Gln Phe Asn Lys Pro Leu Asn Ala Val Val Gln Gln His
        35                  40                  45

Tyr Ala Leu Ala Leu Glu Ala Ala Ala Arg Ala Asp Arg Glu Arg Leu
    50                  55                  60

Glu Gly Arg Ala Arg Gly Val Leu His Gly Leu Pro Cys Thr Val Lys
65                  70                  75                  80

Glu Ser Phe Asp Val Gln Gly Trp Leu Thr Thr Ser Gly Ala His Tyr
                85                  90                  95

Leu Lys Asp Asn Arg Ala Thr Gln Asp Ala Pro Ser Ile Ala Arg Leu
            100                 105                 110

Arg Ala Ala Gly Ala Ile Leu Met Gly Lys Thr Asn Val Pro Met Met
        115                 120                 125

Thr Ala Asp Trp Gln Thr Tyr Asn Asp Leu Tyr Gly Thr Thr His Asn
    130                 135                 140

Leu Trp Asp Arg Gln Arg Ser Pro Gly Gly Ser Ser Gly Gly Ala Ala
145                 150                 155                 160

Val Ala Val Ala Ala Asp Phe Thr Pro Val Glu Phe Gly Ser Asp Leu
                165                 170                 175

Phe Gly Ser Leu Arg Ile Pro Ala His Tyr Thr Gly Val Tyr Ala His
            180                 185                 190

Arg Cys Ser Leu Gly Leu Met Ser Val Arg Gly His Val Pro Gly Gly
        195                 200                 205

Gly Pro Gln Ala Thr Asp Glu Pro Asp Leu Ser Thr Ala Gly Pro Met
    210                 215                 220

Ala Arg Ser Ala Ala Asp Leu Arg Leu Met Met Arg Ala Leu Ser Thr
225                 230                 235                 240

Phe Trp Val Glu Pro Pro Arg Ile Pro Asp Phe Ser Arg Tyr Gln Ala
                245                 250                 255

Lys Ala Asn Tyr Arg Val Cys Thr Trp Phe Ser Ala Pro His His Glu
            260                 265                 270

Ile Asp Gln Gln Ile Ala Gln Arg Phe Gln Ser Phe Ile Asp Lys Leu
        275                 280                 285

Arg Ala Gln Pro Gly Val Glu Val Asp Asp Ala Met Pro Ala Asp Ile
    290                 295                 300

Asp Pro Asp Ala Leu Phe Asp Ile Ala Val Lys Leu Ser Gly Arg Leu
305                 310                 315                 320

Val Ser Thr Ala Leu Asn Gly Arg Gln Arg Leu Thr Ala Gly Leu Ala
                325                 330                 335

Ala Leu Gly Phe Arg Leu Val Gly Lys Leu Ala Asp Val Pro Glu Gly
            340                 345                 350

Ile Thr Ser Tyr Tyr Gln Gly Met Leu Lys Asp Ser Gly Glu Gln Arg
        355                 360                 365

Asn Thr Asp Lys Leu Arg His Glu Tyr Ser Arg Val Ile Glu Thr Leu
    370                 375                 380

Phe Ala Arg Tyr Asp Val Leu Leu Thr Pro Val Ser Pro Val Leu Ala
385                 390                 395                 400

Phe Ala His Met Gln Gln Pro Val Arg Lys Arg Lys Leu Ile Val Asn
                405                 410                 415

Gly Glu Pro Gln Asp Tyr Asn Glu His Leu Phe Trp Asn Met Leu Ala
            420                 425                 430
```

```
Thr Val Phe Gly Leu Pro Ala Thr Val Tyr Pro Leu Ala Lys Thr Met
        435                 440                 445

Asp Glu Leu Pro Cys Gly Ile Gln Ile Ile Ser Gly His Phe His Asp
    450                 455                 460

Asp Val Thr Ile Asn Phe Ala Glu Phe Cys Glu Ser Ile Ser Gly Gly
465                 470                 475                 480

Phe Thr Val Pro Glu Gly Tyr
                485


<210> SEQ ID NO 158
<211> LENGTH: 2154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Met Thr Tyr Ser Glu Ser Asp Ile Ala Ile Val Gly Met Asn Cys Arg
1               5                   10                  15

Tyr Pro Gly Val His Ser Val Ala Ala Phe Glu Thr Val Leu Arg Thr
            20                  25                  30

Gly Cys Asn Ile Leu Asp Pro Lys Val Thr Pro Ser Asn Gly His Asn
        35                  40                  45

His Ile Thr Leu Asn Asn Val Tyr Glu His Met Ala Glu Phe Asp Ala
    50                  55                  60

Asn Phe Phe Gly Tyr Ser Arg Ala Glu Ala Glu Ile Met Asp Pro Gln
65                  70                  75                  80

Gln Arg Val Phe Leu Thr Cys Ala Trp Glu Met Phe Glu Gln Ser Gly
                85                  90                  95

Tyr Asn Pro Lys Gln His Asp Ala Arg Val Gly Leu Tyr Ala Gly Val
            100                 105                 110

Ser Thr Ser Phe Tyr Leu Leu Thr His Leu Met Asn Asn Pro Asp Lys
        115                 120                 125

Leu Ala Gln Leu Gly Gly Leu Gln Ile Met Val Gly Asn Asp Lys Asp
    130                 135                 140

His Leu Thr Ser Gln Leu Ala Tyr Arg Leu Asn Ile Thr Gly Pro Cys
145                 150                 155                 160

Val Thr Val Gln Ala Ser Cys Ala Thr Ser Leu Val Ala Val His Leu
                165                 170                 175

Ala Cys Glu Gly Leu Leu Ser Gly Gln Cys Asp Met Ala Leu Ala Gly
            180                 185                 190

Gly Val Thr Phe Arg Met Glu Glu Gln Arg Ser Tyr Glu Ser His Gly
        195                 200                 205

Asp Gly Leu Gln Ala Glu Asp Gly Leu Ile His Thr Phe Asp Ala Gln
    210                 215                 220

Ala Ser Gly Thr Val Tyr Ser Ser Gly Leu Gly Met Val Leu Leu Lys
225                 230                 235                 240

Arg Ala Thr Asp Ala Gln Val Gln Gly Asp Asn Ile Leu Ala Val Ile
                245                 250                 255

Lys Gly Ser Ala Ile Asn Asn Asp Gly Gly Ala Arg Ser Gly Tyr Thr
            260                 265                 270

Val Pro Gly Val Asp Gly Gln Glu Ala Val Met Ile Glu Ala His Ser
        275                 280                 285
```

```
Leu Ala Glu Val Thr Pro Gln Gln Ile Gln Tyr Leu Glu Leu His Gly
    290                 295                 300

Ser Gly Thr Pro Leu Gly Asp Ala Ile Glu Phe Ala Ala Ile Lys Arg
305                 310                 315                 320

Val Phe Gly Thr Pro Ala Pro Asn Ala Thr Pro Trp Arg Leu Gly Ala
                325                 330                 335

Val Lys Pro Asn Val Gly His Val Glu Met Ala Ser Gly Ile Thr Ser
            340                 345                 350

Leu Ile Lys Thr Val Leu Ser Leu Thr Asn Arg Val Phe Tyr Pro Thr
        355                 360                 365

Leu Asn Phe Gln Arg Ala Asn Pro Gln Leu Gly Leu Glu Asp Ser Pro
    370                 375                 380

Phe Glu Val Val Ser Arg Leu Thr Pro Trp Pro Glu Gly Thr Thr Pro
385                 390                 395                 400

Arg Thr Ala Gly Val Ser Ala Phe Gly Leu Gly Gly Thr Asn Ala His
                405                 410                 415

Leu Val Val Gln Ala Pro Leu Ser Thr Pro Gln Ala Arg Ala Gln Gln
            420                 425                 430

Met Gly Pro Cys Val Val Val Leu Ser Ala Lys Asn His Asn Ala Leu
        435                 440                 445

Glu Gln Met Gln Asn Ala Leu Leu Ala Lys Leu Ala Ala His Pro Glu
    450                 455                 460

Ile Arg Leu Gln Asp Val Ala Tyr Thr Leu Arg His Gly Arg Phe Ser
465                 470                 475                 480

Ala Pro Val Arg Lys Cys Val Ile Ala Glu Asn Cys Thr Gln Leu Ala
                485                 490                 495

Arg Gln Leu Arg Asp Ala Pro Met Val Glu Ala Thr Thr Gly Cys Thr
            500                 505                 510

Ile Tyr Trp Arg Leu Gly His Arg Phe Val Val Ala Leu Glu Thr Leu
        515                 520                 525

Ser Asp Trp Leu Ala Cys Ser Glu Val Leu Ser Gln Ala Val Gly Gln
    530                 535                 540

Leu Leu Glu His Phe Pro Leu Glu Pro Ala Cys Leu Gln Asp Leu Ser
545                 550                 555                 560

Pro Ala Gln Arg Thr Phe Ile Ser Gln Tyr Ala Leu Ile Ala Leu Ile
                565                 570                 575

Asp Glu Arg Glu Thr Leu Asn Val Val Leu Cys Gly Asp Gly Asp Gly
            580                 585                 590

Gly Tyr Ala Ala Ala Val Leu Arg Gly Asp Cys Thr Leu Glu Gln Ala
        595                 600                 605

Trp His Arg Leu Asn Ala Gly Gln Pro Phe Asp Asp Val Pro Thr Asn
    610                 615                 620

Pro Leu Leu Gln Pro Asp Val Cys Ser Leu Met Leu Asp Asp Ala Ala
625                 630                 635                 640

Ser Asp Ala Asn Arg Thr Ala Leu Glu Ala Leu Gly Gln Leu Trp Leu
                645                 650                 655

Ala Gly Val Ser Leu Asp Trp Arg Trp Val Asp Ala Ala Glu Arg Met
            660                 665                 670

Leu Gly Ser Gln Arg Ile Ala Leu Pro Gly Thr Val Phe Thr Pro Gln
        675                 680                 685

Arg Tyr Trp Val Glu Ala Val Arg Pro Ala Thr Phe Ser His Glu Ser
    690                 695                 700

Ser Asn Asn Leu Leu Ser Arg Ala Thr Lys Ser Asp Ile Ile Ala Val
```

```
705                 710                 715                 720

Val Thr Glu Ile Trp Glu Arg Thr Leu Gly Val Ser Ile Asp Asp His
                725                 730                 735

His Ala Ser Phe Phe Glu Leu Gly Gly His Ser Leu Leu Ala Ser Thr
            740                 745                 750

Ile Leu Tyr Asp Ile Gln Gln Arg Tyr Gly Ile Thr Cys Thr Leu Ser
        755                 760                 765

Ala Phe Phe Ala Asp Pro Thr Ile Glu Gly Leu Ser Cys Tyr Leu Leu
    770                 775                 780

Glu Gln Gly Gly Ser Glu Thr Ala Val Ser Ala Leu Pro Asp Thr Val
785                 790                 795                 800

Phe Ala Pro Asp Gln Gln His Leu Pro Phe Pro Leu Thr Asp Val Gln
                805                 810                 815

Gln Ala Tyr Trp Val Gly Arg Arg Lys Ser Leu Gly Leu Gly Asn Ile
            820                 825                 830

Ser Thr His Ile Tyr Val Glu Tyr Glu Leu Gln Gly Leu Asp Glu Thr
        835                 840                 845

Ala Phe Asn Arg Ala Leu Asn Ala Val Ile Ala Arg His Ser Met Leu
    850                 855                 860

Arg Ala Ile Val Asn Asp Asp Gly Met Gln Gln Ile Leu Pro Asn Val
865                 870                 875                 880

Pro Glu Tyr His Val Ala Phe Tyr Thr Thr Gln Cys Glu Asp Ala Phe
                885                 890                 895

Gln Gln Arg Cys Arg Glu Leu Arg Asp Thr Leu Ser His Gln Met Ile
            900                 905                 910

Asp Cys Ser Arg Trp Pro Leu Phe Gln Met Glu Val Val Val Asp Pro
        915                 920                 925

Gln Gln Lys Ala Arg Leu His Val Ser Ile Asp Leu Leu Ile Ala Asp
    930                 935                 940

Ala Trp Ser Leu Glu Leu Phe Ile Arg Glu Leu Ala Tyr His Tyr Arg
945                 950                 955                 960

His Pro Gln Ala Ala Leu Pro Thr Leu Thr Tyr Ser Phe Arg Asp Tyr
                965                 970                 975

Val Leu Thr Leu Lys Ser Tyr Glu Lys Thr Pro Gln Phe Glu Arg Ala
            980                 985                 990

Arg Asp Tyr Trp Arg Ala Arg Ile  Glu Thr Leu Pro Pro  Gly Pro Arg
        995                 1000                1005

Leu Pro  Leu Arg Thr Asp Pro  Thr Lys Leu Glu Asn  Pro Thr Phe
    1010                1015                1020

Val Arg  Arg Ser Tyr Cys Leu  Ser Arg Ala Ile Trp  Gln Arg Leu
    1025                1030                1035

Lys Thr  Gln Ala Gly Gln Met  Ser Ile Thr Pro Thr  Thr Leu Leu
    1040                1045                1050

Leu Thr  Gly Phe Ala Gln Val  Leu Ala Arg Phe Ser  Ser Ser Pro
    1055                1060                1065

His Phe  Ser Leu Asn Leu Thr  Leu Phe Asn Arg Leu  Pro Leu His
    1070                1075                1080

Ala Asp  Ile Asn His Leu Ile  Gly Asp Phe Thr Ala  Leu Thr Leu
    1085                1090                1095

Leu Glu  Ile Asp Met Ser Gln  Gly Glu Thr Leu Gln  Ala Arg Ala
    1100                1105                1110

Asn Val  Ile His Ser Gln Leu  Trp Arg Asp Leu Asp  Asn Arg Leu
    1115                1120                1125
```

```
Phe Gly  Gly Ile Gln Val Ser  Arg Leu Leu Val Gln  Thr His Arg
    1130                 1135                 1140

Asp Pro  Ala Lys Ser Val Ile  Pro Ile Val Phe Thr  Ser Leu Leu
    1145                 1150                 1155

Asn Gln  Tyr Glu Ala Ser Trp  Glu Thr Asp Asp Thr  Leu Phe Asn
    1160                 1165                 1170

Gln Pro  Gln Asp Asp Leu Tyr  Ser Ile Ser Gln Thr  Pro Gln Val
    1175                 1180                 1185

Trp Leu  Asp His Gln Val Met  Glu Arg Asn Gly Glu  Leu His Phe
    1190                 1195                 1200

Asn Trp  Asp Val Val Glu Gln  Leu Phe Glu Pro Ala  Leu Met Asp
    1205                 1210                 1215

Gln Met  Phe Gln Cys Tyr Cys  Gln Leu Leu His Ala  Leu Ala Gln
    1220                 1225                 1230

Arg Pro  Gln Leu Trp His Glu  Thr Gln Asp Val Leu  Ala Leu Pro
    1235                 1240                 1245

Thr Val  Ser Ala Pro Val Thr  Gln Ala Pro Ala Pro  Thr Ala Leu
    1250                 1255                 1260

Leu His  His Gly Leu Leu Arg  Gln Ala Ala Leu Thr  Pro Gln Glu
    1265                 1270                 1275

Thr Ala  Leu Ile Ser Pro Ile  Arg Glu Leu Thr Tyr  Arg Gln Leu
    1280                 1285                 1290

Ser Thr  Ala Ala Asp His Val  Ala Arg Ala Leu Leu  Ala Leu Gly
    1295                 1300                 1305

Val Gln  His Gly Asp Arg Val  Ala Val Val Met Glu  Lys Gly Trp
    1310                 1315                 1320

Gln Gln  Ile Ala Ala Val His  Gly Ile Leu Arg Leu  Gly Ala Val
    1325                 1330                 1335

Tyr Leu  Pro Val Asp Pro Val  Leu Pro Pro Gln Arg  Arg Gln Leu
    1340                 1345                 1350

Leu Leu  Thr Val Gly Glu Val  Arg Val Gln Val Thr  Gln Pro Gly
    1355                 1360                 1365

Leu Thr  Gln Leu Glu Pro Ser  Leu Pro Val Leu Ile  Ile Asp Asp
    1370                 1375                 1380

Gly Met  Leu Asp Thr Pro Ala  Ala Pro Leu Pro Glu  Val Ala Gly
    1385                 1390                 1395

Asp Val  Thr Asp Leu Ala Tyr  Ile Ile Phe Thr Ser  Gly Ser Thr
    1400                 1405                 1410

Gly Thr  Pro Lys Gly Val Met  Ile Asp His Arg Ala  Ala Met Asn
    1415                 1420                 1425

Thr Leu  Glu Asp Ile Asn Glu  Arg Phe Gly Leu Asn  Ala Gln Asp
    1430                 1435                 1440

Arg Val  Phe Gly Leu Ser Ser  Leu Ser Phe Asp Leu  Ser Val Tyr
    1445                 1450                 1455

Asp Ala  Phe Ala Pro Phe Met  Val Gly Ala Ala Leu  Val Leu Pro
    1460                 1465                 1470

Glu Ala  Gly Arg Glu Lys Asp  Pro Arg His Trp Gln  Thr Val Met
    1475                 1480                 1485

Ala His  Gly His Val Ser Val  Trp Asn Ala Val Pro  Ala Leu Met
    1490                 1495                 1500

Gln Met  Leu Cys Glu Tyr His  Ser Gly Asp Arg Met  Ser Tyr Pro
    1505                 1510                 1515
```

-continued

```
Thr Leu  Arg Leu Ala Leu Leu  Ser Gly Asp Trp Ile  Pro Leu Thr
    1520                 1525                 1530

Leu Pro  Glu Gln Met Arg Glu  Arg Leu Asn Glu Thr  Met Asp Ile
    1535                 1540                 1545

Ile Ser  Leu Gly Gly Ala Thr  Glu Cys Ala Ile Trp  Ser Val Tyr
    1550                 1555                 1560

Tyr Pro  Ile Gly Glu Val Glu  Ser Thr Trp Thr Ser  Ile Pro Tyr
    1565                 1570                 1575

Gly Arg  Gly Leu Arg Asn Gln  Pro Val Tyr Val Leu  Asn Ala Gln
    1580                 1585                 1590

Leu Glu  Glu Cys Pro Val Gly  Val Glu Gly Glu Ile  Cys Ile Gly
    1595                 1600                 1605

Gly Met  Gly Leu Ala Gln Gly  Tyr Leu Asn Asp Ala  Glu Lys Thr
    1610                 1615                 1620

Ala Ala  Ser Phe Val Trp Arg  Glu Ala Ser Gly Glu  Arg Ile Tyr
    1625                 1630                 1635

Arg Thr  Gly Asp Arg Gly Arg  Tyr Phe Ala Asp Gly  Gln Val Ala
    1640                 1645                 1650

Phe Leu  Gly Arg Asn Asp Thr  Gln Val Lys Val Asn  Gly Tyr Arg
    1655                 1660                 1665

Ile Glu  Leu Gly Glu Ile Glu  Arg Cys Ile Ala Arg  His Pro Asp
    1670                 1675                 1680

Val Glu  Gln Ser Val Val Val  Ala Val Gly Asn Ser  Gln His Arg
    1685                 1690                 1695

Arg Leu  Val Ala Phe Ala Lys  Leu His Asp Arg His  Gln Ala Gln
    1700                 1705                 1710

Ala Leu  Gln Ala Lys Glu Ala  Glu Ala Ala Ala Leu  Ala Gln Gly
    1715                 1720                 1725

Ile Ile  Val Asn Pro Ala Gln  Arg Leu Ala Phe Lys  Leu Lys Glu
    1730                 1735                 1740

Pro His  Ile Arg Ala Leu Asp  Gly Leu Gly Ile Ala  Leu Thr Ala
    1745                 1750                 1755

Pro Ala  Asp Ser Thr Arg Tyr  Ile Lys Arg Arg Ser  Tyr Arg His
    1760                 1765                 1770

Phe Ser  Ala Gln Lys Thr Thr  Leu Ala Gln Leu Gly  Gln Leu Leu
    1775                 1780                 1785

Ser Gly  Leu Gly Gln Met Arg  Leu Pro Gly Leu Pro  Phe Ala Lys
    1790                 1795                 1800

Tyr Ala  Tyr Ala Ser Ala Gly  Gly Leu Tyr Pro Val  Gln Thr Tyr
    1805                 1810                 1815

Val Tyr  Leu His Pro Asp Lys  Ile Glu Glu Gly Val  Ser Gly Ile
    1820                 1825                 1830

Tyr Tyr  Phe Asp Pro Arg Gln  Ser Cys Leu Met Pro  Val Ala Pro
    1835                 1840                 1845

Glu Val  Glu Leu Asn Ser Gly  Phe His Ala Gly Pro  Asn Gln Ser
    1850                 1855                 1860

Ile Ala  Asp Arg Ala Ala Phe  Thr Leu Phe Met Val  Ala Asp Met
    1865                 1870                 1875

Ala Val  Ile Ser Pro Phe Tyr  Gly Gln Glu Ala Ala  Trp His Phe
    1880                 1885                 1890

Ser Val  Met Glu Ala Gly Thr  Leu Cys His Leu Leu  Glu Glu Asp
    1895                 1900                 1905

Ala Pro  Arg Tyr Gly Leu Gly  Leu Cys Gln Leu Gly  Met Ala Asp
```

```
    1910                1915                1920

Phe Ser  Ala Val Ala Ser His  Phe Gln Leu Ser Pro  His His Arg
    1925                1930                1935

Tyr Val  His Cys Thr Val Gly  Gly Ala Ile Gly Gln  Glu Ala Ala
    1940                1945                1950

Ser Ala  Ala Ala Leu Leu Arg  Asp Phe Ser Thr Tyr  Glu Lys Pro
    1955                1960                1965

Lys Glu  Thr Ala Ala Pro Leu  Asp Met Gln Ser Tyr  Lys Asp Ala
    1970                1975                1980

Met Leu  Arg Gly Leu Arg Gln  Gln Leu Pro Asp Tyr  Met Val Pro
    1985                1990                1995

Ser Asp  Leu Met Leu Ala Thr  Asp Phe Pro Leu Thr  Ala Asn Gly
    2000                2005                2010

Lys Leu  Asp Arg Gln Lys Leu  Gln Leu Gln Gly Glu  Gln Ile Ala
    2015                2020                2025

His Gln  Arg Asp Gly Val Gly  Pro Ile Gln Val Asp  Ser Ala Leu
    2030                2035                2040

Gln Gln  Arg Leu Val Ala Leu  Trp Gln Glu Val Leu  Gly Val Ser
    2045                2050                2055

His Val  Ser Ala Glu Asp Asp  Phe Phe Ser Leu Gly  Gly Ser Ser
    2060                2065                2070

Ile Glu  Leu Val Arg Ile Gln  Gln Ala Leu Glu Ala  Ile Ile Gly
    2075                2080                2085

Gln Glu  Ile Pro Ile Val Asp  Leu Phe Arg Leu Pro  Thr Ile Ala
    2090                2095                2100

Asp Val  Ala Arg Tyr Leu Asp  Glu Gln Leu His Asn  Leu Pro Ala
    2105                2110                2115

Ala His  Asp Ile Val Leu Ala  Gln Ala Glu Val Ser  Gln Val Ser
    2120                2125                2130

Ala Ala  Arg Glu Asn Leu Ala  Leu Arg Arg Lys Arg  Ala Gln Gln
    2135                2140                2145

Gly Glu  Lys Gly Asp Glu
    2150


<210> SEQ ID NO 159
<211> LENGTH: 2166
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Met Thr Ile His His Ala Ala Leu Ala Arg Met Leu Pro Ala Glu Lys
1               5                   10                  15

Lys Glu Lys Leu Leu Arg Gln Leu Ala Gln Ser Gly Val Ser Pro Ser
            20                  25                  30

Arg Ile Pro Ile Ile Lys Ala Asp Pro Ala Gln Ala Ile Pro Leu Ser
        35                  40                  45

Phe Asn Gln Glu Arg Leu Trp Phe Leu Gln Lys Tyr Asp Ser Thr Ala
    50                  55                  60

Thr Asn Tyr Asn Leu Tyr Val Val Tyr Arg Leu His Gly Val Val Asp
65                  70                  75                  80

Met Pro Met Leu Thr Glu Ala Leu Arg His Val Gln Ala Arg His Ala
                85                  90                  95
```

```
Ile Leu Arg Thr Arg Ile Ile Val Arg Asn Asp Arg Pro Cys Gln Val
            100                 105                 110

Ile Asp Asp Ala Ser Ser Leu Val Leu Asp Thr Val Thr Leu Ala Ala
        115                 120                 125

Gln Ala Pro Thr Ser Ala Leu Asp Ala Val Ile Gln Gln Val Ile Asn
    130                 135                 140

Thr Arg Phe Asp Leu Ala Arg Gly Pro Leu Trp Gly Val Thr Gln Ile
145                 150                 155                 160

Ile Gln Pro Asp Gln Gly Cys His Leu Val Phe Cys Ala His His Ile
                165                 170                 175

Ile Ile Asp Gly Ile Ser Leu Arg Leu Leu Phe Asp Glu Leu Gln Gln
            180                 185                 190

Gln Tyr Ala Arg Leu His Ala Gly Asn Glu Thr Ser Leu Pro Pro Pro
        195                 200                 205

Pro Leu Gln Tyr Ala Asp Tyr Ala Phe Trp Gln Arg Glu Trp Phe Gln
    210                 215                 220

Asp Thr Leu Leu Ala Asn Glu Leu Ala Tyr Trp Arg Ala Arg Leu Gln
225                 230                 235                 240

Asp Ala Pro Leu Leu Ser Thr Phe Pro Ser Leu His Pro Arg Pro Ala
                245                 250                 255

Gln Pro Ser Thr His Gly Ser Arg Phe Ser Ile Thr Leu Asp Glu Thr
            260                 265                 270

Leu Ser Leu Ala Leu Lys His Val Ala Arg Thr Gln Glu Thr Thr Pro
        275                 280                 285

Phe Val Leu Met Leu Thr Ala Phe Gln Leu Val Leu Met Arg Tyr Ala
    290                 295                 300

Gln Gln Gln Arg Leu Val Ile Gly Met Pro Val Ser Gly Arg Ile Arg
305                 310                 315                 320

Pro Glu Leu Gln Ser Ser Ile Gly Tyr Tyr Ala Ser Thr Ala Val Ile
                325                 330                 335

Tyr Thr Asp Phe Asn Gly Val Glu Val Gly Arg Glu Ala Leu Gln Arg
            340                 345                 350

Val Lys Ala Ser Val Lys Glu Thr Gln Gly Arg Gln Gln Leu Pro Phe
        355                 360                 365

Glu Asn Leu Val Asn Met Leu Asp Leu Pro Arg Ser Leu Ser His Ser
    370                 375                 380

Pro Leu Phe Gln Ile Leu Tyr Ile Tyr His Asn His Val Thr Pro Arg
385                 390                 395                 400

Ala Phe Thr Leu Ala Gly Ala Tyr Trp Glu Gln Val Thr Tyr His Asn
                405                 410                 415

Gln Thr Val Lys Tyr Asp Met Thr Val Glu Val Phe Gln Asn Asp Ala
            420                 425                 430

Thr Phe Asp Val Ser Phe Glu Tyr Asp Leu Gly Leu Tyr Asp Ala Asp
        435                 440                 445

Val Val Lys Gln Ile Ala Glu Ala Leu Arg Gln His Cys Leu Ser Leu
    450                 455                 460

Thr Ser Ser Leu Glu Thr Pro Ile Gly Ala Ile Pro Leu His Ala Pro
465                 470                 475                 480

Glu Thr Ala Thr Pro Arg Arg Asp Pro Leu Asn Ala Thr Asn Val Pro
                485                 490                 495

Trp Leu Gly Pro Gln Asp Val Leu Arg Ile Ile Glu Gln Arg Cys Val
            500                 505                 510
```

```
Gln His Pro Lys Gln Leu Ala Ile Gln Gln His Asp Gly Thr Leu Thr
        515                 520                 525

Tyr Ala Glu Leu Trp Ala Arg Val Gln Phe Ile Ala Met Arg Phe Arg
    530                 535                 540

Ala His Gly Ile Gln Pro Gly Asp Arg Ile Gly Val Leu Leu Pro Arg
545                 550                 555                 560

His Arg Asp Val Ile Ala Thr Met Leu Ala Thr Trp Phe Val Gly Ala
                565                 570                 575

Cys Tyr Val Pro Phe Asp Ile His Gln Pro Ala Ala Arg Leu Gln Arg
            580                 585                 590

Leu Met Gln Arg Ala Arg Leu Val Cys Leu Val Val Arg Gln Pro Gly
        595                 600                 605

Glu Trp Gly Glu Ile Val Gln Leu Ser Leu Pro Glu Leu Met Gln Asp
    610                 615                 620

Met Ser Asn Ala Ile Arg Tyr Ser Thr Pro Cys Ala Leu Leu Pro Asp
625                 630                 635                 640

Met Gln Ala Tyr Leu Leu Phe Thr Ser Gly Ser Thr Gly Glu Pro Lys
                645                 650                 655

Gly Val Cys Val Val His Arg Gly Leu Leu Asn Leu Leu Leu Asp Met
            660                 665                 670

Gln Arg Thr Phe Ala Val Gly Ser Gln Asp Arg Leu Leu Ser Val Thr
        675                 680                 685

Thr Pro Thr Phe Asp Ile Ser Phe Leu Glu Tyr Leu Leu Pro Leu Ile
    690                 695                 700

Ser Gly Ala Ser Leu Tyr Leu Thr Glu Ala Glu Arg Ala Ala Asp Ser
705                 710                 715                 720

Phe Arg Met Ile Pro Leu Ile Ala Asp Tyr Arg Pro Thr Leu Met Gln
                725                 730                 735

Ala Thr Pro Ser Phe Trp His Gly Leu Leu Met Ala Gly Trp Arg Gly
            740                 745                 750

Asp Pro Glu Leu Cys Val Leu Ala Gly Gly Glu Ala Leu Pro Thr Lys
        755                 760                 765

Val Ala Glu Glu Leu Leu Arg Cys Cys Gly Ser Leu Trp Asn Leu Tyr
    770                 775                 780

Gly Pro Thr Glu Thr Thr Ile Trp Ser Leu Lys Ser Gln Ile Thr Gln
785                 790                 795                 800

Ala Glu Asn Ile Thr Leu Gly Ala Pro Ile Ala Asn Thr Arg Ile Tyr
                805                 810                 815

Ile Leu Asp Asn Glu Gly His Pro Val Pro Gln Gly Val Asp Gly Glu
            820                 825                 830

Leu Tyr Ile Ala Gly Asp Gly Val Ala Gln Gly Tyr Asp Gly Gln Pro
        835                 840                 845

Glu Leu Asn Ala Gln Phe Phe Leu Ser Glu Pro Gly Val Pro Gly Gly
    850                 855                 860

Arg Met Phe Arg Thr Gly Asp Leu Val Arg Ser Asp Ala Gln Gly Gln
865                 870                 875                 880

Leu Phe Phe Val Gly Arg Lys Asp Ser Gln Ile Lys Leu Arg Gly Tyr
                885                 890                 895

Arg Ile Glu Leu Gly Glu Ile Glu Arg Thr Leu Ala Arg His Pro His
            900                 905                 910

Val Asp Ala Ala Val Val Ala Cys Ile Glu Arg Ala Pro Leu His Lys
        915                 920                 925

Ala Leu Ala Ala Phe Ile Ile Thr Ser Glu Pro Pro Ser Leu Phe Glu
```

```
930                935                940

Gln Leu Lys Asn Glu Leu Arg Gln Gln Leu Pro Asp Tyr Met Val Pro
945                950                955                960

Thr Leu Trp Gln Arg Val Ala Asp Phe Pro Asn Thr Asp Asn Gly Lys
                965                970                975

Ile Asp Arg Lys Arg Leu Ala Glu Asn Phe Val Ala Asp Ser Ser Leu
            980                985                990

Val Ser Pro Gln Thr Gln Ala Leu  Ser Asp Thr Glu Gln  Met Leu Leu
        995                1000                1005

Ala Leu  Trp Met Arg Tyr Leu  Pro Ile Lys Asn Val  Asp Pro Glu
    1010                1015                1020

Cys Asp  Phe Phe Arg Leu Gly  Gly His Ser Leu Leu  Ala Val Thr
    1025                1030                1035

Leu Val  Ala Glu Ile Asn Arg  Thr Phe His Cys Ala  Leu Thr Leu
    1040                1045                1050

Lys Asp  Ile Phe His Tyr Ser  Thr Leu Arg Ala Leu  Ser Ala Arg
    1055                1060                1065

Ile Ala  Gln Gln Ser Ile Thr  Asp Ala Ala Ala Ser  Gln Asp Asp
    1070                1075                1080

Trp Val  Ile Val His Asp Pro  Glu His Arg His Gln  Pro Phe Pro
    1085                1090                1095

Leu Thr  Asp Val Gln Arg Ala  Tyr Trp Leu Gly Arg  Gln Thr Gly
    1100                1105                1110

Ala Thr  Ser Ile Ala Thr His  Ile Tyr His Glu Phe  Asp Val Glu
    1115                1120                1125

His Phe  Asn Val Thr Arg Phe  Thr His Ala Val Asn  Ala Leu Ile
    1130                1135                1140

Ala Arg  His Glu Met Leu Arg  Ala Arg Val Leu Pro  Asp Gly Thr
    1145                1150                1155

Gln Gln  Ile Leu Ala Gln Val  Pro Ala Tyr Gln Leu  Glu Gln Arg
    1160                1165                1170

Asp Leu  Ser Ala Leu Ser Pro  Asn Ala Arg Asn Asp  Ala Leu Met
    1175                1180                1185

Ala Ile  Arg Asp Arg Leu Ser  His His Val His Pro  Ala Asp Arg
    1190                1195                1200

Trp Pro  Leu Phe Asp Phe Ser  Tyr Ser Ala Cys Thr  Ala Gln His
    1205                1210                1215

Gly Arg  Leu His Phe Ser Leu  Asp Leu Leu Ile Ala  Asp Ala Leu
    1220                1225                1230

Ser Met  Arg Thr Leu Gln Gln  Glu Leu Met Met Leu  Tyr Arg Glu
    1235                1240                1245

Pro His  Val Ser Leu Pro Leu  Leu Pro Phe Ser Phe  Arg Asp Tyr
    1250                1255                1260

Val Gln  Ala Leu Leu Val Glu  Gln Ala Ser Glu Ala  Tyr Ala Arg
    1265                1270                1275

Asp Gln  Ala Tyr Trp Gln Arg  Ala Leu Pro Gln Leu  Tyr Gly Pro
    1280                1285                1290

Pro Thr  Leu Pro Val Gln Gly  Asp Leu Ala Gln Leu  Ser Ala Ile
    1295                1300                1305

Arg Phe  Val Arg Arg Arg His  Arg Leu Ser Ala His  Asn Trp Gly
    1310                1315                1320

Val Leu  Ser Ala Leu Ala Gln  Arg Thr Arg Ile Thr  Lys Thr Ala
    1325                1330                1335
```

```
Leu Leu  Leu Thr Val Phe Ser  Gln Val Leu Ala Arg  Trp Ser Leu
    1340                 1345                 1350

Ser Pro  Thr Phe Thr Leu Asn  Leu Thr Leu Phe Asn  Arg Pro Gln
    1355                 1360                 1365

Gly Tyr  Pro Asn Ala Glu Ala  Val Ile Gly Asp Phe  Thr Ala Val
    1370                 1375                 1380

Ser Leu  Leu Asn Val Cys Tyr  Asp Ser Gln His Ser  Tyr Ala His
    1385                 1390                 1395

Asn Ala  Gln Arg Ile Gln Val  Gln Leu Trp Glu Asp  Leu Glu His
    1400                 1405                 1410

Arg Arg  Phe Ser Gly Ile Arg  Ala Ser Glu Ala Leu  Ile His Ser
    1415                 1420                 1425

Gly Arg  Phe His Ala Pro Met  Pro Val Val Phe Thr  Ser Met Leu
    1430                 1435                 1440

Asp Ile  Asp Gly Glu Thr Thr  Ala Gln Asp Pro Arg  Asp Thr Thr
    1445                 1450                 1455

Arg Phe  Thr Leu Cys Pro Asp  Ala Asn Ile Thr Gln  Thr Pro Gln
    1460                 1465                 1470

Val Trp  Leu Asp His Gln Val  Ile Glu Leu Ala Gly  Glu Leu His
    1475                 1480                 1485

Phe Asn  Trp Asp Ala Val Glu  Gln Leu Phe Asp Thr  Thr Leu Leu
    1490                 1495                 1500

Asp Gln  Met Phe Gly Ala Tyr  Cys His Ala Leu Gln  Ala Leu Val
    1505                 1510                 1515

Ala Met  Pro Gln Ser Trp Trp  Gly Val Asn Ser Ser  Leu Ala Leu
    1520                 1525                 1530

Pro Thr  Val Ser Ala Pro Val  Thr Gln Ala Pro Ala  Pro Thr Ala
    1535                 1540                 1545

Leu Leu  His His Gly Leu Leu  Arg Gln Ala Ala Leu  Thr Pro Gln
    1550                 1555                 1560

Glu Thr  Ala Leu Ile Ser Pro  Ile Arg Glu Leu Thr  Tyr Arg Gln
    1565                 1570                 1575

Leu Ser  Thr Ala Ala Asp His  Val Ala Arg Ala Leu  Leu Ala Leu
    1580                 1585                 1590

Gly Val  Gln His Gly Asp Arg  Val Ala Val Val Met  Glu Lys Gly
    1595                 1600                 1605

Trp Gln  Gln Ile Ala Ala Val  His Gly Ile Leu Arg  Leu Gly Ala
    1610                 1615                 1620

Val Tyr  Leu Pro Val Asp Pro  Val Leu Pro Pro Gln  Arg Arg Gln
    1625                 1630                 1635

Leu Leu  Leu Thr Val Gly Glu  Val Arg Val Gln Val  Thr Gln Pro
    1640                 1645                 1650

Gly Leu  Thr Gln Leu Glu Pro  Ser Leu Pro Val Leu  Ile Ile Asp
    1655                 1660                 1665

Asp Gly  Met Leu Asp Thr Pro  Ala Ala Pro Leu Pro  Glu Val Ala
    1670                 1675                 1680

Gly Asp  Val Thr Asp Leu Ala  Tyr Ile Ile Phe Thr  Ser Gly Ser
    1685                 1690                 1695

Thr Gly  Thr Pro Lys Gly Val  Met Ile Asp His Arg  Ala Ala Met
    1700                 1705                 1710

Asn Thr  Leu Glu Asp Ile Asn  Glu Arg Phe Gly Leu  Asn Ala Gln
    1715                 1720                 1725
```

```
Asp Arg Val Phe Gly Leu Ser Ser Leu Ser Phe Asp Leu Ser Val
    1730                1735                1740

Tyr Asp Ala Phe Ala Pro Phe Met Val Gly Ala Ala Leu Val Leu
    1745                1750                1755

Pro Glu Ala Gly Arg Glu Lys Asp Pro Arg His Trp Gln Thr Val
    1760                1765                1770

Met Ala His Gly His Val Ser Val Trp Asn Ala Val Pro Ala Leu
    1775                1780                1785

Met Gln Met Leu Cys Glu Tyr His Ser Gly Asp Arg Met Ser Tyr
    1790                1795                1800

Pro Thr Leu Arg Leu Ala Leu Leu Ser Gly Asp Trp Ile Pro Leu
    1805                1810                1815

Thr Leu Pro Glu Gln Met Arg Glu Arg Leu Asn Glu Thr Met Asp
    1820                1825                1830

Ile Ile Ser Leu Gly Gly Ala Thr Glu Cys Ala Ile Trp Ser Val
    1835                1840                1845

Tyr Tyr Pro Ile Gly Glu Val Glu Ser Thr Trp Thr Ser Ile Pro
    1850                1855                1860

Tyr Gly Arg Gly Leu Arg Asn Gln Pro Val Tyr Val Leu Asn Ala
    1865                1870                1875

Gln Leu Glu Glu Cys Pro Val Gly Val Glu Gly Glu Ile Cys Ile
    1880                1885                1890

Gly Gly Met Gly Leu Ala Gln Gly Tyr Leu Asn Asp Ala Glu Lys
    1895                1900                1905

Thr Ala Ala Ser Phe Val Trp Arg Glu Ala Ser Gly Glu Arg Ile
    1910                1915                1920

Tyr Arg Thr Gly Asp Arg Gly Arg Tyr Phe Ala Asp Gly Gln Val
    1925                1930                1935

Ala Phe Leu Gly Arg Asn Asp Thr Gln Val Lys Val Asn Gly Tyr
    1940                1945                1950

Arg Ile Glu Leu Gly Glu Val Lys Ser His Leu Glu Gln Leu Asp
    1955                1960                1965

Ser Val Gly Ser Ala Ala Val Val Cys His Gln Gly Gln Leu Tyr
    1970                1975                1980

Ala Phe Ile Thr Ala Ala Glu Asn Leu His Pro Asp Asp Thr Asp
    1985                1990                1995

Ala Leu Leu Ala Arg Val Arg Ala Gln Leu Ala Val Gln Leu Pro
    2000                2005                2010

Tyr Tyr Leu Leu Pro Gln His Phe Phe Leu Leu Lys Val Leu Pro
    2015                2020                2025

Met Thr Gly Asn Gly Lys Ile Asp Gln Ala Ala Met Val Gln Glu
    2030                2035                2040

Val Ile Gln Arg Met Ser Gln Ser Thr Ser Gln Lys Ser Arg Ala
    2045                2050                2055

Leu Ala His Ala Ser Pro Tyr Glu Gln Gln Val Ala Ala Leu Trp
    2060                2065                2070

Cys Glu Val Leu Gln Arg Glu Gln Ile Gly Leu Asn Asp Asn Phe
    2075                2080                2085

Phe Glu Ala Gly Gly Gly Ser Ile Gln Ile Val Leu Leu His Arg
    2090                2095                2100

Arg Ile Glu Glu Ile Phe Lys Val Thr Val Pro Ile Ala Glu Leu
    2105                2110                2115

Phe Arg Leu Thr Thr Val Lys Arg Ile Ala Gly Tyr Leu Gln Ala
```

```
    2120                2125                2130

Met Gln  Asp Asn Ala Arg Ala  Val Asn Gln Thr Gln  Gln Arg Asp
    2135                2140                2145

Ala Ser  Arg Ser Arg Ala Gln  Gln Arg Leu Val Arg  Arg His Gln
    2150                2155                2160

Arg Gln  Arg
    2165
```

<210> SEQ ID NO 160
<211> LENGTH: 1010
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 160

```
Met Ala Glu Asn Asp Phe Gly Ile Ala Ile Ile Gly Met Ala Gly Arg
1               5                   10                  15

Phe Pro Gln Ala Asp Thr Val Gln Ala Phe Trp Glu Asn Leu Leu Ala
            20                  25                  30

Ser Arg Glu Cys Ile Ser Phe Tyr Ser Asp Glu Glu Leu Leu Ala Met
        35                  40                  45

Gly Ile Ser Pro Glu Phe Val Gln His Pro Asp Tyr Val Lys Ala Lys
    50                  55                  60

Gly Glu Val Ala Asp Ile Asp Lys Phe Asp Ala Ala Phe Phe Gly Ile
65                  70                  75                  80

Ala Pro Arg Glu Ala Glu Leu Met Asp Pro Gln His Arg Val Leu Leu
                85                  90                  95

Glu Thr Ala Trp Ala Ala Phe Glu Asp Ala Gly Tyr Val Ala Ala Asp
            100                 105                 110

Tyr Pro Gly Asp Val Gly Ile Phe Ala Gly Lys Ser Met Asp Ser Tyr
        115                 120                 125

Leu Met Leu Asn Leu Met Pro His Phe Lys Arg Val Phe Ser Ser Gly
    130                 135                 140

Ser Leu Gln Ala Ala Ile Gly Asn Asp Lys Asp Ser Ile Thr Thr Thr
145                 150                 155                 160

Ile Ala Tyr His Leu Asn Leu Arg Gly Pro Ala Ile Thr Val Gln Thr
                165                 170                 175

Ser Ser Ser Thr Ser Leu Val Ala Val Cys Val Ala Cys Gln Ser Leu
            180                 185                 190

Leu Thr Trp Gln Cys Asp Met Ala Ile Ala Gly Gly Val Thr Leu Gly
        195                 200                 205

Pro Pro Ala Lys Thr Gly Tyr Leu Ser Gln Glu Gly Gly Ile Thr Ala
    210                 215                 220

Ala Asp Gly His Cys Arg Ala Phe Ser Asp Asn Ser Ser Gly Phe Val
225                 230                 235                 240

Pro Gly Thr Gly Ala Gly Leu Val Val Leu Lys Arg Val Asp Glu Ala
                245                 250                 255

Leu Arg Asp Gly Asp Asn Ile Tyr Ala Val Ile Lys Gly Phe Ala Val
            260                 265                 270

Asn Asn Asp Gly Ser Glu Lys Ile Ser Tyr Thr Ala Pro Ser Val Asp
        275                 280                 285

Ala Gln Ala Arg Ala Ile Ala Gln Ala Gln Arg Leu Ala Gly Leu Thr
    290                 295                 300
```

```
Pro Gln Asp Ile Thr Tyr Val Glu Ala His Gly Thr Gly Thr Arg Leu
305                 310                 315                 320

Gly Asp Pro Val Glu Phe Ser Ala Leu Ser Gln Ala Phe Ala Gly Ala
                325                 330                 335

Ser Gln Lys Gln Tyr Cys Ala Leu Gly Ser Val Lys Thr Asn Ile Gly
            340                 345                 350

His Leu Asp Thr Ala Ala Gly Val Ala Gly Leu Ile Lys Thr Ala Leu
        355                 360                 365

Ala Val Gln Gln Gly Ile Ile Pro Ala Thr Leu His Phe Glu Arg Pro
    370                 375                 380

Asn Ala Gln Ile Asp Leu Thr Asn Ser Pro Phe Tyr Ile Asn Thr Thr
385                 390                 395                 400

Cys Gln Pro Trp Gln Pro Glu Ser Gly Ile Arg Arg Ala Gly Val Thr
                405                 410                 415

Ser Leu Gly Met Gly Gly Thr Asn Ala His Val Val Leu Glu Gln Ala
            420                 425                 430

Pro Ala Val Asp Leu Gln Ala Arg Ala Pro Val Pro Ala Tyr Ser Ile
        435                 440                 445

Leu Pro Phe Ser Ala Lys Thr Asp Ser Ala Leu Ser Ser Gly Leu Ala
    450                 455                 460

Arg Phe Ala Asp Phe Leu Gln His Glu Ser Leu Pro Asp Arg Arg Asp
465                 470                 475                 480

Leu Ala Trp Thr Leu Ser Gln Gly Arg Lys Ala Phe Ala His Arg Ala
                485                 490                 495

Ala Leu Val Thr Arg Asp Leu His Ala Ala Gly Thr Leu Leu Gln Gln
            500                 505                 510

Ala Ala Thr Ala Pro Phe Ala Arg Gly Val Ala Gln Thr Gln Leu Gly
        515                 520                 525

Leu Gly Leu Leu Phe Ser Gly Gln Gly Ser Gln Tyr Gln Arg Met Gly
    530                 535                 540

His Gln Leu Tyr Gln Val Trp Pro Ala Tyr Ala Asp Ala Phe Asp Arg
545                 550                 555                 560

Cys Ala Thr Leu Leu Glu Arg Glu Tyr Gln Leu Asp Ile Arg His Glu
                565                 570                 575

Leu Phe Arg Ala Glu Val Ser Leu Ala Gln Gly Glu Arg Leu Ala Gln
            580                 585                 590

Thr Cys Leu Thr Gln Pro Leu Leu Phe Ser Val Glu Tyr Ala Leu Ala
        595                 600                 605

Gln Leu Trp Leu Ser Trp Gly Ile Thr Pro Thr Val Met Ile Gly His
    610                 615                 620

Ser Leu Gly Glu Trp Val Ala Ala Thr Leu Ala Gly Val Phe Ser Leu
625                 630                 635                 640

Glu Asp Ala Leu Arg Leu Val Ala Arg Arg Ala Glu Leu Met His Gln
                645                 650                 655

Ala Pro Ser Gly Ala Met Leu Met Val Ala Leu Pro Glu Ala Gln Ile
            660                 665                 670

Arg Ala Leu Ile Thr Ala Pro Leu Ala Ile Ala Ala Val Asn Ala Pro
        675                 680                 685

Asp Tyr Ser Val Ile Ala Gly Pro Thr Ser Glu Ile Leu Ala Val Ser
    690                 695                 700

Gln Arg Leu Thr Glu Gln Asn Ile Ile Asn Lys Arg Leu His Thr Ser
705                 710                 715                 720
```

```
His Ala Phe His Ser Ser Met Met Gln Asp Ala Ala Gln Ala Leu Arg
                725                 730                 735

Gln Ala Phe Glu Asn Val Arg Leu Asn Pro Pro Thr Leu Thr Ile Ile
            740                 745                 750

Ser Thr Val Thr Gly Ala His Val Ser Ala Asp Thr Leu Thr Thr Pro
        755                 760                 765

Asp Tyr Trp Ile Glu Gln Met Leu Met Pro Val Gln Phe Ser Ala Ala
    770                 775                 780

Leu Gln Glu Ala Gln Ala Thr Phe Asp Val Asp Phe Leu Glu Ile Gly
785                 790                 795                 800

Pro Gly Ala Thr Leu Thr Gln Leu Thr Asn Gly His Ala Leu Gly Asp
                805                 810                 815

Arg Leu Ala Phe Ser Ser Leu Pro Ala Gly Ala Arg Ser Ser Asp Glu
            820                 825                 830

His Lys His Ile Leu Asp Thr Val Ala Ala Leu Trp Val Arg Gly His
        835                 840                 845

Asn Ile Asp Leu Ser Ala Phe Ala Gly Glu Gln Pro Arg Arg Val Ser
    850                 855                 860

Leu Pro Thr Tyr Ala Phe Asp Lys Ile Arg Tyr Trp Val Asp Ser Pro
865                 870                 875                 880

Glu Glu Gln Arg Ser Ala Val Thr Pro Val Ala Asp Ala Gly Ser Val
                885                 890                 895

Ile Pro Ser Glu Pro Ser Val Arg Arg Gln Pro Arg Pro Ala Phe Ser
            900                 905                 910

Val Pro Tyr Ala Ala Pro Glu Ser Lys Thr Gln Arg Gly Leu Val Ala
        915                 920                 925

Ile Cys Glu Ala Leu Leu Gly Ile Asp Gly Leu Gly Ile Asp Asp Asn
    930                 935                 940

Phe Phe Glu Ala Gly Gly His Ser Leu Met Leu Gly Met Leu Leu Ala
945                 950                 955                 960

Gln Val Gln Glu Arg Phe Ala Val Thr Leu Ser Phe Phe Asp Val Met
                965                 970                 975

Glu Asp Ala Ser Val Arg Ala Leu Ala Gln Leu Val Glu Gln Glu Gln
            980                 985                 990

Gln Asp Asp Gly Gly Ser Ala Leu  Ala Val Leu Val Asn  Asp Met Ile
        995                 1000                1005

Asn Glu
    1010


<210> SEQ ID NO 161
<211> LENGTH: 1598
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Met Glu Gln Gln Gly Ile Met Arg Gln Leu Pro Thr Asp Asp Gln Thr
1               5                   10                  15

Ile Val Asp Tyr Leu Tyr Arg Ile Ala Gly Glu Tyr Gly Glu Lys Ala
            20                  25                  30

Ala Val Leu Met Gly Asp Ala Ala Leu Ser Tyr His Asp Leu Asn Ala
        35                  40                  45

Arg Ser Asn Gln Leu Ala His Tyr Leu Arg Gly Leu Gly Ile Gly Glu
```

```
    50                  55                  60

Asp Arg Val Val Ala Ile Arg Leu Pro Arg Gly Met Ala Met Leu Ile
65                  70                  75                  80

Ala Ile Phe Ala Ile Val Lys Ala Gly Gly Ala Tyr Leu Pro Leu Ala
                85                  90                  95

Tyr Asn Ala Pro Arg Ser Arg Ile Glu Asn Ile Leu Ser Asn Ser Gly
            100                 105                 110

Ala Val Cys Leu Ile Gly Thr Asp Asp Gly Asp Arg Trp Pro Ile Pro
        115                 120                 125

Arg Val Glu Ile Asp Ser Ala Ala Val Ser Ala Met Pro Thr Thr Asp
    130                 135                 140

Leu Arg Tyr Arg Pro His Ala Arg Gln Leu Ala Tyr Ile Ile Tyr Thr
145                 150                 155                 160

Ser Gly Ser Thr Gly Val Pro Lys Gly Val Ala Thr Glu His Ala Ala
                165                 170                 175

Leu Leu Asn Arg Ile Val Trp Met Gln Asn Ala Tyr Pro Ile Ser Ser
            180                 185                 190

Gln Asp Val Leu Phe Gln Lys Thr Val Tyr Thr Phe Asp Val Ser Val
        195                 200                 205

Trp Glu Met Phe Trp Trp Ala Met Tyr Gly Ala Ser Val Val Leu Leu
    210                 215                 220

Pro Ser Gly Leu Glu Ser Asp Pro Arg Thr Leu Ala Arg Leu Ile Gln
225                 230                 235                 240

Arg His Arg Val Ser Val Val His Phe Val Pro Ser Met Leu Asn Leu
                245                 250                 255

Phe Val Glu Tyr Leu Glu Met Lys Gln Asp Pro Arg Leu Thr Ala Ser
            260                 265                 270

Leu Arg Leu Val Phe Ser Ser Gly Glu Lys Leu Thr Val His Ser Val
        275                 280                 285

Ala Arg Phe Tyr Gln Ser Val Ala Gln Gly Asp Leu Ile Asn Leu Tyr
    290                 295                 300

Gly Pro Thr Glu Ala Ala Ile Asp Val Ser His His Arg Cys Leu Arg
305                 310                 315                 320

Gly Tyr Asp Tyr Asp Asp Ile Pro Ile Gly Gln Ala Ile Asp Gly Cys
                325                 330                 335

Arg Leu Tyr Val Leu Asp Asp His Gly Asn Pro Val Ala Asp Gly Glu
            340                 345                 350

Glu Gly Glu Leu Tyr Leu Ala Gly Ile Gly Leu Ala Arg Gly Tyr Leu
        355                 360                 365

Asn Asn Val Ala Leu Thr Asp Arg Cys Phe Thr Ile His Pro Thr Leu
    370                 375                 380

Arg His Leu Gly Lys Pro Glu Arg Leu Tyr Lys Thr Gly Asp Leu Val
385                 390                 395                 400

Trp Arg Asp Gly Glu Ser Gln Gln Ile His Tyr Ile Gly Arg Asn Asp
                405                 410                 415

Phe Gln Ile Lys Ile Arg Gly Leu Arg Val Glu Leu Gly Glu Ile Glu
            420                 425                 430

Ala His Ala Met Arg Phe Pro Gly Val Gln Gln Ala Val Val Val Ala
        435                 440                 445

Asp Gln Asp Asp Pro Asp Asn Gln Leu Ile Tyr Ala Phe Val Val Ser
    450                 455                 460

Ser Val Pro Leu Asn Leu Ala Ala Leu Met Asp Ala Leu Ser Lys Asn
465                 470                 475                 480
```

```
Leu Pro Ala Tyr Met Leu Pro Asn Arg Leu Leu Ala Met Ser Glu Leu
                485                 490                 495

Pro Leu Ser Asp Asn Gly Lys Cys Cys Arg Lys Thr Leu Leu Asp Leu
            500                 505                 510

Ala Arg Ala Tyr Ser Ala Ser Arg Val Asp Leu Arg Glu Thr Pro Ala
        515                 520                 525

Val Arg Tyr Leu Pro Leu Ser Ser Ala Gln Ser Ser Met Trp Phe Met
    530                 535                 540

Gln Gln Leu Ala Pro His Thr Ala Leu Tyr Asn Asn Pro Thr Ala Leu
545                 550                 555                 560

Leu Leu Glu Gly Glu Leu Asp Arg Thr Arg Met Asp Gly Ala Ile Arg
                565                 570                 575

Gln Leu Met Ser Arg His Thr Leu Leu Arg Ala Met Ala Glu Thr His
            580                 585                 590

Asn Gly Gln Pro Val Leu Ala Val Pro Gln Cys Val Ser Ser Gln Ala
        595                 600                 605

Leu Leu Thr Ile Val Pro Leu Pro Ser Val Ser Asp Asp Asn Ala Leu
    610                 615                 620

Gln Ala Met Ile Asn Gln Arg Ala Ala His Pro Met Pro Leu Thr Ser
625                 630                 635                 640

Gly Thr Pro Leu Cys Arg Phe Glu Leu Leu Thr Leu Asp Asp Asp Arg
                645                 650                 655

Ser Val Leu Leu Ile His Leu His His Ile Ile Ser Asp Gly Trp Ser
            660                 665                 670

Lys Gly Val Leu Leu Arg Glu Leu Gln Ala Ala Tyr Asn Gly Glu Ser
        675                 680                 685

Leu Thr Pro Glu Pro Leu Leu Glu Tyr Ala Asp Tyr Met Glu Tyr Gln
    690                 695                 700

Glu Glu Trp Arg Gln Ser Asp Ala Tyr Gln Asp Ala Met Arg Tyr Trp
705                 710                 715                 720

Gln Asn Thr Leu Ala Gly Thr Leu Pro Ile Leu Asp Ile Pro Thr Asp
                725                 730                 735

Gln Pro Arg Gln Lys Val Ala Arg Tyr Gln Gly Ala Phe Val Ala Phe
            740                 745                 750

Ala Leu Ser Ala Asn Thr Cys Glu Arg Val Leu Ala Ala Ala Arg Ala
        755                 760                 765

Gln Arg Val Ser Leu Tyr Asn Tyr Leu Leu Thr Ala Phe Val Leu Leu
    770                 775                 780

Leu His Arg Asn Ala Arg Gln Gln Glu Tyr Ile Val Gly Met Pro Ile
785                 790                 795                 800

Ala Ala Arg Leu Thr Lys Glu Gln Glu His Met Ile Ala Pro Leu Val
                805                 810                 815

Asn Val Leu Pro Leu Arg Leu Pro Leu Asp Glu Ala Ala Ser Phe Ser
            820                 825                 830

Glu Leu Val Gln Thr Ile Arg Gly Ile Leu Phe Ala Ala Phe Arg His
        835                 840                 845

Gln Arg Leu Glu Phe Thr Asp Ile Val Arg Ala Val Asn Val Asp Arg
    850                 855                 860

Ser Ala Gly His Phe Pro Ile Tyr Gln Cys Met Phe Gln Leu Asp Asn
865                 870                 875                 880

Met Pro Leu Ala Ser Pro Thr Leu Asn Gly Val Asn Val Thr Pro Leu
                885                 890                 895
```

```
Leu Leu Asp Thr Ser Ala Ser Gln Val Asp Ile Ser Leu Ser Met Gln
            900                 905                 910

His Ile Asp Gly Arg Ile Thr Gly Thr Phe Glu Tyr Asp Ala Gly Leu
        915                 920                 925

Tyr Ser Ala Asp Arg Ile Gln His Leu Val Ala Gln Trp Arg Glu Leu
    930                 935                 940

Leu Asp Glu Ala Ser Ser Gln Pro Thr Gln Leu Val Arg Asp Leu Ile
945                 950                 955                 960

Arg Phe Thr Pro Arg Glu His Ala Trp Leu Ala Arg His Asn Ala Thr
                965                 970                 975

Glu Val Ala Leu Pro Pro Val Asp Asn Leu Leu Ala Leu Val Leu Pro
            980                 985                 990

His Cys Gln Gln Arg Pro Thr Gln  Val Ala Leu Arg His  Ala Asp Asp
        995                 1000                1005

Ala Met  Thr Tyr Gly Glu Leu  Gln Gln Ala Thr Met  Gln Met Cys
    1010                 1015                1020

Thr Trp  Leu Arg Ala Gln Gly  Val Lys Arg Gly Glu  Ser Val Ala
    1025                 1030                1035

Leu Gln  Leu Pro Phe Cys Phe  Glu Leu Ile Ile Ala  Gln Leu Ala
    1040                 1045                1050

Ile Leu  Ser Leu Gly Ala Ser  Tyr Val Pro Leu Asp  Gly Asn Ala
    1055                 1060                1065

Pro Ala  Ala Arg Asn Ala Leu  Ile Leu Ala Gln Ala  Thr Pro Cys
    1070                 1075                1080

Met Leu  Leu Val Ala Gln Pro  Leu Glu Ser Pro His  Gly Leu Thr
    1085                 1090                1095

Ile Pro  Trp Val Leu Val Pro  Asp Trp Arg Ser Leu  Leu Thr Glu
    1100                 1105                1110

Ile Pro  Asn Leu Pro Val Ser  Val Ala Pro Asp Ala  Leu Asp Cys
    1115                 1120                1125

Asp Ala  Val Val Ile Phe Thr  Ser Gly Thr Thr Gly  Gln Pro Lys
    1130                 1135                1140

Gly Val  Arg Leu Ser Gln Arg  Asn Leu Val Asn Leu  Thr Ala Ser
    1145                 1150                1155

Phe Ile  Ser Ser Tyr Gln Val  Thr His Gln Asp Val  Leu Leu Pro
    1160                 1165                1170

Ile Thr  Ser Val Ala Ser Ala  Ser Phe Val Gly Glu  Val Leu Pro
    1175                 1180                1185

Leu Leu  Ala Ala Gly Gly Thr  Leu Val Leu Ala Gln  Lys Ala Gln
    1190                 1195                1200

Ser Leu  Asp Ser Asp Ala Leu  Ile Ala Leu Leu Ala  Ser Gln Arg
    1205                 1210                1215

Val Thr  Ile Leu Ser Thr Thr  Pro Ser Leu Ser Ala  Ser Leu Ser
    1220                 1225                1230

Val Leu  Ala Gln Ser Met Gly  Ser Leu Arg Leu Phe  Leu Cys Gly
    1235                 1240                1245

Gly Glu  Ala Leu Glu Tyr Glu  Gln Ile Ala Pro Leu  Leu Pro His
    1250                 1255                1260

Met Ala  Val Val Asn Gly Tyr  Gly Leu Thr Glu Ser  Gly Ile Cys
    1265                 1270                1275

Ser Thr  Tyr Phe Pro Val Ala  Lys Arg Arg Glu Gln  Glu Thr Gly
    1280                 1285                1290

Ala Leu  Pro Ile Gly Arg Pro  Ile Gln Asn Thr Gln  Ala Tyr Val
```

```
    1295                1300                1305

Val Asp  Ala Tyr Asn Arg Leu  Val Pro Pro Gly Ala  Cys Gly Glu
    1310                1315                1320

Leu Cys  Phe Ser Gly Leu Gly  Ile Ser Pro Gly Tyr  Leu Asp Ala
    1325                1330                1335

Arg Gln  Asp Pro Glu Arg Phe  Val Glu Leu Pro Glu  Tyr Pro Gly
    1340                1345                1350

Val Arg  Val Leu Lys Thr Gly  Asp Arg Ala Arg Trp  Ala Thr Asp
    1355                1360                1365

Gly Met  Leu Phe Tyr Leu Gly  Arg Gln Asp Arg Gln  Val Gln Ile
    1370                1375                1380

Arg Gly  Tyr Arg Val Glu Leu  Gly Asp Ile Glu Ser  Leu Leu Lys
    1385                1390                1395

Gln His  Pro Asp Ile Ala Asp  Ala Trp Val Asp Val  Arg Arg Asn
    1400                1405                1410

Ala Ala  Ala Thr Pro Leu Leu  Val Ala Phe Tyr Cys  Ser Val Asn
    1415                1420                1425

Gly Val  Ala Leu Asp Ala Gln  Gln Leu Arg Val Trp  Leu Ser Leu
    1430                1435                1440

Arg Leu  Pro Leu His Met Leu  Pro Leu Leu Tyr Val  Pro Leu Ser
    1445                1450                1455

Ala Met  Pro Leu Gly Val Asn  Gly Lys Ile Asp Pro  Gln Cys Leu
    1460                1465                1470

Pro Leu  Val Asp Leu Arg Gln  Leu Glu Gly Pro Gly  Glu Tyr Val
    1475                1480                1485

Pro Pro  Ala Thr Glu Leu Glu  Gln Arg Leu Ala Glu  Ile Trp Gln
    1490                1495                1500

Gln Leu  Leu Gly Leu Glu Arg  Val Gly Thr Thr Thr  Asn Phe Phe
    1505                1510                1515

Asp Leu  Gly Gly His Ser Leu  Leu Leu Val Gln Met  Gln Gln Tyr
    1520                1525                1530

Ile Gly  Gln Gln Cys Gly Gln  His Val Ala Leu Val  Asp Leu Leu
    1535                1540                1545

Arg Phe  Thr Thr Ile Lys Arg  Leu Ala Glu Phe Leu  Leu Ala Pro
    1550                1555                1560

Asp Ala  Ala Gln Gly Thr Thr  Gly Asp Gln Thr Gln  Leu Arg Ala
    1565                1570                1575

Ala Lys  Gln Arg Leu Ala Phe  Gly His Thr Arg Trp  Ala Ala Thr
    1580                1585                1590

Thr Asp  Ser His His
    1595
```

```
<210> SEQ ID NO 162
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Met Thr Lys Asp Val Ala Leu Met Phe Pro Gly Ser Gly Ser Gln Tyr
1               5                   10                  15

Val Gly Met Ala Arg Trp Leu Tyr Glu Arg Tyr Pro Gln Val Arg Thr
            20                  25                  30
```

```
Leu Phe Asp Glu Ala Ser Gln Ile Thr Glu Arg Asp Met Ala Ala Leu
        35                  40                  45

Cys Leu Ser Gly Thr Leu Val Gln Leu Ala Glu Pro Thr Ala Met Ala
    50                  55                  60

Leu Ala Ile Tyr Thr Thr Ser Val Ala His Phe Val Ala Trp Gln Gln
65                  70                  75                  80

Phe Leu Ala Gln Thr Gly Val His Val Asn Leu Arg Tyr Met Leu Gly
                85                  90                  95

His Ser Leu Gly Glu Tyr Ala Ala Leu Thr Cys Ser Gly Ala Leu Ser
            100                 105                 110

Phe Ser Gln Ala Leu Ala Leu Val Ala Met Arg Ser Arg Leu Ala Ser
        115                 120                 125

Glu Ile Ala Arg Glu Met Asp Ala Ser Thr Thr Ile Ile Lys Gln Gly
    130                 135                 140

Asn Gln Ala Leu Val Ala Ala Ala Cys Glu Val Ala Glu Arg Glu Thr
145                 150                 155                 160

Arg Gln Gln Val Gly Ile Ala Cys Phe Asn Ser Pro Gln Gln Phe Met
                165                 170                 175

Leu Ser Gly Gln Asn Ser Ala Ile Ile Ala Ala Glu Gln Tyr Leu Leu
            180                 185                 190

Asp His Asp Arg Gln Val Glu Val Val Pro Leu Ile Gly Gly Val Pro
        195                 200                 205

Tyr His Ser Pro Leu Leu Lys Pro Cys Gly Gln Gln Leu Arg Lys Ala
    210                 215                 220

Leu Asp Arg Cys Glu Trp Arg Arg Pro Cys Cys Pro Val Ile Ser Asn
225                 230                 235                 240

Val Asn Ala Gln Pro Tyr Pro Asp Thr Val Thr Pro Val Gln Trp Leu
                245                 250                 255

Glu Gln Gln Leu Ser Gln Pro Val Gln Trp Gln Arg Ser Leu Thr Tyr
            260                 265                 270

Leu Thr Gly His Leu Ser Pro Ile Ala Ile Glu Ile Gly Pro Gln Ser
        275                 280                 285

Val Leu Lys Asn Leu Leu Leu Glu Asn Arg Tyr Pro Ala Pro Val Tyr
    290                 295                 300

Ala Phe Asp Asn Arg His Asp Arg Ala Gln Leu Ala Leu Val Leu Gly
305                 310                 315                 320

Asp Asn Met Ala Val Lys Thr Asp Pro Glu Ala Val Arg Arg Gln Arg
                325                 330                 335

Ile Thr Leu Leu Thr Asn Ala Leu Thr Ala Thr Arg His His Arg Ala
            340                 345                 350

Ala Asp Val Ala Ala Ser Ala Gln Leu Lys Glu Leu Leu Ser Arg Phe
        355                 360                 365

Phe Glu Arg Ile Gln Gln Ile Glu Gln Arg Gly Thr Ser Ser Glu Glu
    370                 375                 380

Asp Ile Ala Phe Leu His Glu Leu Leu Glu Gln Gly Phe Gln Leu Lys
385                 390                 395                 400

Gly Ser Ser Gln Ala Glu Ile Asp Ala Cys His Ala Arg Leu Ala Ser
                405                 410                 415

Asp Asn Gly Gly Gln Ala
            420
```

<210> SEQ ID NO 163
<211> LENGTH: 376

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Met Cys Thr Glu Asn Tyr Glu Leu Ala Gln Gln Glu Ala Val Leu Phe
1               5                   10                  15

Ala Lys Gln His Leu Ala Leu Ala Ala Gln Asn Ile Glu Arg Gln Gln
            20                  25                  30

Phe Ile Val Pro Asp Ile Ile Ser Cys Val Ala Gln Ala Gly Tyr Leu
        35                  40                  45

Gly Ala Ser Ile Pro Gln Lys Tyr Gly Gly Arg Gly Tyr Asp Ser Tyr
    50                  55                  60

Gln Leu Cys Ala Leu His Glu Val Met Ala Gly Val His Gly Ser Leu
65                  70                  75                  80

Glu Asn Leu Ile Thr Val Thr Gly Met Val Ser Thr Leu Leu Gln Arg
                85                  90                  95

Val Gly Ser Ala Ala Gln Lys Ala His Tyr Leu Pro Lys Leu Ala Thr
            100                 105                 110

Gly Glu Leu Ile Gly Ala Ile Ala Leu Thr Glu Pro Asn Ile Gly Ser
        115                 120                 125

Asp Leu Val Asn Val Glu Thr Glu Leu Gln Gln Asp Gly Asp Gly Trp
    130                 135                 140

Arg Leu Asn Gly Lys Lys Lys Trp Ile Thr Leu Gly Gln Ile Ala Asp
145                 150                 155                 160

Phe Phe Ile Val Leu Ile His Cys Gly Asn Gln Leu Ala Thr Val Leu
                165                 170                 175

Ile Asp Arg Asn Thr Asp Gly Phe Thr Ile Thr Pro Leu Asn Asp Met
            180                 185                 190

Leu Gly Leu Arg Gly Asn Met Leu Ala Glu Leu His Phe Asn Asp Cys
        195                 200                 205

Arg Leu Lys Glu Asp Ala Leu Leu Gly Pro Leu Thr Pro Gly Val Pro
    210                 215                 220

Leu Ala Val Asn Phe Ala Leu Asn Glu Gly Arg Phe Thr Thr Ala Cys
225                 230                 235                 240

Gly Ser Leu Gly Leu Cys Arg Ala Ala Val Asp Val Ala Ala Arg Tyr
                245                 250                 255

Ile Arg Gln Arg Lys Gln Phe Lys Arg Arg Leu Phe Ser His Gly Ile
            260                 265                 270

Val Gln His Leu Phe Ala Thr Met Leu Thr Gln Thr Arg Ser Ala Gln
        275                 280                 285

Leu Met Cys Phe Ser Ala Ala Glu Tyr Arg Glu Thr Leu His Pro Ala
    290                 295                 300

Met Ile Asn Gln Ile Leu Met Ala Lys Tyr Val Ala Ser Lys Ala Ala
305                 310                 315                 320

Val Asp Val Ala Gly Lys Ala Val Gln Leu Leu Gly Ala Asn Gly Cys
                325                 330                 335

His Ala Asp Tyr Ala Val Glu Arg Tyr Tyr Arg Asp Ala Lys Ile Met
            340                 345                 350

Glu Ile Ile Glu Gly Thr Ser Gln Ile His Glu Ile Gln Ile Ala Met
        355                 360                 365

Asn Tyr Met Met Gly Ser Glu Ala
```

370 375

<210> SEQ ID NO 164
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

```
Met Lys Lys Gln Asp Met Lys Ala Ala Ile Arg Glu Phe Leu Ser Arg
1               5                   10                  15

Ser Leu Arg Gly His Thr Leu Asn Asp Asp Asp Ile Phe Ser Leu
            20                  25                  30

Gly Leu Val His Ser Leu Phe Thr Val Gln Ile Ile Leu Phe Ile Glu
        35                  40                  45

Lys Asn Phe Gln Val Glu Leu Glu Val Ser Glu Leu Lys Thr Glu Gln
    50                  55                  60

Ile Ala Thr Val Asn Lys Ile Val Glu Leu Ile Gln Arg Gln Thr Gly
65                  70                  75                  80

Leu Glu
```

<210> SEQ ID NO 165
<211> LENGTH: 289
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 165

```
Met Met Asn Val Ala Val Ile Gly Ala Gly Val Met Gly Thr Gly Val
1               5                   10                  15

Ala His Asn Met Ala Gln Tyr Gly Ile Ser Thr Asn Val Val Asp Ile
            20                  25                  30

Ser Gln Ser Gln Leu Asp Lys Cys Arg Gln Met Ile Glu Ala Asn Leu
        35                  40                  45

Arg Leu Tyr Asn Phe His Pro Gln His Lys Lys Lys Thr His Ser Thr
    50                  55                  60

Ala Glu Ile Met Glu Asn Ile Arg Phe Thr Thr Glu Leu Asp Asp Ile
65                  70                  75                  80

Val Glu Cys Asp Leu Val Ile Glu Asn Ile Thr Glu Asp Ile Glu Lys
                85                  90                  95

Lys Asn Ala Leu Tyr Thr Arg Met Asn Thr Ile Cys Gly Ala Ser Thr
            100                 105                 110

Val Phe Gly Val Asn Thr Ser Ala Ile Ser Ile Thr Ala Leu Ser Lys
        115                 120                 125

Leu Met Arg His Pro Glu Asn Val Val Gly Val His Phe Met Asn Pro
    130                 135                 140

Val Pro Leu Met His Thr Val Glu Leu Ile Arg Gly Val His Thr Ala
145                 150                 155                 160

Glu Arg Thr Leu Asn Ile Phe His His Leu Phe Ala Gln Leu Asn Lys
                165                 170                 175

Thr Gly Ile Val Val Asn Asp Ser Pro Gly Phe Val Thr Asn Arg Ala
            180                 185                 190
```

```
Met Met Ile Phe Val Asn Glu Ala Ile Phe Met Val Gln Glu Gln Ile
        195                 200                 205

Ala Arg Ala Glu Asp Ile Asp Thr Leu Phe Lys Thr Cys Phe Gly His
    210                 215                 220

Lys Met Gly Pro Leu Gln Thr Ala Asp Leu Ile Gly Leu Asp Thr Ile
225                 230                 235                 240

Leu Gln Ser Leu Gln Val Leu Tyr Glu Ser Phe Asn Asp Asp Lys Tyr
                245                 250                 255

Arg Pro Ser Phe Leu Leu Lys Lys Met Val Asp Ala Gly Tyr Leu Gly
            260                 265                 270

Val Lys Ser Gly Gln Gly Phe Tyr Arg Tyr Gln Gln Thr Tyr Ala Glu
        275                 280                 285

Gln


<210> SEQ ID NO 166
<211> LENGTH: 866
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Met Glu Tyr Ala Ser Glu Met Asn Gly Met Glu Ile Ala Ile Ile Gly
1               5                   10                  15

Met Ala Val Arg Phe Pro Gln Ser Arg Thr Leu His Glu Phe Trp His
            20                  25                  30

Asn Ile Val Gln Gly Lys Glu Cys Val Thr Phe Phe Ser Glu Glu Glu
        35                  40                  45

Leu Leu Ala Glu Gly Val Glu Gln Ser Thr Leu Asp Asn Pro Ala Tyr
    50                  55                  60

Val Arg Ala Lys Pro Tyr Ile Glu Gly Ile Cys Asp Phe Asp Ala Ala
65                  70                  75                  80

Phe Phe Gly Tyr Ser His Lys Glu Ala Gln Thr Leu Asp Pro Lys Ser
                85                  90                  95

Arg Val Leu His Glu Val Ala Tyr His Ala Leu Glu Asp Ala Gly Tyr
            100                 105                 110

Ala Gln Arg Thr Ser Asp Leu Ile Thr Gly Val Phe Val Gly Ala Ser
        115                 120                 125

Glu Asp Val Asp Trp Leu Arg Arg Ser Leu Ser Gln Ile Gly Gly Asp
    130                 135                 140

Ala Leu Asn Arg Phe Glu Ser Gly Ile Tyr Gly His Lys Asp Leu Leu
145                 150                 155                 160

Ala His Leu Ile Ala Tyr Ser Leu Asn Leu Asn Gly Pro Val Tyr Ser
                165                 170                 175

Leu Tyr Thr Ser Cys Ser Thr Ser Leu Ser Ala Thr His Ile Ala Cys
            180                 185                 190

Arg Ser Leu Leu Phe Gly Glu Cys Asp Leu Ala Leu Ala Gly Gly Ile
        195                 200                 205

Thr Ile Asp Leu Pro Gln Lys Ser Gly Tyr Phe Cys Gln Gln Gly Met
    210                 215                 220

Ile His Ser Thr Asp Gly His Cys Arg Pro Phe Asp Ser Gln Ala Ser
225                 230                 235                 240

Gly Thr Leu Phe Gly Asp Gly Ala Gly Val Val Val Leu Arg Arg Leu
                245                 250                 255
```

```
Glu Asp Ala Leu Ala Ala Gly Asp Arg Ile Tyr Ala Val Ile Arg Gly
            260                 265                 270

Ser Ala Val Asn Asn Asp Gly Lys Gln Lys Ile Gly Phe Val Ala Pro
        275                 280                 285

Gly His Glu Gly Gln Lys Ala Val Ile Cys Ala Ala Cys His Leu Ala
    290                 295                 300

Glu Val Ser Pro Glu Ser Ile Gly Tyr Val Glu Thr His Gly Thr Gly
305                 310                 315                 320

Thr Arg Ile Gly Asp Pro Ile Glu Phe Ala Ala Leu Thr Glu Ala Phe
                325                 330                 335

Asp Thr Ser His Arg Gln Tyr Cys Ala Leu Gly Ala Val Lys Ala Asn
            340                 345                 350

Ile Gly His Thr His Ala Ala Ala Gly Val Ala Gly Leu Ile Lys Thr
        355                 360                 365

Ala Leu Val Leu His His Arg Thr Ile Pro Pro Leu Ala Asn Tyr Gln
    370                 375                 380

Met Pro Asn Ser Lys Leu Asp Leu Ala His Ser Pro Phe Tyr Ile Pro
385                 390                 395                 400

Ile Gln Pro Gln Glu Trp Pro Ala Ser Arg Met Pro Pro Arg Ala Gly
                405                 410                 415

Val Ser Ser Phe Gly Ile Gly Gly Thr Asn Val His Met Ile Leu Glu
            420                 425                 430

Gly Leu Asn Pro Ala Val Arg Asp Asp His Asp Gln Val Arg Ala Pro
        435                 440                 445

Val Phe Ile Pro Leu Ser Ala Pro Ser Phe Glu Gln Leu Asp Glu Leu
    450                 455                 460

Thr Gln Gln Leu Thr Pro Leu Leu Ala Thr Leu Asp Ala Ser Thr Leu
465                 470                 475                 480

Ala Tyr Thr Gln Gln Val Ala Arg Pro Val Phe Asp Cys Arg Arg Val
                485                 490                 495

Ile Gln Val Glu Asn Asp Gly Thr Gln Ala Met Leu Ala Ser Leu Asp
            500                 505                 510

Asn Leu Met Pro Asp Ala Pro Trp Gly Leu His Cys Pro Asp Leu Arg
        515                 520                 525

Thr Thr Asn Asp Cys Thr Tyr Ala Gln Trp Leu Ala His Ser Ala His
    530                 535                 540

Tyr Gln Arg Glu Ala Thr Ala Leu Thr Ala Leu Leu Asp Gly Met Asn
545                 550                 555                 560

Ile Pro Pro Ala Tyr Cys His Ala Glu Thr Trp Ala Ala Gln Ala Asn
                565                 570                 575

Ser Ser Leu Leu Ile Arg Gly Cys Gln Thr Ile Ala Ala Leu Lys Thr
            580                 585                 590

Trp Met Asn Leu Leu Pro Thr Leu Thr Leu Leu Ser Gly Ala Gly Thr
        595                 600                 605

Gly Leu Leu Pro Ala Ala Ala Ala Ser Gly Met Ile Ala Thr Gln Asp
    610                 615                 620

Val Leu His Leu Leu Trp Glu Met Glu Gln Lys Ala Leu His Leu Trp
625                 630                 635                 640

Leu Pro Glu Arg His Glu Pro Ile Pro Gly Tyr Val Leu Ala Trp Gln
                645                 650                 655

Gly Asn Pro Ile Thr Asp Ala Gln Arg Asn Asp Arg Gly Phe Trp Ser
            660                 665                 670
```

```
Glu Ala Leu Leu Ala Asp Thr Arg Glu Leu Gly Glu Gly Val His Ser
        675                 680                 685

Ile Asn Trp Val Arg Leu Pro Pro Glu Ile Arg Glu Asp Val Asp Val
    690                 695                 700

Leu Arg Tyr Val Ala Gln Leu Trp Cys Ala Gly Ile Asn Val Asp Trp
705                 710                 715                 720

Ala Val Trp Tyr Gly Thr Pro Leu Pro Gln Arg Gly Ser Ala Ser Ala
                725                 730                 735

Tyr Pro Phe Ala His Asn His Tyr Pro Leu Pro Gly Arg Val Met Gly
            740                 745                 750

Ser Val Glu Thr Gln Pro Glu Ala Gly Pro Glu Thr His His Pro Tyr
        755                 760                 765

Gln Ala Arg Pro Val Leu Ser Val Pro Phe Val Ala Ala His Ser Arg
    770                 775                 780

Gly Met Gln Tyr Ile Thr Gly Leu Met Glu Leu Leu Leu Glu Ile Ser
785                 790                 795                 800

Pro Val Gly Val Asp Asp Asp Phe Phe Glu Leu Gly Gly His Ser Leu
                805                 810                 815

Leu Val Thr Gln Leu Thr Ser Arg Leu Glu Arg Asp Phe Asn Val His
            820                 825                 830

Ile Asp Leu Leu Thr Leu Met Glu Asn Pro Asn Pro Arg Asn Ile Tyr
        835                 840                 845

Ala His Ile Ala Ala Gln Leu Gly Gly Glu Asp Asn Leu Glu Ile Ala
    850                 855                 860

Cys Gln
865


<210> SEQ ID NO 167
<211> LENGTH: 3206
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Met Asp Asn Thr Ser Gly Asp Phe Pro Cys Asn Lys Met Asp Thr Arg
1               5                   10                  15

Lys Gln Leu Pro Leu Thr Pro Ser Gln Gln Gly Phe Leu Phe His Ser
            20                  25                  30

Leu Lys Asp Lys Lys Arg Ser Asn Tyr His Glu His Phe Thr Cys Ile
        35                  40                  45

Phe Ser Gln His Val Asp Ser Ala His Phe Lys Trp Ala Leu Glu Thr
    50                  55                  60

Leu Phe Arg Lys His Glu Cys Phe Arg Thr Asp Tyr Asn Trp Glu Ile
65                  70                  75                  80

Asp Glu Arg Pro Cys Gln Val Val Lys Thr Asp Val Leu Pro Asp Ile
                85                  90                  95

Tyr Val Leu Asp Cys Glu Gln Glu Glu Ile Arg Phe Leu Leu Ala Asn
            100                 105                 110

Asp Asp Ile Ile Ile Pro Val Pro Gln Asp Asp Gly Ile Asp Ala Ile
        115                 120                 125

Ile Pro Gln Leu Leu Gln Ala Asp Leu Lys Tyr Pro Phe Ser Leu Lys
    130                 135                 140

Thr Ile Pro Val Arg Ala Tyr Leu Ile Gln Ser Thr Lys Glu Ser Ala
```

```
145                 150                 155                 160

Phe Ile Leu Ser Tyr His His Ile Val Met Asp Gly Trp Ser Leu Ser
                165                 170                 175

Leu Phe Ile Lys Gln Leu Leu Gln Leu Tyr Gly Ala Ala Val Val Ser
            180                 185                 190

Gly Val Arg Asp Asp Ser Ala Ile Ile Pro Ser Ser Leu Lys Pro Leu
        195                 200                 205

Val Asp Thr Leu Ser Ala Arg Arg His Thr Phe Gln His Asp Tyr Trp
    210                 215                 220

Ala Ala Tyr Leu Arg Glu Gly Thr Pro Thr Cys Ile Val Pro Leu Ser
225                 230                 235                 240

Gln Tyr His Thr Asp Thr Glu Ala Glu Asn Asn Ser Tyr Val Asn Gln
                245                 250                 255

Thr Asn His Val Glu Ile Asn Leu Ser Pro Asp Val Cys Gln Lys Ile
            260                 265                 270

Gln Thr Leu Cys Ser Asp Tyr Arg Ile Thr Pro Ala Val Ile Phe Tyr
        275                 280                 285

Val Ala Trp Gly Ile Leu Leu Gln Arg Trp Cys Tyr Ala Asp Asp Val
    290                 295                 300

Leu Phe Gly Ala Thr Ile Ser Gly Arg Asn Ile Pro Ile Asp Gly Ile
305                 310                 315                 320

Glu Glu Thr Leu Gly Leu Phe Ile Asn Thr Leu Pro Leu Arg Leu Arg
                325                 330                 335

Asp Asp Gly Ala Thr Leu Leu Gln His Leu Gln Arg Met His Gln Thr
            340                 345                 350

Leu Ile Ala His Tyr Ser Asn Glu His Asp Ala Leu Ala Ser Ile Gln
        355                 360                 365

Arg Leu Val His Lys Glu Gly His Ala Gly Asp Leu Phe Asn Thr Leu
    370                 375                 380

Val Val Leu Glu Asn Tyr Pro Val Asp Met Thr Leu Leu Ser Cys Ala
385                 390                 395                 400

Ser Pro Val Ala Ile Arg His Leu Ser Val His Glu Gln Thr His Tyr
                405                 410                 415

Pro Leu Thr Leu Thr Ile Thr Gln Gln Lys Gly Phe Arg Phe Ser Ile
            420                 425                 430

Ala Tyr Ala Leu Asn Tyr Leu Thr Asn Asn Met Ala Gln Ala Leu Leu
        435                 440                 445

Met His Leu Ser Tyr Leu Leu Glu Gln Leu Val Asp Asn Pro Gln Arg
    450                 455                 460

Pro Ile Ala Ala Leu Val Asn Leu Ser Pro Cys Gln Gln Ala Gln Val
465                 470                 475                 480

Leu Gln Pro Tyr Leu Glu Arg Met Ala Cys Arg Asp Trp Asp Ser Gln
                485                 490                 495

Ser Asn Val Ile Glu Gln Phe His Gln Val Ala Ala Thr Ser Pro Ala
            500                 505                 510

Gln Val Ala Val Val Asp Glu Leu Cys Ala Leu Thr Tyr Ser Glu Leu
        515                 520                 525

Ala Ala Gln Ala Glu Gln Leu Ala Ala Tyr Leu Val Gln Gln Gly Val
    530                 535                 540

Met Val Gly Asp Thr Val Gly Ile Ile Ser Glu Arg Arg Val Asn Thr
545                 550                 555                 560

Val Val Ala Ile Ile Ala Ile Met Leu Ile Gly Ala Ala Tyr Val Pro
                565                 570                 575
```

-continued

```
Ile Ser Pro Asp Tyr Pro Val Gly Arg Met Gln Glu Ile Ile Asp Asp
            580                 585                 590

Ser Gly Leu Ala Leu Leu Leu Val His Gly Lys Pro Leu Asp Ala Leu
        595                 600                 605

Asn Val Ala Gln Ser Asp Leu Cys Ala Phe Pro Val Ala Pro Ser Val
    610                 615                 620

Val Phe Pro Val Ile Thr Pro Asp Ser Arg Ala Tyr Val Ile Tyr Ser
625                 630                 635                 640

Ser Gly Ser Thr Gly Lys Pro Lys Gly Ile Ala Val Ala His Arg Gly
                645                 650                 655

Leu Leu Arg Leu Ile Gln Gly Asp Ser Pro Leu Lys Val Glu Ser Gly
            660                 665                 670

Glu Thr Thr Leu Leu Thr Cys Pro Phe Glu Phe Asp Val Ser Val Phe
        675                 680                 685

Glu Met Trp Ser Thr Leu Leu Asn His Gly Lys Leu Val Leu Leu Ser
    690                 695                 700

Lys Gln Ala Leu Leu Asp Ile Asn His Ile Arg Arg Thr Ile Ala Asp
705                 710                 715                 720

Glu Gln Val Ala Arg Ala Trp Phe Thr Ser Ser Leu Phe Asn Ser Tyr
                725                 730                 735

Val Ala Glu Gly Ala Asp Phe Phe Gly Met Leu Gln His Ile Thr Val
            740                 745                 750

Gly Gly Glu Ala Val Ser Ala Trp His Val Asn Asp Val Met Gln Lys
        755                 760                 765

Tyr Pro His Leu Val Val Thr Asn Gly Tyr Gly Pro Thr Glu Asn Thr
    770                 775                 780

Ile Phe Thr Thr Ala Tyr Arg Phe Asn Gly Leu Gln Pro Ala Arg Val
785                 790                 795                 800

Pro Ile Gly Tyr Ala Val Pro Gly Thr Ser Leu Tyr Ile Thr Asp Leu
                805                 810                 815

His Gly His Leu Leu Pro Ile Gly Ala Thr Gly Glu Leu Val Ala Gly
            820                 825                 830

Gly Val Gly Val Ala Ile Gly Tyr Gln Asn Asn Pro Ala Leu Ser Ala
        835                 840                 845

Thr Val Phe Val Pro Asp Pro Phe Ile Pro Gly Gly Met Met Tyr Lys
    850                 855                 860

Thr Gly Asp Tyr Ala Arg Leu Leu Asp Asp Gly Cys Val Asp Cys Phe
865                 870                 875                 880

Gly Arg Lys Asp Gly Gln Ile Lys Ile Asn Gly Gln Arg Ile Glu Thr
                885                 890                 895

Gly Glu Ile Glu Gln Arg Leu Leu Glu Cys Ser Gly Ile Ile Glu Ala
            900                 905                 910

Val Val Val Pro Tyr Arg Val Arg Glu Thr Leu His Ile Ala Ala Val
        915                 920                 925

Val Cys Val Asn Asp Ser Tyr Asp Glu Val Glu Val Arg Gly Gln Leu
    930                 935                 940

Ala Asp Arg Leu Pro Pro Phe Ala Ile Pro Glu Ser Leu Val Val Val
945                 950                 955                 960

Thr Glu Ile Ala Lys Ser His Ser Gly Lys Ala Asp Leu Ala Gln Leu
                965                 970                 975

Arg Tyr Leu Leu Pro Ala Thr Gln Cys Asn Ala Val Ser Thr Thr Ile
            980                 985                 990
```

```
Ser Glu Val His Ser Asp Met Glu  His Ala Leu His Ala  Ile Trp Gln
        995                 1000                 1005

Arg Val  Leu Asp Arg Gln Asp  Ile Asp Ser Asn Ala  Ser Phe Phe
    1010                 1015                 1020

Ala Leu  Gly Gly Thr Ser Leu  Asp Thr Ile Arg Val  Lys Gly Asp
    1025                 1030                 1035

Ile Lys  Arg Gln Leu Gly Leu  Glu Ile Asp Ile Thr  Asp Leu Phe
    1040                 1045                 1050

Lys Tyr  Pro Thr Leu Thr Ala  Leu Ala His Phe Leu  Asp Thr Ala
    1055                 1060                 1065

Val Ser  Pro Glu Asp Ala Ile  Pro Thr Arg Ala Val  Val Tyr Ser
    1070                 1075                 1080

Asp Met  Pro Val Ala Ile Val  Gly Met Ala Gly Arg  Phe Pro Gly
    1085                 1090                 1095

Ala Ala  Asn Ile Ala Ala Leu  Trp Thr Leu Val Val  Gly Gly Glu
    1100                 1105                 1110

Ser Gly  Leu Thr Leu Phe Ser  Asp Glu Glu Leu Arg  Ala His Gly
    1115                 1120                 1125

Val Thr  Pro Asp Thr Leu Lys  Gln Ala Asn Tyr Ile  Lys Thr Lys
    1130                 1135                 1140

Gly Ile  Val Asp Asp His Glu  Trp Phe Asp Ala Asp  Phe Phe Gly
    1145                 1150                 1155

Tyr Thr  Pro Asn Glu Ala Glu  Cys Met Asp Pro Gln  Ile Arg Leu
    1160                 1165                 1170

Leu His  Gln Cys Cys Trp Gln  Thr Leu Glu His Ala  Gly Cys Asp
    1175                 1180                 1185

Pro Ala  Thr Phe Thr Gly Ala  Ile Gly Ile Tyr Ala  Gly Leu Leu
    1190                 1195                 1200

Thr Ser  Pro His Trp Leu Asn  Ala Val Met Gln Asp  Thr Thr Asp
    1205                 1210                 1215

Ser Thr  Ala Leu Tyr Lys Ala  Ser Ile Leu Asn Ile  His Ser Val
    1220                 1225                 1230

Thr Ala  Leu Ile Ala His Ala  Leu Asn Leu Thr Gly  Pro Ala Val
    1235                 1240                 1245

Thr Leu  Asp Thr Ala Cys Ser  Thr Ser Ala Val Ala  Ile His Gln
    1250                 1255                 1260

Ala Cys  Ile Ala Leu Arg Asn  Arg Asp Cys Asp Ala  Ala Leu Ala
    1265                 1270                 1275

Gly Gly  Val Ser Ile Glu Met  Pro Ala Tyr Arg Gly  Tyr Glu Tyr
    1280                 1285                 1290

His Glu  Gly Met Ile Asn Ala  Arg Asp Gly Val Cys  Arg Pro Phe
    1295                 1300                 1305

Asp Ser  Gln Ala Ser Gly Thr  Val Thr Gly Asp Gly  Leu Gly Met
    1310                 1315                 1320

Leu Leu  Leu Lys Arg Leu Asp  Asp Ala Leu Ala Asp  Arg Asp Cys
    1325                 1330                 1335

Ile Tyr  Gly Val Ile Lys Gly  Ser Ala Val Asn Asn  Asp Gly Asn
    1340                 1345                 1350

Asn Lys  Ile Gly Tyr Thr Ala  Pro Ser Val Ile Gly  Gln Ser Thr
    1355                 1360                 1365

Val Ile  Arg Thr Ser Leu Arg  Arg Ala Gly Phe Asp  Ser Asp Ser
    1370                 1375                 1380

Ile Gly  Leu Val Glu Ala His  Gly Thr Gly Thr Val  Leu Gly Asp
```

```
    1385                1390                1395

Pro Ile  Glu Leu Arg Ala Leu  Asn Glu Val Phe Gly  Pro Thr Pro
    1400                1405                1410

Val Pro  Phe Cys Val Val Ser  Ala Leu Lys Ser Asn  Ile Gly His
    1415                1420                1425

Leu Asn  Ser Ala Ala Gly Val  Ala Gly Val Ile Lys  Thr Thr Leu
    1430                1435                1440

Ala Leu  His His Gln Val Leu  Pro Pro Thr Ala His  Phe Arg Gln
    1445                1450                1455

Leu Asn  Pro Ala Ile Asp Leu  Ser Arg Ser Ala Leu  Tyr Val Asn
    1460                1465                1470

Gln Gln  Val Gln Pro Trp Pro  Ser Thr Arg Pro Arg  Arg Ala Leu
    1475                1480                1485

Val Ser  Ser Phe Gly Ile Gly  Gly Thr Asn Ala Ser  Ile Ala Leu
    1490                1495                1500

Glu Ala  His Gln His Glu Asp  Asp Pro Ser Ala Thr  Gly Val Arg
    1505                1510                1515

Asp Ser  Tyr Leu Leu Leu Phe  Ser Ala Lys Thr Pro  Ala Ala Leu
    1520                1525                1530

Glu Leu  Arg Val Ala Ser Thr  Leu Glu Tyr Val Lys  His Gly Val
    1535                1540                1545

Gly Val  Arg Leu Pro Asp Val  Ala Tyr Thr Leu Gln  Thr Gly Arg
    1550                1555                1560

Thr Ala  Phe Asp His Arg Arg  Ala Tyr Leu Val Ser  Arg Gly Ser
    1565                1570                1575

Lys Ile  Asp Leu Ser Cys Ala  Thr Ile Leu Gln Ala  Glu Ile Phe
    1580                1585                1590

Asn Gly  Gln Arg Thr Thr Ala  Glu Ile Cys Phe Met  Phe Pro Gly
    1595                1600                1605

Gln Gly  Ser Gln Tyr His Gly  Met Ala Ser Ala Leu  Tyr Ala His
    1610                1615                1620

Gln Pro  Met Phe Arg Gln His  Met Asp Arg Cys Phe  Ala Ala Phe
    1625                1630                1635

Gln Arg  Tyr Ser Thr Val Asp  Leu Lys Ala Leu Leu  Phe Asp Asp
    1640                1645                1650

Glu Asp  Thr Arg Asp Ile Asp  Gln Thr Gln Phe Thr  Gln Pro Ala
    1655                1660                1665

Leu Phe  Cys Val Glu Tyr Ser  Leu Ala Arg Thr Leu  Ile Asp Leu
    1670                1675                1680

Gly Ile  Thr Pro Asp Ser Met  Ile Gly His Ser Leu  Gly Glu Tyr
    1685                1690                1695

Val Ala  Ala Cys Ile Ala Gly  Val Phe Thr Leu Glu  Asp Ala Leu
    1700                1705                1710

His Val  Ile Glu Ala Arg Gly  Arg Leu Met Gln Ser  Met Arg Pro
    1715                1720                1725

Gly Ser  Met Met Ala Val Tyr  Leu Ser Arg Glu Gln  Leu Thr Pro
    1730                1735                1740

Trp Leu  Ala Ala Glu Arg Gly  Ile Glu Leu Ala Ala  Asn Asn Ser
    1745                1750                1755

Ala His  Phe Cys Val Val Ala  Gly Glu Gln Ala Ala  Ile Ser Arg
    1760                1765                1770

Leu Ser  Thr Arg Leu Val Glu  Gly Gly Ile Gln His  Arg Arg Leu
    1775                1780                1785
```

```
Lys Thr  Ser His Ala Phe His  Ser Ala Met Met Thr  Pro Met Leu
    1790                 1795                 1800

His Asp  Phe Ala Gln Leu Leu  Gly Gln Ile Pro Met  His Ala Pro
    1805                 1810                 1815

His Lys  Arg Phe Ile Ser Asn  Val Ser Gly Thr Trp  Ile Thr Glu
    1820                 1825                 1830

Glu Gln  Ala Thr Ser Pro Asp  Tyr Trp Val Gln Gln  Val Arg Asn
    1835                 1840                 1845

Ala Val  Leu Phe Ser Glu Gly  Ala Ala Gln Leu Leu  Val Gln Pro
    1850                 1855                 1860

Thr Leu  Phe Ile Glu Cys Gly  Pro Gly Asn Thr Leu  Ser Thr Phe
    1865                 1870                 1875

Ile Gln  Gly His Asn Gln Tyr  Ser Asp Gln Pro Thr  Leu Leu Thr
    1880                 1885                 1890

Leu Arg  Lys Ala Asn Ala Ala  Ile Asp Asp Glu His  Met Leu His
    1895                 1900                 1905

Arg Thr  Leu Ala Ala Leu Trp  Val Arg Gly Glu Asn  Ile Asp Trp
    1910                 1915                 1920

Arg Arg  Phe Asn Gln Thr Ala  Leu Gly Lys His Ile  Pro Leu Pro
    1925                 1930                 1935

Asp Tyr  Pro Phe Glu Gln Thr  Tyr Tyr Tyr Arg Tyr  Gly Ala Ala
    1940                 1945                 1950

Leu Ser  Gly Tyr Arg Gln Tyr  Pro Asn Pro Leu Arg  Arg Pro Gln
    1955                 1960                 1965

Asp Glu  Trp Leu Gln Arg Val  Leu Trp Arg Met His  Asp Thr Ser
    1970                 1975                 1980

Leu Arg  Glu Ala Phe Tyr Ala  Pro Gly Glu Leu Ile  Ile Ile Ile
    1985                 1990                 1995

Ser Ala  Asp Gly Asp Lys Leu  Gln Gln Thr Leu Met  Ser Ser Gly
    2000                 2005                 2010

Val Asp  Ser Ile Thr Met Pro  Leu Pro Ile Ser Ser  Glu Asp Asp
    2015                 2020                 2025

Val Trp  Asp Asn Asp Arg Ile  Leu Thr His Phe His  Asp Ile Cys
    2030                 2035                 2040

Ala Leu  Leu Ala His Lys Thr  Tyr Arg Gln Leu His  Cys Leu Tyr
    2045                 2050                 2055

Ala Pro  Gly Ala Glu Ala Gly  Ser Ser Leu Thr Gln  Ser Leu Ser
    2060                 2065                 2070

Gly Leu  Tyr Arg Val Ala Arg  Trp Cys Met His Ser  Thr Thr Pro
    2075                 2080                 2085

Leu Ala  Ser Leu Thr Val Leu  Thr His Gly Ala Phe  Arg Val Gln
    2090                 2095                 2100

Glu Glu  Asp Asn Pro Glu Pro  Thr Leu Ala Ala Leu  Ser Gly Ala
    2105                 2110                 2115

Val Asn  Val Phe Ala Gln Glu  Leu His Pro Thr Glu  Val Arg Leu
    2120                 2125                 2130

Ile Asp  Ile Asp Ala Gln Ser  Ser Asp Glu Asn Leu  Asn Leu Leu
    2135                 2140                 2145

Thr Gln  Arg Leu Ala Pro Lys  Gln Glu Thr Val Met  Ala Leu Arg
    2150                 2155                 2160

Gln Gly  Met Leu Tyr Leu Arg  Arg Phe Ile Pro Thr  Arg Leu Leu
    2165                 2170                 2175
```

```
Ala His  Leu Pro Pro Gln Thr  Gly Cys Ile Pro Gly  Asn Val Leu
    2180                 2185                 2190

Trp Ile  Ile Gly Gly Glu Lys  Gly Ile Gly Arg Met  Ile Gly Glu
    2195                 2200                 2205

Ala Leu  Ala Gln Arg Glu Gly  Val Arg Val Val Leu  Ser Ser Arg
    2210                 2215                 2220

Thr Gly  Tyr His His Glu Ala  Val Gln Gln Asp Ala  Leu Asp Val
    2225                 2230                 2235

Ile His  Cys Asp Val Thr Gln  Ala Glu Ala Val Arg  Ala Cys Leu
    2240                 2245                 2250

Ala Thr  Leu Leu Glu Arg Tyr  Gly Arg Leu Asp Gly  Val Ile Phe
    2255                 2260                 2265

Ala Ala  Asp Ala Thr Thr Thr  Leu Thr Leu His Gln  Leu Ser Glu
    2270                 2275                 2280

Ser Ala  Leu Arg Asp Thr Leu  Thr Val Lys Glu Arg  Gly Thr Ala
    2285                 2290                 2295

Asn Val  Leu His Ala Leu Ala  Gln Arg Asn Leu Leu  Asp Glu Arg
    2300                 2305                 2310

Leu Leu  Leu Leu Phe Cys Asn  Ser Leu Ala Ala Val  Asn Ala Glu
    2315                 2320                 2325

Ile Gly  Gln Thr Gly Tyr Ala  Thr Ala Ser Ala Tyr  Leu Asp Ala
    2330                 2335                 2340

Leu Ala  Gln Gln Leu Arg Thr  Arg Tyr Lys Val Asn  Ala Leu Ser
    2345                 2350                 2355

Ile Gly  Leu Asp Ala Leu Arg  Glu Gln Gly Met Leu  Leu Asp Ala
    2360                 2365                 2370

Ile Asn  Gly Ser Glu Tyr Asp  Val Leu Arg Gly Leu  Arg Pro Leu
    2375                 2380                 2385

Met Thr  Gly Thr Leu Leu Gln  Ala Tyr Lys Gln Gln  Gly Ala Asp
    2390                 2395                 2400

Thr Ser  Tyr Tyr Ala Arg Leu  Ser Pro Glu Ser Asp  Trp Leu Leu
    2405                 2410                 2415

Asp Glu  His Arg Ile Ser Gly  Ile Ala Thr Leu Pro  Gly Thr Gly
    2420                 2425                 2430

Tyr Leu  Ala Leu Ala Tyr Glu  Ala Leu Arg His Tyr  Phe Val Gln
    2435                 2440                 2445

Asp Gln  Ile Cys Ile Asp Glu  Leu Val Phe Leu Ala  Pro Leu Thr
    2450                 2455                 2460

Val Met  Asp Asn Cys Ser Val  Asp Val Phe Val Asp  Ile Ser Pro
    2465                 2470                 2475

Asn Gly  Gln Gly Val Ser Val  Glu Val Lys Ser Met  Thr Glu Arg
    2480                 2485                 2490

Phe Ser  Gly Thr Leu Thr Thr  His Ala Arg Gly Arg  Ala Thr Arg
    2495                 2500                 2505

Leu Met  Val Asp Asp Asn Val  Val Cys Asp Leu Thr  Gly Leu Met
    2510                 2515                 2520

Arg Glu  Met His Thr Ile Thr  Pro Pro Thr Lys Glu  Leu Ser Ser
    2525                 2530                 2535

Thr His  Phe His Tyr Gly Pro  Arg Trp His Ser Val  Gln Gln Leu
    2540                 2545                 2550

Tyr Gly  Asn Thr Ala Gln Thr  Gln Val Phe Ala Thr  Leu Ala Leu
    2555                 2560                 2565

Pro Thr  Val Ala Ala Asn Asp  Thr Ile Ala Leu His  Pro Ala Leu
```

```
    2570                2575                2580

Leu Asp  Ile Ala Ser Ser Val  Val Glu Gln Leu Pro  Gly Phe His
    2585                2590                2595

Thr Asp  Ser Val Pro Phe Leu  Tyr Gln Asp Leu Arg  Leu Tyr Arg
    2600                2605                2610

Pro Leu  Pro Asn Thr Leu His  Val Ala Leu Thr Val  Asn Arg His
    2615                2620                2625

Asp Glu  Glu Gly Asp Ser Tyr  Ala Phe Thr Leu Tyr  Asp Met Ala
    2630                2635                2640

Gly Glu  Met Val Ala Arg Cys  Ala Ala Met Val Lys  Arg Lys Val
    2645                2650                2655

Gln Leu  His Ile Gln Asp Val  Asp Asp Asp Thr Arg  Leu Arg Val
    2660                2665                2670

Pro Ser  Ala Asp Asn Tyr Gln  Leu Arg Leu Ala Ala  Glu Gly Glu
    2675                2680                2685

Gly Ala  Gly Lys Leu Ala Leu  Cys Pro Thr Pro Arg  Leu Ala Leu
    2690                2695                2700

Gly Asp  Ser Gln Val Glu Ile  Glu Val Leu Ala Thr  Gly Leu Asn
    2705                2710                2715

Phe Lys  Asp Val Leu Phe Thr  Thr Gly Leu Leu Arg  Gln Gln Pro
    2720                2725                2730

Gly Glu  Ala Pro Leu Gln Leu  Gly Leu Glu Cys Ala  Gly Arg Ile
    2735                2740                2745

Thr Arg  Val Gly Lys Asn Val  Thr Glu Phe Ala Pro  Gly Glu Asp
    2750                2755                2760

Val Met  Ala Val Leu Asn Gly  Gly Phe Val Gln Tyr  Ala Arg Val
    2765                2770                2775

Glu Ser  Asp Cys Val Val Arg  Lys Pro Ala His Cys  Arg Ile Glu
    2780                2785                2790

Gln Ala  Ala Ala Leu Pro Ile  Ala Tyr Leu Thr Ala  Tyr Tyr Ala
    2795                2800                2805

Leu Val  Val Arg Ala Asn Leu  Gln Pro Gly Glu Arg  Val Leu Ile
    2810                2815                2820

His Ser  Ala Ala Gly Gly Val  Gly Leu Ala Ala Leu  His Ile Ala
    2825                2830                2835

Lys Arg  Cys Gly Ala Gln Ile  Phe Ala Thr Ala Gly  Ser Glu Gln
    2840                2845                2850

Lys Arg  Asp Tyr Leu Leu Ser  Leu Gly Val His Ala  Val Ala Asp
    2855                2860                2865

Ser His  Asp Glu Gln Phe Ala  Ala Thr Leu Leu Thr  Ala Ser Asp
    2870                2875                2880

Gly Gln  Gly Met Asp Val Ile  Leu Asn Ser Leu Thr  Gly Arg Leu
    2885                2890                2895

Leu Asp  Ala Ser Leu Ala Leu  Leu Ala Pro Leu Gly  Arg Phe Leu
    2900                2905                2910

Glu Leu  Gly Ser Lys Asp Ile  Val Glu Asp Lys Ala  Leu Pro Met
    2915                2920                2925

Arg Phe  Phe Ala Gln Gly Gly  Thr Phe Ile Pro Ile  Asn Phe His
    2930                2935                2940

Ala Ala  His Gly Ala Phe Ser  Arg Tyr Leu Gln Gln  Ile Val Ala
    2945                2950                2955

Trp Ile  Asp Asp Asn Thr Leu  Pro Leu Leu Pro Cys  Lys Ser Val
    2960                2965                2970
```

```
Pro Leu Pro Glu Val Ala Arg Ala Phe Ala Thr Leu Thr Thr Pro
    2975                2980                2985

Gln His Ile Gly Lys Val Val Val Thr His Arg Thr Ala Ala Gly
    2990                2995                3000

Met Asp Arg Leu Asn Ala Met Ile Ala Glu Arg Arg Leu Gly Gly
    3005                3010                3015

Tyr Ala Leu Ser Met Ser Asn Ala Glu Val Met Arg Gln Leu Trp
    3020                3025                3030

Pro Ile Leu Asn Thr Arg Ser Pro Trp Ala Gln Leu Leu Leu Ser
    3035                3040                3045

Pro Arg Ala Ile Asp Arg Leu Ala Arg Gly Asn Arg Val Asp Arg
    3050                3055                3060

Gly Val Pro Ser Ala Ala Asn Asp Thr Ile Thr Gln Gln Thr Val
    3065                3070                3075

Lys Lys Arg Pro Arg Pro Glu Ile Gly Val Pro Tyr Ser Pro Ala
    3080                3085                3090

Thr Arg Glu Val Glu Arg Val Leu Cys Gln Ile Leu Glu Glu Tyr
    3095                3100                3105

Leu Gly Leu Asp Arg Val Gly Ile Asp Asp Asn Tyr Ala Glu Leu
    3110                3115                3120

Gly Ala Thr Ser Leu Asp Met Val Gln Leu Ser Gly Gln Met Ala
    3125                3130                3135

Arg His Tyr Pro Gln Val Ser Val Val Ser Leu Tyr Asn His Ala
    3140                3145                3150

Thr Val Arg Gln Leu Ala Thr Phe Cys Gln Pro Pro Glu Gly Glu
    3155                3160                3165

Ser Asn Ala Pro Ser Pro Gln Pro Ala Val Gln Thr Asn Thr Arg
    3170                3175                3180

Ala Asn Gln Ile Ala Lys Arg Ala Leu Gln Ile Ala Lys Asn Thr
    3185                3190                3195

Ala Arg Ser His Thr Ser Leu His
    3200                3205


<210> SEQ ID NO 168
<211> LENGTH: 70
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Met Asp Lys Phe Lys Glu Lys Asn Pro Leu Ser Leu Arg Glu Arg Gln
1               5                   10                  15

Val Leu Arg Met Leu Ala Gln Gly Asp Glu Tyr Ser Gln Ile Ser His
            20                  25                  30

Asn Leu Asn Ile Ser Ile Asn Thr Val Lys Phe His Val Lys Asn Ile
        35                  40                  45

Lys His Lys Ile Gln Ala Arg Asn Thr Asn His Ala Ile His Ile Ala
    50                  55                  60

Asn Arg Asn Glu Ile Ile
65                  70


<210> SEQ ID NO 169
<211> LENGTH: 244
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

```
Met Arg Ile Asp Ile Leu Ile Gly His Thr Ser Phe Phe His Gln Thr
1               5                   10                  15

Ser Arg Asp Asn Phe Leu His Tyr Leu Asn Glu Glu Glu Ile Lys Arg
            20                  25                  30

Tyr Asp Gln Phe His Phe Val Ser Asp Lys Glu Leu Tyr Ile Leu Ser
        35                  40                  45

Arg Ile Leu Leu Lys Thr Ala Leu Lys Arg Tyr Gln Pro Asp Val Ser
    50                  55                  60

Leu Gln Ser Trp Gln Phe Ser Thr Cys Lys Tyr Gly Lys Pro Phe Ile
65                  70                  75                  80

Val Phe Pro Gln Leu Ala Lys Lys Ile Phe Phe Asn Leu Ser His Thr
                85                  90                  95

Ile Asp Thr Val Ala Val Ala Ile Ser Ser His Cys Glu Leu Gly Val
            100                 105                 110

Asp Ile Glu Gln Ile Arg Asp Leu Asp Asn Ser Tyr Leu Asn Ile Ser
        115                 120                 125

Gln His Phe Phe Thr Pro Gln Glu Ala Thr Asn Ile Val Ser Leu Pro
    130                 135                 140

Arg Tyr Glu Gly Gln Leu Leu Phe Trp Lys Met Trp Thr Leu Lys Glu
145                 150                 155                 160

Ala Tyr Ile Lys Tyr Arg Gly Lys Gly Leu Ser Leu Gly Leu Asp Cys
                165                 170                 175

Ile Glu Phe His Leu Thr Asn Lys Lys Leu Thr Ser Lys Tyr Arg Gly
            180                 185                 190

Ser Pro Val Tyr Phe Ser Gln Trp Lys Ile Cys Asn Ser Phe Leu Ala
        195                 200                 205

Leu Ala Ser Pro Leu Ile Thr Pro Lys Ile Thr Ile Glu Leu Phe Pro
    210                 215                 220

Met Gln Ser Gln Leu Tyr His His Asp Tyr Gln Leu Ile His Ser Ser
225                 230                 235                 240

Asn Gly Gln Asn
```

<210> SEQ ID NO 170
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 170

```
Met Ala Val Pro Ser Ser Lys Glu Glu Leu Ile Lys Ala Ile Asn Ser
1               5                   10                  15

Asn Phe Ser Leu Leu Asn Lys Lys Leu Glu Ser Ile Thr Pro Gln Leu
            20                  25                  30

Ala Phe Glu Pro Leu Leu Glu Gly His Ala Lys Gly Thr Thr Ile Ser
        35                  40                  45

Val Ala Asn Leu Val Ser Tyr Leu Ile Gly Trp Gly Glu Leu Val Leu
    50                  55                  60
```

```
His Trp His Asp Gln Glu Ala Lys Gly Lys Thr Ile Ile Phe Pro Glu
65                  70                  75                  80

Glu Gly Phe Lys Trp Asn Glu Leu Gly Arg Leu Ala Gln Lys Phe Tyr
                85                  90                  95

Arg Asp Tyr Glu Asp Ile Thr Glu Tyr Glu Val Leu Leu Ala Arg Leu
            100                 105                 110

Lys Glu Asn Lys Gln Gln Leu Val Ala Leu Ile Glu Arg Phe Ser Asn
        115                 120                 125

Asp Glu Leu Tyr Gly Lys Pro Trp Tyr Asn Lys Trp Thr Arg Gly Arg
    130                 135                 140

Met Ile Gln Phe Asn Thr Ala Ser Pro Tyr Lys Asn Ala Ser Gly Arg
145                 150                 155                 160

Leu Asn Lys Leu Gln Lys Cys Leu Ala Glu
                165                 170


<210> SEQ ID NO 171
<211> LENGTH: 532
<212> TYPE: PRT
<213> ORGANISM: Photorhabdus luminescens

<400> SEQUENCE: 171

Met Lys Ala Lys Asp Val Gln Pro Thr Ile Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Gly Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp Met Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Lys Gly Lys Val Tyr Tyr Met Gly Ala Glu
                165                 170                 175

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
    210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
```

-continued

```
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
    290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
    370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
                405                 410                 415

Val Ala Ala Ile Arg His Asp Cys Ala Ala Ser Gly Ile His Thr Ile
            420                 425                 430

Ala Thr Glu Gln Tyr Asn Gln Asp Ile Val Ser Leu Gly Leu His Ala
        435                 440                 445

Ala Gln Asp Val Leu Glu Met Glu Gln Lys Leu Arg Asn Ile Val Ser
    450                 455                 460

Met Thr Ile Leu Val Ala Cys Gln Ala Ile His Leu Arg Gly Asn Ile
465                 470                 475                 480

Ser Glu Ile Ala Pro Glu Thr Ala Lys Phe Tyr His Ala Val Arg Glu
                485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
        515                 520                 525

Met Leu Glu Glu
    530
```